US010689381B2

(12) United States Patent
Boger

(10) Patent No.: US 10,689,381 B2
(45) Date of Patent: Jun. 23, 2020

(54) VINBLASTINE 20" AMIDES: SYNTHETIC ANALOGS THAT MAINTAIN OR IMPROVE POTENCY AND SIMULTANEOUSLY OVERCOME PGP-DERIVED EFFLUX AND RESISTANCE

(71) Applicant: The Scripps Research Institute, LaJolla, CA (US)

(72) Inventor: Dale Boger, LaJolla, CA (US)

(73) Assignee: The Scripps Research Institute, La Jolla, CA (US)

(*) Notice: Subject to any disclaimer, the term of this patent is extended or adjusted under 35 U.S.C. 154(b) by 0 days.

(21) Appl. No.: 16/052,307

(22) Filed: Aug. 1, 2018

(65) Prior Publication Data
US 2019/0119277 A1    Apr. 25, 2019

Related U.S. Application Data

(60) Provisional application No. 62/559,295, filed on Sep. 15, 2017.

(51) Int. Cl.
| | | |
|---|---|---|
| *C07D 471/22* | (2006.01) | |
| *A61P 35/02* | (2006.01) | |
| *A61P 35/00* | (2006.01) | |
| *C07D 519/04* | (2006.01) | |
| *C07D 487/18* | (2006.01) | |
| *C07D 471/14* | (2006.01) | |

(52) U.S. Cl.
CPC ............ *C07D 471/22* (2013.01); *A61P 35/00* (2018.01); *A61P 35/02* (2018.01)

(58) Field of Classification Search
CPC ......... C07D 471/22; A61P 35/00; A61P 35/02
USPC ....................................................... 540/478
See application file for complete search history.

(56) References Cited

U.S. PATENT DOCUMENTS

| | | | |
|---|---|---|---|
| 4,322,351 A | 3/1982 | Miller et al. | |
| 9,611,271 B2 * | 4/2017 | Boger | C07D 471/14 |
| 2015/0291610 A1 * | 10/2015 | Boger | C07D 471/14 |
| | | | 514/283 |

OTHER PUBLICATIONS

Leggans et al., J. Med, Chem. (2013), 56(3), pp. 628-639.*
Barker et al., ACS Med, Chem. Lett. (2013), 4, pp. 985-988.*
PNAS (2016), 113(35), pp. 9691-9698.*
J. Med, Chem. (2017), 60, pp. 7591-7604 (published Aug. 31, 2017).*
Lukesh et al., *J Med Chem*, 60:7591-7604 (2017).
Lukesh et al., *J Med Chem*, 60:7591-7604 (2017) Supporting Information.
Dr. Dale Boger CV.
Hansch et al., *Chem Rev*, 91:165-195 (1991).
Leggans et al., *Org Lett*, 14(6):1428-1431 (2012).
Hine, *Physical Organic Chemistry*, McGraw-Hill Book Company, Inc., $2^{nd}$ ed., New York, 1962, pp. 87.
Exhibit I, US PTO data base list of titles and numbers of US Patents whose claims recite "Hammett sigma".
*McGraw-Hill Encyclopedia of Science & Technology*, $6^{th}$ ed., McGraw-Hill Book Company, New York, pp. 433-434, (1987).
*Oxford Dictionary of Biochemistry and Molecular Biology*, Smith et al. eds., Oxford University Press, New York, pp. 31 and 94 (1997).
*Merriam-Webster's Medical Desk Dictionary*, Merriam-Webster, Incorporated, Springfield, MA, pp. 31 and 115 (2002).
Streitweiser et al., *Introduction to Organic Chemistry*, $4^{th}$ ed., Prentice Hall, Upper Saddle River, NJ, p. 511 (1992).
Boger, *J Org Chem* 82:11961-11980 (Sep. 25, 2017).
Radakovic and Boger, *Bioorg Med Chem Lett* 28(5):863-865 (Mar. 1, 2018).
Radakovic and Boger, *Bioorg Med Chem Lett* 29:1370-1374 (2019).
Noller, *Chemistry of Organic Compounds*, $2^{nd}$ ed., W.R. Saunders Company, Philadelphia, PA, pp. 28-29 (1957.
*Hawley's Condensed Chemical Dictonary*, $12^{th}$ ed., Van Nostrand Reinhold Company, New York, NY, p. 656 (1993).
Streitweiser et al., *Introduction to Organic Chemistry*, $4^{th}$ ed., Prentice Hall, Upper Saddle River, NJ, p. 46 (1992).
*Oxford Dictionary of Biochemistry and Molecular Biology*, Smith et al. eds., Oxford University Press, New York, NY, p. 346 (1997).
Eliel and Wilen, *Stereochemistry of Organic Compounds*, John Wiley & Sons, Inc., New York, NY, pp. 1197 and 1205 (1994).

* cited by examiner

*Primary Examiner* — John M Mauro
(74) *Attorney, Agent, or Firm* — Husch Blackwell LLP

(57) ABSTRACT

A vinca alkaloid compound substituted at the 20'-position with a carboxamido group is disclosed. The carbonyl of the carboxamido group is bonded to a 20'-amino group and to a ring system that contains up to three 5-, 6- or 7-membered rings that are fused or otherwise bonded together. Each ring can be carbocyclic or heterocyclic, with a heterocyclic ring containing up to three hetero ring atoms that are the same or different and are selected from nitrogen, oxygen and sulfur. The ring system can include up to four substituent groups other than hydrogen that are discussed within. Methods of preparing the compounds are disclosed as are compositions for their use and methods of treatment using d compound. A particularly preferred compound has an activity in specified cancer cell growth inhibition assays that is the same or better than its parental, unsubstituted vinca compound and is not subject to Pgp-mediated efflux.

28 Claims, 2 Drawing Sheets

VINBLASTINE 20" AMIDES: SYNTHETIC ANALOGS THAT MAINTAIN OR IMPROVE POTENCY AND SIMULTANEOUSLY OVERCOME PGP-DERIVED EFFLUX AND RESISTANCE

STATEMENT REGARDING FEDERALLY SPONSORED RESEARCH OR DEVELOPMENT

This invention was made with government support under CA115526 and CA042056 awarded by the National Institutes of Health. The Government has certain rights in the invention.

BACKGROUND ART

The vinca alkaloids constitute a family of indole-indoline dimeric natural product compounds that continue to have a remarkable impact on anticancer drug discovery and treatment [Neuss et al., In *The Alkaloids*; Brossi, A., Suffness, M., Eds.; Academic: San Diego, Calif., 1990; Vol. 37, pp 229-240; Pearce, In *The Alkaloids*; Brossi, A., Suffness, M., Eds.; Academic: San Diego, Calif., 1990; Vol. 37, pp 145-204; and Kuehne et al., In *The Alkaloids*; Brossi, A., Suffness, M., Eds.; Academic: San Diego, Calif., 1990; Vol. 37, pp 77-132]. Originally isolated as trace constituents of the Madagascar periwinkle plant (*Catharanthus roseus* (L.) G.Don) [Noble et al., *Ann. N.Y. Acad. Sci.* 1958, 76, 882-894; and Svoboda et al., *J. Am. Pharm. Assoc. Sci. Ed.* 1959, 48:659-666], are a family of indole-indoline dimeric compounds that contain a four-ring system containing an indole linked to a five-ring system containing an indoline. Two of those natural alkaloid compounds, vinblastine (1) and vincristine (1a), are important clinical agents in the treatment of leukemias, lymphomas and testicular cancer. The semi-synthetic vinca alkaloid compound, vindesine (1b) is used to treat lung cancer and acute leukemia and less often for melanoma, and breast cancer. [*Goodman & Gilman's The Pharmaceutical Basis of Therapeutics*, Hardman et al. Eds., 9th ed., McGraw-Hill, 1257-1260, 1996.]

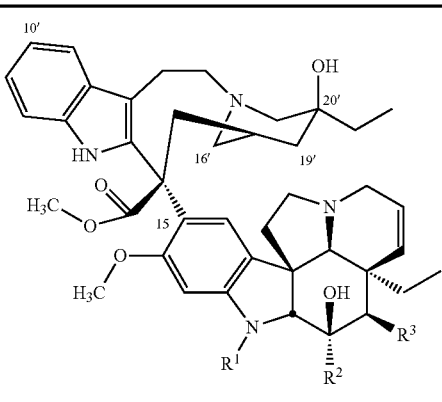

|  | $R^1$ | $R^2$ | $R^3$ |
|---|---|---|---|
| Vinblastine (1) | —CH$_3$ | —C(=O)—OCH$_3$ | —O—C(=O)—CH$_3$ |
| Vincristine (1a) | —CH=O | —C(=O)—OCH$_3$ | —O—C(=O)—CH$_3$ |
| Vindesine (1b) | —CH$_3$ | —C(=O)—NH$_2$ | —OH |

The 19,20'-anhydrovinca alkaloids (anhydrovinca alkaloids) are also active in treating the above diseases, albeit, they are usually somewhat less potently cytotoxic. Thus, the semi-synthetic anhydrovinca alkaloid, vinorelbine, has activity against lung cancer and breast cancer, and anhydrovinblastine is active as is shown hereinafter. Anhydrovincristine and anhydrovindesine are also cytotoxic.

Of the above compounds, vinblastine (1) and vincristine (1a) are the most prominent members of this class, and are among the first plant-derived natural products used in the clinic for the treatment of cancer. These two compounds and three recent semi-synthetic analogs are integral oncology drugs employed today in highly successful combination drug successful combination drug therapies. Their mode of action, which involves disruption of tubulin assembly during mitosis, still remains one of the most successful approaches for inhibiting tumor cell growth [Jordan et al., *Nat. Rev. Cancer* 2004, 4:253-265].

Alterations to the target tubulin could also impact activity and contribute to or be responsible for vinca alkaloid resistance. A series of association studies of clinical data have implicated high level expression of class III β-tubulin as both a prognostic and predictive factor for lower response rates or reduced overall survival in patients receiving tubulin binding drugs [Seve et al., *Lancet Oncol.* 2008; 9:168 and Yang et al., *PLoS One* 2014; 9:e93997]. However, most of the association studies and the supporting cellular studies have examined the impact of class III β-tubulin on taxanes and a much smaller sampling of its impact on vinca alkaloids are represented in the association studies [Sève et al., *Lancet Oncol.* 2008; 9:168 and Yang et al., *PLoS One* 2014; 9:e93997].

Despite the obvious differences in the tubulin binding sites of the taxanes and vinca alkaloids as well as their distinct functional behaviors (stabilization vs destabilization of tubulin dynamics), both taxanes and the vinca alkaloids typically have been lumped together as potentially being negatively impacted by the high expression of class III β-tubulin [Sève et al., *Lancet Oncol.* 2008; 9:168 and Yang et al., *PLoS One* 2014; 9:e93997].

Vinblastine and vincristine are superb drugs even by today's standards. The major limitation to their continued use is the observation of clinical resistance mediated by overexpression of the drug efflux pump phosphoglycoprotein (Pgp) [Persidis, *Nat. Biotechnology* 1999, 17:94-95]. The identification of vinca analogs that might address such resistance, which also results in multidrug resistance (MDR) and is responsible for the majority of all relapses in oncology, has remained a major focus of the field for over 30 years.

Not only would the discovery of a vinca alkaloid such as an illustrated vinblastine analog not susceptible to Pgp efflux serve as an effective replacement for vinblastine in its current clinical uses or in instances of vinblastine resistance, but it could also emerge as a new therapeutic option for other Pgp-derived MDR tumor treatments and constitute a major advance for oncology therapeutics. Thus, Harmsen et al., *Cancer Chemother Pharmacol* 2010 66:765-771, teach that each of vincristine, tamoxifen, vinblastine, docetaxel, cyclophosphamide, Xutamide, ifosfamide and paclitaxel activate PXR-mediated Pgp induction. As a consequence, a contemplated Pgp efflux-insensitive vinca 20' alkaloid amide can be used in place of one or more of those medicaments to inhibit PXR-mediated Pgp induction, while providing a desired anti-cancer therapy.

Despite the efforts focused on vinblastine for the past 40 years that have searched for analogs that effectively overcome vinblastine resistance, little progress has been made [Pearce, In *The Alkaloids*; Brossi, A., Suffness, M., Eds.; Academic: San Diego, Calif., 1990; Vol. 37, pp 145-20]. Recent advances in the total synthesis of vinblastine, vincristine and related natural products have provided access to analogs of the natural products not previously accessible by semisynthetic modification of the natural products [Potier, *J. Nat. Prod.* 1980, 43:72-86; Kutney, *Acc. Chem. Res.* 1993, 26:559-566; Sears et al., *Acc. Chem. Res.* 2015, 48:653-662; Fahy, *Curr. Pharm. Des.* 2001, 7:1181-1197; Langlois et al., *J. Am. Chem. Soc.* 1976, 98:7017-7024; Kutney et al., *Helv. Chim. Acta* 1976, 59:2858-2882; Kuehne et al., *J. Org. Chem.* 1991, 56:513-528; Bornmann et al., *J. Org. Chem.* 1992, 57:1752-1760; Yokoshima et al., *J. Am. Chem. Soc.* 2002, 124:2137-2139; Kuboyama et al., *Proc. Natl. Acad. Sci. U.S.A.* 2004, 101:11966-11970; Magnus et al., *J. Am. Chem. Soc.* 1990, 112:8210-8212; and Ishikawa et al., *J. Am. Chem. Soc.* 2009, 131:4904-4916].

The latest of these efforts has provided a powerful approach to access a variety of vinca alkaloid compounds, particularly vinblastine analogs that contain systematic deep-seated modifications within either the lower vindoline-derived [Ishikawa et al., *J. Am. Chem. Soc.* 2006, 128:10596-10612; Choi et al., *Org. Lett.* 2005, 7:4539-4542; Yuan et al., *Org. Lett.* 2005, 7:741-744; Elliott et al., *Angew. Chem., Int. Ed.* 2006, 45:620-622; Ishikawa et al., *Heterocycles* 2007, 72:95-102; Sears et al., *Org. Lett.* 2015, 17:5460-5463; Wilkie et al., *J. Am. Chem. Soc.* 2002, 124:11292-11294; and Elliott et al., *J. Am. Chem. Soc.* 2006, 128:10589-10595] or upper catharanthine-derived [Fahy, *Curr. Pharm. Des.* 2001, 7:1181-1197] subunits [Vukovic et al., *Tetrahedron* 1988, 44:325-331; Ishikawa et al., *J. Am. Chem. Soc.* 2008, 130:420-421; and Gotoh et al., *J. Am. Chem. Soc.* 2012, 134:13240-13243].

| | $IC_{50}$, nM | |
|---|---|---|
| compound | HCT116 | HCT116/VM46 |
| 1, X = OH | 6.8 | 600 |
| 4, X = H | 60 | 600 |
| 5, X = $N_3$ | 690 | 5500 |
| 6, X = $NH_2$ | 600 | >10000 |

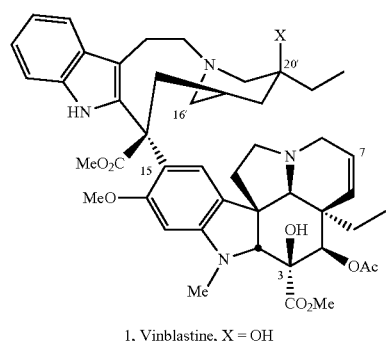

1, Vinblastine, X = OH

| | $IC_{50}$, nM | |
|---|---|---|
| compound | HCT116 | HCT116/VM46 |

2, Catharanthine

3, Vindoline

7, Anhydrovinblastine

20' amides — $R^a$

As a result of these developments, the inventor and his research group have prepared several series of key analogs, systematically exploring and defining the impact individual structural features and substituents have on tubulin binding affinity and tumor cell growth inhibition [Sears et al., *Acc. Chem. Res.* 2015, 48:653-662; and Ishikawa et al., *J. Am. Chem. Soc.* 2009, 131:4904-4916]. Complementary to the studies detailed herein, the impact and role of the vindoline C4 acetate [Campbell et al., *Org. Lett.* 2013, 15:5306-5309; and Yang et al., *Chem. Sci.* 2017, 8:1560-1569], C5 ethyl substituent [Va et al., *J. Am. Chem. Soc.* 2010, 132:8489-8495], $C_6$-$C_7$ double bond [Sasaki et al., *J. Am. Chem. Soc.* 2010, 132:13533-13544; Kato et al., *J. Am. Chem. Soc.* 2010, 132:3685-3687; and Schleicher et al., *J. Med. Chem.* 2013, 56:483-495], and the vindoline core structure itself [Schleicher et al., *J. Med. Chem.* 2013, 56:483-495], and have systematically explored the upper catharanthine-derived subunit C20' ethyl substituent [Allemann et al., *J. Am. Chem. Soc.* 2016, 138:8376-8379; and Allemann et al., Bioorg. Med. Chem. Lett. 2017, 27:3055-3059], C16' methyl ester [Tam et al., Bioorg. Med. Chem. Lett. 2010, 20:6408-6410], and added C10' or C12' indole substitutions have been systematically probed Gotoh et al., ACS Med. Chem. Lett. 2011, 2:948-952].

In addition and in preceding studies, it has been shown that replacement of the C20'-OH with 20' ureas was possible [Leggans et al., Org. Lett. 2012, 14:1428-1431], that substantial [Leggans et al., J. Med. Chem. 2013, 56:628-639] and even remarkable [Carney et al., Proc. Natl. Acad. Sci. U.S.A. 2016, 113:9691-9698] potency enhancements were obtainable with such 20' ureas, and that some exhibited further improvements in activity against vinblastine-resistant tumor cell lines [Barker et al., ACS Med. Chem. Lett. 2013, 4:985-988].

Looking across the vinca alkaloid compounds, is seen that similarities in activity on substitution with the same group at the same position of different vinca alkaloids, and particularly among these three particular alkaloid compounds (1, 1a, and 1b), provide similar results in anti-cancer cell activity increase or decrease. These activity similarities on substitution provide a predictive result across the group of at least the three vinca alkaloids that are vinblastine (1), vincristine (1a) and vindesine (1b).

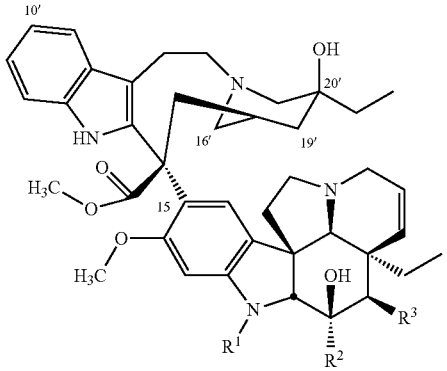

| | $R^1$ | $R^2$ | $R^3$ |
|---|---|---|---|
| Vinblastine (1) | —CH$_3$ | —C(O)—OCH$_3$ | —O—C(O)—CH$_3$ |
| Vincristine (1a) | —CH(O) | —C(O)—OCH$_3$ | —O—C(O)—CH$_3$ |
| Vindesine (1b) | —CH$_3$ | —C(O)—NH$_2$ | —OH |

See, for example, Gotoh et al., ACS Med Chem Lett 2011 2:948-952 and U.S. Pat. No. 8,940,754, where vincristine and vinblastine that had almost identical activities against two cancer call lines and a MDR variety of one of those lines on substitution of each of vincristine and vinblastine at the 10'-position with a fluoro group, provided fluoro-derivative compounds with enhanced, and almost identical activities in those same cancer cell lines. See also, U.S. Pat. No. 7,238,704 where activities among identically substituted vinblastines, vincristines, anhydrovinblastines, anhydro-vincristines are illustrated in and are seen to be similar. Those activities can also be seen to be comparable to the activities of identically substituted vinorelbines that are illustrated in U.S. Pat. No. 7,235,564.

An important extension of these studies is disclosed herein that includes the evaluation of vinblastine 20' amides with a prescribed objective of discovering analogs that match or exceed the potency of vinblastine, but that are not subject to Pgp efflux and its derived vinblastine resistance. Not only did these studies provide vinblastine analogs no longer susceptible to Pgp-derived resistance, but those compounds illustrate the discovery of a site and functionalization strategy for the preparation of now readily accessible vinca alkaloid analogs (3 steps) that improve binding affinity to tubulin (on target affinity) and functional potency in cell-based assays while simultaneously disrupting efflux by Pgp (off target affinity and source of resistance), offering a uniquely powerful approach to discover new, improved, and durable oncology drugs.

BRIEF SUMMARY OF THE INVENTION

The present invention contemplates a 20'-carboxamide-substituted vinca alkaloid compound, and particularly a 20'-amide-substituted vinblastine, vincristine or vindesine, or a pharmaceutically acceptable salt thereof. A contemplated compound corresponds in structure to a compound shown in Table A, below,

TABLE A

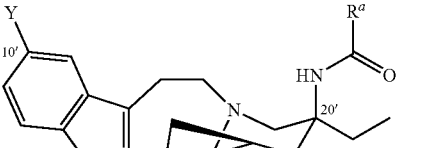

| Vinca Compound | $R^1$ | $R^2$ | $R^3$ |
|---|---|---|---|
| Vinblastine | —CH$_3$ | —C(O)—OCH$_3$ | —O—C(O)—CH$_3$ |
| Vincristine | —CH(O) | —C(O)—OCH$_3$ | —O—C(O)—CH$_3$ |
| Vindesine | —CH$_3$ | —C(O)—NH$_2$ | —OH | wherein

Y— is fluoro (—F) or hydrido (—H), and $R^a$— is a ring system containing up to a total of three 5-, 6- or 7-membered rings that are fused or otherwise directly bonded to each other. That ring system is carbocyclic or heterocyclic in which ring atoms other than carbon are the same or different and are nitrogen (N), oxygen (O) or sulfur (S). A contemplated heterocyclic ring system contains up to three ring heteroatoms.

In addition, up to four substituents that are the same or different are present bonded to ring atoms of the ring system ion place of hydrogens. Those substituents are selected from the group consisting of a $C_1$-$C_7$ hydrocarbyl, trifluoromethyl, phenyl, halogen (fluoro, chloro or bromo), cyano, nitro, $C_1$-$C_7$ acyl, amino, mono- or di-$C_1$-$C_7$ hydrocarbylamino, a nitrogen-bonded heterocyclic ring of 5- or 6 members that can contain 1 or 2 additional ring hetero atoms selected from oxygen, nitrogen, and sulfur, acylamido containing 1-7 carbon atoms, sulfonylamido containing 1-7 carbon atoms, oxycarbonylamido containing 1-7 carbon atoms, $C_1$-$C_7$ hydrocarbyloxy, N—$C_1$-$C_7$ hydrocarbyl acylamido containing 1-7 carbon atoms in the acyl group, N—$C_1$-$C_7$ hydrocarbyl sulfonylamido containing 1-7 carbon atoms in the sulfonamido group, N—$C_1$-$C_7$ hydrocarbyl oxycarbonylamido containing 1-7 carbon atoms in the oxycarbonyl group, trifluoromethoxy, trifluoromethylamino, trifluoromethylamino oxycarbonyl containing 1-7 carbon atoms in the oxycarbonyl group, and $C_1$-$C_7$ hydrocarbylthioxy group.

A contemplated compound exhibits at least the cell growth inhibition activity of the vinca compound of which it is a derivative (vinblastine, vincristine or vindesine) against the mouse leukemia cell line L1210, the human colon cancer cell line HCT116 or the drug-resistant human colon cancer cell line HCT116/VN46 as measured as a minimal inhibition concentration (MIC) of the assayed vinca alkaloid compound. Preferably, a contemplated compound exhibits enhanced activity in at least one of the L1210 and/or HCT116 cell growth inhibition assays by at least 50%, or exhibits a cell growth inhibition MIC for the HCT116/VM46 cell line of 100 nM or less.

A particular aspect of one group of preferred compounds is that such a compound exhibits an enhanced inhibitory activity in one or both of the above L1210 and HCT116 assays of 10 to about 100 times that of its parent, vinblastine. An aspect of some of the first group and other compounds is that cell growth inhibition MIC values against the vinblastine-insensitive cell line HCT116/VM46 are enhanced by about 10 or more times against both the HCT116 cells and the HCT116/VM46 cells. As a consequence, instead of the MIC ratio for inhibition of (HCT116/MV46 cells)/ (HCT116 cells) being about 88, that ratio is about 20 or less, preferably less than about 10, and more preferably about 1 to about 5. The lower ratios of MIC values coupled with a ten-fold or more lessened MIC against HCT116 cells indicates that the assayed compound is not only active against the cell lines, but that the Ppg efflux system of the the HCT116/MV46 cancer cell line that is also present several other cancers is inoperative against the assayed, contemplated vinca alkaloid.

The present invention has several benefits and advantages in addition to those mentioned above.

One benefit of the invention is that a preferred 20'-amide-substituted vinca alkaloid compound is about ten to about one hundred times more potent as a cytotoxic agent against a colorectal carcinoma cancer cell line than is a parental, unsubstituted vinca alkaloid such as vinblastine.

One advantage of the invention is that a preferred 20'-amide-substituted vinca alkaloid compound is also about equal to about about 300 times more potent against multiple drug resistant colorectal carcinoma cancer cell lines than is a parental, unsubstituted vinca alkaloid compound such as vinblastine.

Another benefit of the invention is that a contemplated 20'-amide-substituted vinca alkaloid compound is about ten to about one hundred times more potent as a cytotoxic agent against a leukemia cell line than is the parental, unsubstituted vinca alkaloid.

Another advantage of the invention is that many contemplated 20'-amide-substituted vinca alkaloid compounds can be synthesized in three steps from commercially available starting materials.

Still further benefits and advantages will be apparent to those skilled in the art from the disclosures that follow.

Definitions

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

The words "ortho", "meta" and "para" are used in their usual manner to describe benzenoid compounds that are substituted "1-2", "1-3" and "1-4", respectively. Those same words are also used herein as a convenience to describe those same substitution patterns in aliphatic compounds.

The word "hydrocarbyl" is used herein as a short hand term for a non-aromatic group that includes straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter. A benzyl group is nonetheless considered a hydrocarbyl group herein.

Where a specific aliphatic hydrocarbyl substituent group is intended, that group is recited; i.e., $C_1$-$C_4$ alkyl, methyl or hexenyl. Exemplary hydrocarbyl groups contain a chain of 1 to about 7 carbon atoms, and preferably 1 to about 4 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, iso-amyl, hexyl, benzyl and the like. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, hexenyl, hexadienyl and the like. Examples of alkynyl radicals include ethynyl, 2-propynyl, 3-propynyl, 1-butynyl, 2-butynyl, 3-butynyl, and the like.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, n-propoxy, isopropoxy, allyloxy, n-butoxy, iso-butoxy, sec-butoxy, tert-butoxy, cyclohexenyloxy, benzyloxy groups and the like.

As a skilled worker will understand, a substituent that cannot exist such as a $C_1$ alkenyl group is not intended to be encompassed by the word "hydrocarbyl", although such substituents with two or more carbon atoms are intended.

The term "cyclohydrocarbyl" or "carbocyclic", alone or in combination, means a hydrocarbyl radical that contains 5 to 7 carbon ring atoms, preferably 5 or 6 carbon atoms, and is cyclic. Examples of such cyclohydrocarbyl radicals include cyclopentenyl, cyclohexyl, cycloheptynyl and the like.

The term "aryl", alone or in combination, means a phenyl or naphthyl or other ring system as recited hereinafter that optionally carries one, two, three or four substituents that are the same or different, and are present bonded to ring atoms of the ring system. Those substituents are selected from the group consisting of $C_1$-$C_7$ hydrocarbyl, trifluoromethyl, phenyl, halogen (fluoro, chloro or bromo), cyano, nitro, $C_1$-$C_7$ acyl, amino, mono- or di-$C_1$-$C_7$ hydrocarbylamino, a nitrogen-bonded heterocyclic ring of 5- or 6 members that can contain 1 or 2 additional ring hetero atoms selected from oxygen, nitrogen, and sulfur, acylamido containing 1-7 carbon atoms [—NHC(O)$C_0$-$C_6$], sulfonylamido containing 1-7 carbon atoms [—NHS(O)$_2C_1$-$C_7$], oxycarbonylamido containing 1-7 carbon atoms [—NHC(O)O$C_1$-$C_7$], $C_1$-$C_7$ hydrocarbyloxy [—O$C_1$-$C_7$], N—$C_1$-$C_7$ hydrocarbyl acylamido containing 1-7 carbon atoms in the acyl group [—N($C_1$-$C_7$)C(O)$C_0$-$C_6$], N—$C_1$-$C_7$ hydrocarbyl sulfonylamido containing 1-7 carbon atoms in the sulfonamido group [—N($C_1$-$C_7$)S(O)$_2C_1$-$C_7$], N—$C_1$-$C_7$ hydrocarbyl oxycarbonylamido containing 1-7 carbon atoms in the oxycarbonyl group [—N($C_1$-$C_7$)C(O)$C_0$-$C_6$], trifluoromethoxy [—OCF$_3$], trifluoromethylamino [—NH(CF$_3$)], trifluoromethylamino oxycarbonyl containing 1-7 carbon atoms in the oxycarbonyl group [—NH(CF$_3$)C(O)$C_0$-$C_6$], and $C_1$-$C_7$ hydrocarbylthioxy [—S$C_1$-$C_7$] group. Exemplary unsubstituted and substituted ring systems illustrated and named hereinafter.

The heterocyclyl (heterocyclo or heteterpcyclic ring) is a 5- or 6-membered ring that contains 1 to 3 hetero atoms (non-carbons) in the ring (ring atoms) that independently are nitrogen, oxygen or sulfur atoms in a saturated or partially unsaturated ring that is optionally substituted on one or more ring carbon atoms by a substituent described above. Examples of such heterocyclyl groups are pyrrolidinyl, piperidinyl, piperazinyl, di- and tetrahydropyridyl, 4-($C_1$-$C_6$-hydrocarbyl)-piperidinyl, quinolinyl, 4-phenylpiperidinyl, isoquinolyl, indolinyl, tetrahydroindolinyl, isoindolinyl, tetrahydro-isoindolinyl, morpholinyl, thiomorpholinyl, oxathiazolyl, 1,2,3-triazolyl, 1,2,4-triazolyl, pyrazolyl, 1,2,4-oxadiazinyl and azepinyl groups and the like. A carbocyclic ring fused to a heterocyclic ring is deemed to be a heterocyclic ring system.

A "heteroaryl" group is an aromatic heterocyclic ring that preferably contains one, or two, or three or four atoms in the ring other than carbon. Those heteroatoms can independently be nitrogen, sulfur or oxygen. A heteroaryl group can contain a single 5- or 6-membered ring or a fused ring system having two 6-membered rings or a 5- and a 6-membered ring. Exemplary heteroaryl groups include 6-membered ring substituents such as pyridyl, pyrazyl, pyrimidinyl, and pyridazinyl; 5-membered ring substituents such as 1,3, 5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2, 5-, or 1,3,4-oxadiazolyl and isothiazolyl groups; 6-/5-membered fused ring substituents such as benzothiofuranyl, isobenzothiofuranyl, benzisoxazolyl, benzoxazolyl, purinyl, tetrahydroisoquinolinyl, tetrahydroisoindolinyl, and anthranilyl groups; and 6-/6-membered fused rings such as 1,2-, 1,4-, 2,3- and 2,1-benzopyronyl, quinolinyl, isoquinolinyl, cinnolinyl, quinazolinyl, and 1,4-benzoxazinyl groups. A heteroaryl substituent can also itself be unsubstituted or substituted as can an aryl substituent described above. A heteroaryl ring that is fused to one or two aromatic rings is deemed a heteroaryl ring system herein.

The term "halogen" means fluorine, chlorine or bromine. The term "halohydrocarbyl" means a hydrocarbyl radical having the significance as defined above wherein one or more hydrogens are replaced with a halogen. Examples of such halohydrocarbyl radicals include chloromethyl, 1-bromoethyl, fluoromethyl, difluoromethyl, trifluoromethyl, 1,1,1-trifluoroethyl and the like. The term perfluorohydrocarbyl means a hydrocarbyl group wherein each hydrogen has been replaced by a fluorine atom. Examples of such perfluorohydrocarbyl groups, in addition to trifluoromethyl above, are perfluorobutyl, perfluoroisopropyl, perfluorododecyl and perfluorodecyl. A halohydrocarbyloxy substituent is a halogenated ether such as a trifluoromethoxy group and the like.

In referring to a portion of a chemical compound (a radical) such as a $R^a$ group in this document, a structural formula representing that radical is often depicted including a bond line crossed by a wavy line shown by the symbol "∿" so that neither the entire compound nor the radical itself need be chemically named. This is common practice in organic chemistry.

BRIEF DESCRIPTION OF THE DRAWINGS

In the figures forming a portion of this disclosure.

DETAILED DESCRIPTION OF PREFERRED EMBODIMENTS

Figure 1A:
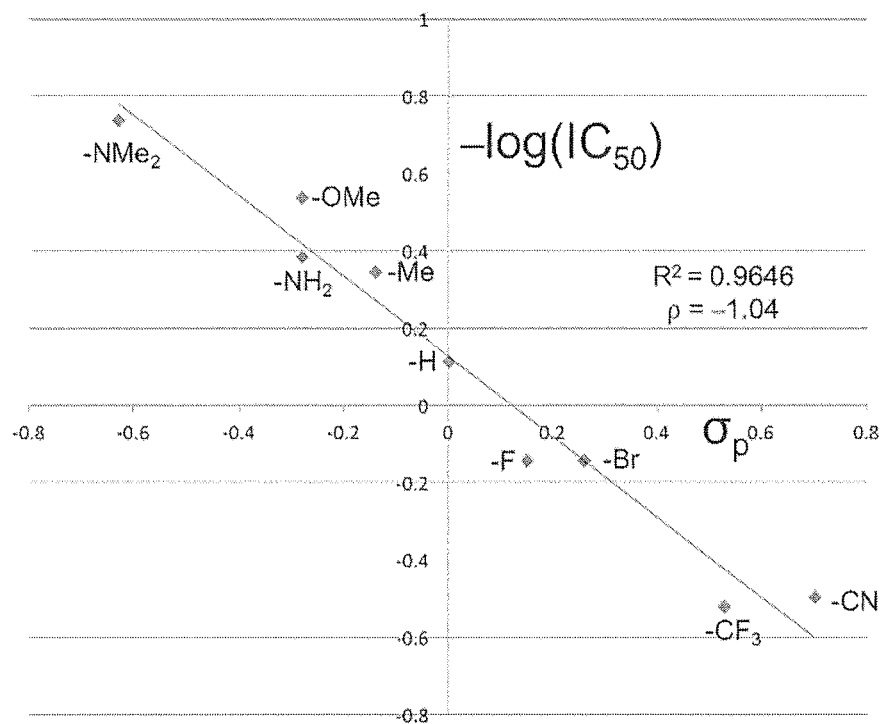
FIG. 1A and FIG. 1B are plots of Hammett $\sigma_p$ constant versus –log IC$_{50}$ (nM) for an initial series of 4-substituted benzamides that were examined in treating HCT116 cells (FIG. 1A) and L1210 cells (FIG. 1B).

The present invention contemplates a 20'-carboxamide-substituted vinca alkaloid compound, and particularly a 20'-carboxamide-substituted vinblastine, vincristine or vindesine, or a pharmaceutically acceptable salt thereof. A 20'-carboxamide-substituted vinblastine is particularly preferred. Unless otherwise stated, "carboxamide" and "amide" are used interchangeably herein.

A contemplated compound corresponds in structure to a compound shown in Table A, below,

TABLE A

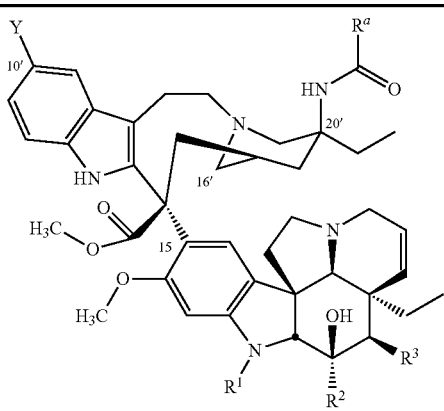

TABLE A-continued

| Vinca Compound | $R^1$ | $R^2$ | $R^3$ |
|---|---|---|---|
| Vinblastine | —$CH_3$ | —C(=O)—$OCH_3$ | —O—C(=O)—$CH_3$ |
| Vincristine | —CH(=O) | —C(=O)—$OCH_3$ | —O—C(=O)—$CH_3$ |
| Vindesine | —$CH_3$ | —C(=O)—$NH_2$ | —OH | wherein

Y— is fluoro (—F) or hydrido (—H), and $R^a$— is a ring system containing up to a total of three 5-, 6- or 7-membered rings that are fused or otherwise directly bonded to each other. A single ring or two fused rings that are 5- and 6-membered or 6- and 6-membered are preferred. The Tables provided hereinbelow illustrate several carbocyclic and heterocyclic ring systems.

As will be seen, a ring ($R^a$-) that is aromatic is preferably bonded directly to the carbonyl group shown in the formula above. By "bonded directly" it is meant that the amido carbonyl group is linked to a carbocyclic or heterocyclic aromatic ring rather than being linked to the ring system via a bond to an aliphatic ring that is bonded or fused to an aromatic ring. These differences in bonding can be seen for two fused ring carbocyclic compounds in Table 4. There, in Compounds 121 and 124 the phenyl (aromatic) ring is bonded to the amido carbonyl carbon, whereas in Compounds 122 and 125 the carbonyl carbon atom is bonded to a saturated ring that is fused to the aromatic ring.

That ring system is carbocyclic or heterocyclic in which ring atoms other than carbon are the same or different and are nitrogen (N), oxygen (O) or sulfur (S). A contemplated heterocyclic ring system contains up to three ring heteroatoms. One or two hetero atoms are preferred per heterocyclic ring system.

In addition, up to four substituents that are the same or different are present bonded to ring atoms of the ring system. More preferably, one or two ring system substituents are preferred. Those substituents are selected from the group consisting of a $C_1$-$C_7$ hydrocarbyl, trifluoromethyl, phenyl, halogen (fluoro, chloro or bromo), cyano, nitro, $C_1$-$C_7$ acyl, amino, mono- or di-$C_1$-$C_7$ hydrocarbylamino, a nitrogen-bonded heterocyclic ring of 5- or 6 members that can contain 1 or 2 additional ring hetero atoms selected from oxygen, nitrogen, and sulfur, acylamido containing 1-7 carbon atoms, sulfonylamido containing 1-7 carbon atoms, oxycarbonylamido containing 1-7 carbon atoms, $C_1$-$C_7$ hydrocarbyloxy, N—$C_1$-$C_7$ hydrocarbyl acylamido containing 1-7 carbon atoms in the acyl group, N—$C_1$-$C_7$ hydrocarbyl sulfonylamido containing 1-7 carbon atoms in the sulfonamido group, N—$C_1$-$C_7$ hydrocarbyl oxycarbonylamido containing 1-7 carbon atoms in the oxycarbonyl group, trifluoromethoxy, trifluoromethylamino, trifluoromethylamino oxycarbonyl containing 1-7 carbon atoms in the oxycarbonyl group, and $C_1$-$C_7$ hydrocarbylthioxy group.

Ring system substituents having Hammett sigma values whose sum is zero or less are preferred. Hammett sigma values are well known in the art. Tables of Hammett sigma values for the para ($\sigma_p$) and meta ($\sigma_m$) positions are available widely in the art. One particularly useful set of values can be found in Hansch et al., *Chem. Rev.* 1991, 91:165-195.

A substituent also is preferably free of electronic charge at physiological pH values (pH 7.2-7.4). Looked at differently, a basic substituent preferably has a pKa value that is at least one pH unit above 7.2-7.4, and preferably two two units above 7.2-7.4, whereas an acidic substituent has a pKa value one pH unit below 7.2-7.4, and preferably two pH units below 7.2-7.4.

Illustrative particularly preferred compounds correspond in structure to the following structural formulas:

TABLE A

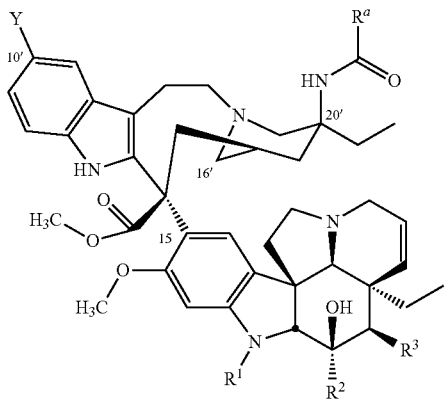

| Vinca Compound | $R^1$ | $R^2$ | $R^3$ |
|---|---|---|---|
| Vinblastine | —$CH_3$ | —C(=O)—$OCH_3$ | —O—C(=O)—$CH_3$ |
| Vincristine | —CH(=O) | —C(=O)—$OCH_3$ | —O—C(=O)—$CH_3$ |
| Vindesine | —$CH_3$ | —C(=O)—$NH_2$ | —OH | where Y is hydrido or fluoro; and $R^a$ is one or more of the following:

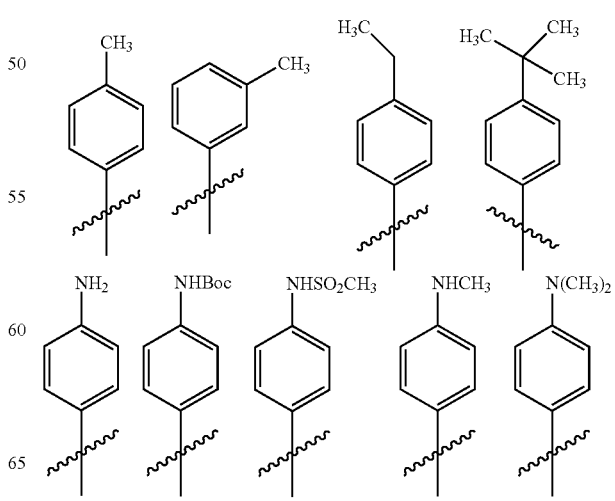

-continued
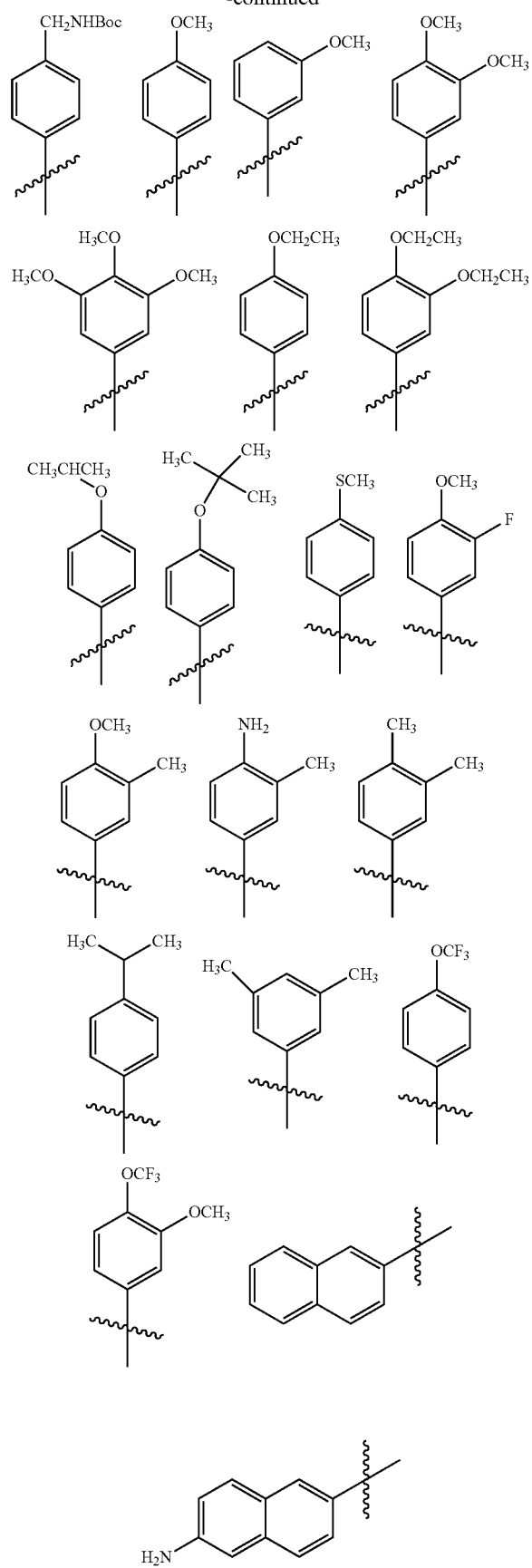
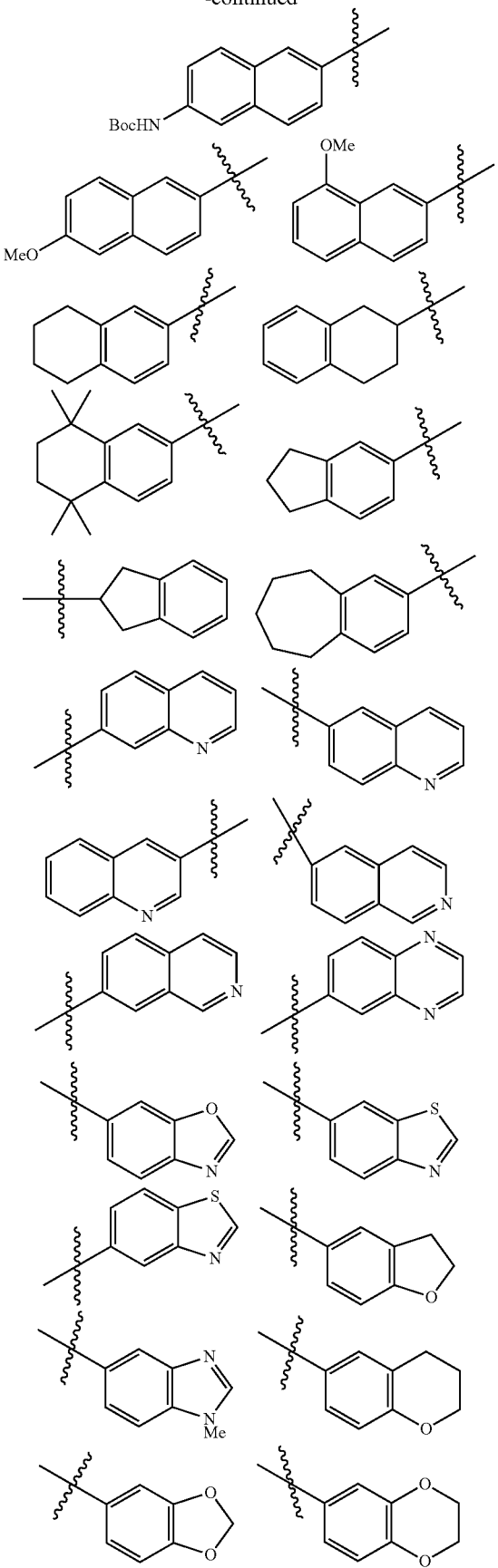

-continued

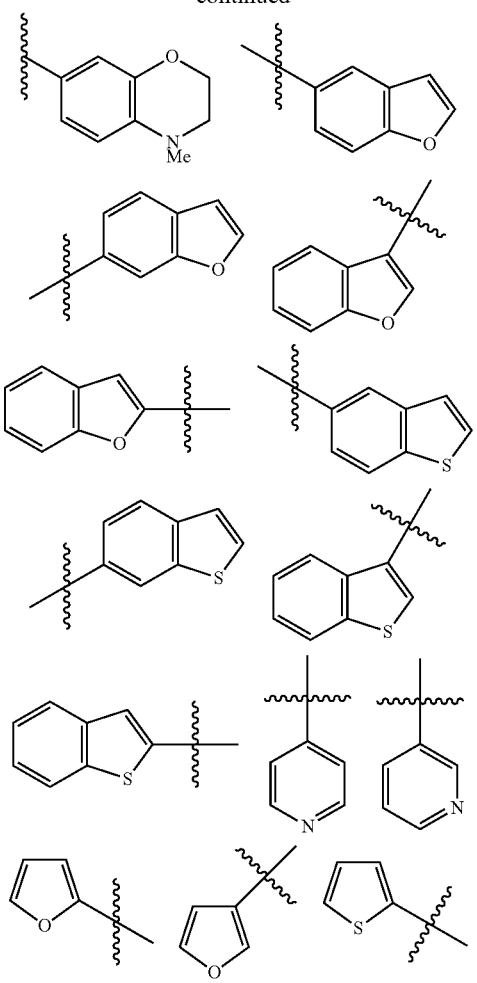

When Y is fluoro, $R^a$ is preferably one or more of the following:

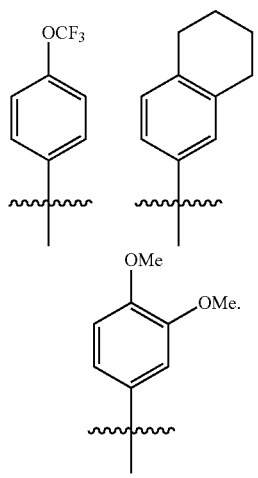

Pharmaceutical Composition and Methods

A contemplated 20-amide-substituted vinca alkaloid compound can also be used in the manufacture of a medicament (pharmaceutical composition) that is useful at least for inhibiting the proliferation (growth) of hematologic cancer cells such as leukemia or lymphoma cells, as well as cells of carcinomas such as non-small cell lung cancers, sarcomas, melanomas, neuromas and the like. It is to be understood that a contemplated contemplated 20-amide-substituted vinca alkaloid compound can and often does exhibit activities in the standard assays illustrated herein.

The differences in activity can be exhibited in one two or all of the common assays used herein as well is other assays or circumstances that are not illustrated here. In the common inhibitory assay against L1210 or HCT166 cancer cells, a contemplated 20-amide-substituted vinca alkaloid compound is more active than its corresponding vinblastine, vincristine or vindesine parent compound by at least fifty percent so that where vinblastine exhibits a minimal inhibitory concentration (MIC) of 6 nM, a contemplated compound exhibits a MIC of about 3 nM or less. In the common inhibition assay against HCT116/VM46 cells, a contemplated compound exhibits a MIC of less than about 100 nM, whereas use of vinblastine exhibits a MIC of 600 nM. As will be seen by the following data, some contemplated 20-amide-substituted vinca alkaloid compounds were about 100-times as active as vinblastine against L1210 and HCT116 cells and up to about 400-times as active as vinblastine against the HCT116/VM46 cell line.

A contemplated compound, medicament or pharmaceutical composition containing the same inhibits that growth by contacting those cancerous cells in vitro, or in vivo as in a subject in need thereof, as is a parent compound. When so used, pharmaceutically acceptable salts, buffers and the like are typically present that collectively are referred to as pharmaceutically acceptable diluents as compared to those that can be present in a composition that is not intended for pharmaceutical use, as in an in vitro assay or drying synthesis.

A contemplated compound can be provided for use by itself, or as a pharmaceutically acceptable salt. The contemplated compounds are amines. Parental vinblastine has reported pKa values of 5.4 and 7.4, whereas vincristine has reported pKa values of 6.04 and 7.67. [*The Merck Index*, 13$^{th}$ ed. Merck & Co., Whitehouse Station, N.J., 2001, pages 1778-1779.] Both compounds are sold commercially as their sulfate salts. Vindesine is reported to have pKa values of 6.04 and 7.67 [*The Merck Index*, 12$^{th}$ ed., Merck and Co., Whitehouse Station, N.J., 1996, page 1704]. Vindesine is also commercially available as the sulfate salt.

Exemplary salts useful for a contemplated compound include but are not limited to the following: sulfate, hydrochloride, hydro bromides, acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenyl-propionate, picrate, pivalate, propionate, succinate, tartrate, thiocyanate, tosylate, mesylate and undecanoate.

The reader is directed to Berge, *J. Pharm. Sci.* 1977 68(1):1-19 for lists of commonly used pharmaceutically acceptable acids and bases that form pharmaceutically acceptable salts with pharmaceutical compounds.

In some cases, a salt can also be used as an aid in the isolation, purification or resolution of the compounds of this invention. In such uses, the acid used and the salt prepared need not be pharmaceutically acceptable.

As is seen from the data herein, a contemplated compound is active in in vitro assay studies at picomolar to micromolar amounts. When used in an assay such as an in vitro assay, a contemplated compound is present in the composition in an amount that is sufficient to provide a concentration of about 0.1 nM to about 1000 nM, preferably about 1 nM to about 50 nM to a contact cells to be assayed.

A contemplated pharmaceutical composition contains a cancerous cell proliferation-inhibiting amount of a contemplated 20'-amide-substituted vinca alkaloid compound or a pharmaceutically acceptable salt thereof dissolved or dispersed in a physiologically (pharmaceutically) acceptable carrier. That amount is typically about the same amount to a little less than the amount of a parental vinca alkaloid used to treat the same cancer. Such a composition can be administered to mammalian cells in vitro as in a cell culture to contact those cells, or the cells can be contacted in vivo as in a living, host mammal in need.

More usually, anti-neoplastic drugs such as a 20'-amide-substituted vinca alkaloid contemplated here are administered parenterally in vivo in a weight amount per square meter of the recipient's body surface area (bsa). For adults, this amount is typically about 1 to about 20 mg/m2 bsa, and about one-half those amounts for children, with an amount being chosen so that the maximal amount does not cause leukopenia. Children weighing about 10 kg or less are typically dosed at about 0.05 mg/kg.

For example, vinblastine sulfate is typically administered to adults at 3.7 mg/m$^2$ bsa for the first dose, 5.5 mg/m$^2$ bsa for the second weekly dose, 7.4 mg/m$^2$ bsa for the third weekly dose, 9.25 mg/m$^2$ bsa for the fourth weekly dose and 11.1 mg/m$^2$ bsa for the fifth weekly dose. Dosages typically do not exceed 18.5 mg/m$^2$ bsa, and should not be increased if the white-cell count falls to approximately 3000 cells/mm$^3$. Usual dosages for adults are about 5.5 to 7.4 mg/m$^2$ bsa. Dosages of a contemplated 20'-amide-substituted vinca alkaloid compound or its pharmaceutically acceptable salt typically do not exceed those of the parent compound and can be less.

A contemplated composition is typically administered in vivo to a subject in need thereof a plurality of times within one month, such as weekly, and can be administered over a period of several months to several years. More usually, a contemplated composition is administered a plurality of times over a course of treatment.

In usual practice, a contemplated 20'-amide-substituted vinca alkaloid compound is administered to treat the same disease state in the same amount and at the same intervals as is a parental, 20'-hydroxy-vinca alkaloid. A contemplated 20'-amide-substituted vinca alkaloid can be utilized as a first course of treatment, and is preferably administered if there is relapse after a first or later course of treatment, particularly where multiple drug resistance is shown or suspected (indicated).

A contemplated pharmaceutical composition can be administered orally (perorally) or parenterally, which is preferred, in a formulation containing conventional nontoxic pharmaceutically acceptable carriers, adjuvants, and vehicles as desired. The term parenteral as used herein includes subcutaneous injections, intravenous (which is most preferred), intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Solid dosage forms for oral administration can include capsules, tablets, pills, powders, and granules. The amount of a contemplated compound in a solid dosage form is as discussed previously, an amount sufficient to provide a concentration of about 0.1 nM to about 1000 nM, preferably about 1 nM to about 50 nM, in the serum or blood plasma. A solid dosage form can also be administered a plurality of times during a one week time period.

In such solid dosage forms, a compound of this invention is ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

A contemplated pharmaceutical composition is preferably adapted for parenteral administration. Thus, a pharmaceutical composition is preferably in liquid form when administered, and most preferably, the liquid is an aqueous liquid, although other liquids are contemplated as discussed below, and a presently most preferred composition is an injectable preparation.

Thus, injectable preparations, for example, sterile injectable aqueous or oleaginous solutions or suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline.

Other liquid pharmaceutical compositions include, for example, solutions suitable for parenteral administration. Sterile water solutions of a 20'-amide-substituted vinca alkaloid active component or sterile solution of the active component in solvents comprising water, ethanol, or propylene glycol are examples of liquid compositions suitable for parenteral administration. In some aspects, a contemplated 20'-amide-substituted vinca alkaloid is provided as a dry powder that is to be dissolved in an appropriate liquid medium such as sodium chloride for injection prior to use.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of an injectable composition. Dimethyl acetamide, surfactants including ionic and non-ionic detergents, polyethylene glycols can be used. Mixtures of solvents and wetting agents such as those discussed above are also useful. Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

A mammal in need of treatment (a subject) and to which a pharmaceutical composition containing a contemplated compound is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where an in vitro assay is contemplated, a sample to be assayed such as cells and tissue can be used. These in vitro compositions typically contain the water, sodium or potassium chloride, and one or more buffer salts such as and acetate and phosphate salts, Hepes or the like, a metal ion chelator such as EDTA that are buffered to a desired pH value such as pH 4.0-8.5, preferably about pH 7.2-7.4, depending on the assay to be performed, as is well known.

Preferably, the pharmaceutical composition is in unit dosage form. In such form, the composition is divided into unit doses containing appropriate quantities of the active compound. The unit dosage form can be a packaged preparation, the package containing discrete quantities of the preparation, for example, in vials or ampules.

In another preferred embodiment, a contemplated 20'-amide-substituted vinca alkaloid is administered with one or more other anti-neoplastic compounds. Such joint therapy is well known in the art, with other drugs such as cisplatin, 5-fluorouracil and the like being co-administered. That co-administration is usually physically separate administrations of each compound that are timed so that the two or more active agents can act in concert.

Results and Discussion

Synthesis of Vinblastine C20' Amides

The extensive series of nearly 200 vinblastine analogs replacing the C20' alcohol with substituted or functionalized C20' amides was obtained through acylation of 20'-aminovinblastine (6), derived from reduction of the hydroazidation product 5, with either an acid chloride (Method 1, 2 equiv RCOCl, 4 equiv i-Pr$_2$NEt, CH$_2$Cl$_2$, 23° C., 2 hours) or a carboxylic acid (Method 2, 2 equiv RCO$_2$H, 4 equiv EDCI, 0.2 equiv DMAP, DMF, 23° C., 12 hours), as illustrated in Scheme 1, below.

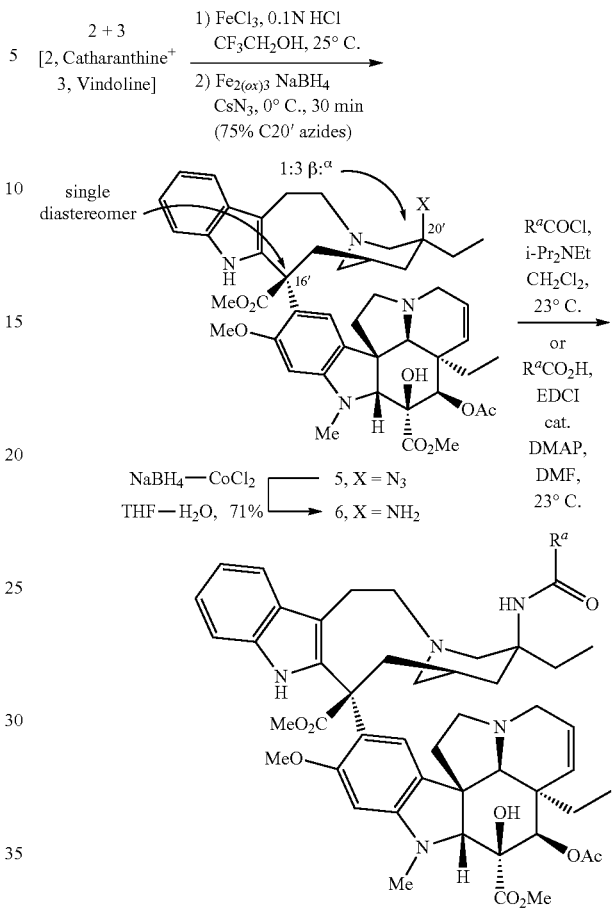

The former procedure (Method 1) that uses an acid chloride generally provided the better yields and avoids the added purification challenges of removing residual coupling reagents from the reaction products.

Notably, the precursor azide 5 is available directly in a single step from commercially available vindoline (3) and catharanthine (2) by enlisting first their Fe(III)-promoted coupling (5 equiv FeCl$_3$, 0.1 N aq HCl/CF$_3$CH$_2$OH, 25° C., 2 hours) [Vukovic et al., Tetrahedron 1988, 44:325-331], which proceeds by single electron oxidative fragmentation of catharanthine and installs exclusively the C16' natural stereochemistry [Ishikawa et al., J. Am. Chem. Soc. 2008, 130:420-421; and Gotoh et al., J. Am. Chem. Soc. 2012, 134:13240-13243]. Subsequent in situ Fe(III)-mediated free radical hydrogen atom transfer hydroazidation of anhydrovinblastine (10 equiv Fe$_2$(ox)$_3$, 20 equiv NaBH$_4$, 30 equiv CsN$_3$, aq HCl/CF$_3$CH$_2$OH, 0° C., 30 minutes) provided 20'-azidovinblastine (5) directly as a mixture C20' diastereomers, but with exclusive control of the critical C16' stereochemistry [Ishikawa et al., J. Am. Chem. Soc. 2009, 131:4904-4916; and Leggans et al., Org. Lett. 2012, 14:1428-1431].

An X-ray structure determination conducted on the major diastereomer of the reaction revealed that it possessed the unnatural vinblastine C20' stereochemistry (leurosidine stereochemistry) and that the minor diastereomer of the reaction possessed the natural C20' vinblastine stereochemistry [Ishikawa et al., J. Am. Chem. Soc. 2009, 131:4904-4916; and Leggans et al., Org. Lett. 2012, 14:1428-1431].

This powerful hydrogen atom transfer-initiated free radical reaction was developed to provide a general method for functionalization of alkenes with use of a wide range of free radical traps beyond $O_2$ (air) used for vinblastine itself and was explored explicitly to provide the late-stage, divergent [Boger et al., *J. Org. Chem.* 1984, 49:4050-4055] preparation of vinblastine analogs that bear altered C20' functionality at a site previously inaccessible for systematic exploration. In addition to other free radical traps that were introduced that included azide, the broad alkene substrate scope was defined, the Markovnikov addition regioselectivity was established, the remarkable functional group tolerance was demonstrated, alternative Fe(III) salts and initiating hydride sources were shown to support the reaction, its underlying free radical reaction mechanism was defined, and mild reaction conditions (0-25° C., 5-30 min) were developed that are remarkably forgiving to the reaction parameters [Leggans et al., *Org. Lett.* 2012, 14:1428-1431; and Barker et al., *J. Am. Chem. Soc.* 2012, 134:13588-13591].

In the course of examination the 20' amide analogs of vinblastine, a reported Ritter amidation reaction conducted on vinblastine or anhydrovinblastine was reexamined. This reaction was used to provide a limited series of 20' amides [Miller et al., U.S. Pat. No. 4,322,351 (1982)]. Although this reaction was reported to proceed in very modest conversions (5-10%), the present interest was in its disclosure as providing a single diastereomer that possesses the natural 20' vinblastine stereochemistry.

By enlisting acetonitrile as the trap of the intermediate carbocation under conditions and in a reaction detailed in this work, it was found that the reaction does indeed provide a single 20' diastereomer in low yield (<10%) as described and shown in eq. 1, below [Miller et al., U.S. Pat. No. 4,322,351 (1982)]. However, the product 8 of the

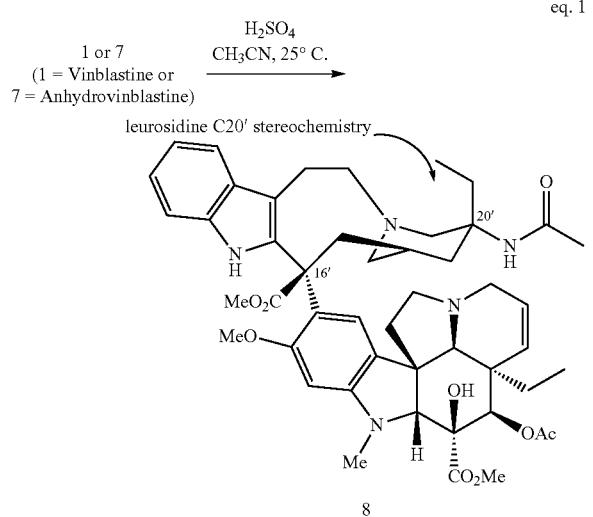

eq. 1 reaction from vinblastine (1) was found to possess the unnatural (leurosidine) 20' stereochemistry and was shown to be identical in all respects with an authentic sample of this unnatural 20' acetamide diastereomer. In retrospect, this is not surprising given the now recognized preference for α-face C20' addition, but was conducted at a time this knowledge and the powerful modern day characterization techniques were unavailable. The analogous reaction starting with anhydrovinblastine (7) failed to provide any acetamido product.

Consequently, the work detailed herein, expanding on the three examples disclosed (20' formamide, acetamide and trifluoroacetamide) along with the vinblastine hydroazidation reaction [Leggans et al., *Org. Lett.* 2012, 14:1428-1431, represent the only authentic 20' amides disclosed and examined to date in the art.

Biological Activity

As previously highlighted, the only major limitation to the clinical use of vinblastine and vincristine is the observation of clinical resistance mediated by overexpression of the drug efflux pump phosphoglycoprotein (Pgp). The identification of analogs that might address such resistance has remained a major focus for over 40 years and would represent a major advance for oncology therapeutics.

With this objective in mind, all analogs prepared to date in the inventor's laboratories, including the 20' amides detailed herein, were screened simultaneously for growth inhibition activity against HCT116 (human colon cancer cell line) and a matched resistant cell line (HCT116/VM46) that is approximately 100-fold resistant by virtue of the clinically relevant overexpression of Pgp. This well-designed set of functional assays simultaneously provides a direct measure of both functional activity (HCT116) and the analog susceptibility to Pgp efflux (resistance, HCT116/VM46). Key members were assessed for tubulin binding affinity for correlation with functional activity and those that emerged as candidates that avoid Pgp efflux were examined in efflux assays to confirm their behavior toward Pgp and related efflux transporters. The cell growth inhibition activity against the L1210 (mouse leukemia) tumor cell line was also measured and the results were qualitatively and quantitatively ($IC_{50}$) nearly identical to those observed with the HCT116 cell line.

The results are presented and discussed below in groups of amides that embody related structural characteristics. Notably and importantly, the results below indicate that the source of vinblastine clinical resistance is not derived from changes in the drug target and impact on drug binding (tubulin). Rather, it is derived from binding and efflux by an off target protein (Pgp). These results display distinguishable structure-activity relationships, one impacting potency (tubulin binding) and a second impacting resistance (Pgp binding and efflux). As important and as interesting as the former are in the discussions below, it is the remarkable discovery of a small subset of 20' amides that avoid Pgp efflux and overcome resistance, displaying equal activity against both HCT116 and HCT116/VM46, that became a driving focus of these efforts.

Alkyl 20' Amides

Several important trends were observed with simple aliphatic 20' amides that influenced subsequent studies. These data are shown in Table 1 below.

TABLE 1

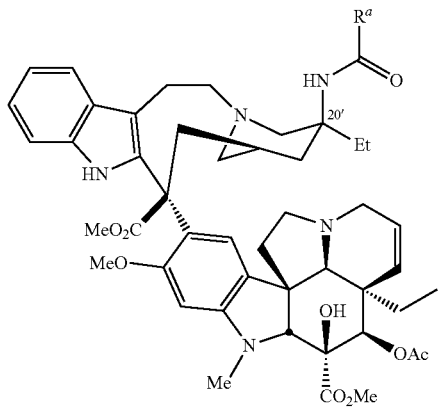

| compound | L1210 | HCT116 | HCT116/VM46 | ratio[a] |
|---|---|---|---|---|
| Vinblastine (1) | 6.0 | 6.8 | 600 | 88 |
| $R^a$ = H (9)[b] | 65 | 85 | 6500 | 76 |
| $R^a$ = methyl (10)[b] | 65 | 90 | 7500 | 83 |
| $R^a$ = CF$_3$ (11)[b] | 660 | 690 | 8100 | 12 |
| $R^a$ = ethyl (12) | 60 | 60 | 2100 | 35 |
| $R^a$ = i-propyl (13) | 70 | 90 | 1400 | 16 |
| $R^a$ = t-butyl (14) | 2800 | 3600 | 4100 | 1.1 |
| $R^a$ = n-pentyl (15) | 55 | 40 | 450 | 11 |
| $R^a$ = n-heptyl (16) | 50 | 60 | 420 | 7 |
| $R^a$ = cyclopropyl (17) | 5.5 | 6.1 | 95 | 16 |
| $R^a$ = cyclobutyl (18) | 5.4 | 5.4 | 85 | 16 |
| $R^a$ = cyclopentyl (19) | 30 | 25 | 380 | 15 |
| $R^a$ = cyclohexyl (20) | 55 | 70 | 760 | 11 |
| $R^a$ = benzyl (21) | 55 | 55 | 550 | 10 |
| $R^a$ = CHPh$_2$ (22) | 760 | 3800 | 5100 | 1.3 |
| $R^a$ = vinyl (23) | 7.0 | 6.0 | 520 | 87 |

[a]IC$_{50}$ HCT116-VM46/HCT116.
[b]Reported in ref. 41.

First, the small series of Compounds 9-11, examined at the time the 20' azidation reaction was generalized [Leggans et al., *Org. Lett.* 2012, 14:1428-1431], revealed that the simplest of the aliphatic amides (Compounds 9 and 10) reduced activity approximately 10-fold, that both Compounds 9 and 10 displayed an approximate 80-fold resistance with HCT116/VM46 similar to vinblastine, that both 9 and 10 were 10-fold more active than the corresponding free amine Compound 6, and that the increased electron-withdrawing properties of the acyl group of the trifluoroacetamide Compound 11 was further and significantly detrimental to compound potency. These trends continued to be observed throughout the expanded and more systematic series of aliphatic amides summarized in Table 1 with some important notable exceptions.

Thus, only the sterically most bulky aliphatic amides (Compounds 14 and 22) were not tolerated and these led to further reductions in activity. Three of the smaller aliphatic amides (Compounds 17, 18 and 23) uniquely matched the potency of vinblastine in the vinblastine-sensitive L1210 and HCT116 cell lines. These three compounds displayed activity that was improved over both the small or larger aliphatic amides, and two (Compounds 17 and 18) improved (reduced) the differential activity between the vinblastine-sensitive and -resistant HCT116 cell lines.

Most significantly, a well-defined trend was observed among all the 20' amides against the vinblastine-resistant HCT116/VM46 cell line. The 20' amides with the more hydrophobic substituents displayed a smaller differential in activity between the vinblastine-sensitive and -resistant cell lines (ratio=HCT116-VM46/HCT116), indicating less effective Pgp efflux in the resistant cell line. Moreover, this differential in activity smoothly and progressively diminished as the hydrophobic nature of the substituent increased (ratio: R=Me>Et>i-Pr, c-Pr, c-Bu>c-pentyl>c-hexyl>benzyl>n-heptyl).

Finally, the acrylamide Compound 23 matched, but did not exceed the activity of vinblastine. It proved to be more active than most, but not all of the simple aliphatic 20' amides and possesses the potential for covalent capture at a tubulin binding site. However, no evidence of such behavior has been found and, as detailed below, improved activity has been observed with substituted acrylamides less prone to putative covalent capture.

Benzoyl 20' Amides

The initial exploration of aryl versus aliphatic 20' amides led to analogs displaying activity that merited a detailed and systematic examination of such compounds (Table 2, below). The parent unsubstituted 20' benzamide Compound 24 proved to be >5-fold more potent than vinblastine and >50-fold more potent than the saturated cyclohexyl counterpart Compound 20. But like 20, Compound 24 also displayed a smaller differential in activity between the sensitive and resistant HCT116 cell lines than vinblastine (25-fold vs 88-fold), indicating it also embodied characteristics that make it a less effective substrate for Pgp.

TABLE 2

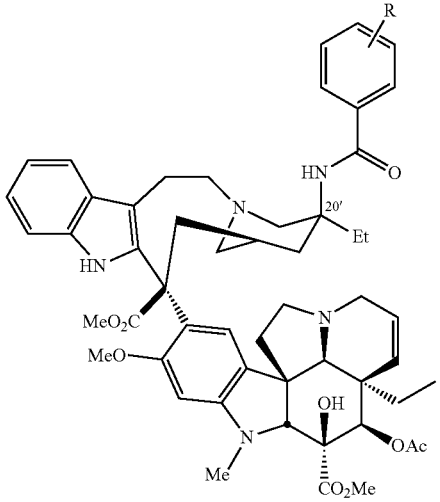

| compound | L1210 | HCT116 | HCT116/VM46 | ratio[a] |
|---|---|---|---|---|
| Vinblastine (1) | 6.0 | 6.8 | 600 | 88 |
| R = H (24) | 1.1 | 0.8 | 20 | 25 |
| R = 4-Me (25) | 0.5 | 0.45 | 4.5 | 10 |
| R = 3-Me (26) | 0.5 | 0.7 | 3 | 4.3 |
| R = 2-Me (27) | 55 | 50 | 540 | 11 |
| R = 3,4-Me$_2$ (28) | 3 | 4.5 | 7.6 | 1.7 |
| R = 3,5-Me$_2$ (29) | 5.4 | 6 | 9.2 | 1.5 |
| R = 4-Et (30) | 0.65 | 0.7 | 3.4 | 4.9 |
| R = 3,5-Et$_2$ (31) | 4.2 | 6.4 | 66 | 10 |
| R = 4-iPr (32) | 5.4 | 6.4 | 13 | 2 |
| R = 3-iPr (33) | 7.5 | 8.7 | 65 | 7.5 |
| R = 4-nPr (34) | 4.3 | 4.8 | 35 | 7 |
| R = 4-nBu (35) | 30 | 20 | 70 | 3.5 |
| R = 4-iBu (36) | 25 | 10 | 65 | 6.5 |
| R = 4-sBu (37) | 25 | 15 | 65 | 4 |
| R = 4-tBu (38) | 0.6 | 1.9 | 55 | 17 |
| R = 4-CF$_3$ (39) | 4.3 | 3.3 | 55 | 17 |

TABLE 2-continued

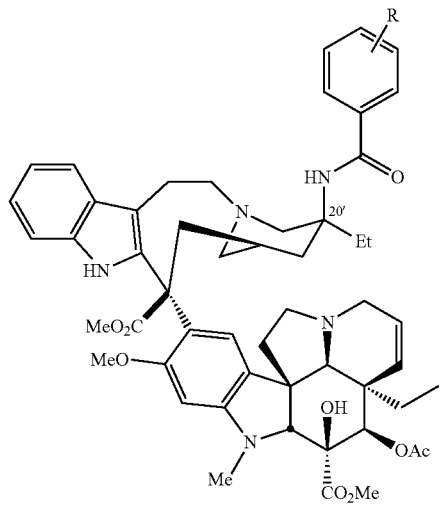

| compound | L1210 | HCT116 | HCT116/VM46 | ratio[a] |
|---|---|---|---|---|
| R = 3-CF3 (40) | 6.2 | 6.4 | 40 | 6 |
| R = 2-CF3 (41) | 45 | 60 | 540 | 10 |
| R = 4-Ph (42) | 5.5 | 5.4 | 60 | 11 |
| R = 4-cHex (43) | 40 | 30 | 60 | 2 |
| R = 4-F (44) | 1.8 | 1.4 | 25 | 18 |
| R = 3-F (45) | 5.7 | 5.3 | 25 | 5 |
| R = 2-F (46) | 8.4 | 7.7 | 75 | 10 |
| R = 4-Cl (47) | 3.1 | 3.2 | 50 | 16 |
| R = 3-Cl (48) | 4.2 | 2.7 | 20 | 7 |
| R = 2-Cl (49) | 50 | 55 | 390 | 7 |
| R = 3,4-Cl2 (50) | 8.5 | 8.7 | 80 | 9 |
| R = 4-Br (51) | 2.7 | 1.4 | 10 | 7 |
| R = 3-Br (52) | 5 | 6.3 | 60 | 10 |
| R = 3,4-Br2 (53) | 60 | 40 | 80 | 2 |
| R = 4-CN (54) | 4.4 | 3.1 | 60 | 20 |
| R = 4-CN,3-Me (55) | 4.8 | 6.2 | 65 | 10 |
| R = 4-NO2 (56) | 6.1 | 6.1 | 60 | 10 |
| R = 4-NH2 (57) | 0.4 | 0.4 | 4.8 | 12 |
| R = 4-NHAc (58) | 1.6 | 0.8 | 55 | 70 |
| R = 4-NHCO2Me (59) | 1.5 | 0.8 | 55 | 70 |
| R = 4-NHBoc (60) | 0.3 | 0.3 | 30 | 100 |
| R = 4-NHSO2Me (61) | 0.4 | 0.3 | 50 | 165 |
| R = 4-NHMe (62) | 0.38 | 0.33 | 6.2 | 19 |
| R = 4-NMeBoc (63) | 4.1 | 3.9 | 35 | 9 |
| R = 4-NMe2 (64) | 0.18 | 0.18 | 4.1 | 23 |
| R = 4-CH2NH2 (65) | 25 | 3.5 | 470 | 130 |
| R = 4-CH2NHBoc (66) | 0.76 | 0.7 | 50 | 70 |
| R = 4-OMe (67) | 0.25 | 0.3 | 7.6 | 25 |
| R = 3-OMe (68) | 0.6 | 0.8 | 8.7 | 11 |
| R = 2-OMe (69) | 30 | 10 | 100 | 10 |
| R = 3,4-(OMe)2 (70) | 0.06 | 0.07 | 1.4 | 20 |
| R = 3,4,5-(OMe)3 (71) | 0.09 | 0.1 | 2.4 | 24 |
| R = 4-OEt (72) | 0.6 | 0.6 | 2.8 | 4.7 |
| R = 3,4-(OEt)2 (73) | 0.4 | 0.5 | 6.0 | 12 |
| R = 4-OiPr (74) | 0.7 | 0.8 | 6.6 | 8 |
| R = 4-OtBu (75) | 0.6 | 0.6 | 6.8 | 11 |
| R = 4-OPh (76) | 5.2 | 6.5 | 50 | 8 |
| R = 4-OBn (77) | 5.4 | 5.7 | 55 | 10 |
| R = 4-OCF3 (78) | 5.9 | 4.4 | 8.4 | 2 |
| R = 3-OCF3 (79) | 4.8 | 5.9 | 50 | 9 |
| R = 2-OCF3 (80) | 450 | 480 | 620 | 1.3 |
| R = 4-OCHF2 (81) | 5.9 | 1.7 | 17 | 10 |
| R = 4-OMe,3-OCF3 (82) | 1.7 | 2.2 | 17 | 10 |
| R = 4-OCF3,3-OMe (83) | 1.3 | 1.7 | 6.9 | 4 |
| R = 4-SMe (84) | 0.4 | 0.5 | 6.8 | 14 |
| R = 3-SMe (85) | 5.4 | 2.3 | 20 | 9 |
| R = 4-SEt (86) | 4.9 | 6.1 | 35 | 6 |
| R = 4-SiPr (87) | 4.3 | 4.6 | 55 | 12 |
| R = 4-SO2F (88) | 20 | 30 | 310 | 10 |
| R = 3-SO2F (89) | 40 | 30 | 570 | 19 |
| R = 3-F,4-OMe (90) | 0.6 | 0.6 | 30 | 50 |

TABLE 2-continued

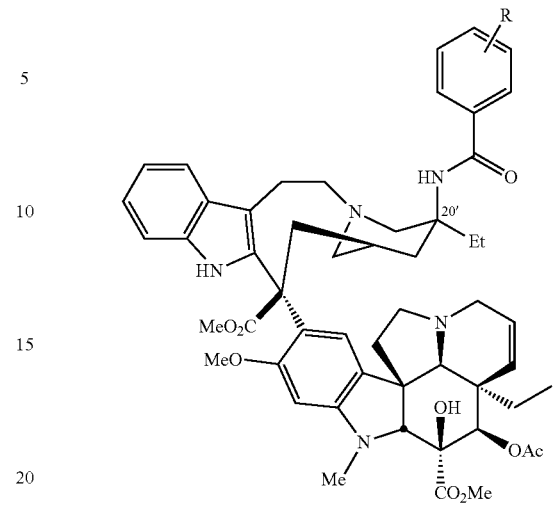

| compound | L1210 | HCT116 | HCT116/VM46 | ratio[a] |
|---|---|---|---|---|
| R = 2-F,4-OMe (91) | 6.2 | 6.4 | 70 | 11 |
| R = 3-Cl,4-OMe (92) | 3.7 | 5.1 | 8.9 | 1.7 |
| R = 3-8r,4-OMe (93) | 5.1 | 6.2 | 40 | 6 |
| R = 3-Cl,4-OEt (94) | 4.2 | 6.1 | 40 | 7 |
| R = 3-Br,4-OEt (95) | 3.9 | 6.2 | 50 | 8 |
| R = 3,5-Cl2,4-OMe (96) | 3.1 | 4.2 | 25 | 6 |
| R = 3-Me,4-OMe (97) | 0.6 | 0.7 | 5.2 | 7 |
| R = 4-Me,3-OMe (98) | 4.2 | 3.3 | 6.9 | 2.1 |
| R = 3,5-Me2,4-OMe (99) | 0,5 | 0.65 | 3.5 | 5 |
| R = 3,5-Me2,4-OBn (100) | 30 | 30 | 80 | 2.7 |
| R = 3-NH2,4-Me (101) | 0.6 | 0.7 | 25 | 36 |
| R = 3-NHBoc,4-Me (102) | 6 | 7.1 | 90 | 13 |
| R = 3-NHAc,4-Me (103) | 5.4 | 4.3 | 330 | 77 |
| R = 4-NH2,3-Me (104) | 0.6 | 0,6 | 7.8 | 13 |
| R = 4-NHBoc,3-Me (105) | 5.6 | 5.8 | 30 | 5 |
| R = 3-N-morpholino (106) | 4.8 | 2.8 | 30 | 11 |
| R = 3-NHCOPh,4-Me (107) | 30 | 7.6 | 240 | 32 |

[a]IC50 HCT116-VM46/HCT116.

Early in these studies, a small but key series of 4-substituted benzamides was prepared to probe the electronic impact of substituents as well as several related analogs to establish sites amenable to substitution. These studies revealed that both 4-, 3-substitution and 3,4-disubstitution of the phenyl ring were well tolerated and that any given substituent provided nearly equivalent activity when placed at either site (4-(para)>3-(meta)), but that o-substitution reduced the relative potency by 10-fold or more (potency: p→m→>o-substitution) when the o-substituent was other than fluoro (—F), as in Compound 46.

Figure 1B:
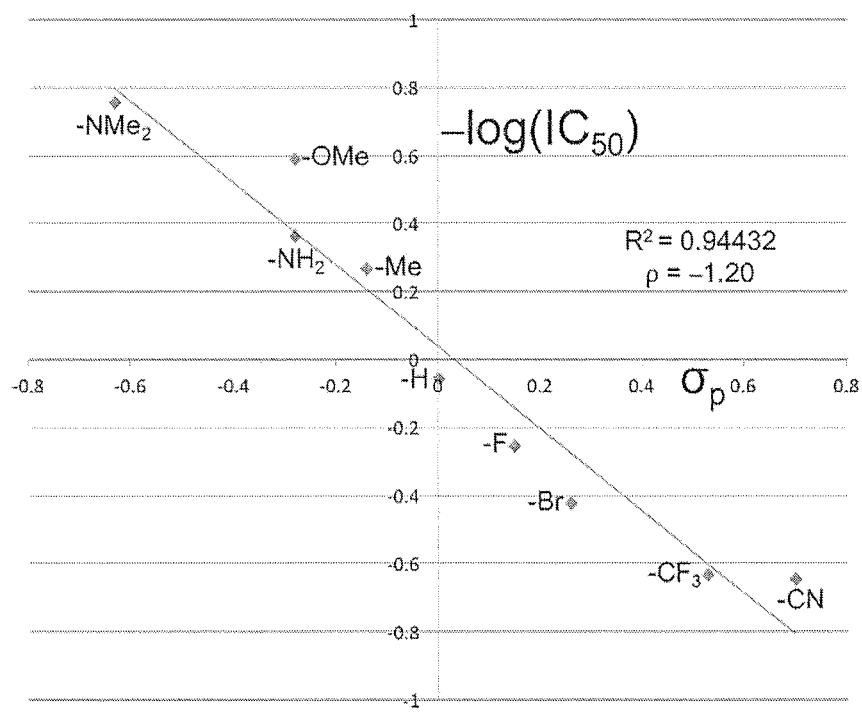

In addition, the initial 4-substituted benzamides that were examined were found to display a well-defined trend in which electron-donating substituents improved potency, whereas electron-withdrawing substituents reduced activity. Plots of the substituent Hammett $\sigma_p$ constants versus −log IC$_{50}$ (nM) revealed a linear relationship with slopes ($\rho$ value) of −1.04 (HCT116) and −1.20 (L1210), indicating a large and remarkably well defined electronic contribution to the behavior of the analogs (FIGS. 1A and 1B).

Figure 2:
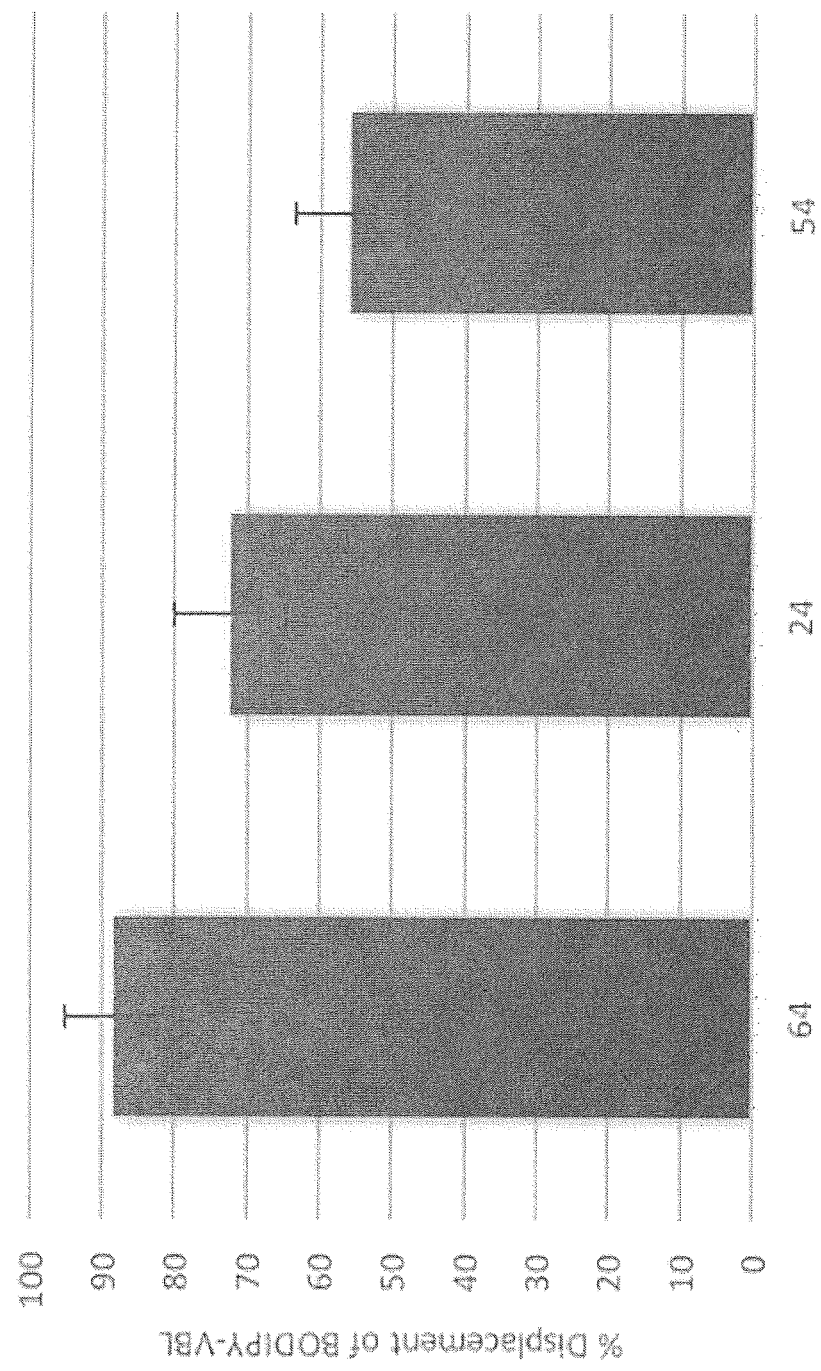
FIG. 2 is a graph that utilizes a tubulin binding assay measuring the percent (%) displacement of tubulin-bound BODIPY-vinblastine under conditions where vinblastine results in 50% displacement. Compounds 64 (88±5%), 24 (72±4%), and 54 (56±5%) are the 20' benzamide derivatives containing a 4-NMe$_2$, 4-H, and 4-CN substituent, respectively.

Throughout these studies, periodic measurements of relative tubulin binding affinities established that the substituent effects on activity correlated with relative target tubulin binding affinities. In initial studies on the 20' benzamide substituent effects, three derivatives (Compounds 24, 54 and 64; R=H, CN, and NMe$_2$, respectively) from the Hammett plot set were examined (FIG. 2).

Consistent with their relative potencies, the three derivatives displayed the same clear trends in their ability to displace tubulin bound BODIPY-vinblastine [Carney et al., Proc. Natl. Acad. Sci. U.S.A. 2016, 113:9691-9698] (Compounds 64>24>54). This direct correlation of functional cell growth inhibition activity with target tubulin binding affinity and the relative magnitude of the effects indicate that the properties of these C20' amides are derived predominately, if not exclusively, from target effects on tubulin.

Retrospective modeling of the analogs bound to tubulin detailed later herein suggest that this pronounced effect arises from the electronic impact of the substituent on the Lewis basicity of the amide carbonyl, enhancing its ability to serve as a H-bond acceptor for the backbone NH of β-tubulin Tyr224. Notably, this complements the requisite H-bond donor property of the secondary 20' amides (tertiary amides are inactive) in which the secondary amide NH mimics the tertiary alcohol of vinblastine itself and H-bonds to the backbone amide carbonyl of Pro222.

Further, the early studies revealed that further increasing the hydrophobic character of the benzamide generally reduced the differential in activity between the sensitive and resistant HCT116 cell lines (e.g. compare Compounds 24 and 25-29). This paradox of increasing potency through addition of a typically polar electron-donating substituent, enhancing target tubulin binding, while simultaneously disrupting Pgp transport by further decreasing the polarity of the 20' benzamide is chronicled in the subsequent extensive studies that are reported in Table 2, above.

Within this series, there are several vinblastine analogs that display stunning potencies (e.g. Compounds 57, 60-62, 64, 67, 70, 71 and 73), others that display substantially improved potencies (10-fold) and attractive reduced differentials in activity (<10-fold; e.g. Compounds 25, 26, 30, 72, 74, 97 and 99), and many that display substantially improved differentials in activity (<10-fold). There are even those that indicate surprisingly large p-substituents are well tolerated (e.g. t-Bu in Compound 38). Many of these would be attractive analogs of vinblastine for further study. For us and the prescribed objective of discovering analogs that match or exceed the potency of vinblastine, but which are not subject to Pgp efflux derived resistance (ratio differential <2-fold), it is the analog Compounds 28, 29, 32, 78, 92, and 98 that met these defined parameters. Of these, it was Compound 28 that was selected for additional study.

20' Acrylamides

A small series of substituted 20' acrylamides was prepared and examined in part for comparison with the unsubstituted acrylamide 23 (Table 3, below).

TABLE 3

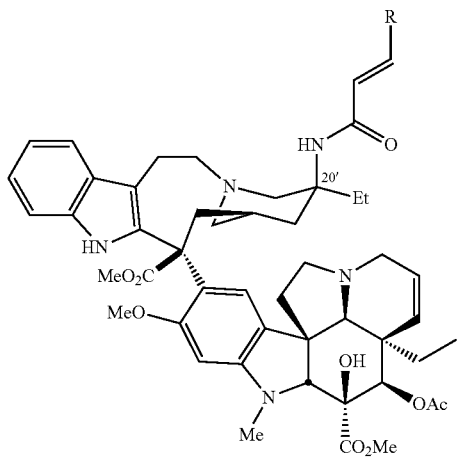

| compound | IC$_{50}$ (nM) | | | ratio$^a$ |
| --- | --- | --- | --- | --- |
| | L1210 | HCT116 | HCT116/VM46 | |
| Vinblastine (1) | 6.0 | 6.8 | 600 | 88 |
| R = H (23) | 7.0 | 6.0 | 520 | 87 |
| R = Ph (108) | 0.8 | 0.9 | 20 | 22 |
| R = 4-Pyr (109) | 0.6 | 0.7 | 50 | 71 |
| R = 3-Pyr (110) | 5.9 | 5.7 | 320 | 60 |
| R = 2-Pyr (111) | 0.7 | 0.7 | 25 | 36 |
| R = 3-furanyl (112) | 0.7 | 0.7 | 20 | 29 |
| R = 2-furanyl (113) | 1.3 | 1.3 | 30 | 23 |
| R = 3-thienyl (114) | 0.5 | 0.6 | 20 | 35 |

$^a$IC$_{50}$ HCT116-VM46/HCT116.

Thus, addition of an aryl group to the terminus of the acrylamide was found to provide vinblastine analogs as much as 10-fold more potent than either Compound 23 or vinblastine itself. Although the number of comparisons is small, the differential in activity between the vinblastine-sensitive HCT116 and vinblastine-resistant HCT116/VM46 cell lines decreased with the increased hydrophobic character of the aryl substitute (Pyr>furanyl, thienyl>Ph). This proved consistent with the observations made with the 20' benzoyl amides of Table 2 where increased hydrophobic character reduced the activity differential. In fact, the activity of the benzoyl amide Compound 24 proved essentially indistinguishable from the phenyl-substituted acrylamide Compound 108, both in terms of their potency and this activity differential.

As indicated earlier, no evidence of covalent capture at a tubulin binding site with Compounds 23 or 108-114 and the improved activity with the substituted acrylamides less prone to putative covalent capture is consistent with enhanced tubulin binding affinity derived simply through non-covalent interactions.

Polycyclic Benzoyl-Like 20' Amides

An important series of benzoyl-like 20' amides was examined that contained additional rings fused to the aromatic core, Table 4, below. In essence, these compounds represent variations on the 1- or 2-naphthyl amides of Compounds 115 and 116.

TABLE 4

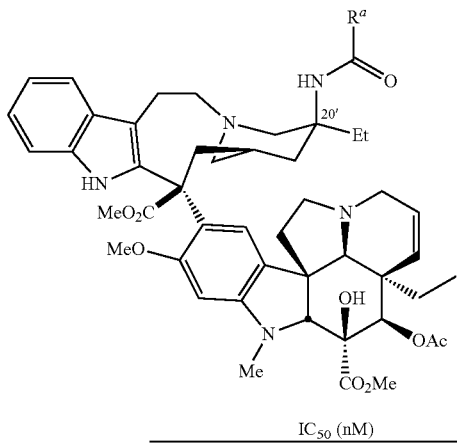

| compound | IC$_{50}$ (nM) | | | ratio[a] |
|---|---|---|---|---|
| | L1210 | HCT116 | HCT116/VM46 | |
| Vinblastine (1) | 6.0 | 6.8 | 600 | 88 |
| R$^a$ = 1-naphthyl (115) | 60 | 65 | 220 | 3.4 |
| R$^a$ = 2-naphthyl (116) | 1.9 | 2.3 | 6.4 | 2.8 |
| 117 | 0.7 | 0.8 | 7.4 | 10 |
| 118 | 5 | 6.5 | 60 | 9 |
| 119 | 2.5 | 3.5 | 20 | 5.7 |
| 120 | 10 | 13 | 70 | 5.4 |
| 121 | 3.3 | 4.9 | 8.7 | 1.8 |
| 122 | 420 | 580 | 960 | 1.7 |
| 123 | 7.4 | 7.8 | 50 | 6.4 |
| 124 | 5 | 5.6 | 11 | 2 |
| 125 | 30 | 15 | 80 | 5.3 |
| 126 | 6.1 | 4.8 | 35 | 7 |
| R$^a$ = 2-anthracenyl (127) | 40 | 60 | 150 | 2.5 |

[a] IC$_{50}$ HCT116-VM46/HCT116.

Although the 1-naphthyl amide Compound 115 was found to be roughly 10-fold less potent than vinblastine, the 2-naphthyl 20' amide Compound 116 was determined to be approximately 3-fold more potent. Most significantly, the activity of Compound 116 against the resistant HCT116/VM46 cell line was substantially improved such that the differential in activity versus HCT116 was less than 3-fold, indicating that it is no longer effectively subject to Pgp efflux-derived resistance. Although the sensitivity of HCT116 toward Compound 116 was not significantly improved, the improvement in activity against HCT116/VM46 was suggestive that it is no longer a substrate for Pgp efflux. In this series and like the 20' benzamide series, polar electron-donating substituents in conjugation with the amide carbonyl often improved activity (e.g. Compound 117) but did so at the expense of the differential potency against the sensitive and resistant HCT116 cell lines. The amides in which the carbonyl was attached directly to the aryl ring were more effective than the bicyclic systems attached at an aliphatic site (e.g. Compounds 121 and 124 vs 122 and 125).

In general and consistent with expectations, the derivatives with the greater hydrophobic character led to reduced differentials in activity between the sensitive and resistant HCT116 cell lines. The amides bearing the saturated fused six- or five-membered rings (Compounds 121 and 124) exhibited the unique combination of slightly improved potency relative to vinblastine (about 2-fold) and little differential activity (<2-fold) and proved to be essentially indistinguishable from Compound 28 (3,4-dimethylbenzoylamide). These compounds are similar in activity to the parent benzamide Compound 24, but with an even better improvement in activity against the resistant HCT116/VM116 cell line.

As detailed earlier and like Compound 28, Compound 121 exhibited a profile of activity that was sought at the start of these studies and both became key compounds that were further profiled.

Monocyclic Heterocyclic 20' Amides

A systematic series of 20' amides were examined that contain a single heterocyclic ring. Data for these compounds are shown in Table 5.

TABLE 5

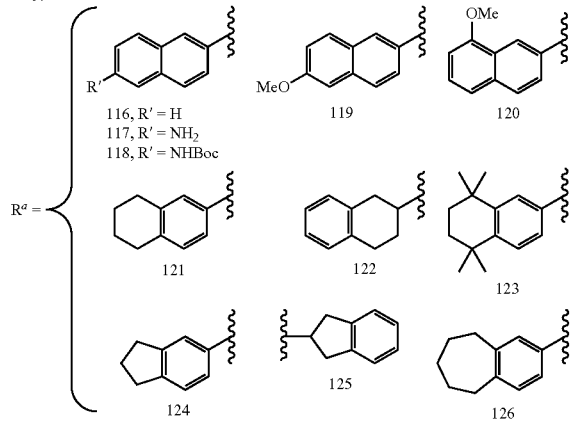

| compound | IC$_{50}$ (nM) | | | ratio[a] |
|---|---|---|---|---|
| | L1210 | HCT116 | HCT116/VM46 | |
| Vinblastine (1) | 6.0 | 6.8 | 600 | 88 |
| R$^a$ = 4-Pyr (128) | 0.4 | 0.4 | 55 | 138 |
| R$^a$ = 3-Pyr (129) | 0.7 | 0.6 | 50 | 83 |
| R$^a$ = 2-Pyr (130) | 55 | 50 | 460 | 9 |
| R$^a$ = 2-pyrazinyl (131) | 40 | 20 | 550 | 28 |
| R$^a$ = 4-pyridazinyl (132) | 30 | 9 | 700 | 78 |
| R$^a$ = 3-furanyl (133) | 0.7 | 0.6 | 6.3 | 11 |
| R$^a$ = 2-furanyl (134) | 0.7 | 0.7 | 12 | 17 |
| R$^a$ = 3-thienyl (135) | 0.5 | 0.7 | 7.7 | 11 |
| R$^a$ = 2-thienyl (136) | 0.6 | 0.6 | 6.7 | 11 |
| R$^a$ = 4-oxazolyl (137) | 4.5 | 4 | 90 | 22 |
| R$^a$ = 5-oxazolyl (138) | 3.9 | 3.5 | 65 | 19 |
| R$^a$ = 4-thiazolyl (139) | 5.6 | 6.3 | 80 | 13 |
| R$^a$ = 5-thiazolyl (140) | 1.8 | 0.6 | 45 | 75 |
| R$^a$ = 5-N$^1$Me-Imid (141) | 4 | 2.2 | 80 | 36 |
| R$^a$ = 4-N$^1$Me-Imid (142) | 80 | 50 | >1000 | nd |
| R$^a$ = 3-isoxazolyl (143) | 4.5 | 7 | 90 | 13 |
| 144 | 70 | 35 | 3500 | 100 |
| 145 | 460 | 450 | 5200 | 12 |

TABLE 5-continued

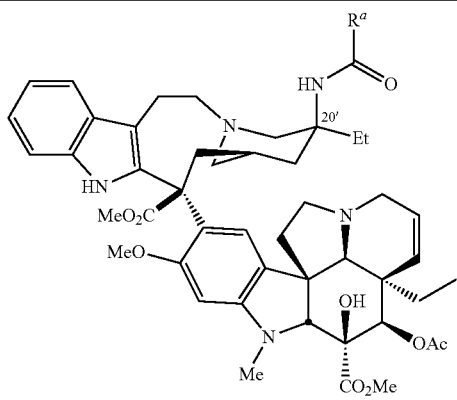

| compound | L1210 | HCT116 | HCT116/VM46 | ratio[a] |
|---|---|---|---|---|
| 146 | 4200 | >10000 | >10000 | nd |
| 147 | 50 | 45 | 500 | 11 |
| 148 | 5300 | 4400 | 6600 | 1.5 |

[a] $IC_{50}$ HCT116-VM46/HCT116.

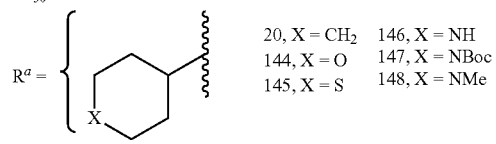

$R^a = $ 
20, X = $CH_2$     146, X = NH
144, X = O          147, X = NBoc
145, X = S          148, X = NMe

In general, the potency of the series against the sensitive cell lines followed trends in which the more hydrophobic and more electron-rich heterocyclic amides displayed the greatest activity (furanyl, thienyl>oxazolyl, thiazoyl, isoxazolyl>imidazoyl, pyrazinyl, pyridazinyl). The exceptions to this generalization are the 4- and 3-pyridyl amide Compounds 128 and 129 that proved to be among the most potent analogs in this series despite their polarity and electron-deficient character.

Similarly, the differential in activity against the sensitive and resistant HCT116 cell lines also generally increased as the polarity or heteroatom count in the heterocycle increased (furanyl, thienyl<oxazolyl, thiazolyl, isoxazolyl<imidazoyl, pyrazinyl, pyridazinyl, pyridyl). Within this series, impressive potency was observed with the 3-furanyl and 2-thienyl amides (Compounds 133 and 136), displaying activity ($IC_{50}$=600-700 pM) 10-fold greater than vinblastine and roughly 2-fold better than the 20' benzamide Compound 24 with additional improved reductions in the differential activity (11-fold vs 88-fold and 25-fold) for the sensitive and resistant HCT116 cell lines. Interestingly, the 4- and 3-pyridyl amide Compounds 128 and 129 were among the most potent compounds in the series ($IC_{50}$=400-700 pM), whereas the 2-pyridyl amide 130 was among the least potent. However, both Compounds 128 and 129 displayed the largest differential in activity against the sensitive and resistant HCT116 cell lines (138-fold and 83-fold, respectively).

The saturated heterocyclic amide Compounds 144-148 proved to be much less potent than vinblastine and less potent than most of the aromatic heterocyclic 20' amides. In the small series examined, the compounds appear to follow trends where the more polar substituents not only led to progressive losses in activity, but also increase the differential in activity between the sensitive and resistant HCT116 cell lines. An instructive comparison is the activity of Compound 144 versus Compound 20 in which a polar oxygen atom is introduced into the all carbon six-membered ring. Although the two compounds proved nearly equipotent against the sensitive cell lines, Compound 144 proved to be much less active in the resistant HCT116 cell line, displaying a differential in activity (100-fold) similar to that of vinblastine (88-fold) and much greater than Compound 20 (11-fold).

Polycyclic Heterocyclic 20' Amides

An important series of heterocyclic amides that contain two fused aromatic or non-aromatic rings was examined that also provided important insights into structural features that can enhance potency or disrupt Pgp-derived resistance. Data for these compounds is shown in Table 6, below

TABLE 6

| compound | L1210 | HCT116 | HCT116/VM46 | ratio[a] |
|---|---|---|---|---|
| Vinblastine (1) | 6.0 | 6.8 | 600 | 88 |
| $R^a$ = 7-quinolyl (149) | 0.6 | 0.7 | 8.2 | 12 |
| $R^a$ = 6-quinolyl (150) | 0.6 | 0.6 | 4.9 | 8 |
| $R^a$ = 3-quinolyl (151) | 0.7 | 0.6 | 5.7 | 9 |
| $R^a$ = 2-quinolyl (152) | 40 | 40 | 270 | 7 |
| $R^a$ = 7-isoquinolyl (153) | 0.4 | 0.4 | 3.7 | 9 |
| $R^a$ = 6-isoquinolyl (154) | 0.6 | 0.6 | 7.3 | 12 |
| $R^a$ = 6-quinoxalyl (155) | 0.6 | 0.6 | 7.5 | 13 |
| $R^a$ = 2-quinoxalyl (156) | 6.2 | 5.9 | 60 | 10 |
| $R^a$ = 6-benzfuranyl (157) | 3.3 | 2.2 | 6.5 | 3 |
| $R^a$ = 5-benzfuranyl (158) | 5 | 3.8 | 25 | 7 |
| $R^a$ = 3-benzfuranyl (159) | 4 | 4.6 | 35 | 8 |
| $R^a$ = 2-benzfuranyl (160) | 1.8 | 1.1 | 15 | 14 |
| 161 | 0.3 | 0.25 | 2.4 | 10 |
| $R^a$ = 6-benzthiophenyl (162) | 3.1 | 2.9 | 7.7 | 2.7 |
| $R^a$ = 5-benzthiophenyl (163) | 4.2 | 4.9 | 16 | 3.3 |
| $R^a$ = 3-benzthiophenyl (164) | 5.2 | 5.7 | 20 | 3.3 |
| $R^a$ = 2-benzthiophenyl (165) | 3.1 | 1.9 | 9.2 | 4.9 |
| 166 | 0.7 | 0.6 | 8 | 13 |
| $R^a$ = 6-benzoxazolyl (167) | 0.6 | 0.6 | 30 | 50 |
| $R^a$ = 5-benzoxazolyl (168) | 5.4 | 5.1 | 70 | 14 |
| $R^a$ = 2-benzoxazolyl (169) | 60 | 60 | 190 | 3.2 |
| $R^a$ = 6-benzthiazolyl (170) | 0.5 | 0.6 | 20 | 33 |
| $R^a$ = 5-benzthiazolyl (171) | 0.6 | 0.7 | 25 | 36 |
| $R^a$ = 2-benzthiazolyl (172) | 180 | 80 | 470 | 6 |
| 173 | 0.4 | 0.5 | 1.8 | 3.8 |
| 174 | 0.6 | 0.8 | 8.7 | 11 |
| 175 | 0.6 | 0.5 | 5.3 | 11 |
| 176 | 0.3 | 0.3 | 4.9 | 16 |

TABLE 6-continued

[Structure of vinblastine analog with R$^a$-HN-C(=O)- group at C20', showing indoline, MeO$_2$C, MeO, OH, OAc, CO$_2$Me, N-Me substituents]

| compound | L1210 | HCT116 | HCT116/VM46 | ratio$^a$ |
|---|---|---|---|---|
| R$^a$ = 5-indolinyl (177) | 5.1 | 6.7 | 60 | 9 |
| R$^a$ = N-Boc-5-indolinyl (178) | 35 | 15 | 90 | 6 |

IC$_{50}$ (nm)

$^a$IC$_{50}$ HCT116-VM46/HCT116.

R$^a$ = {161 (benzofuran-5-yl), 166 (1-methylbenzimidazol-5-yl), 173 (chroman-6-yl), 174 (1,3-benzodioxol-5-yl), 175 (2,3-dihydro-1,4-benzodioxin-6-yl), 176 (4-methyl-3,4-dihydro-2H-1,4-benzoxazin-6-yl)}

The trends observed with incorporation of a series of polycyclic heterocycles, which constitute benzo-fused versions of the monocyclic 20' heteroaromatic amides (Table 4), are instructive. First and foremost, the differential in activity between the sensitive and resistant HCT116 cell lines for each benzo-fused heterocycle generally improved (diminished) relative to its companion monocyclic heterocycle. This behavior is analogous to the comparison of benzamide Compound 24 and its benzo-fused counterpart Compound 116 (2-naphthyl amide), and likely reflects the increased hydrophobic character of the benzo-fused heterocycle.

For the heterocycles containing a basic nitrogen, acyl linkage at the site adjacent to the basic nitrogen with Compounds 152, 156, 169 and 172 (2-quinolyl, 2-quinoxalyl, 2-benzoxazolyl, 2-benzthiazolyl) led to substantial reductions in activity, an observation analogous to that made with the pyridyl series with Compounds 128-130.

Otherwise, the heterocycle acyl linkage site proved remarkably flexible tolerating most possibilities. Notably, derivatives were not generally examined that might represent the distinguishing linkage sites of 2- vs 1-naphtyl where the linkage site is adjacent to a ring fusion center and found to be detrimental. However, the productive activity maintained by the 3-benzofuranyl and 3-benzthiophenyl amide Compounds 159 and 164 suggest such linkages should not be ruled out.

The potencies of many of the heterocyclic amides were found to be superb with nearly all exceeding the activity of vinblastine. The potency comparisons of each benzo-fused heterocycle with its companion monocyclic heterocyclic amide was more variable, although most were found to maintain or even improve on this activity.

These generalizations are perhaps best depicted in comparing the quinolyl and isoquinolyl amide series Compounds 149-154 with the pyridyl series of Compounds 128-130. These maintained the exceptional potency (IC$_{50}$=400-700 pM) observed in the pyridyl series (IC$_{50}$=400-600 pM), also exhibited a substantial loss in activity when the acyl substitution site was ortho to the basic nitrogen (about 100-fold, 152), and exhibited a substantially improved (diminished) differential in activity between the sensitive and resistance HCT116 cell lines for the potent variants (about 10-fold vs 100-fold).

Within this series, the 6-benzfuranyl and 6-benzthiophenyl amides (Compounds 157 and 162) displayed activity (IC$_{50}$=2-3 nM) 2- to 3-fold greater than vinblastine with additional and superb improved reductions in the differential activity for the sensitive and resistant HCT116 cell lines (3-fold and 2.7-fold vs 88-fold), and proved very comparable to the 2-naphthyl amide Compounds 116.

Even more significant, a series polycyclic heterocyclic 20' amides was examined in which the fused heterocycle was saturated versus aromatic (Compounds 161 and 173-176). In essence, those examined represent benzoyl amides substituted with a para electron-donating substituent incorporated into a fused ring system, some of which introduce more hydrophobic character. In general, such amides displayed the superb potency that accompanies the introduction of a para electron-donating substituent (IC$_{50}$=300-800 pM). Of these, Compound 173 emerged as the most attractive vinblastine analog. It is >10-fold more potent than vinblastine against the sensitive cell lines (IC$_{50}$=400-500 pM), >300-fold more active against the resistant HCT116 cell line (IC$_{50}$=1.8 nM), and displays a differential in activity of only 3.8-fold. As a result and like Compounds 28 and 121, Compound 173 exhibited a profile of activity sought to be discover at the start of these studies and became a key compound that was further profiled.

C20' Sulfonamides

A small series of C20' sulfonamides was also prepared in a single step from Compound 6 (1.5 equiv RSO$_2$Cl, 2 equiv i-Pr$_2$NEt, 0.05 M CH$_2$Cl$_2$, 23° C., 16 hours; Method 3) and examined (Table 7). No compound in this series approached the potency of vinblastine. In the cases where a comparison C20' amide was prepared, the corresponding sulfonamide compounds (179 vs 24, 180 vs 25, 181 vs 67 and 185 vs 116) proved to be approximately 50-100 times less active.

TABLE 7

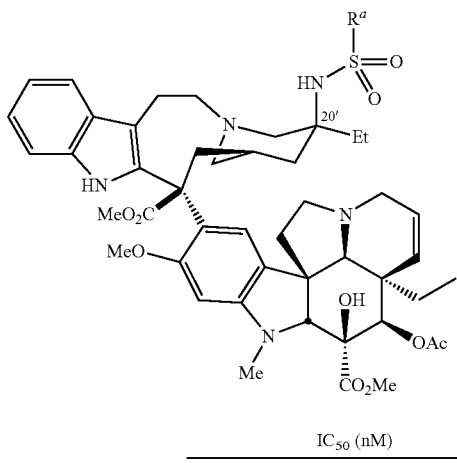

| compound | IC$_{50}$ (nM) | | | |
|---|---|---|---|---|
| | L1210 | HCT116 | HCT116/VM46 | ratio[a] |
| Vinblastine (1) | 6.0 | 6.8 | 600 | 88 |
| R$^a$ = Ph (179) | 45 | 50 | 680 | 14 |
| R$^a$ = 4-MePh (180) | 40 | 30 | 330 | 11 |
| R$^a$ = 4-MeOPh (181) | 35 | 30 | 240 | 8 |
| R$^a$ = 3-NO$_2$Ph (182) | 450 | 490 | 430 | 0.9 |

TABLE 7-continued

| | | | | |
|---|---|---|---|---|
| R$^a$ = 2-NO$_2$Ph (183) | 360 | 420 | 440 | 1 |
| R$^a$ = 2,4,6-Me$_3$Ph (184) | 500 | 580 | 710 | 1.2 |
| R$^a$ = 2-naphthyl (185) | 50 | 60 | 440 | 8 |
| R$^a$ = 5-Me$_2$N-1-naphthyl (186) | 30 | 30 | 60 | 2 |

[a]IC$_{50}$ HCT116-VM46/HCT116.

In recent work, the incorporation of a fluorine atom at the 10' position of vinblastine provided a compound (187) with a nearly 10-fold improvement in activity over vinblastine itself [Gotoh et al., *ACS Med. Chem. Lett.* 2011, 2:948-952]. It was of interest to determine whether the incorporation of both the 10'-F substituent and a 20' amide would have the same effect of enhancing the potency of the vinblastine 20' amide analog and also establishing whether a 10'-F substituent would impact the improved differential in activity against the matched sensitive and resistant HCT116 cell line.

Three key 20' amides also containing a 10'-F substituent were prepared, each of which constitutes 10'-F derivatives of 20' amides that displayed superb or improved reductions in the differential activity (Table 8). In each case, the potency of 20' amide analog was maintained (189 vs 121 and 190 vs 70) or enhanced (188 vs 78) and the improvement in the activity differential observed with the parent 10'-H analogs was maintained (189) or was further improved (188 and 190). The latter

TABLE 8

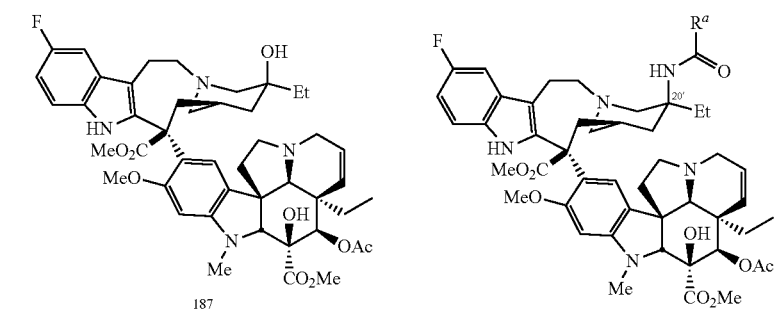

| compound | IC$_{50}$ (nm) | | | |
|---|---|---|---|---|
| | L1210 | HCT116 | HCT116/VM46 | ratio[a] |
| Vinblastine (1) | 6.0 | 6.8 | 600 | 88 |
| 187 | 0.6 | 0.7 | 30 | 43 |
| 188 | 0.6 | 0.7 | 1.0 | 1.4 |
| 189 | 5 | 6.2 | 19 | 3 |
| 190 | 0.06 | 0.08 | 0.9 | 11 |

[a]IC$_{50}$ HCT116-VM46/HCT116.

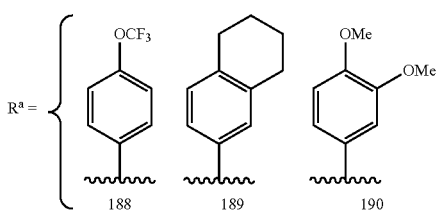

compound 190 is notable in that it is exceptionally potent (IC$_{50}$=60-80 pM) against the vinblastine-sensitive cell lines and even displays sub-nanomolar activity against the vinblastine-resistant HCT116 cell line (IC$_{50}$=900 pM against HCT116/VM46), representing a >600-fold improvement in this activity.

1361:59-168; and Youdim et al., *Drug Discov. Today* 2003, 8:97-1003]. The results are summarized in Table 10, where the compounds demonstrate little or no Pgp transport (or efflux), while maintaining the intrinsic permeability of vinblastine.

TABLE 10

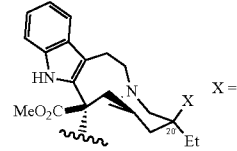

| | (1, vinblastine) | 173 | 121 | 28 |
|---|---|---|---|---|
| IC$_{50}$ (nM), HCT116 | 6.8 | 0.5 | 4.9 | 4.5 |
| IC$_{50}$ (nM), HCT116/VM46 | 600 (88)$^a$ | 1.8 (3.8)$^a$ | 8.7 (1.8)$^a$ | 7.6 (1.7)$^a$ |
| P$_{app}$ (x 10$^{-6}$ cm/s), B to A$^b$ | 38.2 ± 2.0 | 1.5 ± 0.2 | 2.0 ± 0.6 | 3.2 ± 0.9 |
| Efflux ratio$^b$ | 16.2 | 2.2 | 1.3 | 1.5 |
| % Pgp ATPase activity$^c$ | 87% | nd | 0% | nd |

$^a$Fold resistance derived from Pgp overexpression.
$^b$Caco-2 cells, bidirectional permeability.
$^c$Pgp ATPase activity in membranes.
nd = not done Additional Assessments of Compounds 28, 121 and 173

From the series of 20' amides prepared and examined, three compounds (28, 121 and 173) were chosen for further evaluation. The set consists of a small series of hydrophobic aryl amides that are essentially equipotent with (Compounds 28 and 121) or more potent (Compound 173) than vinblastine against sensitive tumor cell lines (e.g. HCT116) and that maintain this potency against the matched resistant human tumor cell line (HCT116/VM46).

The tubulin binding properties of the three compounds were examined alongside vinblastine for their relative ability to displace tubulin bound BODIPY-vinblastine [Carney et al., *Proc. Natl. Acad. Sci. U.S.A.* 2016, 113:9691-9698]. Like the prior comparisons summarized in FIG. 2, the cell-based functional activity of the compounds correlated directly with their relative tubulin binding affinities (Table 9). Thus, the affinities of

TABLE 9

| compd | % displacement | IC$_{50}$ (nM, HCT116) |
|---|---|---|
| 1 | 61 ± 13% | 6.8 |
| 28 | 67 ± 8% | 4.5 |
| 121 | 63 ± 5% | 4.9 |
| 173 | 98 ± 7% | 0.5 |

Compounds 28 and 121 were essentially indistinguishable from or perhaps slightly better than that of vinblastine, whereas the affinity of Compound 173 was established to be significantly higher than that of vinblastine (Compound 1).

The observations made with the three compounds also indicated that the derivatives are not subject to resistance derived from Pgp overexpression as found in HCT116/VM46. These results suggested they are no longer effective substrates for Pgp efflux and that this type of modification may disrupt binding and transport by Pgp. This was confirmed in two widely used secondary assays (Caco-2 bidirectional permeability and stimulated Pgp ATPase activity in membranes) [Polli et al., *J. Pharmacol. Exp. Ther.* 2001, 299:20-628; Litman et al., *Biochim. Biophys. Acta* 1997, At the start of these studies, this type of result was viewed as an initial complete success for the studies—the discovery of vinblastine analogs that matched or exceeded the potency of the clinical drugs, but that would not be subject to clinical resistance derived from Pgp overexpression and efflux.

Models of 28, 121 and 173 Bound to Tubulin

The binding site for vinblastine lies at the head-to-tail tubulin α/β dimer-dimer interface. As depicted in the X-ray co-crystal structures of tubulin bound complexes [Gigant et al., *Nature* 2005, 435, 519-522; and Waight et al., *Plos One* 2016, 11, e0160890], vinblastine is nearly completely buried in the protein binding site. It adopts a T-shaped bound conformation with C3/C4 (bottom of T) lying at the solvent interface and the C20' site (top corner of T) extends deepest into the binding pocket lying at one corner. In contrast to early expectations based on the steric constraints of the tubulin binding site surrounding the vinblastine C20' center, large 20' substituents such as those detailed herein are accommodated.

The C20' alcohol extends toward a narrow channel that leads from the buried C20' site to the opposite face of the protein, representing the continuation of the protein-protein interaction defined by the tubulin dimer-dimer interface. Even without adjusting the proteins found in the vinblastine-bound X-ray structures, the modeled 20' amides extend into this narrow channel, continuing along the tubulin α/β dimer-dimer protein-protein interface. The newly introduced vinblastine 20' amide forms two key H-bonds in which the amide N—H serves as a H-bond donor for the backbone carbonyl of Pro222 (2.0 Å) and the amide carbonyl serves as a H-bond acceptor for the backbone amide N—H of Tyr224 (3.0 Å). These H-bonds serve to anchor the orientation of the 20' amides such that the attached acyl group extends into the adjacent narrow channel.

In this orientation, not only are substituents on the benzamides accommodated at either the 3- or 4-position, but such electron-donating substituents that increase the Lewis basicity of the amide carbonyl would be expected to increase the strength of the H-bond with Tyr224, accounting for the enhanced tubulin binding affinity and the resulting increased activity in cell-based functional assays.

Further Tubulin-Related Studies

Alterations to the target tubulin could also impact activity and contribute to or be responsible for vinca alkaloid resistance. A series of association studies of clinical data have implicated high level expression of class III p-tubulin as both a prognostic and predictive factor for lower response rates or reduced overall survival in patients receiving tubulin binding drugs [Sève et al., Lancet Oncol. 2008; 9:168 and Yang et al., PLoS One 2014; 9:e93997]. However, most of the association studies and the supporting cellular studies have examined the impact of class III β-tubulin on taxanes and a much smaller sampling of its impact on vinca alkaloids are represented in the association studies [Sève et al., Lancet Oncol. 2008; 9:168 and Yang et al., PLoS One 2014; 9:e93997].

Despite the obvious differences in the tubulin binding sites of the taxanes and vinca alkaloids as well as their distinct functional behaviors (stabilization vs destabilization of tubulin dynamics), both taxanes and the vinca alkaloids typically have been lumped together as potentially being negatively impacted by the high expression of class III β-tubulin [Sève et al., Lancet Oncol. 2008, 9:168 and Yang et al., PLoS One 2014, 9:e93997].

A series of the key vinblastine analogs was examined that emerged from these studies in additional cell-based functional cell growth inhibition assays for their sensitivity to the high expression of class III β-tubulin and report the results herein. The key analogs that were examined alongside vinblastine (1) are 10'-fluorovinblastine (187) [U.S. Pat. No. 8,940,754], three vinblastine 20' amides 28, 121 and 173 that displayed no susceptibility to Pgp efflux and are insensitive to Pgp overexpression resistance [Lukesh et al. J. Med. Chem. 2017, 60:7591], and a series of vinblastine 20' ureas $9^c$, $58^c$, $60^c$ and $61^c$ [numbered as in WO 2017/210206] that includes the ultrapotent analogs $58^c$, $60^c$ and $61^c$ [Barker et al., ACS Med. Chem. Lett., 2013, 4:985 and Carney et al., Proc. Natl. Acad. Sci. USA, 2016, 113:9691; WO 2017/210206].

In primary studies, these compounds were screened for growth inhibition activity against HCT116 (human colon cancer cell line) and a matched resistant cell line (HCT116/VM46) that is approximately 100-fold resistant by virtue of the overexpression of Pgp. This well-designed set of cell-based assays simultaneously provided a direct measure of both functional activity (HCT116) and the analog susceptibility to Pgp efflux (resistance, HCT116/VM46).

Key members were assessed for tubulin binding affinity for correlation with functional activity and those that showed no sensitivity to Pgp overexpression, including Compounds 28, 121 and 173, were examined in efflux assays to confirm their behavior toward Pgp and related efflux transporters [Lukesh et al. J. Med. Chem. 2017, 60:7591]. The cell growth inhibition activity against the L1210 (mouse leukemia) cell line was also measured and the results were qualitatively and quantitatively ($IC_{50}$) nearly identical to those observed with the HCT116 cell line.

In these studies, the HCT116 human tumor cell line was found to accurately reflect activity observed against a larger panel of clinically relevant human tumor-derived cell lines [Sears et al., Acc. Chem. Res. 2015, 48:653; Boger, J. Org. Chem. 2017, 82:11961; Barker et al., ACS Med. Chem. Lett., 2013, 4:985; Carney et al., Proc. Natl. Acad. Sci. USA, 2016, 113:9691; Lukesh et al. J. Med. Chem. 2017, 60:7591; Tam et al., Bioorg. Med. Chem. Lett. 2010, 20 6408; and Gotoh et al., ACS Med. Chem. Lett., 2011, 2:948]. Alongside that prior data, the cell growth inhibition activity of the analog Compounds 187, 28, 121, 173, $9^c$, $58^c$, $60^c$ and $61^c$ (superscripted "c" compound numbers are as used in WO 2017/206210) against the human A549 cell line (human non-small cell lung cancer) and a matched cell line A549-T24 insensitive to taxol are reported below. [Goncalves et al., Proc. Natl. Acad. Sci. USA. 2001, 98:11737; Kavallaris et al., Brit. J. Cancer. 1999, 80:1020; and Kavallaris et al., J. Clin. Invest. 1997, 100:1282].

After its original generation and characterization, this taxol-resistant cell line (A549-T24) was found to embody an increased expression of class III β-tubulin that was correlated with the loss in taxol sensitivity with no alteration in Pgp expression [Goncalves et al., Proc. Natl. Acad. Sci. USA. 2001, 98:11737; Kavallaris et al., Brit. J. Cancer. 1999, 80:1020; and Kavallaris et al., J. Clin. Invest. 1997, 100:1282]. As a result, the comparison of cell growth inhibition of candidate drugs against A549 vs A549-T24 has been used to characterize potential resistance due to increased expression of class III β-tubulin [Goncalves et al., Proc. Natl. Acad. Sci. USA. 2001, 98:11737; Kavallaris et al., Brit. J. Cancer. 1999, 80:1020; and Kavallaris et al., J. Clin. Invest. 1997, 100:1282].

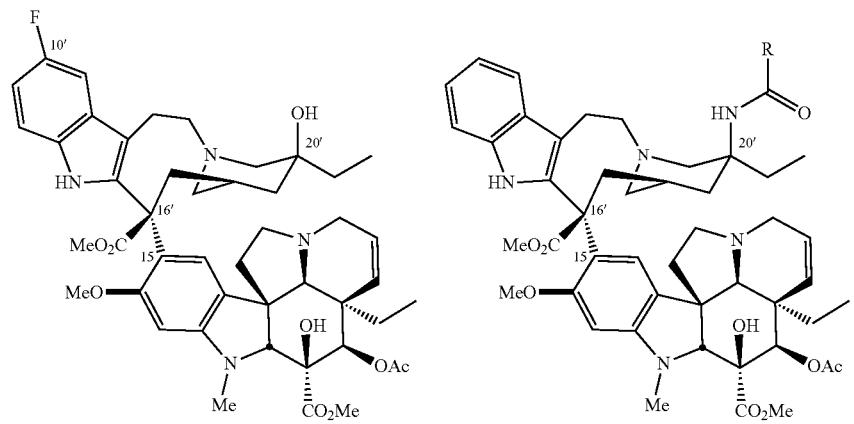

187, 10'-Fluorovinblastine

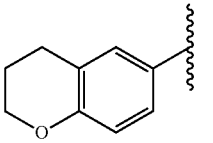

R = 173, 28, 9[c], 121

| Cell Line[a] | IC$_{50}$ (nM) | | | | | | |
|---|---|---|---|---|---|---|---|
| | 1 | 187 | 28 | 121 | 173 | 9[c] | Taxol |
| L1210 | 6.0 | 0.7 | 3.0 | 3.0 | 0.4 | 0.5 | |
| HCT116 | 6.8 | 0.8 | 4.5 | 4.9 | 0.5 | 0.6 | 4.1 |
| HCT116/VM46 | 600 (88) | 80 (100) | 7.6 (1.7) | 8.7 (1.8) | 1.8 (3.8) | 7.5 (12) | >200[b] (>50) |
| A549 | 7.7 | 2.9 | 5.0 | 7.6 | 1.4 | 0.7 | 7.1 |
| A549-T24 | 6.7 (<1) | 0-8 (<1) | 2.5 (<1) | 6.5 (<1) | 0.8 (<1) | 0.7 (1) | 70 (10) |

[a]L1210 (mouse leukemia), HCT116 (human colon), HCT116/VM46 (human colon, vinblastine resistant, Pgp overexpression), A549 (human non small cell lung), A549-T24 (human non small cell lung, taxol resistant, class III β-tubulin high expression).
[b]Highest concentration tested. Measured fold resistant vs wt HCT116 or wt A549 is presented in parentheses.
[c]As numbered in WO/2017/210206. All compounds were >95% pure.

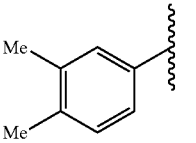

R = 58[c], 60[c], 61[c]

| Cell Line[a] | IC$_{50}$ (nM) Compound | | | |
|---|---|---|---|---|
| | 58[c] | 60[c] | 61[c] | Taxol |
| L1210 | 0.06 | 0.06 | 0.06 | |
| HCT116 | 0.07 | 0.07 | 0.07 | 4.1 |
| HCT116/VM46 | 0.88 (13) | 0.83 (12) | 0.87 (12) | >200[b] (>50) |
| A549 | 0.17 | 0.19 | 0.53 | 7.1 |
| A549-T24 | 0.13 (<1) | 0.09 (<1) | 0.26 (<1) | 70 (10) |

See notes above.

Consistent with prior reports, A549-T24 proved insensitive to taxol treatment, exhibiting a 10-fold loss in potency relative to wild type A549 cells (IC$_{50}$=70 vs 7.1 nM) [Goncalves et al., *Proc. Natl. Acad. Sci. USA.* 2001, 98:11737; Kavallaris et al., *Brit. J. Cancer.* 1999, 80:1020; and Kavallaris et al., *J. Clin. Invest.* 1997, 100:1282]. In contrast, vinblastine as well as all the enumerated vinblastine analogs did not exhibit any loss in sensitivity toward A549-T24. In fact, most showed slight increases in potency (1-3.6 fold, avg=1.8 fold), suggesting they may be even more effective in the presence of expressed class III β-tubulin.

In retrospect, this may not be surprising. Class III β-tubulin increases the instability and dynamics of microtubule assembly, potentially countering the stabilizing effects of bound taxol, but enhancing the destabilizing effects of the vinca alkaloids. Most significant within this series of analogs are the results with Compounds $58^c$, $60^c$ and $61^c$ [Lukesh et al. *J. Med. Chem.* 2017, 60:7591; WO 2017/206210]. They match or exceed the potency of vinblastine, they display equipotent or more potent activity against A549-T24 than even wild type A549 cells (1.2-2 fold) and, as detailed earlier [Lukesh et al. *J. Med. Chem.* 2017, 60:7591; WO 2017/206210], they uniquely display no sensitivity to the overexpression of Pgp (HCT116/VM46 vs HCT116) and are not subject to efflux by Pgp or related drug efflux transporters [Lukesh et al. *J. Med. Chem.* 2017, 60:7591; WO 2017/206210].

The results not only suggest that (1) vinblastine and related analogs are not likely to be prone to resistance derived from high expression of class III β-tubulin unlike the taxanes, but also that (2) association studies of clinical data with tubulin binding drugs [Seve et al., *Lancet Oncol.* 2008, 9:168 and Yang et al., *PLoS One* 2014, 9:e93997] should treat taxanes and the vinca alkaloids as distinct drug classes likely to exhibit different sources of on target resistance.

Conclusions

A site and powerful functionalization strategy on vinblastine was exploited that provided access to analogs that simultaneously maintain or improve cell-based functional activity, maintain or improve target tubulin binding affinity, and simultaneously disrupt off target activity (Pgp efflux) responsible for clinical resistance. Thus, an extensive and systematic series of synthetic vinblastine 20' amides were prepared in three steps from commercially available material, targeting a site inaccessible to traditional divergent functionalization [Borman et al., In *The Alkaloids*; Brossi, A., Suffness, M., Eds.; Academic: San Diego, 1990; Vol. 37, pp 133-144].

Many such 20' amides were found to exhibit substantial and some even remarkable potency increases, many exhibited further improvements in activity against a Pgp overexpressing resistant tumor cell line, and an important subset of the vinblastine analogs displayed little or no differential in activity against a matched pair of vinblastine-sensitive and -resistant (Pgp overexpressing) cell lines. The improvements in potency directly correlated with improvements in target tubulin binding affinity, and the reduction in differential functional activity against the sensitive and resistant cell lines was found to correlate with analogous reductions in Pgp derived efflux.

Well defined structure-activity relationships and a structural model were developed in the studies that confidently account for the structural features that improve functional and target tubulin binding activity and key insights into structural characteristics [Hitchcock, *J. Med. Chem.* 2012, 55, 4877-4895] that can be used to simultaneously disrupt off target Pgp binding and/or efflux responsible for clinical drug resistance were obtained. Members of this class of vinblastine 20' amides have the potential of not only serving as vinblastine replacements in the clinic, addressing clinical resistance limiting its continued use, but can also offer opportunities for the development of powerful new frontline treatment options in instances of other multidrug resistant (MDR) tumors (overexpression of Pgp) refractory to most other chemotherapeutic drugs [Persidis, Nat. Biotechnology 1999, 17:94-95].

EXPERIMENTAL SECTION

General Chemistry Procedures

All commercial reagents were used without further purification unless otherwise noted. All reactions were performed in oven-dried (200° C.) glassware and under an inert atmosphere of Ar unless otherwise noted.

Column chromatography was performed with silica gel 60 (43-60 Å). TLC was performed on Whatman® silica gel (250 μm) $F_{254}$ glass plates and spots visualized by UV. PTLC was performed on Whatman® silica gel (250 and 500 μm) $F_{254}$ glass plates.

Optical rotations were determined on a Rudolph Research Analytical Autopol III automatic polarimeter using the sodium D line (λ=589 nm) at room temperature (23° C.) and are reported as follows: $[\alpha]_D^{23}$, concentration (c=g/100 mL), and solvent. FT-IR spectroscopy was conducted on a Nicolet™ 380 FT-IR instrument.

$^1$H NMR was recorded on a Bruker 600 MHz spectrometer. Chemical shifts are reported in ppm from an internal standard of residual CHCl$_3$ (7.26 for $^1$H). Proton chemical data are reported as follows: chemical shift (δ), multiplicity (ovlp=overlapping, br=broad, s=singlet, d=doublet, t=triplet, q=quartet, m=multiplet), coupling constant, and integration. High resolution mass spectra were obtained at The Scripps Research Institute Mass Spectrometry Facility on an Agilent ESI-TOF/MS using Agilent ESI-L low concentration tuning mix as internal high resolution calibration standards. The purity of each tested compound (>95%) was determined on an Agilent 1100 LC/MS instrument using a ZORBAX® SB-C18 column (3.5 mm, 4.6 mm×50 mm, with a flow rate of 0.75 mL/min and detection at 220 and 254 nm) with a 10-98% acetonitrile/water/0.1% formic acid gradient (two different gradients). A table of the established purity for each tested compound is provided hereinafter.

General Methods for the Synthesis of Vinblastine 20' Amides

Method 1

A solution of 20'-aminovinblastine [Leggans et al., *Org. Lett.* 2012, 14:1428-1431] (6, 3.5 mg, 0.004 mmol) in CH$_2$Cl$_2$ (0.1 mL) was treated with 4 μL of i-Pr$_2$NEt (0.016 mmol) followed by addition of the acid chloride (0.008 mmol). The reaction mixture was stirred for 2 hours at room temperature before being quenched with the addition of saturated aqueous NaHCO$_3$ (3 mL). The mixture was extracted with 10% MeOH in CH$_2$Cl$_2$ (3 mL), and washed with saturated aqueous NaCl (3 mL). The organic layer was dried over Na$_2$SO$_4$, and concentrated under reduced pressure. PTLC (SiO$_2$, EtOAc:MeOH:Et$_3$N=95:5:5) purification provided the pure products; yields (35-98%).

Method 2

A solution 20'-aminovinblastine [Leggans et al., *Org. Lett.* 2012, 14:1428-1431] (6, 4 mg, 0.005 mmol) in DMF (0.1 mL) was treated with EDCI (0.02 mmol), DMAP (20 mol %) and the carboxylic acid (0.01 mmol). The reaction mixture was allowed to stir at room temperature overnight (about 18 hours), after which it was diluted with the addition of 10% MeOH in CH$_2$Cl$_2$ (3 mL) and aqueous 10% citric acid or 1 M HCl (3 mL). The aqueous layer was further extracted with 10% MeOH in CH$_2$Cl$_2$, and the combined organic phase was washed with saturated aqueous NaHCO$_3$ (3 mL), and saturated aqueous NaCl (3 mL). The organic layer was dried over Na$_2$SO$_4$, and concentrated under reduced pressure. PTLC (SiO$_2$, EtOAc:MeOH:Et$_3$N=95:5: 5) purification provided the pure products; yields (20-98%).

Method 3

A solution of 20'-aminovinblastine [Leggans et al., *Org. Lett.* 2012, 14:1428-1431] (6, 4 mg, 0.005 mmol) in anhydrous CH$_2$Cl$_2$ (0.1) was treated with i-Pr$_2$NEt (0.01 mmol) and the sulfonyl chloride (0.008 mmol). The resulting mixture was allowed to stir at room temperature overnight (about 18 hours), after which it was diluted with the addition of saturated aqueous NaHCO$_3$ (2 mL). The mixture was extracted with 10% MeOH in CH$_2$Cl$_2$, and washed with saturated aqueous NaCl (3 mL). The combined organic extracts were dried over Na$_2$SO$_4$ and concentrated under reduced pressure. PTLC (SiO$_2$, EtOAc:MeOH:Et$_3$N=97:3: 3) purification provided the pure products; yields (41-54%).

Compound 28

Method 1 was followed using 8.0 mg of 20'-aminovinblastine (6, 0.01 mmol) to provide 4.7 mg of Compound 28 as a white solid, yield: 50%. $^1$H NMR (600 MHz, CDCl$_3$) δ 9.83 (br s, 2H), 8.02 (s, 1H), 7.82-7.76 (m, 2H), 7.44 (d, J=7.2 Hz, 1H), 7.24 (d, J=7.7 Hz, 1H), 7.14-7.07 (m, 2H), 6.64 (s, 1H), 6.12 (s, 1H), 6.08 (s, 1H), 5.85 (d, J=5.7 Hz, 1H), 5.48 (s, 1H), 5.30 (d, J=10.3 Hz, 1H), 4.00 (br s, 1H), 3.81 (s, 3H), 3.80 (s, 3H), 3.75 (s, 1H), 3.58 (s, 3H), 3.42-3.36 (m, 2H), 3.30 (td, J=9.5, 4.8 Hz, 1H), 3.22 (t, J=8.7 Hz, 1H), 3.10 (dd, J=14.6, 7.2 Hz, 2H), 2.83 (d, J=16.2 Hz, 1H), 2.72 (s, 3H), 2.67 (s, 1H), 2.45-2.41 (m, 1H), 2.35 (s, 3H), 2.30 (s, 3H), 2.17 (s, 1H), 2.11 (s, 3H), 2.02-1.98 (m, 1H), 1.85-1.78 (m, 2H), 1.62-1.59 (m, 4H), 1.42 (t, J=7.4 Hz, 1H), 1.37-1.31 (m, 2H), 1.26-1.23 (m, $^3$H), 0.82 (t, J=7.0 Hz, 3H), 0.77 (t, J=6.2 Hz, 3H); HRESI-TOF m/z 942.5012 (C$_{55}$H$_{67}$N$_5$O, +H$^+$, required 942.5011). [α]$_D^{23}$–39 (c 0.027, CHCl$_3$).

Compound 121

Method 2 was followed using 8.4 mg of 20'-aminovinblastine (6, 0.01 mmol) to provide 4.0 mg of Compound 121 as a white solid, yield: 42%. $^1$H NMR (600 MHz, CDCl$_3$) δ 9.86 (br s, 1H), 8.05 (s, 1H), 7.76 (s, 2H), 7.48-7.46 (m, 1H), 7.19 (d, J=8.2 Hz, 1H), 7.16 (d, J=6.7 Hz, 1H), 7.12-7.10 (m, 2H), 6.66 (s, 1H), 6.14 (s, 1H), 6.10 (s, 1H), 5.88-5.87 (m, 1H), 5.50 (s, 1H), 5.33 (d, J=10.2 Hz, 1H), 4.00 (br s, 1H), 3.84 (s, 3H), 3.82 (s, 3H), 3.78-3.77 (m, 1H), 3.60 (s, 3H), 3.44-3.38 (m, 2H), 3.33 (td, J=9.5, 4.8 Hz, 1H), 3.26-3.23 (m, 1H), 3.14-3.10 (m, 2H), 2.91-2.87 (m, 2H), 2.84-2.83 (m, 1H), 2.82-2.81 (m, 1H), 2.75 (s, 3H), 2.71-2.69 (m, 1H), 2.48-2.43 (m, 1H), 2.39-2.36 (m, 1H), 2.20 (s, 3H), 2.13 (s, 1H), 1.88-1.85 (m, 1H), 1.83-1.82 (m, 4H), 1.61 (s, 3H), 1.54-1.51 (m, 1H), 1.44 (t, J=7.4 Hz, 1H), 1.37-1.33 (m, 2H), 1.28 (s, 2H), 0.92-0.89 (m, 1H), 0.84 (t, J=6.9 Hz, 3H), 0.80-0.78 (m, 3H); HRESI-TOF m/z 968.5164 (C$_{57}$H$_{69}$N$_5$O$_9$+H$^+$, required 968.5168). [α]$_D^{23}$–55 (c 0.069, CHCl$_3$).

Compound 173

Method 2 was followed using 8.0 mg of 20'-aminovinblastine (6, 0.01 mmol) to provide 3.5 mg of Compound 173 as a pale white solid, yield: 37%. $^1$H NMR (600 MHz, CDCl$_3$) δ 9.84 (br s, 1H), 8.06-8.04 (m, 1H), 7.91 (s, 1H), 7.58-7.50 (m, 2H), 7.30-7.38 (m, 1H), 7.19-7.16 (m, 2H), 6.78-6.77 (m, 2H), 6.53 (s, 1H), 6.11 (s, 1H), 5.88 (s, 1H), 5.47 (s, 1H), 5.32 (d, J=9.8 Hz, 1H), 4.21 (t, J=4.6 Hz, 2H), 3.82-3.82 (m, 6H), 3.76 (br s, 1H), 3.63 (s, 3H), 3.51 (s, 1H), 3.42-3.37 (m, 2H), 3.31-3.25 (m, 2H), 3.15-3.10 (m, 2H), 2.91 (s, 1H), 2.82-2.79 (m, 2H), 2.74 (s, 3H), 2.66-2.62 (m, 1H), 2.45-2.41 (m, 1H), 2.32-2.30 (m, 2H), 2.19 (s, 3H), 2.13-2.12 (m, 2H), 2.11-2.09 (m, 1H), 2.01 (br s, 1H), 1.69-1.66 (m, 4H), 1.55-1.52 (m, 2H), 1.33-1.28 (m, 5H), 0.89-0.84 (m, 6H); HRESI-TOF m/z 970.4961 (C$_{56}$H$_{67}$N$_5$O$_{10}$+H$^+$, required 970.4960). [α]$_D^{23}$–76 (c 0.059, CHCl$_3$).

Ritter Reaction Used to Prepare 20'-acetamidoleurosidine (8)

A solution containing 22 mg of vinblastine sulfate in 0.6 mL of anhydrous acetonitrile was prepared. 60 µL of 18 M sulfuric acid was added. The resulting solution was stirred at ambient temperature for 7 hours and then overnight (about 18 hours) at 0° C. Next, 318 mg of Na$_2$CO$_3$ and 2 mL of anhydrous MeOH were added. This mixture was stirred for 15 minutes before 4 mL of a saturated aqueous NaCl was added. The reaction volume was increased to 8 mL by the addition of water. This diluted mixture was stirred for about 15 minutes, after which time it was extracted four times with an equal volume of benzene. The combined organic layer was dried over Na$_2$SO$_4$, and concentrated under reduced pressure. PTLC (SiO$_2$, EtOAc:MeOH:Et$_3$N=97:3:3) provided three products. The first product was recovered vinblastine (5.5 mg). The second product was 20'-acetamidoyl-leurosidine (8, 1.2 mg) and its structure was confirmed by comparison with a sample prepared from authentic 20'-aminoleurosidine. The third product (1.8 mg) was leurosidine. For 20'-amidoleurosidine (Compound 8): $^1$H NMR (600 MHz, CDCl$_3$) δ 9.81 (s, 1H), 7.98 (s, 1H), 7.52 (d, J=7.8 Hz, 1H), 7.21-7.14 (m, 1H), 7.14-7.08 (m, 3H), 6.50 (s, 1H), 6.16 (s, 1H), 6.08 (s, 1H), 5.88-5.80 (m, 1H), 5.45 (s, 1H), 5.28 (d, J=10.2 Hz, 1H), 3.79 (s, 3H), 3.77 (s, 1H), 3.76 (s, 3H), 3.66-3.61 (m, 1H), 3.59 (s, 3H), 3.40-3.34 (m, 1H), 3.33-3.27 (m, 1H), 3.27-3.21 (m, 2H), 3.15 (t, J=14.4 Hz, 1H), 3.04 (dd, J=14.5, 5.9 Hz, 1H), 2.97 (d, J=10.7 Hz, 1H), 2.91-2.83 (m, 1H), 2.83-2.77 (m, 1H), 2.73 (s, 3H), 2.71-2.64 (m, 2H), 2.63 (s, 1H), 2.47-2.41 (m, 1H), 2.31 (dq, J=14.8, 7.5 Hz, 1H), 2.27-2.22 (m, 1H), 2.22-2.15 (m, 1H), 2.09 (s, 3H), 1.88 (s, 3H), 1.78 (dt, J=14.4, 7.4 Hz, 1H), 1.75-1.68 (m, 1H), 1.43 (dq, J=14.3, 7.2 Hz, 1H), 1.36-1.27 (m, 1H), 1.07-0.99 (m, 1H), 0.96 (d, J=15.1 Hz, 1H), 0.81 (t, J=7.4 Hz, 3H), 0.78 (t, J=7.4 Hz, 3H); $^{13}$C NMR (151 MHz, CDCl$_3$) δ 174.5, 171.8, 171.1, 169.8, 158.1, 153.1, 135.0, 130.9, 130.2, 129.4, 124.6, 123.3, 123.0, 122.6, 119.2, 118.3, 117.0, 110.8, 94.5, 83.5, 79.8, 76.6, 65.8, 56.8, 56.0, 54.4, 53.4, 52.6, 52.4, 50.5, 44.7, 43.5, 42.8, 38.6, 37.1, 30.9, 30.7, 30.1, 24.7, 21.3, 8.6, 8.2; IR (film) ν$_{max}$ 3467, 2958, 1738, 1666, 1459, 1229, 1039, 749 cm$^{-1}$; HRESI-TOF m/z 852.4547 (C$_{48}$H$_{61}$N$_5$O$_9$+H$^+$, required 852.4542). [α]$_D^{23}$+13 (c 0.31, CHCl$_3$). Identical in all respects with reported data and an authentic sample [Leggans et al., *Org. Lett.* 2012, 14:1428-1431].

Cell Growth Inhibition Assay

Compounds were tested for their cell growth inhibition of L1210 (ATCC no. CCL-219, mouse lymphocytic leukemia), HCT116 (ATCC no. CCL-247, human colorectal carcinoma), and HCT116/VM46 (a vinblastine-resistant strain of HCT116) cells in culture. A population of cells (>1×10$^6$ cells/mL as determined with a hemocytometer) was diluted with Dulbecco's Modified Eagle Medium (DMEM, Gibco) containing 10% fetal bovine serum (FBS, Gibco) to give a final concentration of 30,000 cells/mL. To each well of a 96-well plate (Corning® Costar®) was added 100 µL of the cell media solution with a multichannel pipet. The cultures were incubated at 37° C. in an atmosphere of 5% CO$_2$ and 95% humidified air for 24 hours.

The test compounds were then added to the plate as follows: test compounds were diluted in DMSO to a concentration of 1 mM. 10-Fold serial dilutions in DMSO were next performed on a separate 96-well plate. Fresh culture media (100 µL) was added to each well of cells resulting in 200 µL of medium per well followed by 2 µL of each test agent. Compounds were tested in duplicate (n=2-8 times) at six concentrations between 0-1000 nM or 0-10000 nM. Following the addition of compound, cultures were incubated for an additional 72 hours.

A phosphatase assay was used to establish $IC_{50}$ values as follows: the media was removed from each well and treated with 100 µL of phosphatase solution (100 mg phosphatase substrate in 30 mL of 0.1 M NaDAc, pH 5.5, 0.1% Triton® X-100 buffer). The plates were incubated at 37° C. for 5 minutes (L1210) or 15 min (HCT116 and HCT116/VM46). After the given incubation time, 50 µL of 0.1 N NaOH was added to each well and the absorption at 405 nm was determined using a 96 well plate reader. Given that the absorption is directly proportional to the number of living cells, $IC_{50}$ values were calculated and reported values represent the average of 4-16 determinations (SD±10%).

Tubulin Binding Competition Assay [Carney et al., *Proc. Natl. Acad. Sci. U.S.A.* 2016, 113:9691-9698]

Tubulin (0.1 mg/mL, 0.91 µM) was incubated with BODIPY-vinblastine (BODIPY-VBL, 1.8 µM) for 15 minutes at 37° C. in PEM buffer containing 850 µM GTP. Subsequently, a competitive ligand (vinblastine, Compound 64, 24, or 54) was added to the solution at a final concentration of 18 µM. After incubation for 60 minutes at 37° C., 100 µL aliquots from each incubation were measured in a fluorescence microplate reader (FI; ex 480 nm, em 514 nm). Control studies were performed with BODIPY-VBL in the absence of a competitive ligand (control 1, maximum FI enhancement) and in the absence of tubulin (control 2, no FI enhancement). Percent (%) BODIPY-VBL displacement was calculated by the formula: (control 1 FI−experiment FI)/(Control 1 FI−Control 2 FI)×100%. Reported values are the average of 5 measurements±SD.

Efflux and Permeability Assays

The amount of drug-stimulated Pgp ATPase activity generated by either vinblastine or analog Compound 121 was determined using a MDR1 PREDEASY™ ATPase Kit Assay Protocol (SOLVO Biotechnology, Version Number: 1.2) purchased from Sigma-Aldrich (St. Louis, Mo.) and following the manufacturer's protocol Polli et al., *J. Pharmacol. Exp. Ther.* 2001, 299, 620-628; and Litman et al., *Biochim. Biophys. Acta* 1997, 1361, 159-168]. The Caco-2 cell permeability assay was conducted comparing vinblastine, and Compounds 28, 121, and 173 by following a previously published procedure [Youdim et al., *Drug Discov. Today* 2003, 8, 997-1003] and was conducted by Sekisui XenoTech, LLC (Kansas City, Kans.).

Abbreviations Used

DMAP, 4-(dimethylamino)pyridine; DMF, dimethylformamide; DMSO, dimethylsulfoxide; EDCI, 1-ethyl-3-(3-dimethylaminopropyl)carbodiimide; MDR, multidrug resistant; Pgp, P-glycoprotein.

Compound 9

A solution of 20T-aminovinblastine [Leggans et al., *Org. Lett.* 2012, 14:1428-1431] (6, 7.9 mg, 0.009 mmol) in formic acid (400 µL, 10.4 mmol) was treated with acetic anhydride (60 µL, 0.64 mmol). The reaction mixture was stirred for 2 hours at room temperature before being quenched with the addition of saturated aqueous NaHCO$_3$ (1 mL). The mixture was extracted with 10% MeOH in CH$_2$Cl$_2$, and washed with saturated aqueous NaCl (1 mL). The organic layer was dried over Na$_2$SO$_4$, and concentrated under reduced pressure. PTLC (SiO$_2$, EtOAc:MeOH: Et$_3$N=97:3:3) purification provided Compound 9 as a white solid in 72%. $^1$H NMR (600 MHz, CDCl$_3$) δ 9.81 (br s, 1H), 8.31 (s, 1H), 8.02 (br s, 1H), 7.50 (d, J=7.8 Hz, 1H), 7.14-7.11 (m, 3H), 6.63 (s, 1H), 6.09 (s, 1H), 5.79 (dd, J=10.1, 3.6 Hz, 1H), 5.46 (s, 1H), 5.29 (d, J=9.8 Hz, 1H), 3.76 (s, 6H), 3.73 (s, 1H), 3.67-3.64 (m, 1H), 3.58 (s, 3H), 3.40-3.36 (m, 2H), 3.39-3.16 (m, 3H), 3.09-3.03 (m, 1H), 2.82-2.79 (m, 1H), 2.70 (s, 3H), 2.60 (s, 1H), 2.45-2.40 (m, 1H), 2.31 (d, J=12.8 Hz, 1H), 2.20-2.16 (m, 2H), 2.10 (s, 3H), 1.82-1.78 (m, 2H), 1.69 (s, 1H), 1.55-1.32 (m, 3H), 1.24-1.22 (m, 3H), 0.82 (t, J=7.4 Hz, 3H), 0.77 (t, J=7.4 Hz, 3H); IR (film) $v_{max}$ 3466, 2924, 2850, 1737, 1686, 1612, 1460, 1232, 1039, 734 cm$^{-1}$; HRESI-TOF m/z 838.4376 (C$_{47}$H$_{59}$N$_5$O$_9$+H$^+$, required 838.4386). $[\alpha]_D^{23}$+13 (c 0.034, CHCl$_3$).

Compound 10

Method 1 was followed using 2.0 mg of 20'-aminovinblastine (6, 0.02 mmol) to provide Compound 10 as a white solid, yield: 61%. $^1$H NMR (600 MHz, CDCl$_3$) δ 9.80 (s, 1H), 8.01 (s, 1H), 7.51 (d, J=7.8 Hz, 1H), 7.21-7.08 (m, 3H), 6.63 (s, 1H), 6.10 (s, 1H), 5.85 (dd, J=10.2, 5.0 Hz, 1H), 5.48 (s, 1H), 5.37 (s, 1H), 5.30 (d, J=10.2 Hz, 1H), 3.83-3.71 (m, 9H), 3.60 (s, 3H), 3.42-3.33 (m, 2H), 3.37-3.13 (m, 3H), 3.12-3.06 (m, 1H), 2.82 (d, J=16.2 Hz, 1H), 2.71 (s, 3H), 2.66 (s, 1H), 2.59 (d, J=13.6 Hz, 1H), 2.44 (dt, J=11.2, 9.7 Hz, 1H), 2.36-2.31 (m, 1H), 2.23-2.16 (m, 2H), 2.16 (s, 3H), 2.11 (s, 3H), 1.93 (d, J=14.6 Hz, 1H), 1.85-1.76 (m, 2H), 1.70-1.55 (m, 2H), 1.35 (dq, J=14.4, 7.2 Hz, 1H), 1.25 (s, 1H), 1.22-1.11 (m, 2H), 0.82 (t, J=7.4 Hz, 3H), 0.75 (t, J=7.4 Hz, 3H); HRESI-TOF m/z 852.4542 (C48H$_{61}$N$_5$O$_9$+H$^+$, required 852.4542). $[\alpha]_D^{23}$−31 (c 0.06, CHCl$_3$).

Compound 11

A solution of 20'-aminovinblastine[41] (6, 2.0 mg, 0.002 mmol) in THF (2 mL) cooled to −78° C. was treated with trifluoroacetic anhydride (300 µL, 2.1 mmol). The reaction mixture was stirred for 10 hours at −78° C. before being quenched with the addition of deionized H$_2$O (2 mL). The mixture was extracted with 10% MeOH in CH$_2$Cl$_2$, and washed with saturated aqueous NaCl (1 mL). The organic layer was dried over Na$_2$SO$_4$, and concentrated under reduced pressure. PTLC (SiO$_2$, EtOAc:MeOH:Et$_3$N=97:3: 3) purification provided Compound 11 as a white solid in 67%. $^1$H NMR (600 MHz, CDCl$_3$) δ 9.83 (br s, 1H), 8.06 (br s, 1H), 7.51 (d, J=8.4 Hz, 1H), 7.17-7.14 (m, 1H), 7.13-7.07 (m, 3H), 6.62 (s, 1H), 6.27 (s, 1H), 6.11 (s, 1H), 5.83 (s, 1H), 5.49 (s, 1H), 5.29 (d, J=11.8 Hz, 1H), 3.80 (s, 3H), 3.79 (s, 3H), 3.74 (s, 1H), 3.65 (t, J=10.2 Hz, 1H), 3.61 (s, 3H), 3.50-3.43 (m, 1H), 3.39 (d, J=15.5 Hz, 1H), 3.32-3.27 (m, 2H), 3.24 (d, J=12.8 Hz, 1H), 3.15-3.04 (m, 2H), 2.81 (d, J=15.1 Hz, 1H), 2.70 (s, 3H), 2.68 (d, J=14.2 Hz, 1H). 2.64 (s, 1H), 2.46-2.41 (m, 1H), 2.30 (d, J=13.2 Hz, 1H), 2.25-2.16 (m, 2H), 2.11 (s, 3H), 2.02-1.99 (m, 1H), 1.94 (d, J=13.2 Hz, 1H), 1.83-1.75 (s, 2H), 1.65-1.62 (m, 2H) 1.34-1.28 (m, 2H), 0.81 (t, J=7.5 Hz, 3H), 0.77 (t, J=7.5 Hz, 3H); IR (film) $v_{max}$ 3587, 2926, 1740, 1616, 1502, 1458, 1228, 1034, 736 cm$^{-1}$; HRESI-TOF m/z 906.4246 (C$_{48}$H$_{58}$F$_3$N$_5$O$_9$+H$^+$, required 906.4259). $[\alpha]_D^{23}$+3 (c 0.15, CHCl$_3$).

Compound 12

Method 1 was followed using 2.0 mg of 20'-aminovinblastine (6, 0.02 mmol) to provide 1.4 mg of Compound 12 as a white solid, yield: 67%. $^1$H NMR (600 MHz, CDCl$_3$) δ 9.92 (br s, 1H), 8.01 (br s, 1H), 7.50 (d, J=7.8 Hz, 1H), 7.16-7.14 (m, 1H), 7.12-7.09 (m, 2H), 6.62 (s, 1H), 6.09 (s, 1H), 5.85 (dd, J=10.1, 3.9 Hz, 1H), 5.46 (s, 1H), 5.40 (s, 1H), 5.31-5.29 (m, 1H), 4.13-4.04 (m, 1H), 3.79 (s, 3H), 3.79 (s, 3H), 3.73 (s, 1H), 3.58 (s, 3H), 3.38-3.34 (m, 2H), 3.31-3.27 (m, 1H), 3.25-3.22 (m, 1H), 3.19-3.18 (m, 1H), 3.10-3.07 (m, 1H), 2.82 (d, J=16.1 Hz, 1H), 2.70 (s, 3H), 2.58 (d, J=13.5 Hz, 1H), 2.46-2.42 (m, 1H), 2.39-2.37 (m, 1H), 2.32 (d, J=13.2 Hz, 1H), 2.20-2.15 (m, 1H), 2.11 (s, 3H), 2.08-2.06 (m, 1H), 1.81-1.76 (m, 2H), 1.64-1.60 (m, 7H), 1.27 (t, J=7.6 Hz, 3H), 1.25-1.24 (m, 3H), 0.81 (t, J=7.3 Hz, 3H), 0.72 (t, J=7.4 Hz, 3H); ESI-MS m/z 866.3 ($C_{49}H_{63}N_5O_9$+H$^+$, required 866.47).

Compound 1

Method 2 was followed providing Compound 13 in 39% yield. $^1$H NMR (600 MHz, CDCl$_3$) δ 9.80 (s, 1H), 8.03 (s, 1H), 7.50 (d, J=7.8 Hz, 1H), 7.19-7.07 (m, 3H), 6.63 (s, 1H), 6.10 (s, 1H), 5.85 (dd, J=9.9, 4.1 Hz, 1H), 5.48 (s, 1H), 5.40 (s, 1H), 5.30 (d, J=10.2 Hz, 1H), 3.84-3.76 (m, 7H), 3.74 (s, 1H), 3.62 (d, J=6.0 Hz, 1H), 3.59 (s, 3H), 3.43-3.34 (m, 2H), 3.34-3.16 (m, 4H), 3.09 (d, J=6.1 Hz, 1H), 2.81 (d, J=16.0 Hz, 1H), 2.71 (s, 3H), 2.59 (d, J=13.9 Hz, 1H), 2.53-2.40 (m, 2H), 2.32 (d, J=14.7 Hz, 1H), 2.24-2.15 (m, 2H), 2.11 (s, 3H), 1.88 (d, J=14.4 Hz, 1H), 1.85-1.76 (m, 2H), 1.69-1.60 (m, 2H), 1.37-1.28 (m, 7H), 1.24-1.16 (m, 2H), 0.82 (t, J=7.4 Hz, 3H), 0.79-0.75 (m, 1H), 0.72 (t, J=7.4 Hz, 3H); HRESI-TOF m/z 880.4856 ($C_{50}H_{65}N_5O_9$+H$^+$, required 880.4855). [α]$_D^{23}$+0.02 (c 0.3, CHCl$_3$).

Compound 14

Method 1 was followed using 4.8 mg of 20'-aminovinblastine (6, 0.06 mmol) to provide Compound 14 as a white solid, yield: 470. $^1$H NMR (600 MHz, CDCl$_3$) δ 8.03 (s, 1H), 7.49 (d, J=7.8 Hz, 1H), 7.15-7.13 (m, 1H), 7.11-7.08 (m, 2H), 6.61 (s, 1H), 6.09 (s, 1H), 5.84 (dd, J=10.2, 3.9 Hz, 1H), 5.64 (s, 1H), 5.47 (s, 1H), 5.29 (d, J=10.2 Hz, 1H), 3.79 (s, 3H), 3.78 (s, 3H), 3.76-3.73 (m, 2H), 3.58 (s, 3H), 3.37 (dd, J=15.7, 4.6 Hz, 2H), 3.29 (td, J=9.5, 4.6 Hz, 1H), 3.25-3.23 (d, J=12.2 Hz, 1H), 3.21-3.16 (m, 2H), 3.07-3.05 (m, 1H), 2.81 (d, J=16.1 Hz, 1H), 2.70 (s, 3H), 2.65 (s, 1H), 2.58 (d, J=13.6 Hz, 1H), 2.43 (td, J=10.4, 6.7 Hz, 1H), 2.31-2.29 (m, 1H), 2.19-2.16 (m, 2H), 2.10 (s, 3H), 1.86 (d, J=14.5 Hz, 1H), 1.82-1.77 (m, 2H), 1.67-1.57 (m, 3H), 1.34 (s, 9H), 1.22-1.20 (m, 2H), 1.18 (d, J=5.5 Hz, 1H), 0.80 (t, J=7.4 Hz, 3H), 0.69 (t, J=7.4 Hz, 3H); ESI-MS m/z 894.5 ($C_{48}H_{61}N_5O_9$+H$^+$, required 894.50).

Compound 15

Method 1 was followed providing Compound 15 in 60% yield. $^1$H NMR (600 MHz, CDCl$_3$) δ 9.76 (br s, 1H), 8.04 (s, 1H), 7.53 (d, J=7.9 Hz, 1H), 7.44 (d, J=7.4 Hz, 1H), 7.26-7.23 (m, 1H), 7.19-7.15 (m, 3H), 6.66-6.64 (m, 1H), 6.43 (s, 1H), 6.12 (s, 1H), 5.92-5.90 (m, 1H), 5.51-5.49 (m, 1H), 5.45 (s, 1H), 5.40 (s, 1H), 5.37-5.31 (m, 2H), 3.87-3.73 (m, 8H), 3.69-3.65 (m, 2H), 3.47-3.36 (m, 3H), 3.36-3.28 (m, 2H), 3.25-3.19 (m, 1H), 3.11-3.04 (m, 2H), 3.00-2.83 (m, 5H), 2.76 (s, 3H), 2.68 (s, 1H), 2.56-2.54 (m, 1H), 2.39-2.32 (m, 2H), 2.31-2.25 (m, 3H), 2.16-2.08 (m, 2H), 2.07-2.04 (m, 1H), 1.76-1.69 (m, 3H), 1.29-1.27 (m, 2H), 1.19-1.13 (m, 1H), 0.98-0.86 (m, 8H), 0.85-0.82 (m, 2H); HRESI-TOF m/z 908.5169 ($C_{52}H_{69}N_5O_9$+H$^+$, required 908.5168). [α]$_D^{23}$+12 (c 0.16, CHCl$_3$).

Compound 16

Method 1 was followed providing Compound 16 in 53% yield. $^1$H NMR (600 MHz, CDCl$_3$) δ 9.80 (s, 1H), 8.04 (s, 1H), 7.53 (d, J=7.9 Hz, 1H), 7.21-7.14 (m, 2H), 7.14-7.10 (m, 1H), 6.65 (s, 1H), 6.12 (s, 1H), 5.88 (dd, J=10.3, 5.0 Hz, 1H), 3.86-3.74 (m, 8H), 3.64-3.61 (m, 3H), 3.44-3.31 (m, 4H), 3.31-3.18 (m, 4H), 3.14-3.09 (m, 2H), 2.85-2.83 (m, 2H), 2.73 (s, 3H), 2.69 (s, 1H), 2.61 (d, J=13.5 Hz, 2H), 2.47 (td, J=10.4, 6.6 Hz, 2H), 2.43-2.30 (m, 4H), 2.25-2.17 (m, 3H), 2.13 (s, 3H), 1.93-1.83 (m, 3H), 1.83-1.77 (m, 2H), 1.77-1.72 (m, 2H), 1.47-1.20 (m, 6H), 0.90 (dt, J=8.9, 6.8 Hz, 4H), 0.84 (t, J=7.4 3H), 0.76 (t, J=7.4 Hz, 3H); HRESI-TOF m/z 936.5480 ($C_{54}H_{73}N_5O_9$+H$^+$, required 936.5481). [α]$_D^{23}$+7 (c 0.11, CHCl$_3$).

Compound 17

Method 1 was followed using 4.4 mg of 20'-aminovinblastine (6, 0.05 mmol) to provide Compound 17 as a white solid, yield: 44%. $^1$H NMR (600 MHz, CDCl$_3$) δ 8.02 (s, 1H), 7.51 (d, J=7.8 Hz, 1H), 7.15 (t, J=7.2 Hz, 1H), 7.11-7.08 (m, 2H), 6.63 (s, 1H), 6.09 (s, 1H), 5.85 (dd, J=10.1, 4.1 Hz, 1H), 5.56 (s, 1H), 5.46 (s, 1H), 5.30 (s, 1H), 3.84 (t, J=14.0 Hz, 1H), 3.79 (s, 3H), 3.79 (s, 3H), 3.73 (s, 1H), 3.60 (s, 3H), 3.39-3.35 (m, 2H), 3.31-3.27 (m, 2H), 3.19-3.15 (m, 1H), 3.10-3.07 (m, 1H), 2.81 (d, J=16.1 Hz, 1H), 2.70 (s, 3H), 2.66 (s, 1H), 2.56 (d, J=13.7 Hz, 1H), 2.45-2.42 (m, 1H), 2.35 (d, J=13.2 Hz, 1H), 2.25-2.17 (m, 1H), 2.10 (s, 3H), 1.83-1.77 (m, 4H), 1.69-1.67 (m, 2H), 1.53-1.51 (m, 2H), 1.35-1.31 (m, 2H), 1.26-1.20 (m, 2H), 0.99-0.98 (m, 2H), 0.81 (t, J=7.4 Hz, 3H), 0.75 (t, J=7.3 Hz, 5H); ESI-MS m/z 878.5 ($C_{50}H_{63}N_5O_9$+H$^+$, required 878.47).

Compound 18

Method 1 was followed using 4.7 mg of 20'-aminovinblastine (6, 0.06 mmol) to provide Compound 18 as a white solid, yield: 51%. $^1$H NMR (600 MHz, CDCl$_3$) δ 9.90 (s, 1H), 8.02 (s, 1H), 7.49 (d, J=7.8 Hz, 1H), 7.16-7.13 (m, 1H), 7.11-7.08 (m, 2H), 6.61 (s, 1H), 6.09 (s, 1H), 5.84 (dd, J=10.2, 3.8 Hz, 1H), 5.46 (s, 1H), 5.29-5.28 (m, 2H), 3.79 (s, 6H), 3.74-3.70 (m, 2H), 3.59 (s, 3H), 3.38-3.35 (m, 2H), 3.30-3.27 (m, 1H), 3.19-3.14 (m, 2H), 3.09-3.07 (m, 1H), 2.81 (d, J=16.1 Hz, 1H), 2.70 (s, 3H), 2.65 (s, 1H), 2.58 (d, J=13.6 Hz, 1H), 2.43-2.38 (m, 2H), 2.32 (d, J=13.1 Hz, 1H), 2.27-2.24 (m, 2H), 2.19-2.16 (m, 2H), 2.10 (s, 3H), 2.03 (s, 1H), 2.00-1.97 (m, 1H), 1.88-1.84 (m, 2H), 1.82-1.75 (m, 3H), 1.69-1.65 (m, 3H), 1.56-1.53 (m, 2H), 1.33 (dd, J=14.4, 7.3 Hz, 1H), 1.26-1.23 (m, 2H), 1.19 (dd, J=14.5, 5.7 Hz, 1H), 0.80 (t, J=7.4 Hz, 3H), 0.71 (t, J=7.4 Hz, 3H); ESI-MS m/z 892.5 ($C_{51}H_{65}N_5O_9$+H$^+$, required 892.49).

Compound 19

Method 1 was followed using 5.1 mg of 20'-aminovinblastine (6, 0.06 mmol) to provide Compound 19 as a white solid, yield: 47%. $^1$H NMR (600 MHz, CDCl$_3$) δ 9.81 (br s, 1H), 8.02 (s, 1H), 7.50 (d, J=7.8 Hz, 1H), 7.16-7.13 (m, 1H), 7.11-7.08 (m, 2H), 6.61 (s, 1H), 6.09 (s, 1H), 5.84 (dd, J=10.2, 3.8 Hz, 1H), 5.46 (s, 1H), 5.41 (s, 1H), 5.29 (d, J=10.2 Hz, 1H), 3.79 (s, 6H), 3.73 (s, 1H), 3.67-3.65 (m, 1H), 3.59 (s, 3H), 3.36 (dd, J=15.8, 3.6 Hz, 2H), 3.29 (td, J=9.5, 4.7 Hz, 1H), 3.25-3.21 (m, 2H), 3.19-3.17 (m, 1H), 2.81 (d, J=16.1 Hz, 1H), 2.70 (s, 3H), 2.67-2.64 (d, J=6.6 Hz, 1H), 2.57 (d, J=13.7 Hz, 1H), 2.43 (td, J=10.4, 6.6 Hz, 1H), 2.32 (d, J=13.3 Hz, 1H), 2.22-2.16 (m, 2H), 2.08 (s, 3H), 2.01-1.99 (m, 2H), 1.90-1.73 (m, 7H), 1.68-1.65 (m, 3H), 1.63-1.58 (m, 3H), 1.54-1.51 (m, 1H), 1.26-1.24 (m, 2H), 1.20 (dd, J=14.5, 5.5 Hz, 1H), 0.80 (t, J=7.4 Hz, 3H), 0.72 (t, J=7.4 Hz, 3H); ESI-MS m/z 906.5 ($C_{52}H_{67}N_5O_9$+H$^+$, required 906.50).

Compound 20

Method 1 was followed using 5.2 mg of 20'-aminovinblastine (6, 0.06 mmol) to provide Compound 20 as a white solid, yield: 52%. $^1$H NMR (600 MHz, CDCl$_3$) δ 9.88 (s, 1H), 8.05 (s, 1H), 7.50 (d, J=7.8 Hz, 1H), 7.15-7.13 (m, 1H), 7.01-7.08 (m, 2H), 6.60 (s, 1H), 6.09 (s, 1H), 5.83 (dd, J=10.2, 4.5 Hz, 1H), 5.46 (s, 1H), 5.37 (s, 1H), 5.27 (s, 1H), 3.78 (s, 6H), 3.72 (s, 2H), 3.59 (s, 3H), 3.38-3.34 (m, 2H), 3.28 (td, J=9.5, 4.6 Hz, 1H), 3.24-3.19 (m, 2H), 3.09-3.07 (m, 1H), 2.81 (d, J=16.1 Hz, 1H), 2.69 (s, 3H), 2.64 (s, 1H), 2.57 (d, J=13.6 Hz, 1H), 2.43 (td, J=10.3, 6.8 Hz, 1H), 2.32 (d, J=13.2 Hz, 1H), 2.22-2.16 (m, 3H), 2.09 (s, 3H), 2.06-

2.03 (m, 2H), 1.83-1.78 (m, 6H), 1.69 (d, J=12.3 Hz, 2H), 1.65-1.62 (m, 2H), 1.55-1.50 (m, 3H), 1.26-1.23 (m, 3H), 1.19 (dd, J=14.5, 5.7 Hz, 2H), 0.79 (t, J=7.3 Hz, 3H), 0.70 (t, J=7.4 Hz, 3H); HRESI-TOF m/z 920.5168 ($C_{53}H_{69}N_5O_9$+H$^+$, required 920.5168). [α]$_D^{23}$+27 (c 0.87, CHCl$_3$).

Compound 21

Method 1 was followed using 5.3 mg of 20'-aminovinblastine (6, 0.06 mmol) to provide Compound 21 as a white solid, yield: 61%. $^1$H NMR (600 MHz, CDCl$_3$) δ 8.03 (s, 1H), 7.48-7.45 (m, 3H), 7.36 (t, J=7.5 Hz, 2H), 7.30-7.27 (m, 2H), 7.16-7.14 (m, 1H), 7.10-7.08 (m, 2H), 6.56 (s, 1H), 6.08 (s, 1H), 5.84 (dd, J=10.2, 4.0 Hz, 1H), 5.47 (s, 1H), 5.29-5.28 (m, 2H), 3.80 (s, 3H), 3.79 (s, 3H), 3.72-3.71 (m, 2H), 3.64 (s, 3H), 3.38-3.33 (m, 2H), 3.31-3.27 (m, 2H), 3.09 (t, J=12.2 Hz, 1H), 3.03 (d, J=13.4 Hz, 1H), 2.87 (dd, J=14.7, 4.5 Hz, 1H), 2.82-2.77 (t, J=13.1 Hz, 2H), 2.69 (s, 3H), 2.63 (s, 1H), 2.51 (d, J=13.4 Hz, 1H), 2.40 (dd, J=17.1, 10.4 Hz, 1H), 2.20-2.14 (m, 3H), 2.10 (s, 3H), 1.90 (t, J=7.0 Hz, 2H), 1.81-1.74 (m, 3H), 1.35-1.28 (m, 3H), 1.26-1.24 (m, 1H), 1.09 (dd, J=14.4, 5.6 Hz, 1H), 0.81 (t, J=7.4 Hz, 3H), 0.63 (t, J=7.4 Hz, 3H); ESI-MS m/z 928.5 ($C_{54}H_{65}N_5O_9$+H$^+$, required 928.49).

Compound 22

Method 1 was followed using 4.0 mg of 20'-aminovinblastine (6, 0.06 mmol) to provide 3.05 mg of Compound 22 as a white solid, yield: 62%. $^1$H NMR (CDCl$_3$, 600 MHz) δ 9.79 (s, 1H), 8.02 (s, 1H), 7.53 (d, J=7.2 Hz, 2H), 7.46 (d, J=7.8 Hz, 4H), 7.33 (t, J=7.5 Hz, 4H), 7.17-7.10 (m, 3H), 6.60 (s, 1H), 6.10 (s, 1H), 5.85 (dd, J=4.8, 10.2 Hz, 1H), 5.58 (s, 1H), 5.49 (s, 1H), 5.30 (d, J=10.2 Hz, 1H), 5.09 (s, 1H), 3.83-3.73 (m, 8H), 3.64 (s, 3H), 3.39-3.34 (m, 2H), 3.31-3.27 (m, 1H), 3.20 (d, J=13.2 Hz, 1H), 3.09-3.05 (m, 1H), 2.81-2.68 (m, 4H), 2.64-2.54 (m, 5H), 2.44-2.39 (m, 1H), 2.22-2.17 (m, 2H), 2.11 (s, 3H), 2.00 (d, J=14.4 Hz, 1H), 1.89-1.78 (m, 3H), 1.52-1.49 (m, 2H), 1.37-1.34 (m, 2H), 1.16-1.13 (m, 2H), 0.84-0.81 (m, 3H), 0.72-0.70 (m, 3H); IR (film) ν$_{max}$ 3467, 2926, 1739, 1671, 1500, 1228, 745 cm$^{-1}$; HRESI-TOF m/z 1004.5178 ($C_{60}H_{69}N_5O_9$+H$^+$, required 1004.5168). [α]$_D^{23}$+6 (c 0.15, CHCl$_3$).

Compound 23

Method 1 was followed using 6.3 mg of 20'-aminovinblastine (6, 0.08 mmol) to provide 4.8 mg of Compound 23 as a white solid, yield: 72%. $^1$H NMR (600 MHz, CDCl$_3$) δ 8.00 (s, 1H), 7.48 (d, J=7.6 Hz, 1H), 7.16-7.13 (m, 3H), 7.11-7.08 (m, 1H), 6.62 (s, 1H), 6.34-6.32 (m, 1H), 6.27 (d, J=10.1 Hz, 1H), 6.09 (s, 1H), 5.85-5.83 (m, 1H), 5.68 (d, J=9.9 Hz, 1H), 5.56 (s, 1H), 5.46 (s, 1H), 5.29 (s, 3H), 3.79 (s, 6H), 3.74 (s, 2H), 3.59 (s, 3H), 3.38-3.36 (m, 2H), 3.29-3.21 (m, 2H), 3.16-3.09 (m, 2H), 2.81 (d, J=15.7 Hz, 1H), 2.70 (s, 3H), 2.66 (s, 1H), 2.45-2.38 (m, 3H), 2.25-2.15 (m, 2H), 2.10 (s, 3H), 1.80-1.78 (m, 4H), 1.50-1.48 (m, 1H), 1.34-1.24 (m, 5H), 0.81 (t, J=6.6 Hz, 3H), 0.76-0.74 (m, 3H); ESI-MS m/z 864.3 ($C_{49}H_{61}N_5O_9$+H$^+$, required 864.45).

Compound 24

Method 1 was followed using 2.0 mg of 20'-aminovinblastine (6, 0.02 mmol) to provide Compound 24 as a white solid, yield: 43%. $^1$H NMR (600 MHz, CDCl$_3$) δ 9.98 (s, 1H), 8.03 (s, 3H), 7.49-7.48 (m, 3H), 7.45 (d, J=7.9 Hz, 1H), 7.13 (d, J=7.3 Hz, 1H), 7.10-7.07 (m, 2H), 6.64 (s, 1H), 6.11-6.10 (m, 2H), 5.85 (dd, J=10.0, 4.3 Hz, 1H), 5.47 (s, 1H), 5.30-5.28 (m, 1H), 3.98 (br s, 1H), 3.80 (s, 3H), 3.79 (s, 3H), 3.74 (s, 3H), 3.58 (s, 3H), 3.40-3.38 (m, 2H), 3.31 (dt, J=9.5, 4.8 Hz, 1H), 3.20-3.19 (m, 1H), 3.11-3.10 (m, 2H), 2.83 (d, J=16.0 Hz, 1H), 2.71 (s, 3H), 2.67-2.66 (m, 1H), 2.47-2.46 (m, 1H), 2.41 (d, J=13.5 Hz, 1H), 2.34 (d, J=13.4 Hz, 1H), 2.20-2.17 (m, 1H), 2.11 (s, 3H), 1.81-1.76 (m, 2H), 1.61-1.58 (m, 3H), 1.34-1.31 (m, 2H), 1.25-1.24 (m, 4H), 0.81 (t, J=7.3 Hz, 3H), 0.76 (t, J=7.4 Hz, 3H); ESI-MS m/z 914.5 ($C_{53}H_{63}N_5O_9$+H$^+$, required 914.47).

Compound 25

Method 1 was followed using 5.5 mg of 20'-aminovinblastine (6, 6.8 μmol) to provide 4.4 mg of Compound 25 as a pale yellow resin, yield: 70%. $^1$H NMR (CDCl$_3$, 600 MHz) δ 9.86 (br s, 1H), 8.03 (s, 1H), 7.82-7.76 (m, 2H), 7.44 (d, J=8.4 Hz, 1H), 7.29 (d, J=8.4 Hz, 1H), 7.15-7.06 (m, 3H), 6.64 (s, 1H), 6.12 (s, 1H), 6.08 (s, 1H), 5.85 (dd, J=4.5, 10.5 Hz, 1H), 5.48 (s, 1H), 5.31-5.29 (m, 1H), 3.99 (br s, 1H), 3.81 (s, 3H), 3.80 (s, 3H), 3.75 (s, 1H), 3.60 (s, 3H), 3.41-3.36 (m, 2H), 3.30 (td, J=4.6, 10.5 Hz, 1H), 3.25-3.06 (m, 4H), 2.83 (d, J=16.2 Hz, 1H), 2.72-2.66 (m, 4H), 2.48-2.34 (m, 5H), 2.22-2.17 (m, 1H), 2.11 (s, 3H), 1.99 (br s, 1H), 1.85-1.77 (m, 3H), 1.67 (br s, 3H), 1.36-1.32 (m, 2H), 1.27-1.25 (m, 2H), 0.82 (t, J=7.2 Hz, 3H), 0.77 (t, J=7.5 Hz, 3H); IR (film) ν$_{max}$ 3460, 2930, 1739, 1496, 1228, 1040 cm$^{-1}$; HRESI-TOF m/z 928.4838 ($C_{54}H_{65}N_5O_9$+H$^+$, required 928.4855).

Compound 26

Method 2 was followed providing Compound 26 in 23% yield. $^1$H NMR (500 MHz, CDCl$_3$) δ 8.03 (s, 1H), 7.91-7.76 (m, 2H), 7.46 (d, J=8.2 Hz, 1H), 7.37 (t, J=7.6 Hz, 1H), 7.31 (d, J=7.2 Hz, 1H), 7.18-7.04 (m, 3H), 6.65 (s, 1H), 6.12 (s, 1H), 6.09 (s, 1H), 5.85 (dd, J=10.2, 3.7 Hz, 1H), 5.48 (s, 1H), 5.30 (d, J=10.9 Hz, 1H), 4.04-3.84 (m, 2H), 3.84-3.79 (m, 6H), 3.75 (s, 1H), 3.57 (s, 3H), 3.45-3.34 (m, 2H), 3.34-3.18 (m, 3H), 3.17-3.02 (m, 3H), 2.82 (d, J=16.3 Hz, 1H), 2.72 (s, 3H), 2.67 (s, 1H), 2.49-2.40 (m, 5H), 2.35 (d, J=13.9 Hz, 1H), 2.25-2.15 (m, 1H), 2.11 (s, 3H), 1.87-1.77 (m, 3H), 1.40-1.31 (m, 4H), 0.84-0.74 (m, 7H); HRESI-TOF m/z 928.4856 ($C_{54}H_{65}N_5O_9$+H$^+$, required 928.4855). [α]$_D^{23}$−10 (c 0.2, CHCl$_3$).

Compound 27

Method 2 was followed providing Compound 27 in 31% yield. $^1$H NMR (600 MHz, CDCl$_3$) δ 9.82 (s, 1H), 8.08 (s, 1H), 7.88 (s, 1H), 7.50 (d, J=7.9 Hz, 1H), 7.35-7.25 (m, 2H), 7.21-7.06 (m, 3H), 6.64 (s, 1H), 6.11 (s, 1H), 5.88-5.83 (m, 1H), 5.72 (s, 1H), 5.49 (s, 1H), 5.30 (d, J=10.2 Hz, 1H), 3.95 (t, J=13.6 Hz, 1H), 3.80 (s, 3H), 3.77 (s, 3H), 3.74 (s, 1H), 3.65-3.59 (m, 3H), 3.59 (s, 3H), 3.46-3.34 (m, 2H), 3.30 (dt, J=9.5, 4.5 Hz, 1H), 3.28-3.21 (m, 2H), 3.21-3.15 (m, 1H), 3.13-3.05 (m, 1H), 2.82 (d, J=16.2 Hz, 1H), 2.71 (s, 3H), 2.70-2.66 (m, 2H), 2.54 (s, 3H), 2.52-2.38 (m, 1H), 2.35-2.30 (m, 2H), 2.27-2.15 (m, 1H), 2.11 (s, 3H), 2.10-1.97 (m, 1H), 1.92-1.76 (m, 2H), 1.73-1.45 (m, 1H), 1.39-1.23 (m, 3H), 0.88-0.78 (m, 8H); HRESI-TOF m/z 928.4855 ($C_{54}H_{65}N_5O_9$+H$^+$, required 928.4855). [α]$_D^{23}$−22 (c 0.07, CHCl$_3$).

Compound 28

Method 1 was followed using 8.0 mg of 20'-aminovinblastine (6, 0.01 mmol) to provide 4.7 mg of Compound 28 as a white solid, yield: 50%. $^1$H NMR (600 MHz, CDCl$_3$) δ 9.83 (br s, 2H), 8.02 (s, 1H), 7.82-7.76 (m, 2H), 7.44 (d, J=7.2 Hz, 1H), 7.24 (d, J=7.7 Hz, 1H), 7.14-7.07 (m, 2H), 6.64 (s, 1H), 6.12 (s, 1H), 6.08 (s, 1H), 5.85 (d, J=5.7 Hz, 1H), 5.48 (s, 1H), 5.30 (d, J=10.3 Hz, 1H), 4.00 (br s, 1H), 3.81 (s, 3H), 3.80 (s, 3H), 3.75 (s, 1H), 3.58 (s, 3H), 3.42-3.36 (m, 2H), 3.30 (td, J=9.5, 4.8 Hz, 1H), 3.22 (t, J=8.7 Hz, 1H), 3.10 (dd, J=14.6, 7.2 Hz, 2H), 2.83 (d, J=16.2 Hz, 1H), 2.72 (s, 3H), 2.67 (s, 1H), 2.45-2.41 (m, 1H), 2.35 (s, 3H), 2.30 (s, 3H), 2.11 (s, 3H), 2.02-1.98 (m, 1H), 1.85-1.78 (m, 2H), 1.62-1.59 (m, 4H), 1.42 (t, J=7.4 Hz, 1H), 1.37-1.31 (m, 2H), 1.26-1.23 (m, 3H), 0.82 (t, J=7.0 Hz, 3H), 0.77 (t, J=6.2 Hz, 3H); HRESI-TOF m/z 942.5012 ($C_{55}H_{67}N_5O_9$+H$^+$, required 942.5011). $[\alpha]_D^{23}$ −39 (c 0.27, CHCl$_3$).

Compound 29

Method 1 was followed providing Compound 29 in 61% yield. $^1$H NMR (600 MHz, CDCl$_3$) δ 9.83 (s, 1H), 8.02 (s, 1H), 7.64 (s, 2H), 7.47 (d, J=8.0 Hz, 1H), 7.17-7.06 (m, 4H), 6.64 (s, 1H), 6.11 (s, 1H), 6.08 (s, 1H), 5.88-5.82 (m, 1H), 5.48 (s, 1H), 5.30 (d, J=10.2 Hz, 1H), 4.05-3.95 (s, 2H), 3.81 (s, 3H), 3.80 (s, 3H), 3.75 (s, 1H), 3.54 (s, 3H), 3.45-3.35 (m, 2H), 3.35-3.27 (m, 1H), 3.26-3.22 (m, 2H), 3.16-3.06 (m, 1H), 2.83 (d, J=16.1 Hz, 1H), 2.72 (s, 3H), 2.71-2.65 (m, 2H), 2.50-2.42 (m, 2H), 2.40 (s, 6H), 2.34 (d, J=13.4 Hz, 1H), 2.23-2.16 (m, 2H), 2.11 (s, 3H), 1.87-1.76 (m, 2H), 1.39-1.30 (m, 1H), 1.26-1.24 (m, 2H), 0.94-0.86 (m, 4H), 0.82 (t, J=7.4 Hz, 3H), 0.76 (t, J=7.4 Hz, 3H); HRESI-TOF m/z 942.5012 ($C_{55}H_{67}N_5O_9$+H$^+$, required 942.5011). $[\alpha]_D^{23}$ −38 (c 0.09, CHCl$_3$).

Compound 30

Method 1 was followed providing Compound 30 in 52% yield. $^1$H NMR (500 MHz, D$_2$O) δ 9.83 (s, 1H), 8.03 (s, 1H), 7.96 (d, J=7.8 Hz, 2H), 7.45 (d, J=7.9 Hz, 1H), 7.31 (d, J=8.0 Hz, 2H), 7.16-7.04 (m, 3H), 6.65 (s, 1H), 6.12 (s, 1H), 6.08 (s, 1H), 5.91-5.78 (m, 1H), 5.48 (s, 1H), 5.30 (d, J=10.2 Hz, 1H), 4.06-3.90 (m, 2H), 3.81 (s, 3H), 3.80 (s, 3H), 3.75 (s, 1H), 3.60 (s, 3H), 3.44-3.34 (m, 2H), 3.31 (td, J=9.4, 4.4 Hz, 1H), 3.20 (q, J=11.2 Hz, 2H), 3.16-3.06 (m, 2H), 2.85-2.80 (m, 1H), 2.72 (s, 3H), 2.71-2.68 (m, 2H), 2.67 (s, 2H), 2.50-2.39 (m, 2H), 2.36 (d, J=14.0 Hz, 1H), 2.25-2.15 (m, 1H), 2.11 (s, 3H), 1.89-1.75 (m, 3H), 1.34 (dd, J=13.8, 6.4 Hz, 3H), 1.27-1.23 (m, 4H), 1.12 (d, J=6.7 Hz, 2H), 0.84-0.79 (m, 4H), 0.77 (t, J=7.4 Hz, 3H); HRESI-TOF m/z 942.5011 ($C_{55}H_{67}N_5O_9$+H$^+$, required 942.5011). $[\alpha]_D^{23}$ −0.06 (c 0.4, CHCl$_3$).

Compound 31

Method 2 was followed providing Compound 31 in 46% yield. $^1$H NMR (600 MHz, CDCl$_3$) δ 9.83 (s, 1H), 8.02 (s, 1H), 7.67 (s, 2H), 7.48 (d, J=7.9 Hz, 1H), 7.18 (s, 1H), 7.16-7.06 (m, 2H), 6.65 (s, 1H), 6.11 (s, 1H), 6.10 (s, 1H), 5.85 (dd, J=10.5, 4.4 Hz, 1H), 5.49 (s, 1H), 5.30 (d, J=10.5 Hz, 1H), 4.05-3.95 (m, 2H), 3.80 (s, 3H), 3.79 (s, 3H), 3.75 (s, 1H), 3.50 (s, 3H), 3.46-3.22 (m, 6H), 3.14-3.10 (m, 2H), 2.82 (d, J=16.1 Hz, 1H), 2.77-2.65 (m, 4H), 2.49-2.42 (m, 1H), 2.40 (d, J=13.2 Hz, 1H), 2.31 (d, J=14.4 Hz, 1H), 2.25-2.16 (m, 1H), 2.11 (s, 3H), 1.87-1.76 (m, 2H), 1.63-1.53 (m, 6H), 1.39-1.30 (m, 2H), 1.28-1.23 (m, 7H), 0.91-0.80 (m, 4H), 0.77 (t, J=7.5 Hz, 3H); HRESI-TOF m/z 970.5332 ($C_{57}H_{71}N_5O_9$+H$^+$, required 970.5324). $[\alpha]_D^{23}$ −29 (c 0.07, CHCl$_3$).

Compound 32

Method 2 was followed providing Compound 32 in 53% yield. $^1$H NMR (600 MHz, CDCl$_3$) δ 9.87 (br s, 1H), 8.06 (s, 1H), 7.90-7.86 (m, 2H), 7.43 (d, J=8.4 Hz, 1H), 7.39 (d, J=8.4 Hz, 1H), 7.17-7.09 (m, 3H), 6.67 (s, 1H), 6.14 (s, 1H), 6.10 (s, 1H), 5.85 (dd, J=4.5, 10.5 Hz, 1H), 5.51 (s, 1H), 5.33-5.31 (m, 2H), 3.84 (br s, 1H), 3.81 (s, 3H), 3.77 (s, 3H), 3.75 (s, 1H), 3.58 (s, 3H), 3.38-3.35 (m, 2H), 3.30 (td, J=4.6, 10.5 Hz, 1H), 3.25-3.06 (m, 4H), 2.83 (d, J=16.2 Hz, 1H), 2.72-2.66 (m, 4H), 2.48-2.34 (m, 5H), 2.22-2.17 (m, 1H), 2.11 (s, 3H), 1.99 (br s, 1H), 1.85-1.77 (m, 3H), 1.67 (br s, 3H), 1.36-1.28 (m, 6H), 1.27-1.25 (m, 2H), 0.82 (t, J=7.2 Hz, 3H), 0.77 (t, J=7.5 Hz, 3H); HRESI-TOF m/z 956.5168 ($C_{56}H_{65}N_5O_9$+H$^+$, required 956.5168). $[\alpha]_D^{23}$ −2 (c 0.15, CHCl$_3$).

Compound 33

Method 2 was followed providing Compound 33 in 49% yield. $^1$H NMR (600 MHz, CDCl$_3$) δ 9.84 (s, 1H), 8.03 (s, 1H), 7.87 (s, 1H), 7.84 (s, 1H), 7.47 (d, J=8.0 Hz, 1H), 7.43-7.36 (m, 2H), 7.18-7.07 (m, 2H), 6.65 (s, 1H), 6.11 (s, 1H), 6.10 (s, 1H), 5.85 (dd, J=10.4, 4.3 Hz, 1H), 5.48 (s, 1H), 5.36-5.33 (m, 1H), 5.30 (d, J=10.3 Hz, 1H), 4.05-3.95 (m, 1H), 3.81 (s, 3H), 3.80 (s, 3H), 3.75 (s, 1H), 3.55 (s, 3H), 3.45-3.27 (m, 3H), 3.27-3.23 (m, 2H), 3.15-3.10 (m, 2H), 3.05-2.98 (m, 1H), 2.82 (d, J=16.1 Hz, 1H), 2.75-2.63 (m, 5H), 2.50-2.37 (m, 2H), 2.33 (d, J=13.1 Hz, 1H), 2.26-2.15 (m, 1H), 2.13-2.05 (m, 5H), 2.02-1.97 (m, 1H), 1.97-1.75 (m, 3H), 1.37-1.18 (m, 4H), 0.88 (t, J=6.9 Hz, 3H), 0.85-0.80 (m, 5H), 0.78 (t, J=7.5 Hz, 3H); HRESI-TOF m/z 956.5165 ($C_{56}H_{69}N_5O_9$+H$^+$, required 956.5168). $[\alpha]_D^{23}$ −16 (c 0.05, CHCl$_3$).

Compound 34

Method 1 was followed providing Compound 34 in 61% yield. $^1$H NMR (600 MHz, CDCl$_3$) δ 9.85 (s, 1H), 8.03 (s, 1H), 7.95 (d, J=7.7 Hz, 2H), 7.45 (d, J=7.9 Hz, 1H), 7.29 (d, J=7.9 Hz, 2H), 7.17-7.04 (m, 3H), 6.65 (s, 1H), 6.12 (s, 1H), 6.07 (s, 1H), 5.87-5.83 (m, 1H), 5.48 (s, 1H), 5.30 (d, J=10.2 Hz, 1H), 4.05-3.95 (m, 2H), 3.81 (s, 3H), 3.80 (s, 3H), 3.75 (s, 1H), 3.60 (s, 3H), 3.42-3.34 (m, 2H), 3.31 (td, J=9.5, 4.6 Hz, 1H), 3.27-3.16 (m, 2H), 3.15-3.05 (m, 2H), 2.83 (d, J=16.1 Hz, 1H), 2.72 (s, 3H), 2.69-2.60 (m, 4H), 2.50-2.39 (m, 3H), 2.36 (d, J=13.6 Hz, 1H), 2.26-2.16 (m, 2H), 2.11 (s, 3H), 1.87-1.75 (m, 2H), 1.65 (d, J=7.5 Hz, 2H), 1.37-1.30 (m, 1H), 1.27-1.23 (m, 3H), 0.93 (t, J=7.3 Hz, 3H), 0.82 (t, J=7.4 Hz, 3H), 0.77 (t, J=7.4, 3H); HRESI-TOF m/z 956.5191 ($C_{56}H_{69}N_5O_9$+H$^+$, required 956.5168). $[\alpha]_D^{23}$ −25 (c 0.11, CHCl$_3$).

Compound 35

Method 2 was followed providing Compound 35 in 36% yield. $^1$H NMR (600 MHz, CDCl$_3$) δ 9.85 (s, 1H), 8.03 (s, 1H), 7.95 (d, J=7.8 Hz, 2H), 7.50-7.39 (m, 1H), 7.29 (d, J=8.0 Hz, 2H), 7.17-7.07 (m, 2H), 6.65 (s, 1H), 6.12 (s, 1H), 6.07 (s, 1H), 5.85 (dd, J=10.5, 4.2 Hz, 1H), 5.48 (s, 1H), 5.30 (d, J=10.3 Hz, 1H), 4.05-3.05 (m, 2H), 3.81 (s, 3H), 3.80 (s, 3H), 3.75 (s, 1H), 3.60 (s, 3H), 3.43-3.27 (m, 3H), 3.27-3.16 (m, 2H), 3.16-3.06 (m, 2H), 2.72 (s, 3H), 2.69-2.62 (m, 3H), 2.49-2.40 (m, 2H), 2.36 (d, J=14.2 Hz, 1H), 2.24-2.16 (m, 2H), 2.11 (s, 3H), 2.02-1.99 (m, 1H), 1.87-1.77 (m, 1H), 1.66-1.58 (m, 2H), 1.38-1.30 (m, 2H), 1.31-1.25 (m, 6H), 0.91 (t, J=7.3 Hz, 3H), 0.90-0.83 (m, 2H), 0.82 (t, J=7.4 Hz, 3H), 0.77 (t, J=7.5 Hz, 3H); HRESI-TOF m/z 970.5325 ($C_{57}H_{71}N_5O_9$+H$^+$, required 970.5324). $[\alpha]_D^{23}$ +11 (c 0.04, CHCl$_3$).

Compound 36

Method 2 was followed providing Compound 36 in 39% yield. $^1$H NMR (600 MHz, CDCl$_3$) δ 8.03 (s, 1H), 7.94 (d, J=7.7 Hz, 2H), 7.47-7.42 (m, 1H), 7.17-7.04 (m, 3H), 6.65 (s, 1H), 6.12 (s, 1H), 6.07 (s, 1H), 5.85 (dd, J=10.6, 4.4 Hz, 1H), 5.48 (s, 1H), 5.30 (d, J=10.2 Hz, 1H), 4.04-3.97 (m, 2H), 3.81 (s, 3H), 3.80 (s, 3H), 3.75 (s, 3H), 3.60 (s, 3H), 3.43-3.17 (m, 5H), 3.16-3.05 (m, 2H), 2.83 (d, J=16.0 Hz, 1H), 2.72 (s, 3H), 2.67 (s, 1H), 2.51 (d, J=6.8 Hz, 2H), 2.49-2.40 (m, 2H), 2.37 (d, J=14.0 Hz, 1H), 2.24-2.16 (m, 2H), 2.13 (s, 1H), 2.11 (s, 3H), 1.93-1.83 (m, 1H), 1.83-1.74 (m, 2H), 1.30-1.22 (m, 5H), 0.89-0.80 (m, 9H), 0.77 (t, J=7.5 Hz, 3H); HRESI-TOF m/z 970.5322 ($C_{57}H_{71}N_5O_9$+H$^+$, required 970.5324). $[\alpha]_D^{23}$ +6 (c 0.08, CHCl$_3$).

Compound 38

Method 1 was followed using 2.2 mg of 20'-aminovinblastine (6, 2.7 µmol) to provide Compound 38 as a white solid, yield: 44%. $^1$H NMR (600 MHz, CDCl$_3$) δ 9.85 (s, 1H), 8.03 (d, J=0.4 Hz, 1H), 7.96-7.95 (m, 2H), 7.49 (d, J=8.2 Hz, 2H), 7.45 (d, J=7.8 Hz, 1H), 7.14-7.05 (m, 3H), 6.64 (s, 1H), 6.11 (s, 1H), 6.07 (s, 1H), 5.84 (dd, J=10.0, 4.6 Hz, 1H), 5.47 (s, 1H), 5.29 (t, J=4.9 Hz, 1H), 4.01-3.96 (m, 2H), 3.81 (s, 3H), 3.79 (s, 3H), 3.74 (s, 1H), 3.59 (s, 3H), 3.40-3.35 (m, 2H), 3.32-3.27 (m, 1H), 3.23-3.21 (m, 2H), 3.13-3.09 (m, 2H), 2.82 (d, J=16.2 Hz, 1H), 2.71 (s, 3H), 2.68-2.66 (m, 1H), 2.48-2.40 (m, 2H), 2.36 (d, J=13.5 Hz, 1H), 2.21-2.16 (m, 1H), 2.10 (s, 3H), 1.85-1.77 (m, 3H), 1.62-1.52 (m, 3H), 1.32 (s, 9H), 1.25 (s, 2H), 0.81 (t, J=7.2 Hz, 3H), 0.76 (t, J=7.4 Hz, 3H); ESI-MS m/z 970.5 ($C_{57}H_{71}N_5O_9$+H$^+$, required 970.53).

Compound 39

Method 1 was followed using 2.5 mg of 20'-aminovinblastine (6, 3.1 µmol) to provide Compound 39 as a pale clear resin, yield: 75%. $^1$H NMR (CDCl$_3$, 600 MHz) δ 8.18-8.14 (m, 2H), 8.02 (s, 1H), 7.77 (d, J=7.8 Hz, 2H), 7.71 (d, J=8.4 Hz, 1H), 7.45 (d, J=7.8 Hz, 1H), 7.16-7.06 (m, 3H), 6.66 (s, 1H), 6.12 (s, 1H), 6.08 (s, 1H), 5.86 (dd, J=4.2, 10.8 Hz, 1H), 5.48 (s, 1H), 5.31-5.29 (m, 2H), 3.99 (br s, 1H), 3.82 (s, 3H), 3.80 (s, 3H), 3.76 (s, 1H), 3.60 (s, 2H), 3.44-3.36 (m, 2H), 3.32-3.29 (m, 1H), 3.26-3.22 (m, 1H), 3.18-3.11 (m, 3H), 2.83 (d, J=15.6 Hz, 1H), 2.74 (s, 3H), 2.68 (s, 1H), 2.46-2.44 (m, 2H), 2.35 (d, J=13.8 Hz, 1H), 2.22-2.18 (m, 1H), 2.11 (s, 3H), 2.03-1.98 (m, 1H), 1.85-1.79 (m, 4H), 1.39-1.33 (m, 2H), 1.26-1.23 (m, 2H), 0.89-0.77 (m, 6H); HRESI-TOF m/z 982.4568 ($C_{54}H_{62}F_3N_5O_9$+H$^+$, required 982.4572).

Compound 40

Method 1 was followed using 2.6 mg of 20'-aminovinblastine (6, 3.2 µmol) to provide Compound 40, yield: 75%. $^1$H NMR (CDCl$_3$, 600 MHz) δ 8.30-8.20 (m, 3H), 8.04 (s, 1H), 7.80-7.76 (m, 1H), 7.65 (t, J=7.8 Hz, 1H), 7.56 (t, J=7.8 Hz, 1H), 7.45 (d, J=8.4 Hz, 1H), 7.16-7.07 (m, 3H), 6.63 (s, 1H), 6.13-6.12 (m, 2H), 5.85 (dd, J=4.8, 10.2 Hz, 1H), 5.47 (s, 1H), 5.31-5.29 (m, 1H), 3.93 (br s, 1H), 3.81-3.80 (m, 6H), 3.75 (s, 1H), 3.56 (s, 2H), 3.46-3.44 (m, 1H), 3.37 (dd, J=4.8, 16.2 Hz, 1H), 3.30-3.27 (m, 2H), 3.21-3.20 (m, 1H), 3.15-3.14 (m, 1H), 2.82 (d, J=16.2 Hz, 1H), 2.72 (s, 3H), 2.67 (s, 1H), 2.47-2.42 (m, 3H), 2.37-2.24 (m, 1H), 2.21-2.17 (m, 2H), 2.11 (s, 3H), 1.93-1.90 (m, 1H), 1.84-1.78 (m, 2H), 1.62-1.59 (m, 1H), 1.42-1.40 (m, 1H), 1.36-1.32 (m, 2H), 1.26-1.23 (m, 2H), 0.83-0.80 (m, 6H); IR (film) $v_{max}$ 3464, 2931, 1737, 1664, 1503, 1227, 1167, 1126, 738 cm$^{-1}$; HRESI-TOF m/z 982.4574 ($C_{54}H_{62}F_3N_5O_9$+H$^+$, required 982.4572).

Compound 41

Method 1 was followed using 2.7 mg of 20'-aminovinblastine (6, 3.3 µmol) to provide 2.0 mg of Compound 41 as an off-white resin, yield: 61%. $^1$H NMR (CDCl$_3$, 600 MHz) δ 9.77 (br s, 1H), 8.19 (s, 1H), 8.06 (s, 1H), 7.74 (d, J=8.4 Hz, 1H), 7.68 (t, J=7.5 Hz, 1H), 7.55 (t, J=7.8 Hz, 1H), 7.49 (d, J=7.8 Hz, 1H), 7.17-7.09 (m, 3H), 6.64 (s, 1H), 6.11 (s, 1H), 5.86 (dd, J=4.8, 10.2 Hz, 1H), 5.74 (s, $^1$H), 5.48 (s, 1H), 5.31-5.30 (m, 1H), 3.95-3.91 (m, 1H), 3.80 (s, 3H), 3.78 (s, 3H), 3.75 (s, 1H), 3.64-3.59 (m, 4H), 3.44-3.37 (m, 2H), 3.31 (td, J=4.8, 9.6 Hz, 1H), 3.24-3.19 (m, 3H), 3.10-3.08 (m, 1H), 2.82 (d, J=15.6 Hz, 1H), 2.72 (s, 3H), 2.67 (s, 1H), 2.48-2.43 (m, 1H), 2.35-2.30 (m, 2H), 2.23-2.18 (m, 1H), 2.11 (s, 3H), 2.09-2.06 (m, 1H), 1.89-1.69 (m, 5H), 1.37-1.31 (m, 2H), 1.25 (s, 1H), 0.89-0.81 (m, 6H); HRESI-TOF m/z 982.4568 ($C_{54}H_{62}F_3N_5O_9$+H$^+$, required 982.4572).

Compound 42

Method 1 was followed using 2.4 mg of 20'-aminovinblastine (6, 3.7 µmol) to provide 2.8 mg of Compound 42 as a pale yellow resin, yield: 75%. $^1$H NMR (CDCl$_3$, 600 MHz) δ 9.87 (br s, 1H), 8.11 (d, J=4.2 Hz, 1H), 8.04 (s, 1H), 7.71 (d, J=8.4 Hz, 1H), 7.62 (dd, J=1.2, 8.4 Hz, 2H), 7.45 (t, J=7.8 Hz, 3H), 7.38-7.27 (m, 2H), 7.15-7.06 (m, 3H), 6.66 (s, $^1$H), 6.15 (s, 1H), 6.13 (s, 1H), 5.85 (dd, J=4.5, 10.5 Hz, 1H), 5.48 (s, 1H), 5.31-5.29 (m, 1H), 4.02 (br s, 1H), 3.82 (s, 3H), 3.80 (s, 3H), 3.72 (s, 1H), 3.60 (s, 3H), 3.45-3.35 (m, 3H), 3.31 (td, J=9.6, 4.2 Hz, 1H), 3.25-3.20 (m, 1H), 3.13-3.08 (m, 2H), 2.83 (d, J=16.2 Hz, 1H), 2.72 (s, 3H), 2.68 (s, 1H), 2.47-2.37 (m, 3H), 2.22-2.17 (m, 1H), 2.11 (s, 3H), 2.00 (br s, 1H), 1.86-1.77 (m, 3H), 1.62 (br s, 1H), 1.42-1.32 (m, 3H), 1.26-1.21 (m, 2H), 0.83-0.80 (m, 6H); IR (film) $v_{max}$ 3467, 2927, 1738, 1502, 1228, 1039 cm$^{-1}$; HRESI-TOF m/z 990.4993 ($C_{59}H_{67}N_5O_9$+H$^+$, required 959.5011).

Compound 43

Method 2 was followed providing Compound 43 in 41% yield. $^1$H NMR (600 MHz, CDCl$_3$) δ 9.84 (s, 1H), 8.03 (s, 1H), 7.95 (d, J=7.9 Hz, 2H), 7.45 (d, J=7.9 Hz, 1H), 7.32 (d, J=8.0 Hz, 2H), 7.17-7.04 (m, 3H), 6.65 (s, 1H), 6.12 (s, 1H), 6.07 (s, 1H), 5.85 (dd, J=10.4, 4.5 Hz, 1H), 5.48 (s, 1H), 5.30 (d, J=10.2 Hz, 1H), 4.04-3.96 (m, 2H), 3.81 (s, 3H), 3.80 (s, 3H), 3.75 (s, 1H), 3.60 (s, 3H), 3.43-3.27 (m, 3H), 3.25-3.18 (m, 2H), 3.15-3.06 (m, 2H), 2.83 (d, J=16.1 Hz, 1H), 2.72 (s, 3H), 2.71-2.65 (m, 2H), 2.58-2.52 (m, 1H), 2.48-2.39 (m, 2H), 2.36 (d, J=13.7 Hz, 1H), 2.25-2.14 (m, 1H), 2.11 (s, 3H), 1.89-1.71 (m, 3H), 1.68-1.56 (m, 3H), 1.46-1.30 (m, 4H), 1.30-1.26 (m, 3H), 1.25 (s, 3H), 0.88 (t, J=6.9 Hz, 2H), 0.82 (t, J=7.4 Hz, 3H), 0.76 (t, J=7.4 Hz, 3H); HRESI-TOF m/z 996.5485 ($C_{59}H_{73}N_5O_9$+H$^+$, required 996.5481). $[α]_D^{23}$ −33 (c 0.08, CHCl$_3$).

Compound 44

Method 1 was followed using 2.8 mg of 20'-aminovinblastine (6, 3.5 µmol) to provide Compound 44 as a white solid, yield: 52%. $^1$H NMR (600 MHz, CDCl$_3$) δ 8.06-8.00 (m, 4H), 7.44 (d, J=7.9 Hz, 1H), 7.18-7.05 (m, 5H), 6.64 (s, 1H), 6.11 (s, 1H), 6.03 (s, 1H), 5.85 (dd, J=10.2, 4.5 Hz, 1H), 5.47 (s, 1H), 5.30 (d, J=8.9 Hz, 1H), 4.00-3.97 (m, 2H), 3.81 (s, 3H), 3.79 (s, 3H), 3.74 (s, 1H), 3.59 (s, 3H), 3.41-3.09 (m, 9H), 2.83-2.80 (m, 1H), 2.73 (d, J=0.9 Hz, 3H), 2.67 (s, 1H), 2.47-2.43 (m, 2H), 2.35-2.33 (m, 1H), 2.10 (s, 3H), 1.81 (td, J=15.8, 6.9 Hz, 3H), 1.37-1.32 (m, 2H), 1.25 (s, 1H), 0.88-0.84 (m, 2H), 0.81 (t, J=7.3 Hz, 3H), 0.77 (t, J=7.3 Hz, 3H); ESI-MS m/z 932.3 ($C_{53}H_{62}FN_5O_9$+H$^+$, required 932.46).

Compound 45

Method 1 was followed using 2.6 mg of 20'-aminovinblastine (6, 3.2 µmol) to provide Compound 45 as a white solid, yield: 46%. $^1$H NMR (600 MHz, CDCl$_3$) δ 8.04 (s, 1H), 7.83-7.81 (m, 1H), 7.71-7.66 (m, 1H), 7.49-7.44 (m, 2H), 7.20 (t, J=7.7 Hz, 1H), 7.14 (t, J=7.5 Hz, 1H), 7.10-7.06 (m, 2H), 6.63 (s, 1H), 6.11 (s, 1H), 6.06 (s, 1H), 5.84 (dd, J=9.8, 4.5 Hz, 1H), 5.47 (s, 1H), 5.29 (d, J=10.3 Hz, 1H), 3.96-3.91 (m, 2H), 3.80 (s, 3H), 3.79 (s, 3H), 3.74 (s, 1H), 3.60 (s, 3H), 3.42-3.35 (m, 2H), 3.29 (td, J=9.5, 4.7 Hz, 1H), 3.24-3.22 (m, 1H), 3.16-3.09 (m, 3H), 2.81 (d, J=16.2 Hz, 1H), 2.71 (s, 3H), 2.66 (s, 1H), 2.44 (dd, J=17.5, 11.2 Hz, 2H), 2.36 (d, J=13.6 Hz, 1H), 2.21-2.16 (m, 1H), 2.10 (s, 3H), 1.84-1.77 (m, 5H), 1.52 (s, 1H), 1.37-1.30 (m, 2H), 1.24 (s, 1H), 0.82-0.76 (m, 6H); ESI-MS m/z 932.3 ($C_{53}H_{62}FN_5O_9$+H$^+$, required 932.46).

Compound 46

Method 1 was followed using 2.3 mg of 20'-aminovinblastine (6, 4.1 µmol) to provide Compound 46 as a white solid, yield: 41%. $^1$H NMR (600 MHz, CDCl$_3$) δ 8.14 (t, J=7.7 Hz, 1H), 8.05 (s, 1H), 7.46-7.45 (m, 2H), 7.29 (t, J=7.6 Hz, 1H), 7.18-7.06 (m, 4H), 6.75 (d, J=13.4 Hz, 1H), 6.56 (s, 1H), 6.09 (s, 1H), 5.83 (dd, J=9.7, 4.5 Hz, 1H), 5.45 (s, 1H), 5.29 (s, 1H), 5.27 (d, J=9.9 Hz, 1H), 3.79 (s, 3H), 3.77 (s, 3H), 3.73 (s, 1H), 3.48-3.42 (m, 3H), 3.37-3.24 (m, 4H), 3.18-3.11 (m, 2H), 2.82-2.78 (m, 2H), 2.70 (s, 3H), 2.63 (s, 1H), 2.49 (d, J=13.5 Hz, 1H), 2.41 (dd, J=17.0, 9.7 Hz, 1H), 2.32 (d, J=14.2 Hz, 1H), 2.20-2.15 (m, 2H), 2.09 (s, 3H), 1.84-1.74 (m, 4H), 1.41-1.36 (m, 1H), 1.32-1.28 (m, 1H), 1.25 (d, J=2.5 Hz, 2H), 0.87 (t, J=6.8 Hz, 2H), 0.82-0.77 (m, 6H); HRESI-TOF m/z 932.3 ($C_{53}H_{62}FN_5O_9$+H$^+$, required 932.46).

Compound 47

Method 1 was followed using 3.3 mg of 20'-aminovinblastine (6, 4.1 µmol) to provide 2.9 mg of Compound 47 as a yellow resin, yield: 75%. $^1$H NMR (CDCl$_3$, 600 MHz) δ 8.13-7.97 (m, 3H), 7.84-7.78 (m, 1H), 7.48-7.42 (m, 3H), 7.16-7.08 (m, 3H), 6.65 (s, 1H), 6.12 (s, 1H), 6.05 (s, 1H), 5.86-5.85 (m, 1H), 5.48 (s, 1H), 5.31-5.30 (m, 1H), 3.98 (br s, 1H), 3.82-3.80 (m, 6H), 3.75 (s, 1H), 3.60 (s, 3H), 3.41-3.35 (m, 2H), 3.32-3.29 (m, 3H), 3.25-3.20 (m, 1H), 3.11-3.08 (m, 2H), 2.83 (d, J=16.2 Hz, 1H), 2.72 (s, 3H), 2.67 (s, 1H), 2.46-2.41 (m, 2H), 2.33 (d, J=13.8 Hz, 1H), 2.23-2.15 (m, 1H), 2.11 (s, 3H), 2.00-1.97 (m, 1H), 1.85-1.76 (m, 2H), 1.66-1.62 (m, 2H), 1.36-1.33 (m, 2H), 1.25 (s, 1H), 0.83-0.76 (m, 6H); IR (film) $\nu_{max}$ 3466, 2929, 1735, 1227, 1039, 739 cm$^{-1}$; HRESI-TOF m/z 948.4302 ($C_{53}H_{62}ClN_5O_9$+H$^+$, required 948.4309).

Compound 48

Method 1 was followed using 4.7 mg of 20'-aminovinblastine (6, 5.8 µmol) to provide 3.3 mg of Compound 48 as a pale yellow resin, yield: 60%. $^1$H NMR (CDCl$_3$, 600 MHz) δ 8.05 (br s, 1H), 7.99-7.88 (m, 2H), 7.49-7.43 (m, 3H), 7.16-7.07 (m, 3H), 6.63 (s, 1H), 6.12 (s, 1H), 6.06 (s, 1H), 5.85 (dd, J=4.5, 10.5 Hz, 1H), 5.48 (s, 1H), 5.31-5.29 (m, 1H), 3.92 (br s, 1H), 3.81-3.80 (m, 6H), 3.75 (s, 1H), 3.58 (s, $^3$H), 3.42 (d, J=13.2 Hz, 1H), 3.38 (dd, J=4.8, 16.8 Hz, 1H), 3.31-3.26 (m, 2H), 3.20-3.11 (m, 3H), 2.83 (d, J=16.2 Hz, 1H), 2.72 (s, 3H), 2.67 (s, 1H), 2.47-2.42 (m, 2H), 2.35 (d, J=13.8 Hz, 1H), 2.21-2.17 (m, 2H), 2.11 (s, 3H), 1.95-1.90 (m, 1H), 1.85-1.77 (m, 2H), 1.62-1.59 (m, 1H), 1.38-1.32 (m, 2H), 1.27-1.24 (m, 2H), 0.81 (t, J=7.2 Hz, 3H), 0.78 (t, J=7.5 Hz, 3H); IR (film) $\nu_{max}$ 3466, 2931, 1736, 1502, 1227, 737 cm$^{-1}$; HRESI-TOF m/z 948.4305 ($C_{53}H_{62}ClN_5O_9$+H$^+$, required 948.4309).

Compound 49

Method 1 was followed using 5.6 mg of 20'-aminovinblastine (6, 6.9 µmol) to provide 3.3 mg of Compound 49 as an off-white resin, yield: 75%. $^1$H NMR (CDCl$_3$, 600 MHz) δ 9.85 (br s, 1H), 8.07 (s, 1H), 8.03 (s, 1H), 7.49 (d, J=7.8 Hz, 1H), 7.44-7.43 (m, 1H), 7.39-7.35 (m, 2H), 7.16-7.08 (m, 3H), 6.61 (s, 1H), 6.10 (s, 1H), 5.94 (s, 1H), 5.85 (dd, J=4.2, 10.2 Hz, 1H), 5.48 (s, 1H), 5.30-5.29 (m, 1H), 3.86-3.84 (m, 1H), 3.80-3.78 (m, 6H), 3.74 (s, 1H), 3.56 (s, 3H), 3.48 (s, 1H), 3.43-3.36 (m, 2H), 3.32-3.09 (m, 5H), 2.81 (d, J=16.2 Hz, 1H), 2.71 (s, 3H), 2.65 (s, 1H), 2.47-2.42 (m, 1H), 2.37-2.31 (m, 2H), 2.22-2.16 (m, 2H), 2.11 (s, 3H), 1.98-1.93 (m, 1H), 1.85-1.78 (m, 2H), 1.66-1.61 (m, 2H), 1.35-1.24 (m, 4H), 0.89 (t, J=7.5 Hz, 3H), 0.81 (t, J=7.5 Hz, 3H); HRESI-TOF m/z 948.4305 ($C_{53}H_{62}ClN_5O_9$+H$^+$, required 948.4309).

Compound 50

Method 1 was followed using 3.9 mg of 20'-aminovinblastine (6, 4.8 µmol) to provide 3.0 mg of Compound 50 as a yellow resin, yield: 75%. $^1$H NMR (CDCl$_3$, 600 MHz) δ 8.09 (d, J=1.8 Hz, 1H), 8.05 (s, 1H), 7.83 (dd, J=2.4, 8.4 Hz, 1H), 7.58 (d, J=8.4 Hz, 1H), 7.50 (d, J=8.4 Hz, 1H), 7.33 (d, J=7.8 Hz, 1H), 7.16-7.06 (m, 3H), 6.60 (s, 1H), 6.11 (s, 1H), 6.07 (s, 1H), 5.85 (dd, J=4.2, 10.2 Hz, 1H), 5.46 (s, 1H), 5.31-5.29 (m, 1H), 4.07 (br s, 1H), 3.82 (s, 3H), 3.80 (s, 3H), 3.75 (s, 1H), 3.62 (s, 3H), 3.38-3.34 (m, 2H), 3.26 (td, J=4.8, 9.6 Hz, 2H), 3.22-3.20 (m, 1H), 3.18-3.14 (m, 1H), 2.76 (d, J=16.2 Hz, 1H), 2.72 (s, 3H), 2.67 (s, 1H), 2.43-2.39 (m, 2H), 2.20-2.16 (m, 2H), 2.11 (s, 3H), 2.01-1.99 (m, 1H), 1.92-1.89 (m, 1H), 1.83-1.76 (m, 1H), 1.60-1.49 (m, 1H), 1.35-1.30 (m, 2H), 1.27-1.25 (m, 2H), 0.81 (t, J=7.2 Hz, 6H); IR (film) $\nu_{max}$ 3466, 2925, 1734, 1460, 1228, 1031, 739 cm$^{-1}$; HRESI-TOF m/z 982.3919 ($C_{53}H_{61}Cl_2N_5O_9$+H$^+$, required 982.3919).

Compound 51

Method 2 was followed providing Compound 51 in 41% yield. $^1$H NMR (600 MHz, CDCl$_3$) δ 9.82 (s, 1H), 8.00 (s, 1H), 7.94 (d, J=7.4 Hz, 2H), 7.64 (d, J=8.4 Hz, 2H), 7.45 (d, J=7.9 Hz, 1H), 7.17-7.04 (m, 3H), 6.66 (s, 1H), 6.12 (s, 1H), 6.05 (s, 1H), 5.85 (dd, J=10.2, 5.1 Hz, 1H), 5.48 (s, 1H), 5.33-5.28 (m, 1H), 3.99-3.94 (m, 2H), 3.82 (s, 3H), 3.80 (s, 3H), 3.75 (s, 1H), 3.60 (s, 3H), 3.43-3.37 (m, 2H), 3.37-3.25 (m, 2H), 3.25-3.15 (m, 1H), 3.14-3.06 (m, 2H), 2.83 (d, J=16.0 Hz, 1H), 2.72 (s, 3H), 2.69-2.64 (m, 2H), 2.50-2.38 (m, 2H), 2.35-2.29 (m, 1H), 2.20 (ddd, J=15.2, 9.0, 6.4 Hz, 1H), 2.11 (s, 3H), 2.00-1.95 (m, 1H), 1.87-1.76 (m, 3H), 1.35 (dt, J=14.2, 6.4 Hz, 2H), 1.27-1.24 (m, 1H), 0.96-0.74 (m, 7H); HRESI-TOF m/z 992.3802 ($C_{53}H_{62}N_5O_9Br$+H$^+$, required 992.3803). [α]$_D^{23}$ −34 (c 0.07, CHCl$_3$).

Compound 52

Method 1 was followed providing Compound 52 in 52% yield. $^1$H NMR (CDCl$_3$, 600 MHz) δ 9.83 (s, 1H), 8.12 (t, J=1.2 Hz, 1H), 8.03 (s, 1H), 8.01-7.97 (m, 1H), 7.63 (ddd, J=8.1, 2.1, 0.9 Hz, 1H), 7.47 (d, J=7.9 Hz, 1H), 7.38 (t, J=7.9 Hz, 1H), 7.17-7.05 (m, 3H), 6.64 (s, 1H), 6.12 (s, 1H), 6.05 (s, 1H), 5.85 (dd, J=10.2, 5.0 Hz, 1H), 5.48 (s, 1H), 5.32-5.27 (m, 1H), 3.97-3.83 (m, 2H), 3.81 (s, 3H), 3.80 (s, 3H), 3.75 (s, 1H), 3.57 (s, 3H), 3.44-3.33 (m, 2H), 3.33-3.20 (m, 2H), 3.17-3.09 (m, 3H), 2.86-2.79 (m, 1H), 2.72 (m, 3H), 2.70-2.65 (m, 2H), 2.49-2.37 (m, 2H), 2.35-2.29 (m, 1H), 2.25-2.16 (m, 1H), 2.11 (s, 3H), 2.11-2.03 (m, 1H), 1.93-1.89 (m, 2H), 1.87-1.76 (m, 2H), 1.37-1.30 (m, 2H), 1.27-1.23 (m, 1H), 0.82 (t, J=7.4 Hz, 3H), 0.77 (t, J=7.5 Hz, 3H); HRESI-TOF m/z 992.3805 ($C_{53}H_{62}BrN_5O_5$+H$^+$, required 992.3803). [α]$_D^{23}$ −41 (c 0.12, CHCl$_3$).

Compound 53

Method 2 was followed providing Compound 53 in 43% yield. $^1$H NMR (600 MHz, CDCl$_3$) δ 9.82 (s, 1H), 8.23 (d, J=2.3 Hz, 1H), 8.03-7.99 (m, 1H), 7.90 (s, 1H), 7.76 (d, J=8.3 Hz, 1H), 7.46 (d, J=8.0 Hz, 1H), 7.19-7.05 (m, 3H), 6.65 (s, 1H), 6.11 (s, 1H), 6.02 (s, 1H), 5.85 (dd, J=9.9, 4.6 Hz, 1H), 5.48 (s, 1H), 5.30 (d, J=10.5 Hz, 1H), 3.81 (s, 3H), 3.80 (s, 3H), 3.75 (s, 1H), 3.58 (s, 3H), 3.44-3.27 (m, 3H), 3.26-3.19 (m, 1H), 3.12-3.05 (m, 3H), 2.82 (d, J=16.6 Hz, 1H), 2.78-2.65 (m, 5H), 2.47-2.36 (m, 2H), 2.30 (d, J=13.0 Hz, 1H), 2.25-2.15 (m, 1H), 2.11 (s, 3H), 1.94-1.71 (m, 4H), 1.39-1.28 (m, 1H), 1.26-1.23 (m, 5H), 0.92-0.79 (m, 3H), 0.76 (t, J=7.5 Hz, 3H); HRESI-TOF m/z 1070.2904 ($C_{53}H_{61}Br_2N_5O_9$+H$^+$, required 1070.2909). [α]$_D^{23}$ −9 (c 0.05, CHCl$_3$).

Compound 54

Method 2 was followed providing Compound 54 as an off-white resin in 15% yield. $^1$H NMR (CDCl$_3$, 600 MHz) δ 9.80 (br s, 1H), 8.19 (d, J=8.4 Hz, 1H), 7.99 (s, 1H), 7.81 (d, J=8.4 Hz, 1H), 7.46-7.44 (m, 2H), 7.16-7.07 (m, 3H), 6.67 (s, 1H), 6.12 (s, 1H), 6.10 (s, 1H), 5.86 (dd, J=4.2, 10.2 Hz, 1H), 5.48 (s, 1H), 5.30 (d, J=10.2 Hz, 1H), 4.10-3.93 (m, 2H), 3.82 (s, 3H), 3.80 (s, 3H), 3.76 (s, 1H), 3.60 (s, 3H), 3.43-3.35 (m, 2H), 3.31 (td, J=4.2, 9.6 Hz, 1H), 3.23-3.20 (m, 1H), 3.07-3.05 (m, 3H), 2.82 (d, J=16.2 Hz, 1H), 2.72 (s, 3H), 2.68 (s, 1H), 2.46 (td, J=10.8, 6.6 Hz, 1H), 2.40 (d, J=13.2 Hz, 1H), 2.31 (d, J=13.8 Hz, 1H), 2.26-2.19 (m, 2H), 2.17 (s, 1H), 2.11 (s, 3H), 2.00-1.97 (m, 1H), 1.85-1.80 (m, 2H), 1.43-1.34 (m, 4H), 1.25 (s, 1H), 0.83 (t, J=7.5 Hz, 3H), 0.77 (t, J=7.2 Hz, 3H); IR (film) $\nu_{max}$ 3869, 2924, 1742, 1230 cm$^{-1}$; HRESI-TOF m/z 939.4647 ($C_{54}H_{62}N_6O_9$+H$^+$, required 939.4651). [α]$_D^{23}$ −26 (c 0.05, CHCl$_3$).

Compound 55

Method 2 was followed providing Compound 55 in 41% yield. $^1$H NMR (600 MHz, CDCl$_3$) δ 9.81 (s, 1H), 8.03 (s, 1H), 8.00-7.94 (m, 2H), 7.74 (d, J=8.1 Hz, 1H), 7.45 (d, J=7.9 Hz, 1H), 7.14 (t, J=7.3 Hz, 1H), 7.11 (d, J=7.9 Hz, 1H), 7.08 (td, J=7.3, 1.2 Hz, 1H), 6.66 (s, 1H), 6.12 (s, 1H), 6.08 (s, 1H), 5.86 (ddd, J=10.2, 5.0, 1.6 Hz, 1H), 5.48 (s, 1H), 5.32 (d, J=10.2 Hz, 1H), 4.08-3.90 (m, 2H), 3.82 (s, 3H), 3.80 (s, 3H), 3.76 (s, 1H), 3.59 (s, 3H), 3.45-3.34 (m, 1H), 3.31 (td, J=9.5, 4.5 Hz, 1H), 3.25-3.19 (m, 1H), 3.12-3.06 (m, 2H), 2.83 (d, J=16.1 Hz, 1H), 2.72 (s, 3H), 2.71-2.67 (m, 2H), 2.66 (s, 3H), 2.49-2.43 (m, 1H), 2.41 (d, J=13.3 Hz, 1H), 2.31 (d, J=13.3 Hz, 1H), 2.25-2.16 (m, 1H), 2.11 (s, 3H), 2.02-1.95 (m, 1H), 1.86-1.77 (m, 3H), 1.40-1.32 (m, 2H), 1.25 (s, 3H), 0.95-0.80 (m, 4H), 0.77 (t, J=7.5 Hz, 3H); HRESI-TOF m/z 970.5332 (C$_{57}$H$_{71}$N$_5$O$_9$+H$^+$, required 970.5324). [α]$_D^{23}$−5 (c 0.08, CHCl$_3$).

Compound 56

Method 1 was followed providing Compound 56 as a pale yellow resin in 75% yield. $^1$H NMR (CDCl$_3$, 600 MHz) δ 8.37-8.36 (m, 2H), 8.26-8.25 (m, 2H), 7.99 (s, 1H), 7.44 (d, J=7.8 Hz, 1H), 7.17-7.07 (m, 3H), 6.67 (s, 1H), 6.13-6.11 (m, 2H), 5.86 (dd, J=4.8, 10.2 Hz, 1H), 5.43 (s, 1H), 5.32-5.30 (m, 2H), 3.96-3.94 (m, 1H), 3.82-3.80 (m, 6H), 3.76 (s, 1H), 3.62 (s, 3H), 3.43-3.35 (m, 2H), 3.30 (td, J=4.8, 9.6 Hz, 1H), 3.23-3.20 (m, 1H), 3.09 (br s, 2H), 2.83 (d, J=16.2 Hz, 1H), 2.73 (s, 3H), 2.68 (s, 1H), 2.48-2.40 (m, 3H), 2.32 (d, J=13.8 Hz, 1H), 2.23-2.18 (m, 2H), 2.11 (s, 3H), 1.97 (br s, 1H), 1.84-1.79 (m, 3H), 1.38-1.35 (m, 2H), 1.27-1.20 (m, 3H), 0.89-0.77 (m, 6H); IR (film) ν$_{max}$ 3461, 2934, 1736, 1524, 1227, 1040 cm$^{-1}$; HRESI-TOF m/z 959.4551 (C$_{53}$H$_{62}$N$_6$O$_{11}$+H$^+$, required 959.4549).

Compound 57

A solution of Compound 60 (3 mg, 2.9 μmol) in anhydrous CH$_2$Cl$_2$ (100 μL) was cooled to 0° C. TFA (100 μL) was added and the reaction mixture was stirred at the same temperature for 30 minutes. The solvent was removed and the crude residue taken up with 10% MeOH:CH$_2$Cl$_2$, washed with saturated aqueous NaHCO$_3$, saturated aqueous NaCl, and dried over Na$_2$SO$_4$. Evaporation in vacuo yielded the crude product that was purified by PTLC (SiO$_2$) to provide Compound 57 (89% yield) as an off-white resin. $^1$H NMR (CDCl$_3$, 600 MHz) δ 9.85 (br s, 1H), 8.02 (s, 1H), 7.87 (d, J=7.8 Hz, 2H), 7.44 (d, J=8.4 Hz, 1H), 7.15-7.05 (m, 4H), 6.72 (d, J=8.4 Hz, 1H), 6.64 (s, 1H), 6.12 (s, 1H), 5.97 (s, 1H), 5.85 (dd, J=4.8, 10.2 Hz, 1H), 5.48 (s, 1H), 5.30 (d, 1H), 3.99 (br s, 1H), 3.91 (br s, 1H), 3.82 (s, 3H), 3.80 (s, 3H), 3.75 (s, 1H), 3.60 (s, 3H), 3.39-3.35 (m, 2H), 3.30 (td, J=4.8, 9.6 Hz, 1H), 3.24-3.11 (m, 4H), 3.07-3.04 (m, 1H), 2.07-2.03 (m, 1H), 2.83 (d, J=16.2 Hz, 1H), 2.72 (s, 3H), 2.67 (s, 1H), 2.48-2.42 (m, 2H), 2.35 (d, J=13.8 Hz, 1H), 2.21-2.16 (m, 2H), 2.11 (s, 3H), 1.85-1.76 (m, 2H), 1.41 (br s, 1H), 1.36-1.31 (m, 2H), 1.27-1.25 (m, 2H), 0.81 (t, J=7.2 Hz, 3H), 0.77 (t, J=7.5 Hz, 3H); IR (film) ν$_{max}$ 3448, 2928, 1609, 1243, 1037 cm$^{-1}$; HRESI-TOF m/z 929.4830 (C$_{53}$H$_{64}$N$_6$O$_9$+H$^+$, required 929.4807).

Compound 58

Method 2 was followed providing Compound 58 in 34% yield. $^1$H NMR (600 MHz, CDCl$_3$) δ 8.06-8.02 (s, 2H), 7.66 (d, J=8.1 Hz, 2H), 7.48-7.45 (m, 1H), 7.24 (s, 1H), 7.20-7.14 (m, 2H), 6.68 (s, 1H), 6.15 (s, 1H), 6.07 (s, 1H), 5.88 (dd, J=10.3, 4.5 Hz, 1H), 5.51 (s, 1H), 5.33 (s, 2H), 4.05-3.95 (m, 1H), 3.85 3.80 (m, 6H), 3.77 (s, 1H), 3.63 (s, 3H), 3.44-3.40 (m, 1H), 3.40-3.37 (m, 1H), 335-3.30 (m, 1H), 3.28-3.22 (m, 1H), 3.16-3.08 (m, 3H), 2.85 (d, J=16.0 Hz, 1H), 2.74 (s, 3H), 2.72-2.67 (m, 2H), 2.52-2.41 (m, 2H), 2.37 (d, J=13.7 Hz, 1H), 2.26-2.23 (m, 2H), 2.22 (s, 3H), 2.14 (s, 3H), 2.05-2.01 (m, 2H), 1.90-1.79 (m, 2H), 1.30-1.26 (m, 3), 0.93-0.82 (m, 5H), 0.80 (t, J=7.4 Hz, 3H); HRESI-TOF m/z 971.4906 (C$_{55}$H$_{66}$N$_6$O$_{10}$+H$^+$, required 971.4913). [α]$_D^{23}$−16 (c 0.05, CHCl$_3$).

Compound 60

Method 2 was followed providing Compound 60 as a yellow resin in 60% yield. $^1$H NMR (CDCl$_3$, 600 MHz) δ 9.88 (br s, 1H), 8.02-7.98 (m, 2H), 7.49-7.44 (m, 2H), 7.14-7.05 (m, 3H), 6.65 (s, 1H), 6.60 (s, 1H), 6.12 (s, 1H), 6.04 (s, 1H), 5.85 (dd, J=4.5, 10.5 Hz, 1H), 5.48 (s, 1H), 5.31-5.29 (m, 1H), 3.98 (br s, 1H), 3.81 (s, 3H), 3.80 (s, 3H), 3.75 (s, 1H), 3.60 (s, 3H), 3.41-3.36 (m, 2H), 3.30 (td, J=4.6, 9.5 Hz, 1H), 3.24-3.20 (m, 1H), 3.16-3.04 (m, $^3$H), 2.83 (d, J=16.2 Hz, 1H), 2.72 (s, 3H), 2.68-2.66 (m, 2H), 2.48-2.40 (m, 2H), 2.33 (d, J=13.8 Hz, 1H), 2.22-2.17 (m, 2H), 2.11 (s, 3H), 2.00 (br s, 1H), 1.85-1.77 (m, 3H), 1.63 (br s, 1H), 1.51 (s, 9H), 1.36-1.31 (m, 2H), 1.27-1.25 (m, 2H), 0.82 (t, J=7.5 Hz, 3H), 0.77 (t, J=7.5 Hz, 3H); IR (film) ν$_{max}$ 3463, 2933, 1730, 1500, 1232, 1159, 1044 cm$^{-1}$; HRESI-TOF m/z 1029.5325 (C$_{58}$H$_{72}$N$_6$O$_{11}$+H$^+$, required 1029.5332).

Compound 61

Method 2 was followed providing Compound 61 in 43% yield. $^1$H NMR (600 MHz, CDCl$_3$) δ 8.10 (d, J=8.2 Hz, 2H), 8.03 (s, 1H), 7.48-7.45 (m, 1H), 7.34 (d, J=8.5 Hz, 2H), 7.22-7.01 (m, 3H), 6.68 (s, 1H), 6.15 (s, 1H), 6.07 (s, 1H), 5.88 (dd, J=10.4, 4.9 Hz, 1H), 5.51 (s, 1H), 5.33 (d, J=10.0 Hz, 1H), 4.05-4.02 (m, 1H), 3.85-3.81 (m, 7H), 3.78 (s, 1H), 3.63 (s, 3H), 3.43-3.40 (m, 2H), 3.36-3.29 (m, 2H), 3.28-3.19 (m, 1H), 3.17-3.09 (m, 2H), 3.08 (s, 3H), 2.85 (d, J=16.5 Hz, 1H), 2.75 (s, 3H), 2.72-2.67 (m, 2H), 2.51-2.44 (m, 2H), 2.38-2.35 (m, 1H), 2.25-2.20 (m, 1H), 2.14 (s, 3H), 1.85-1.81 (m, 4H), 0.91 (t, J=6.9 Hz, 3H), 0.87-0.81 (m, 6H), 0.80 (t, J=7.5 Hz, 3H); HRESI-TOF m/z 1007.4575 (C$_{54}$H$_{66}$N$_6$O$_{11}$S+H$^+$, required 1007.4583). [α]$_D^{23}$−27 (c 0.03, CCl$_3$).

Compound 62

Generated by Boc deprotection of Compound 63 with 4 M HCl in dioxane (92% yield). $^1$H NMR (600 MHz, CDCl$_3$) δ 8.04 (s, 1H), 7.92 (d, J=8.1 Hz, 2H), 7.49-7.43 (m, 1H), 7.20-6.98 (m, 3H), 6.67-6.63 (m, 2H), 6.15 (s, 1H), 5.99 (s, 1H), 5.87 (dd, J=10.4, 4.9 Hz, 1H), 5.50 (s, 1H), 5.38-5.25 (m, 1H), 4.11-3.99 (m, 2H), 3.85-3.80 (m, 7H), 3.77 (s, 1H), 3.63 (s, 3H), 3.44-3.36 (m, 2H), 3.26-3.20 (m, 2H), 2.89 (m, 3H), 2.88-2.83 (m, 2H), 2.74 (s, 3H), 2.71-2.66 (m, 2H), 2.50-2.44 (m, 2H), 2.41-2.34 (m, 2H), 2.28-2.17 (m, 1H), 2.13 (s, 3H), 2.05-2.01 (m, 1H), 1.88-1.80 (m, 1H), 1.28 (m, 4H), 0.91 (t, J=6.9 Hz, 2H), 0.88-0.86 (m, 2H), 0.84 (t, J=7.3 Hz, 3H), 0.79 (t, J=7.4 Hz, 3H), HRESI-TOF m/z 943.4964 (C$_{54}$H$_{66}$N$_6$O$_9$+H$^+$, required 943.4964). [α]r$_D^{23}$−21 (c 0.02, CHCl$_3$).

Compound 63

Method 2 was followed providing Compound 63 in 41% yield. $^1$H NMR (600 MHz, CDCl$_3$) δ 9.86 (s, 1H), 8.03 (s, 1H), 7.48 (d, J=7.9 Hz, 1H), 7.46 (s, 1H), 7.4 (d, J=8.4 Hz, 1H), 7.19-7.07 (m, 4H), 6.68 (s, 1H), 6.15 (s, 1H), 6.08 (s, 1H), 5.88 (dd, J=10.5, 4.8 Hz, 1H), 5.51 (s, 1H), 5.34-5.32 (m, 1H), 5.14 (s, 1H), 4.03-3.98 (m, 2H), 3.83 (d, J=7.7 Hz, 3H), 3.78-3.77 (m, 2H), 3.62 (s, 1H), 3.44-3.42 (m, 3H), 3.38 (s, 1H), 3.37-3.30 (m, 3H), 3.27-3.17 (m, 2H), 3.17-3.08 (m, 3H), 2.85 (d, J=15.9 Hz, 2H), 2.75 (s, 1H), 2.70 (s, 1H), 2.49-2.43 (m, 3H), 2.40-2.34 (m, 2H), 2.22 (dt, J=15.1, 8.1 Hz, 2H), 2.14 (s, 1H), 1.88-1.81 (m, 2H), 1.57 (s, 9H), 1.47 (s, 3H), 1.40-1.33 (m, 2H), 1.28 (s, 3H), 0.92-0.83 (m, 4H), 0.79 (t, J=7.5 Hz, 3H); HRESI-TOF m/z 1043.5487 (C$_{59}$H$_{74}$N$_6$O$_{11}$+H$^+$, required 1043.5488). [α]$_D^{23}$−15 (c 0.03, CHCl$_3$).

Compound 64

Method 1 was followed providing Compound 64 as an off-white resin in 75% yield. $^1$H NMR (CDCl$_3$, 600 MHz) δ 9.88 (br s, 1H), 8.03 (s, 1H), 7.92 (s, 1H), 7.44-7.42 (m, 1H), 7.13-7.06 (m, 3H), 6.75-6.69 (m, 2H), 6.64 (s, 1H), 6.12 (s, 1H), 5.98 (s, 1H), 5.86-5.84 (m, 1H), 5.47 (s, 1H), 5.31-5.29 (m, 1H), 3.99 (br s, 1H), 3.82-3.80 (m, 6H), 3.75 (s, 1H), 3.71-3.69 (m, 2H), 3.61 (br s, 2H), 3.39-3.35 (m, 2H), 3.30 (td, J=4.6, 9.5 Hz, 1H), 3.23-3.21 (m, 1H), 3.16-3.13 (m, 1H), 3.01 (s, 6H), 2.85 (d, J=14.4 Hz, 1H), 2.72 (s, 3H), 2.68-2.65 (m, 2H), 2.45-2.42 (m, 1H), 2.39-2.36 (m, 1H), 2.21-2.16 (m, 2H), 2.11 (s, 3H), 1.85-1.77 (m, 2H), 1.70-1.68 (m, 2H), 1.34-1.32 (m, 2H), 1.25 (s, 2H), 0.84-0.77 (m, 6H); IR (film) $v_{max}$ 3470, 2928, 1738, 1608, 1230, 1041 cm$^{-1}$; HRESI-TOF m/z 957.5122 (C$_{55}$H$_{68}$N$_6$O$_9$+H$^+$, required 959.5120).

Compound 65

A solution of Compound 66 (14 mg, 13 μmol) in anhydrous CH$_2$Cl$_2$ (1.0 mL) was cooled to 0° C. TFA (1.0 mL) was added and the reaction mixture was stirred at that temperature for 30 minutes. The solvent was removed and the crude residue taken up with 10% MeOH:CH$_2$Cl$_2$, washed with saturated aqueous NaHCO$_3$, saturated aqueous NaCl, and dried over Na$_2$SO$_4$. Evaporation in vacuo yielded the crude product that was purified by PTLC (SiO$_2$) to provide Compound 65 (12.5 mg, 100%) as an off-white solid. $^1$H NMR (600 MHz, CDCl$_3$) δ 9.83 (br s, 2H), 8.05-7.99 (m, 2H), 7.54-7.45 (m, 3H), 7.19-1.16 (m, 1H), 7.14-7.11 (m, 1H), 6.64 (br s, 2H), 6.15-6.14 (m, 1H), 6.12-6.11 (m, 1H), 5.88 (dd, J=10.1, 4.7 Hz, 1H), 5.49 (s, 1H), 5.33 (d, J=9.9 Hz, 1H), 4.61-4.59 (m, 2H), 4.01 (br s, 1H), 3.84 (s, 3H), 3.83 (s, 3H), 3.78 (s, 1H), 3.64-3.63 (m, 3H), 3.40 (dd, J=16.7, 4.7 Hz, 2H), 3.35-3.31 (td, J=9.4, 4.8 Hz, 2H), 3.14-3.11 (m, 2H), 2.85 (d, J=16.5 Hz, 1H), 2.75 (s, 3H), 2.69-2.69 (m, 1H), 2.51-2.48 (m, 2H), 2.20 (s, 2H), 2.13 (s, 3H), 2.04-2.02 (m, 1H), 1.87-1.80 (m, 3H), 1.60-1.56 (m, 2H), 1.45-1.36 (m, 3H), 1.28-1.27 (m, 4H), 0.92-0.82 (m, 6H); ESI-MS m/z 943.5 (C$_{54}$H$_{66}$N$_6$O$_9$+H$^+$, required 943.50).

Compound 66

Method 2 was followed using 26.6 mg of 20'-aminovinblastine (6, 0.033 mmol) to provide 10.1 mg of Compound 66 as a white solid, yield: 29%. $^1$H NMR (600 MHz, CDCl$_3$) δ 9.83 (br s, 1H), 8.16 (s, 1H), 7.99 (s, 1H), 7.68 (d, J=7.9 Hz, 2H), 7.58 (d, J=7.7 Hz, 1H), 7.32-7.31 (m, 2H), 7.19 (d, J=7.5 Hz, 1H), 7.15 (t, J=7.6 Hz, 2H), 6.91 (br s, 1H), 6.54 (s, 1H), 6.11 (s, 1H), 5.88-5.86 (m, 1H), 5.48 (s, 1H), 5.32 (d, J=10.1 Hz, 1H), 4.94 (br s, 1H), 4.35-4.34 (m, 2H), 3.81 (s, 3H), 3.80 (s, 3H), 3.75 (s, 1H), 3.63 (s, 3H), 3.39-3.34 (m, 2H), 3.32-3.30 (m, 1H), 3.27-3.26 (m, 1H), 3.13 (d, J=10.1 Hz, 2H), 2.81 (d, J=16.2 Hz, 1H), 2.74 (s, 3H), 2.65 (s, 1H), 2.53 (q, J=7.2 Hz, 1H), 2.45-2.40 (m, 1H), 2.32-2.29 (m, 1H), 2.12 (s, 3H), 1.84-1.78 (m, 2H), 1.72-1.67 (m, 1H), 1.57-1.54 (m, 1H), 1.46 (s, 9H), 1.35-1.30 (m, 2H), 1.28 (s, 3H), 1.12-1.09 (m, 1H), 0.86-0.83 (m, 6H); ESI-MS m/z 1043.5 (C$_{59}$H$_{74}$N$_6$O$_{11}$+H$^+$, required 1043.55).

Compound 67

Method 1 was followed using 3.0 mg of 20'-aminovinblastine (6, 0.04 mmol) to provide Compound 67 as a white solid, yield: 56%. $^1$H NMR (600 MHz, CDCl$_3$) δ 9.84 (s, 1H), 8.00-7.99 (m, 3H), 7.44 (d, J=8.0 Hz, 1H), 7.14-7.05 (m, 3H), 6.97 (d, J=8.6 Hz, 2H), 6.64 (s, 1H), 6.11 (s, 1H), 6.01 (s, 1H), 5.84 (dd, J=10.0, 4.4 Hz, 1H), 5.47 (s, 1H), 5.30-5.28 (m, 1H), 4.01-3.96 (m, 2H), 3.84 (s, 3H), 3.81 (s, 3H), 3.79 (s, 3H), 3.74 (s, 1H), 3.59 (s, 3H), 3.39-3.35 (m, 2H), 3.32-3.28 (m, 1H), 3.24-3.04 (m, 5H), 2.82 (d, J=16.2 Hz, 1H), 2.71 (s, 3H), 2.66 (t, J=6.6 Hz, 2H), 2.47-2.41 (m, 2H), 2.35 (d, J=13.7 Hz, 1H), 2.21-2.16 (m, 1H), 2.10 (s, 3H), 1.84-1.77 (m, 3H), 1.35-1.31 (m, 2H), 1.25 (s, 1H), 0.88-0.86 (m, 1H), 0.81 (t, J=7.3 Hz, 3H), 0.76 (t, J=7.4 Hz, 3H); ESI-MS m/z 944.3 (C$_{54}$H$_{65}$N$_5$O$_{10}$+H$^+$, required 944.48).

Compound 68

Method 1 was followed using 3.4 mg of 20'-aminovinblastine (6, 0.04 mmol) to provide Compound 68 as a white solid, yield: 39%. $^1$H NMR (600 MHz, CDCl$_3$) δ 9.85 (br s, 1H), 8.04 (s, 1H), 7.60 (s, 1H), 7.50 (d, J=0.3 Hz, 1H), 7.45 (d, J=7.5 Hz, 1H), 7.39 (t, J=7.9 Hz, 1H), 7.13 (d, J=7.2 Hz, 1H), 7.10-7.07 (m, 2H), 7.03 (dd, J=8.2, 1.7 Hz, 1H), 6.63 (s, 1H), 6.11-6.09 (m, 2H), 5.85-5.83 (m, 1H), 5.47 (s, 1H), 5.29-5.28 (m, 1H), 3.93-3.91 (m, 1H), 3.86 (s, 3H), 3.79 (s, 6H), 3.74 (s, 1H), 3.57 (s, 3H), 3.41-3.35 (m, 2H), 3.30 (td, J=9.5, 4.7 Hz, 1H), 3.23-3.20 (m, 1H), 3.12-3.10 (m, 2H), 2.82 (d, J=16.1 Hz, 1H), 2.71 (s, 3H), 2.66 (s, 1H), 2.40 (d, J=13.5 Hz, 1H), 2.35 (d, J=13.8 Hz, 1H), 2.21-2.16 (m, 1H), 2.09 (s, 3H), 1.91-1.89 (m, 2H), 1.84-1.77 (m, 2H), 1.63-1.59 (m, 4H), 1.34-1.31 (m, 2H), 1.26-1.24 (m, 2H), 0.80 (t, J=7.4 Hz, 3H), 0.78-0.75 (m, 3H); ESI-MS m/z 944.3 (C$_{54}$H$_{65}$N$_5$O$_{10}$+H$^+$, required 944.48).

Compound 69

Method 1 was followed using 2.7 mg of Compound 6 (0.03 mmol) to provide 1.6 mg of Compound 69 as a white solid, yield: 51%. $^1$H NMR (600 MHz, CDCl$_3$) δ 9.87 (s, 1H), 8.25 (d, J=7.7 Hz, 1H), 8.02-8.00 (m, 2H), 7.45-7.42 (m, 2H), 7.10-7.09 (m, 1H), 7.08-7.05 (m, 2H), 7.03-7.02 (d, J=8.3 Hz, 1H), 6.59 (s, 1H), 6.09 (s, 1H), 5.85-5.82 (m, 1H), 5.45 (s, 1H), 5.27 (s, 1H), 4.09 (s, 3H), 4.07 (s, 2H), 3.79 (s, 3H), 3.76 (s, 3H), 3.73 (s, 3H), 3.35-3.34 (m, 2H), 3.28-3.27 (m, 2H), 3.13-3.12 (m, 1H), 3.03-3.02 (m, 1H), 2.81 (d, J=16.2 Hz, 1H), 2.70 (s, 3H), 2.64 (s, 1H), 2.39 (d, J=14.2 Hz, 1H), 2.25-2.23 (m, 1H), 2.18 2.15 (m, 1H), 2.09 (s, 3H), 1.84-1.73 (m, 7H), 1.33-1.29 (m, 3H), 1.24 (s, 2H), 0.78 (t, J=7.2 Hz, 6H); ESI-MS m/z 944.3 (C$_{54}$H$_{65}$N$_5$O$_{10}$+H$^+$, required 944.48).

Compound 70

Method 2 was followed providing Compound 70 in 31% yield. $^1$H NMR (600 MHz, CDCl$_3$) δ 9.82 (s, 1H), 8.02 (s, 1H), 7.56 (s, 1H), 7.48-7.39 (m, 2H), 7.16-7.04 (m, 3H), 6.98-6.89 (m, 1H), 6.12 (s, 1H), 6.10-6.05 (m, 1H), 5.91-5.84 (m, 1H), 5.48 (s, 1H), 5.34-5.28 (m, 1H), 3.97 (s, 3H), 3.92 (s, 3H), 3.90 (d, J=5.1 Hz, 3H), 3.82 (s, 3H), 3.80 (s, 3H), 3.40-3.34 (m, 2H), 3.31 (d, J=4.9 Hz, 1H), 3.07 (s, 2H), 2.96 (s, 1H), 2.88 (s, 1H), 2.83 (d, J=16.4 Hz, 1H), 2.72 (s, 3H), 2.49-2.39 (m, 2H), 2.11 (s, 3H), 2.03-1.93 (m, 2H), 1.88-1.77 (m, 3H), 0.90-0.81 (m, 8H); HRESI-TOF m/z 974.4908 (C$_{55}$H$_{67}$N$_5$O$_{11}$+H$^+$, required 974.4915). [α]$_D^{23}$ −26 (c 0.2, CHCl$_3$).

Compound 71

Method 1 was followed using 2.4 mg of 20'-aminovinblastine (6, 0.03 mmol) to provide Compound 71 as a white solid, yield: 50%. $^1$H NMR (600 MHz, CDCl$_3$) δ 8.04 (s, 1H), 7.48 (d, J=7.7 Hz, 1H), 7.31 (s, 1H), 7.18 (s, 2H), 7.15 (d, J=7.3 Hz, 1H), 7.10 (dd, J=14.4, 7.5 Hz, 2H), 6.61 (s, 1H), 6.09 (s, 1H), 6.02 (s, 1H), 5.84 (dd, J=10.3, 4.0 Hz, 1H), 5.46 (s, 1H), 5.29 (d, J=10.3 Hz, 1H), 3.92 (s, 6H), 3.89 (d, J=3.3 Hz, 2H), 3.87 (s, 3H), 3.79 (s, 3H), 3.76 (s, 3H), 3.74 (s, 1H), 3.71-3.68 (m, 1H), 3.49 (s, 3H), 3.43 (d, J=12.9 Hz, 1H), 3.36 (td, J=13.3, 4.3 Hz, 2H), 3.31-3.24 (m, 2H), 3.20-3.10 (m, 2H), 2.81 (d, J=16.2 Hz, 1H), 2.70 (s, 3H), 2.65 (s, 1H), 2.46-2.37 (m, 2H), 2.31 (d, J=14.5 Hz, 1H), 2.21-2.16 (m, 1H), 2.10 (s, 3H), 1.83-1.75 (m, 4H), 1.69-1.67 (m, 1H), 1.33 (dd, J=14.2, 6.9 Hz, 2H), 0.88-0.85 (m, 1H), 0.80 (t, J=7.4 Hz, 3H), 0.76 (t, J=7.2 Hz, 3H); ESI-MS m/z 1004.5 (C$_{56}$H$_{69}$N$_5$O$_{12}$+H$^+$, required 1004.50).

Compound 72

Method 1 was followed providing Compound 72 in 51% yield. ¹H NMR (500 MHz, CDCl₃) δ 9.83 (s, 1H), 8.11-7.89 (m, 3H), 7.44 (d, J=7.9 Hz, 1H), 7.20-7.03 (m, 3H), 7.02-6.89 (m, 2H), 6.65 (s, 1H), 6.12 (s, 1H), 6.02 (s, 1H), 5.85 (dd, J=10.1, 4.5 Hz, 1H), 5.48 (s, 1H), 5.30 (d, J=10.2 Hz, 1H), 4.07 (q, J=7.0 Hz, 2H), 4.05-3.90 (m, 2H), 3.82 (s, 3H), 3.80 (s, 3H), 3.75 (s, 1H), 3.60 (s, 3H), 3.42-3.34 (m, 2H), 3.33-3.28 (m, 1H), 3.26-3.03 (m, 4H), 2.82 (d, J=16.2 Hz, 1H), 2.72 (s, 3H), 2.67-2.65 (m, 1H), 2.50-2.39 (m, 2H), 2.36 (d, J=13.4 Hz, 1H), 2.26-2.14 (m, 1H), 2.11 (s, 3H), 2.05-1.97 (m, 1H), 1.90-1.75 (m, 3H), 1.42 (t, J=7.0 Hz, 4H), 1.37-1.26 (m, 3H), 0.86-0.73 (m, 7H); HRESI-TOF m/z 958.4960 (C₅₅H₆₇N₅O₁₀+H⁺, required 958.4960). [α]$_D^{23}$ −0.06 (c 0.4, CHCl₃).

Compound 73

Method 2 was followed providing Compound 73 in 53% yield. ¹H NMR (600 MHz, CDCl₃) δ 8.05 (s, 1H), 7.49-7.46 (m, 2H), 7.42-7.38 (m, 2H), 7.23 (t, J=7.2 Hz, 1H), 7.15 (t, J=7.9 Hz, 2H), 6.93 (d, J=8.7 Hz, 2H), 6.84 (d, J=8.4 Hz, 1H), 6.48 (s, 1H), 6.15 (s, 1H), 6.00 (s, 1H), 5.92 (dd, J=9.8, 5.3 Hz, 1H), 5.44 (s, 1H), 5.32 (s, 1H), 5.14 (s, 1H), 4.24-4.14 (m, 5H), 3.88-3.84 (m, 5H), 3.72-3.70 (m, 2H), 3.49-3.44 (m, 2H), 3.38 (t, 1H), 3.32-3.26 (m, 2H), 3.19-3.16 (m, 2H), 3.09-3.03 (m, 2H), 2.95 (s, 2H), 2.78 (s, 2H), 2.67-2.64 (m, 1H), 2.25-2.22 (m, 1H), 2.16-2.07 (m, 4H), 1.50 (td, J=6.9, 5.2 Hz, 6H), 1.26-1.23 (m, 4H), 0.97 (t, J=7.3 Hz, 3H), 0.92-0.86 (m, 4H), 0.83-0.79 (m, 4H); HRESI-TOF m/z 1002.5219 (C₅₇H₇₁N₅O₁₁+H⁺, required 1002.5219). [α]$_D^{23}$ −2 (c 0.19, CHCl₃).

Compound 74

Method 2 was followed providing Compound 74 in 97% yield. ¹H NMR (600 MHz, CDCl₃) δ 9.86 (br s, 1H), 8.06 (s, 1H), 7.80-7.73 (m, 2H), 7.22 (d, J=8.4 Hz, 1H), 7.19 (d, J=8.4 Hz, 1H), 7.17-7.09 (m, 3H), 6.67 (s, 1H), 6.14 (s, 1H), 6.10 (s, 1H), 5.85 (dd, J=4.5, 10.5 Hz, 1H), 5.51 (s, 1H), 5.33-5.31 (m, 2H), 3.84 (br s, 1H), 3.81 (s, 3H), 3.77 (s, 3H), 3.75 (s, 1H), 3.58 (s, 3H), 3.38-3.35 (m, 2H), 3.30 (td, J=4.6, 10.5 Hz, 1H), 3.25-3.06 (m, 4H), 2.83 (d, J=16.2 Hz, 1H), 2.72-2.66 (m, 4H), 2.48-2.34 (m, 5H), 2.22-2.17 (m, 2H), 2.11 (s, 3H), 1.99 (br s, 1H), 1.85-1.77 (m, 3H), 1.67 (br s, 3H), 1.36-1.28 (m, 6H), 1.27-1.25 (m, 2H), 0.82 (t, J=7.5 Hz, 3H), 0.77 (t, J=7.5 Hz, 3H); HRESI-TOF m/z 972.5117 (C₅₆H₆₉N₅O₁₀+H⁺, required 972.5117). [α]$_D^{23}$ −0.44 (c 0.11, CHCl₃).

Compound 75

Method 2 was followed providing Compound 75 as a clear resin in 70% yield. ¹H NMR (CDCl₃, 600 MHz) δ 8.04 (s, 1H), 7.95 (d, J=7.8 Hz, 2H), 7.45 (d, J=7.8 Hz, 1H), 7.15-7.07 (m, 5H), 6.65 (s, 1H), 6.12 (s, 1H), 6.03 (s, 1H), 5.85 (dd, J=4.5, 9.9 Hz, 1H), 5.48 (s, 1H), 5.30 (s, 1H), 4.01-3.97 (m, 1H), 3.81 (s, 3H), 3.80 (s, 3H), 3.75 (s, 1H), 3.60 (s, 3H), 3.49 (s, 1H), 3.41-3.36 (m, 2H), 3.30 (td, J=4.8, 9.3 Hz, 1H), 3.26-3.18 (m, 2H), 3.14-3.11 (m, 2H), 2.83 (d, J=16.2 Hz, 1H), 2.72-2.67 (m, 4H), 2.48-2.41 (m, 2H), 2.35 (d, J=13.8 Hz, 1H), 2.22-2.17 (m, 1H), 2.11 (s, 3H), 2.00 (br s, 1H), 1.85-1.77 (m, 3H), 1.48-1.32 (m, 11H), 1.27-1.25 (m, 2H), 0.81 (t, J=7.2 Hz, 3H), 0.77 (t, J=7.5 Hz, 3H); IR (film) ν$_{max}$ 3465, 2931, 1738, 1493, 1241, 1160 cm⁻¹; HRESI-TOF m/z 986.5261 (C₅₇H₇₁N₅O₁₀+H⁺, required 986.5273).

Compound 76

Method 1 was followed providing Compound 76 as a pale yellow resin in 70% yield. ¹H NMR (CDCl₃, 600 MHz) δ 9.83 (br s, 1H), 8.02-8.00 (m, 2H), 7.86 (br s, 1H), 7.45-7.36 (m, 3H), 7.21-6.96 (m, 7H), 6.64 (s, 1H), 6.11 (s, 1H), 6.04 (s, 1H), 5.86-5.85 (m, 1H), 5.55 (d, J=5.4 Hz, 1H), 5.31-5.29 (m, 1H), 3.99 (br s, 1H), 3.81 (s, 3H), 3.80 (s, 3H), 3.75 (s, 1H), 3.57 (s, 3H), 3.39-3.35 (m, 2H), 3.32-3.28 (m, 2H), 3.17-3.10 (m, 3H), 2.84 (d, J=15.6 Hz, 1H), 2.72 (s, 3H), 2.67 (s, 1H), 2.47-2.41 (m, 1H), 2.36-2.33 (m, 2H), 2.18-2.17 (m, 2H), 2.11 (s, 3H), 2.09-2.04 (m, 2H), 1.92-1.80 (m, 2H), 1.61 (br s, 1H), 1.35-1.33 (m, 2H), 1.26-1.25 (m, 2H), 0.89-0.80 (m, 6H); IR (film) ν$_{max}$ 2926, 1738, 1613, 1488, 1237, 1040, 740 cm⁻¹; HRESI-TOF m/z 1006.4962 (C₅₉H₆₇N₅O₁₀+H⁺, required 1006.4960).

Compound 77

Method 2 was followed providing Compound 77 in 42% yield. ¹H NMR (600 MHz, CDCl₃) δ 9.84 (s, 1H), 8.04-7.97 (m. 3H), 7.45 (d, J=7.8 Hz, 1H), 7.44-7.40 (m, 2H), 7.37 (t, J=7.6 Hz, 2H), 7.35-7.29 (m, 1H), 7.17-7.03 (m, 5H), 6.65 (s, 1H), 6.12 (s, 1H), 6.02 (s, 1H), 5.85 (dd, J=10.3, 4.5 Hz, 1H), 5.48 (s, 1H), 5.30 (d, J=10.3 Hz, 1H), 5.11 (s, 2H), 4.05-3.95 (m, 2H), 3.81 (s, 3H), 3.80 (s, 3H), 3.75 (s, 1H), 3.56 (s, 3H), 3.44-3.34 (m, 2H), 3.31 (td, J=9.5, 4.7 Hz, 1H), 3.26-3.04 (m, 4H), 2.83 (d, J=16.1 Hz, 1H), 2.72 (s, 3H), 2.67 (t, J=6.9 Hz, 2H), 2.50-2.39 (m, 1H), 2.35 (d, J=13.7 Hz, 1H), 2.24-2.16 (m, 1H), 2.11 (s, 3H), 2.04-1.96 (m, 1H), 1.89-1.74 (m, 3H), 1.36-1.20 (m, 3H), 0.94-0.83 (m, 2H), 0.81 (t, J=7.4 Hz, 3H), 0.77 (t, J=7.4 Hz, 3H); HRESI-TOF m/z 1020.5116 (C₆₀H₆₉N₅O₁₀+H⁺, required 1020.5117). [α]$_D^{23}$ −2 (c 0.16, CHCl₃).

Compound 78

Method 2 was followed providing Compound 77 as an off-white resin in 75% yield. ¹H NMR (CDCl₃, 600 MHz) δ 8.11 (d, J=7.8 Hz, 2H), 7.45 (d, J=8.4 Hz, 1H), 7.33 (d, J=8.4 Hz, 2H), 7.16-7.07 (m, 3H), 6.65 (s, 1H), 6.12 (s, 1H), 6.06 (s, 1H), 5.86 (dd, J=4.8, 10.8 Hz, 1H), 5.48 (s, 1H), 5.30 (d, J=9.6 Hz, 1H), 4.02-3.97 (m, 1H), 3.82 (s, 3H), 3.80 (s, 3H), 3.75 (s, 1H), 3.60 (s, 3H), 3.42-3.36 (m, 2H), 3.31 (td, J=4.2, 9.6 Hz, 1H), 3.26-3.21 (m, 1H), 3.17-3.10 (m, 4H), 2.82 (d, J=15.6 Hz, 1H), 2.72-1.68 (m, 5H), 2.48-2.42 (m, 1H), 2.34 (d, J=13.8 Hz, 1H), 2.22-2.17 (m, 1H), 2.11 (s, 3H), 1.98 (br s, 1H), 1.85-1.77 (m, 3H), 1.48 (br s, 1H), 1.38-1.34 (m, 2H), 1.27-1.25 (m, 3H), 0.83 (t, J=7.2 Hz, 3H), 0.77 (t, J=7.5 Hz, 3H); IR (film) ν$_{max}$ 3464, 2933, 1738, 1497, 1254, 1224, 1041 cm⁻¹; HRESI-TOF m/z 998.4512 (C₅₄H₆₂F₃N₅O₁₀+H⁺, required 998.4521).

Compound 79

Method 2 was followed providing Compound 79 in 33% yield. ¹H NMR (600 MHz, CDCl₃) δ 9.81 (s, 1H), 8.02 (s, 1H), 7.88 (s, 1H), 7.55 (t, J=8.0 Hz, 1H), 7.46 (d, J=8.0 Hz, 1H), 7.36 (d, J=8.6 Hz, 1H), 7.21-7.05 (m, 3H), 6.65 (s, 1H), 6.12 (s, 1H), 6.08 (s, 1H), 5.88-5.78 (m, 1H), 5.49 (s, 1H), 5.33-5.28 (m, 1H), 4.02-3.86 (m, 2H), 3.82 (s, 3H), 3.80 (s, 3H), 3.75 (s, 1H), 3.57 (s, 3H), 3.45-3.35 (m, 2H), 3.35-3.27 (m, 1H), 3.27-3.20 (m, 1H), 3.15-3.08 (m, 2H), 2.82 (d, J=16.2 Hz, 1H), 2.72 (s, 3H), 2.70-2.65 (m, 2H), 2.50-2.43 (m, 1H), 2.40 (d, J=13.1 Hz, 1H), 2.32 (d, J=13.8 Hz, 1H), 2.24-2.16 (m, 2H), 1.97-1.75 (m, 2H), 1.34 (dd, J=14.6, 6.0 Hz, 1H), 1.56-1.51 (m, 3H), 1.30-1.23 (m, 5H), 0.95-0.85 (m, 1H), 0.83 (t, J=7.4 Hz, 3H), 0.78 (t, J=7.4 Hz, 3H); HRESI-TOF m/z 998.4519 (C₅₄H₆₂F₃N₅O₁₀+H⁺, required 998.4521). [α]$_D^{23}$ −27 (c 0.08, CHCl₃).

Compound 80

Method 1 was followed providing Compound 80 in 67% yield. ¹H NMR (600 MHz, CDCl₃) δ 8.20 (dd, J=7.8, 1.8 Hz, 1H), 8.06 (s, 1H), 7.55-7.43 (m, 4H), 7.37 (d, J=7.8 Hz, 1H), 7.19-7.08 (m, 3H), 6.61 (s, 1H), 6.13 (s, 1H), 5.86 (dd, J=10.2, 5.0 Hz, 1H), 5.50 (s, 1H), 5.31 (d, J=7.8 Hz, 1H), 3.82 (s, 3H), 3.80 (s, 3H), 3.72-3.69 (m, 1H), 3.62 (d, J=13.6 Hz, 1H), 3.50-3.42 (m, 4H), 3.42-3.36 (m, 1H), 3.35-3.27 (m, 2H), 3.24-3.12 (m, 3H), 2.81 (t, J=8.0 Hz, 2H), 2.73 (s, 3H), 2.66 (s, 2H), 2.48-2.43 (m, 2H), 2.32 (d, J=14.3 Hz, 1H), 2.23-2.19 (m, 2H), 2.13 (s, 3H), 2.03-1.91 (m, 1H), 1.71-1.65 (m, 1H), 1.42-1.26 (m, 4H), 0.98-0.85 (m, 5H), 0.82 (t, J=7.4 Hz, 3H); HRESI-TOF m/z 998.4519 ($C_{54}H_{62}F_3N_5O_{10}$+H$^+$, required 998.4521). $[\alpha]_D^{23}$ −9 (c 0.18, CHCl$_3$).

Compound 81

Method 2 was followed providing Compound 81 in 45% yield. $^1$H NMR (600 MHz, CDCl$_3$) δ 9.83 (s, 1H), 8.09 (d, J=8.3 Hz, 2H), 8.00 (s, 1H), 7.48-7.42 (m, 1H), 7.23 (d, J=8.5 Hz, 2H), 7.16-7.05 (m, 4H), 6.66 (s, 1H), 6.12 (s, 1H), 6.05 (s, 1H), 5.86 (dd, J=10.4, 4.4 Hz, 1H), 5.48 (s, 1H), 5.30 (d, J=10.4 Hz, 1H), 3.99 (s, 1H), 3.82 (s, 3H), 3.80 (s, 3H), 3.75 (s, 1H), 3.60 (s, 3H), 3.46-3.36 (m, 3H), 3.34-3.26 (m, 2H), 3.22 (t, J=12.0 Hz, 1H), 3.12-3.08 (m, 2H), 2.83 (d, J=16.0 Hz, 1H), 2.72 (s, 3H), 2.68 (d, J=11.0 Hz, 2H), 2.47 (dd, J=10.7, 6.6 Hz, 1H), 2.42 (d, J=13.9 Hz, 1H), 2.33 (d, J=13.7 Hz, 1H), 2.22-2.17 (m, 1H), 2.11 (s, 3H), 1.97 (s, 1H), 1.88-1.78 (m, 3H), 1.40-1.30 (m, 3H), 1.22 (d, J=7.2 Hz, 1H), 1.19 (q, J=7.2 Hz, 2H), 1.16-1.11 (m, 2H); HRESI-TOF m/z 980.4617 ($C_{54}H_{63}F_2N_5O_{10}$+H$^+$, required 980.4616). $[\alpha]_D^{23}$ −5 (c 0.29, CHCl$_3$).

Compound 82

Method 1 was followed using 2.5 mg of 20'-aminovinblastine (6, 0.003 mmol) to provide 1.0 mg of Compound 82 as a white solid, yield: 32%. $^1$H NMR (600 MHz, CDCl$_3$) δ 9.74 (br s, 2H), 8.11 (s, 1H), 8.06-8.04 (m, 2H), 7.47 (s, 1H), 7.20 (d, J=7.7 Hz, 1H), 7.14-7.08 (m, 2H), 6.43 (s, 1H), 6.12 (s, 1H), 5.96 (s, 1H), 5.90 (dd, J=9.4, 3.8 Hz, 1H), 5.43 (s, 1H), 5.33 (d, J=10.2 Hz, 1H), 3.99 (s, 1H), 3.97 (s, 3H), 3.84 (s, 3H), 3.80 (s, 3H), 3.76-3.74 (m, 1H), 3.68 (s, 3H), 3.45-3.39 (m, 2H), 3.35 (s, 1H), 3.26-3.25 (m, 1H), 3.20-3.17 (m, 2H), 2.85 (d, J=15.9 Hz, 1H), 2.75 (s, 3H), 2.67 (s, 1H), 2.56-2.52 (m, 1H), 2.17 (s, 1H), 2.11 (s, 3H), 2.01-1.97 (m, 1H), 1.82-1.77 (m, 2H), 1.62-1.58 (m, 3H), 1.45 (d, J=7.1 Hz, 1H), 1.32-1.30 (m, 2H), 1.24-1.22 (m, 4H), 0.88 (t, J=6.5 Hz, 3H), 0.79 (t, J=7.4 Hz, 3H); ESI-TOF m/z 1012.5 ($C_{55}H_{64}F_3N_5O_{10}$+H$^+$, required 1012.47). $[\alpha]_D^{23}$ −24 (c 0.019, CHCl$_3$)

Compound 83

Method 2 was followed providing Compound 83 in 41% yield. $^1$H NMR (600 MHz, CDCl$_3$) δ 9.84 (s, 1H), 8.04 (s, 1H), 7.68 (d, J=1.7 Hz, 1H), 7.49 (d, J=8.0 Hz, 1H), 7.37 (d, J=8.3 Hz, 1H), 7.20-7.08 (m, 3H), 6.68 (s, 1H), 6.14 (s, 1H), 6.11 (s, 1H), 5.91-5.88 (m, 1H), 5.51 (s, 1H), 5.36-5.30 (m, 1H), 3.99 (s, 1H), 3.95-3.90 (m, 1H), 3.83-3.81 (m, 6H), 3.78 (s, 2H), 3.60 (s, 3H), 3.47-3.30 (m, 4H), 3.30-3.09 (m, 4H), 2.85 (d, J=16.2 Hz, 1H), 2.74-2.70 (m, 5H), 2.52-2.40 (m, 2H), 2.35 (d, J=13.5 Hz, 1H), 2.23 (dt, J=15.3, 8.1 Hz, 1H), 2.14 (s, 3H), 1.93-1.79 (m, 3H), 1.40-1.33 (m, 3H), 1.28 (s, 3H), 0.90-0.79 (m, 8H); HRESI-TOF m/z 1028.4633 ($C_{55}H_{64}F_3N_5O_{11}$+H$^+$, required 1028.4627). $[\alpha]_D^{23}$ +12 (c 0.07, CHCl$_3$).

Compound 84

Method 2 was followed providing Compound 84 in 61% yield. $^1$H NMR (600 MHz, CDCl$_3$) δ 9.80 (s, 1H), 8.04 (s, 1H), 7.98 (s, 1H), 7.83-7.81 (m, 1H), 7.55 7.53 (m, 1H), 7.34 (d, J=8.0 Hz, 2H), 7.23-7.21 (m, 1H), 7.14 (d, J=8.0 Hz, 2H), 6.45 (s, 1H), 6.14 (s, 1H), 6.08-6.03 (m, 1H), 5.94-5.88 (m, 1H), 5.52-5.48 (m, 1H), 5.45 (s, 1H), 5.36-5.31 (m, 1H), 3.9-3.82 (m, 8H), 3.82 (s, 3H), 3.72-3.70 (m, 2H), 3.64-3.61 (m, 1H), 3.43-3.36 (m, 1H), 3.33 (td, J=9.5, 5.0 Hz, 1H), 3.20-3.18 (m, 1H), 3.09-3.05 (m, 2H), 2.88-2.85 (m, 2H), 2.79-2.75 (m, 2H), 2.71-2.69 (m, 2H), 2.53 (s, 3H), 2.24-2.20 (m, 1H), 2.14 (s, 3H), 2.01-1.97 (m, 1H), 1.61-1.59 (m, 4H), 1.28 (s, 2H), 0.99-0.95 (m, 2H), 0.92-0.79 (m, 7H); HRESI-TOF m/z 960.4577 ($C_{54}H_{65}N_5O_9S$+H$^+$, required 960.4576). $[\alpha]_D^{23}$ −8 (c 0.19, CHCl$_3$).

Compound 85

Method 2 was followed providing Compound 85 in 54% yield. $^1$H NMR (600 MHz, CDCl$_3$) δ 9.78 (s, 1H), 8.09-8.02 (m, 1H), 7.77 (s, 1H), 7.59 (d, J=7.0 Hz, 1H), 7.45-7.39 (m, 3H), 7.23 (t, J=7.6 Hz, 1H), 7.15 (t, J=7.8 Hz, 2H), 6.45 (s, 1H), 6.15 (s, 1H), 6.06 (s, 1H), 5.92 (dd, J=10.5, 4.9, 1H), 5.45 (s, 1H), 5.35 (d, J=10.6 Hz, 1H), 3.86 (s, 3H), 3.82 (s, 3H), 3.71 (s, 2H), 3.51-3.36 (m, 2H), 3.35-3.29 (m, 2H), 2.90-2.82 (m, 1H), 2.79-2.75 (m, 4H), 2.69 (s, 1H), 2.56 (s, 3H), 2.27-2.19 (m, 1H), 2.10 (s, 3H), 2.03-1.99 (m, 1H), 1.87-1.77 (m, 3H), 1.63-1.59 (m, 4H), 1.34-1.31 (m, 4H), 0.99 (t, J=7.3 Hz, 3H), 0.91 (t, J=7.0 Hz, 3H), 0.87-0.79 (m, 5H); HRESI-TOF m/z 960.4577 ($C_{54}H_{65}N_5O_9S$+H$^+$, required 960.4576). $[\alpha]_D^{23}$ −12 (c 0.26, CHCl$_3$).

Compound 86

Method 2 was followed providing Compound 86 in 43% yield. $^1$H NMR (600 MHz, CDCl$_3$) δ 9.84 (s, 1H), 8.02 (s, 1H), 7.95 (d, J=8.0 Hz, 1H), 7.45 (d, J=8.0 Hz, 1H), 7.38 (d, J=8.2 Hz, 2H), 7.17-7.04 (m, 3H), 6.65 (s, 1H), 6.12 (s, 1H), 6.05 (s, 1H), 5.85 (dd, J=10.3, 4.6 Hz, 1H), 5.48 (s, 1H), 5.30 (d, J=10.2 Hz, 1H), 4.03-3.93 (m, 2H), 3.81 (s, 3H), 3.80 (s, 3H), 3.75 (s, 1H), 3.60 (s, 3H), 3.43-3.27 (m, 3H), 3.26-3.11 (m, 2H), 3.10-3.05 (m, 2H), 2.99 (q, J=7.4 Hz, 2H), 2.83 (d, J=16.1 Hz, 1H), 2.72 (s, 3H), 2.70-2.65 (m, 2H), 2.49-2.39 (m, 2H), 2.34 (d, J=13.3 Hz, 1H), 2.25-2.17 (m, 1H), 2.11 (s, 3H), 2.03-1.97 (m, 1H), 1.89-1.74 (m, 2H), 1.34 (t, J=7.4 Hz, 3H), 1.27-1.23 (m, 4H), 0.88 (t, J=6.9 Hz, 1H), 0.85-0.80 (m, 4H), 0.77 (t, J=7.5 Hz, 3H); HRESI-TOF m/z 974.4733 ($C_{55}H_{67}SN_5O_9$+H$^+$, required 974.4732). $[\alpha]_D^{23}$ −24 (c 0.09, CHCl$_3$).

Compound 87

Method 2 was followed providing Compound 87 in 32% yield. $^1$H NMR (600 MHz, CDCl$_3$) δ 9.84 (s, 1H), 8.02 (s, 1H), 7.96 (d, J=7.9 Hz, 2H), 7.47-7.42 (m, 3H), 7.17-7.04 (m, 3H), 6.65 (s, 1H), 6.12 (s, 1H), 6.06 (s, 1H), 5.85 (dd, J=10.7, 4.8 Hz, 1H), 5.48 (s, 1H), 5.30 (d, J=10.4 Hz, 1H), 4.03-3.95 (m, 2H), 3.81 (s, 3H), 3.80 (s, 3H), 3.75 (s, 1H), 3.60 (s, 3H), 3.49 (sep, J=6.7 Hz, 1H), 3.42-3.34 (m, 3H), 3.31 (td, J=9.6, 4.6 Hz, 1H), 3.27-3.11 (m, 2H), 3.11-3.06 (m, 2H), 2.83 (d, J=16.1 Hz, 1H), 2.72 (s, 3H), 2.67 (s, 1H), 2.49-2.39 (m, 2H), 2.34 (d, J=13.4 Hz, 1H), 2.24-2.16 (m, 2H), 2.11 (s, 3H), 2.02-1.98 (m, 1H), 1.87-1.77 (m, 1H), 1.32 (d, J=6.7 Hz, 6H), 1.26-1.23 (m, 4H), 0.91-0.84 (m, 1H), 0.82 (t, J=7.3 Hz, 3H), 0.77 (t, J=7.5 Hz, 3H); HRESI-TOF m/z 988.4896 ($C_{56}H_{69}SN_5O_9$+H$^+$, required 988.4889). $[\alpha]_D^{23}$ +5 (c 0.18, CHCl$_3$).

Compound 88

Method 2 was followed providing Compound 88 in 32% yield. $^1$H NMR (600 MHz, CDCl$_3$) δ 9.69 (s, 1H), 8.67 (s, 1H), 8.50 (s, 1H), 8.51 (s, 1H), 8.32-8.18 (m, 3H), 8.13 (s, 1H), 7.98-7.84 (m, 4H), 7.53 (d, J=7.8 Hz, 4H), 7.43 (s, 3H), 7.19-7.04 (m, 2H), 6.82 (s, 1H), 5.94 (s, 1H), 5.48 (m, 1H), 4.54 (m, 1H), 4.45 (s, 1H), 4.12 (d, J=7.3 Hz, 2H), 3.93 (s, 3H), 3.91 (s, 3H), 3.90-3.82 (m, 2H), 3.73 (m, 2H), 3.66 (s, 3H), 3.64-3.58 (m, 2H), 3.49 (s, 1H), 3.42-3.28 (m, 2H), 3.18-3.00 (m, 2H), 2.96 (s, 1H), 2.14-2.04 (m, 4H), 0.92 (t, J=6.7 Hz, 2H), 0.88-0.75 (m, 9H); HRESI-TOF m/z 994.4275 ($C_{53}H_{63}N_5O_{12}S$+H$^+$, required 994.4223). $[\alpha]_D^{23}$ −4 (c 0.19, CHCl$_3$).

Compound 89

Method 2 was followed providing Compound 89 in 34% yield. $^1$H NMR (600 MHz, CDCl$_3$) δ 9.79 (s, 1H), 8.50 (d, J=9.6 Hz, 1H), 8.23-8.16 (m, 2H), 8.02 (s, 1H), 7.80 (t, J=7.6 Hz, 2H), 7.41 (dd, J=15.4, 8.4 Hz, 2H), 6.81 (d, J=8.1 Hz, 1H), 6.46 (d, J=9.4 Hz, 1H), 6.24 (s, 1H), 5.92-5.88 (m, 1H), 5.43 (s, 1H), 5.34 (s, 1H), 5.12 (s, 1H), 3.86-3.79 (m, 9H), 3.68 (s, 3H), 3.66 (s, 3H), 3.41 (d, J=6.5 Hz, 1H), 3.35 (s, 3H), 3.05 (s, 1H), 2.93 (d, J=11.9 Hz, 3H), 2.85-2.79 (m, 1H), 2.75 (s, 3H), 1.94-1.86 (m, 1H), 1.78 (dt, J=16.0, 7.7 Hz, 3H), 1.12 (d, J=6.8 Hz, 3H), 1.01 (t, J=7.3 Hz, 3H), 0.92 (d, J=6.7 Hz, 3H), 0.44 (t, J=7.2 Hz, 3H); HRESI-TOF m/z 994.4236 ($C_{53}H_{63}N_5O_{12}S+H^+$, required 994.4223). $[\alpha]_D^{23}$ −2 (c 0.23, CHCl$_3$).

Compound 90

Method 1 was followed using 5.0 mg of 20'-aminovinblastine (6, 0.006 mmol) to provide 5.0 mg of Compound 90 as a white solid, yield: 85%. $^1$H NMR (600 MHz, CDCl$_3$) δ 9.74 (br s, 2H), 8.03 (s, 1H), 7.84 (d, J=6.7 Hz, 1H), 7.74 (d, J=11.4 Hz, 1H), 7.54 (d, J=7.6 Hz, 1H), 7.14-7.03 (m, 3H), 6.65 (s, 1H), 6.13 (s, 1H), 6.00 (s, 1H), 5.85 (dd, J=9.6, 4.0 Hz, 1H), 5.48 (s, 1H), 5.30 (d, J=10.1 Hz, 1H), 4.12 (q, J=7.1 Hz, 1H), 3.94 (s, 3H), 3.83 (s, 3H), 3.80 (s, 3H), 3.75 (s, 1H), 3.62 (s, 3H), 3.41-3.35 (m, 2H), 3.31 (td, J=9.5, 4.6 Hz, 1H), 3.23 (t, J=11.9 Hz, 1H), 3.13-3.10 (m, 2H), 2.83 (d, J=15.8 Hz, 1H), 2.72 (s, 3H), 2.67 (s, 1H), 2.44-2.38 (m, 1H), 2.24-2.17 (m, 1H), 2.11 (s, 3H), 2.05 (s, 3H), 1.83-1.80 (m, 2H), 1.65-1.52 (m, 3H), 1.36-1.29 (m, 2H), 1.28-1.25 (m, 5H), 0.82 (t, J=7.2 Hz, 3H), 0.78 (t, J=7.5 Hz, 3H); HRESI-TOF m/z 962.4715 ($C_{54}H_{64}FN_5O_{10}+H^+$, required 962.4710). $[\alpha]_D^{23}$ −25 (c 0.20, CHCl$_3$).

Compound 91

Method 1 was followed using 4.1 mg of 20'-aminovinblastine (6, 0.05 mmol) to provide Compound 91 as a white solid, yield: 39%. $^1$H NMR (600 MHz, CDCl$_3$) δ 8.10 (t, J=9.1 Hz, 1H), 8.05 (s, 1H), 7.47 (d, J=7.9 Hz, 1H), 7.13-7.08 (m, 2H), 7.09 (s, 1H), 6.82 (dd, J=8.9, 2.3 Hz, 1H), 6.72 (d, J=14.4 Hz, 1H), 6.68 (d, J=14.1 Hz, 1H), 6.58 (br s, 1H), 6.10 (s, 1H), 5.84 (dd, J=10.2, 4.6 Hz, 1H), 5.46 (s, 1H), 5.28, (d, J=9.9 Hz, 1H), 3.84 (s, 3H), 3.79 (s, 3H), 3.78 (s, 3H), 3.74 (br s, 2H), 3.49 (br s, 2H), 3.37 (t, J=13.2 Hz, 1H), 3.37-3.35 (m, 1H), 3.30-3.26 (m, 2H), 3.12 (t, J=15.3 Hz, 2H), 2.81 (d, J=16.0 Hz, 1H), 2.71 (s, 3H), 2.64 (s, 1H), 2.41 (br s, 2H), 2.30 (d, J=13.2 Hz, 1H), 2.21-2.14 (m, 1H), 2.10 (s, 3H), 1.85-1.75 (m, 7H), 1.33-1.29 (m, 2H), 1.25 (s, 1H), 0.79 (t J=7.2 Hz, 6H); IR (film) ν$_{max}$ 3464, 2931, 1739, 1660, 1619, 1498, 1458, 1370, 1331, 1238, 1154, 1103, 1036, 953, 839, 739, 456 cm$^{-1}$; HRESI-TOF m/z 962.4700 ($C_{54}H_{64}FN_5O_{10}+H^+$, required 962.4710).

Compound 92

Method 2 was followed providing Compound 92 in 47% yield. $^1$H NMR (600 MHz, CDCl$_3$) δ 8.06-8.03 (m, 2H), 8.01-7.99 (m, 1H), 7.48 (d, J=8.0 Hz, 1H), 7.20-7.07 (m, 3H), 7.04 (d, J=8.7 Hz, 1H), 6.66 (s, 1H), 6.14 (s, 1H), 6.02 (s, 1H), 5.50 (s, 1H), 5.34-5.31 (m, 1H), 3.97 (s, 3H), 3.84 (s, 3H), 3.82 (s, 3H), 3.62 (s, 3H), 3.46-3.36 (m, 1H), 3.37-3.23 (m, 2H), 3.21-3.10 (m, 3H), 2.85 (d, J=16.1 Hz, 1H), 2.74 (s, 3H), 2.72-2.68 (m, 1H), 2.50-2.45 (m, 2H), 2.37 (d, J=13.5 Hz, 1H), 2.27-2.18 (m, 2H), 2.13 (s, 3H), 1.89-1.79 (m, 2H), 1.40-1.33 (m, 1H), 1.30-1.18 (m, 3H), 0.89-0.82 (m, 10H), 0.80 (t, J=7.5 Hz, 3H); HRESI-TOF m/z 978.4410 ($C_{54}H_{64}N_5O_{10}Cl+H^+$, required 978.4414). $[\alpha]_D^{23}$ −16 (c 0.08, CHCl$_3$).

Compound 93

Method 2 was followed providing Compound 93 in 37% yield. $^1$H NMR (600 MHz, CDCl$_3$) δ 9.83 (s, 1H), 8.19 (d, J=2.1 Hz, 1H), 8.05-8.00 (m, 2H), 7.46 (d, J=8.0 Hz, 1H), 7.17-7.03 (m, 3H), 6.98 (d, J=8.6 Hz, 1H), 6.64 (s, 1H), 6.12 (s, 1H), 5.99 (s, 1H), 5.85 (dd, J=10.1, 4.4 Hz, 1H), 5.48 (s, 1H), 5.30 (d, J=10.1 Hz, 1H), 3.94 (s, 3H), 3.82 (s, 3H), 3.80 (s, 3H), 3.75 (s, 1H), 3.59 (s, 3H), 3.43-3.27 (m, 3H), 3.25-3.20 (m, 2H), 3.17-3.07 (m, 3H), 2.83 (d, J=16.0 Hz, 1H), 2.72 (s, 3H), 2.69-2.64 (m, 2H), 2.50-2.39 (m, 2H), 2.33 (d, J=13.6 Hz, 1H), 2.24-2.16 (m, 2H), 2.11 (s, 3H), 1.85-1.78 (m, 2H), 1.38-1.30 (m, 2H), 1.28-1.23 (m, 3H), 0.91-0.79 (m, 4H), 0.77 (t, J=7.4 Hz, 3H); HRESI-TOF m/z 1022.3905 ($C_{54}H_{64}BrN_5O_{10}+H^+$, required 1022.3909). $[\alpha]_D^{23}$ −44 (c 0.04, CHCl$_3$).

Compound 94

Method 2 was followed providing Compound 94 in 33% yield. $^1$H NMR (600 MHz, CDCl$_3$) δ 9.84 (s, 1H), 8.04-8.00 (m, 2H), 7.94 (s, 1H), 7.46 (d, J=7.9 Hz, 1H), 7.17-7.05 (m, 3H), 6.99 (d, J=8.6 Hz, 1H), 6.64 (s, 1H), 6.12 (s, 1H), 5.99 (s, 1H), 5.88-5.82 (m, 1H), 5.48 (s, 1H), 5.30 (d, J=10.3 Hz, 1H), 4.19-4.11 (m, 2H), 3.96-3.90 (m, 2H), 3.81 (s, 3H), 3.80 (s, 3H), 3.75 (s, 1H), 3.59 (s, 3H), 3.43-3.20 (m, 4H), 3.16-3.08 (m, 3H), 2.83 (d, J=16.0 Hz, 1H), 2.72 (s, 3H), 2.70-2.65 (m, 2H), 2.49-2.39 (m, 2H), 2.34 (d, J=13.8 Hz, 1H), 2.25-2.15 (m, 2H), 2.11 (s, 3H), 1.97-1.93 (m, 1H), 1.87-1.75 (m, 2H), 1.48 (t, J=7.0 Hz, 3H), 1.37-1.30 (m, 2H), 1.28-1.24 (s, 2H), 0.81 (t, J=7.4 Hz, 3H), 0.77 (t, J=7.4 Hz, 3H); HRESI-TOF m/z 992.4577 ($C_{55}H_{66}ClN_5O_{10}+H^+$, required 992.4571). $[\alpha]_D^{23}$ −45 (c 0.05, CHCl$_3$).

Compound 95

Method 2 was followed providing Compound 95 in 41% yield. $^1$H NMR (600 MHz, CDCl$_3$) δ 9.83 (s, 1H), 8.02 (s, 1H), 7.99 (s, 1H), 7.46 (d, J=8.0 Hz, 1H), 7.19-7.05 (m, 4H), 6.95 (d, J=8.6 Hz, 1H), 6.64 (s, 1H), 6.12 (s, 1H), 5.98 (s, 1H), 5.85 (dd, J=10.2, 4.5 Hz, 1H), 5.48 (s, 1H), 5.30 (d, J=10.3 Hz, 1H), 4.18-4.11 (m, 2H), 3.96-3.90 (m, 2H), 3.81 (s, 3H), 3.80 (s, 3H), 3.75 (s, 1H), 3.58 (s, 3H), 3.43-3.34 (m, 2H), 3.31 (td, J=9.5, 4.6 Hz, 1H), 3.27-3.06 (m, 4H), 2.83 (d, J=16.0 Hz, 1H), 2.72 (s, 3H), 2.68-2.64 (m, 3H), 2.49-2.38 (m, 2H), 2.33 (d, J=13.2 Hz, 1H), 2.24-2.16 (m, 2H), 2.11 (s, 3H), 1.87-1.75 (m, 1H), 1.48 (t, J=7.0 Hz, 3H), 1.37-1.30 (m, 2H), 1.28-1.23 (m, 2H), 0.91-0.80 (m, 4H), 0.77 (t, J=7.5 Hz, 3H); HRESI-TOF m/z 1036.4056 ($C_{55}H_{66}BrN_5O_{10}+H^+$, required 1036.4066). $[\alpha]_D^{23}$ −28 (c 0.09, CHCl$_3$).

Compound 96

Method 1 was followed using 2.5 mg of 20'-aminovinblastine (6, 0.003 mmol) to provide 2.6 mg of Compound 96 as a white solid, yield: 86%. $^1$H NMR (600 MHz, CDCl$_3$) δ 9.80 (br s, 1H), 8.05 (s, 1H), 7.80 (s, 1H), 7.72 (dd, J=5.4, 3.5 Hz, 1H), 7.53 (dd, J=5.4, 3.9 Hz, 1H), 7.40 (d, J=7.5 Hz, 1H), 7.21 (d, J=7.2 Hz, 1H), 7.14 (t, J=8.5 Hz, 1H), 6.43 (s, 1H), 6.12 (s, 1H), 5.95 (s, 1H), 5.89 (dd, J=10.6, 4.6 Hz, 1H), 5.43 (s, 1H), 5.33 (d, J=10.3 Hz, 1H), 4.37 (q, J=7.2 Hz, 1H), 3.95 (s, 3H), 3.84 (s, 3H), 3.80 (s, 3H), 3.77-3.73 (m, 1H), 3.68 (m, 3H), 3.47-3.40 (m, 2H), 3.33-3.28 (m, 1H), 3.19-3.16 (m, 1H), 3.11-3.03 (m, 2H), 2.84 (d, J=18.4 Hz, 1H), 2.74 (s, 3H), 2.69-2.67 (m, 1H), 2.35 (t, J=7.7 Hz, 1H), 2.17 (s, 1H), 2.11 (s, 3H), 2.02-1.98 (m, 1H), 1.81-1.76 (m, 2H), 1.66-1.62 (m, 2H), 1.43 (t, J=7.2 Hz, 3H), 1.37 (t, J=7.2 Hz, 2H), 1.16-1.10 (m, $^3$H), 0.88 (t, J=6.5 Hz, 3H), 0.79 (t, J=7.4 Hz, 3H); HRESI-TOF m/z 1012.4028 ($C_{54}H_{63}Cl_2N_5O_{10}+H^+$, required 1012.4025).

Compound 97

Method 2 was followed providing Compound 97 in 47% yield. $^1$H NMR (600 MHz, CDCl$_3$) δ 9.87 (s, 1H), 8.04 (s, 1H), 7.91 (d, J=8.5 Hz, 1H), 7.85 (s, 1H), 7.47 (d, J=8.0 Hz, 1H), 7.19-7.06 (m, 3H), 6.91 (d, J=8.6 Hz, 1H), 6.67 (s, 1H), 6.14 (s, 1H), 6.05 (s, 1H), 5.88 (dd, J=10.6, 4.3 Hz, 1H), 5.50 (s, 1H), 5.35-5.30 (m, 1H), 4.07-4.00 (m, 2H), 3.89 (s, 3H), 3.84 (s, 3H), 3.83 (s, 3H), 3.77 (s, 1H), 3.61 (s, 3H), 3.44-3.38 (m, 2H), 3.36-3.29 (m, 1H), 3.28-3.22 (m, 2H), 3.17-3.14 (m, 1H), 3.11-3.08 (m, 1H), 2.85 (d, J=16.1 Hz, 1H), 2.74 (s, 3H), 2.72-2.67 (m, 2H), 2.52-2.43 (m, 2H), 2.39 (d, J=14.1 Hz, 1H), 2.31 (s, 3H), 2.26-2.14 (m, 1H), 2.14 (s, 3H), 1.99 (s, 1H), 1.90-1.79 (m, 2H), 1.37 (dt, J=14.1, 6.5 Hz, 1H), 1.28 (s, 3H), 0.93-0.87 (m, 1H), 0.84

(t, J=7.4 Hz, 3H), 0.79 (t, J=7.5 Hz, 3H); HRESI-TOF m/z 958.4960 ($C_{55}H_{67}N_5O_{10}$+H$^+$, required 958.496). $[\alpha]_D^{23}$ −22 (c 0.07, CHCl$_3$).

Compound 98

Method 2 was followed providing Compound 98 in 32% yield. $^1$H NMR (600 MHz, CDCl$_3$) δ 9.86 (s, 1H), 8.05 (s, 1H), 7.56 (s, 1H), 7.53-7.45 (m, 2H), 7.26 (d, J=7.6 Hz, 1H), 7.19-7.06 (m, 3H), 6.67 (s, 1H), 6.14 (s, 1H), 5.91-5.85 (m, 1H), 5.51 (s, 1H), 5.32 (d, J=10.2 Hz, 1H), 4.03-3.98 (m, 2H), 3.94 (s, 3H), 3.85-3.80 (m, 5H), 3.77 (s, 3H), 3.60 (s, 3H), 3.46-3.37 (m, 2H), 3.37-3.29 (m, 1H), 3.28-3.20 (m, 2H), 3.17-3.08 (m, 2H), 2.85 (d, J=16.0 Hz, 1H), 2.74 (s, 3H), 2.72-2.68 (m, 2H), 2.52-2.41 (m, 2H), 2.37 (d, J=13.9 Hz, 1H), 2.27 (s, 3H), 2.25-2.18 (m, 1H), 2.13 (s, 3H), 1.90-1.78 (m, 2H), 1.39-1.34 (m, 1H), 1.28 (s, 2H), 0.92-0.82 (m, 6H), 0.80 (t, J=7.5 Hz, 3H); HRESI-TOF m/z 958.4961 ($C_{55}H_{67}N_5O_{10}$+H$^+$, required 958.4960). $[\alpha]_D^{23}$−20 (c 0.10, CHCl$_3$).

Compound 99

Method 2 was followed providing Compound 99 in 41% yield. $^1$H NMR (600 MHz, CDCl$_3$) δ 8.04 (s, 1H), 7.73 (s, 2H), 7.49 (d, J=7.9 Hz, 1H), 7.20-7.07 (m, 3H), 6.67 (s, 1H), 6.14 (s, 1H), 6.06 (s, 1H), 5.88 (dd, J=10.2, 4.2 Hz, 1H), 5.50 (s, 1H), 5.33 (d, J=9.2 Hz, 1H), 4.08-4.00 (m, 2H), 3.84 (s, 3H), 3.83 (s, 3H), 3.77 (s, 1H), 3.76 (s, 3H), 3.59 (s, 3H), 3.47-3.40 (m, 2H), 3.40-3.31 (m, 2H), 3.29-3.24 (m, 3H), 3.18-3.08 (m, 3H), 2.85 (d, J=16.1 Hz, 1H), 2.73-2.67 (m, 3H), 2.50-2.45 (m, 2H), 2.39 (s, 6H), 2.14 (s, 3H), 1.89-1.79 (m, 2H), 1.40-1.35 (m, 2H), 1.28 (s, 3H), 0.93-0.82 (m, 5H), 0.79 (t, J=7.5 Hz, 3H); HRESI-TOF m/z 972.5110 ($C_{56}H_{69}N_5O_{10}$+H$^+$, required 972.5117). $[\alpha]_D^{23}$−40 (c 0.11, CHCl$_3$).

Compound 100

Method 2 was followed providing Compound 100 in 36% yield. $^1$H NMR (600 MHz, CDCl$_3$) δ 9.86 (s, 1H), 8.05 (s, 1H), 7.76 (s, 2H), 7.52-7.47 (m, 3H), 7.46-7.33 (m, 3H), 7.20-7.08 (m, 3H), 6.67 (s, 1H), 6.14 (s, 1H), 6.08 (s, 1H), 5.91-5.85 (m, 1H), 5.51 (s, 1H), 5.33 (d, J=10.1 Hz, 1H), 4.85 (s, 2H), 4.10-4.00 (m, 2H), 3.84 (s, 3H), 3.83 (s, 3H), 3.77 (s, 1H), 3.58 (s, 3H), 3.47-3.37 (m, 2H), 3.33 (td, J=9.5, 4.6 Hz, 1H), 3.18-3.10 (m, 2H), 2.86 (d, J=16.2 Hz, 1H), 2.75 (s, 3H), 2.52-2.44 (m, 2H), 2.41 (s, 6H), 2.39-2.36 (m, 2H), 2.27-2.17 (m, 2H), 2.14 (s, 3H), 2.05-2.01 (m, 1H), 1.90-1.79 (m, 3H), 1.42-1.35 (m, 3H), 0.94-0.82 (m, 6H), 0.80 (t, J=7.5 Hz, 3H); HRESI-TOF m/z 1048.5425 ($C_{62}H_{73}N_5O_{10}$+H$^+$, required 1048.5430). $[\alpha]_D^{23}$−40 (c 0.11, CHCl$_3$).

Compound 101

Generated via Boc deprotection of Compound 102 with 4 M HCl in dioxane (95% yield). $^1$H NMR (600 MHz, CDCl$_3$) δ 9.84 (s, 1H), 7.97 (s, 1H), 7.69 (s, 1H), 7.48-7.44 (m, 1H), 7.34-7.31 (m, 1H), 7.20-7.07 (m, 4H), 6.72 (s, 1H), 6.15 (s, 1H), 6.05 (s, 1H), 5.89 (dd, J=10.5, 4.7 Hz, 1H), 5.51 (s, 1H), 5.35 (d, J=10.3 Hz, 1H), 4.28-4.18 (m, 4H), 3.86 (s, 3H), 3.83 (s, 3H), 3.82-3.80 (m, 1H), 3.78 (s, 1H), 3.64 (s, 3H), 3.45-3.39 (m, 2H), 3.37-3.29 (m, 1H), 3.27-3.17 (m, 2H), 3.16-3.12 (m, 1H), 3.07-3.02 (m, 1H), 2.86 (d, J=16.1 Hz, 1H), 2.76 (s, 3H), 2.73 (s, 1H), 2.68 (d, J=14.0 Hz, 1H), 2.52-2.44 (m, 2H), 2.36 (d, J=13.6 Hz, 1H), 2.21 (s, 3H), 2.14 (s, 3H), 2.06-2.01 (m, 1H), 1.88-1.80 (m, 2H), 1.44-1.29 (m, 2H), 0.93-0.84 (m, 6H), 0.78 (t, J=7.5 Hz, 3H); HRESI-TOF m/z 943.4964 ($C_{54}H_{66}N_6O_9$+H$^+$, required 943.4964). $[\alpha]_D^{23}$−72 (c 0.03, CHCl$_3$)

Compound 102

Method 2 was followed providing Compound 102 in 39% yield. $^1$H NMR (600 MHz, CDCl$_3$) δ 8.28 (s, 1H), 8.00 (s, 1H), 7.75 (s, 1H), 7.46 (d, J=7.8 Hz, 1H), 7.32 (d, J=8.0 Hz, 1H), 7.19-7.06 (m, 3H), 6.70 (s, 1H), 6.14 (s, 1H), 6.12 (s, 1H), 5.88 (dd, J=10.3, 4.7 Hz, 1H), 5.51 (s, 1H), 5.33 (d, J=10.4 Hz, 1H), 4.10-4.02 (m, 2H), 3.84 (s, 3H), 3.83 (s, 3H), 3.78 (s, 1H), 3.61 (s, 3H), 3.46-3.30 (m, 3H), 3.28-3.11 (m, 2H), 3.10-3.06 (m, 1H), 2.85 (d, J=16.1 Hz, 1H), 2.75 (s, 3H), 2.72-2.68 (m, 2H), 2.50-2.41 (m, 1H), 2.33 (s, 3H), 2.26-2.19 (m, 2H), 2.14 (s, 3H), 1.89-1.79 (m, 2H), 1.50 (s, 9H), 1.42-1.32 (m, 1H), 0.95-0.84 (m, 11H), 0.80 (t, J=7.5 Hz, 3H); HRESI-TOF m/z 1043.5485 ($C_{59}H_{74}N_6O_{11}$+H$^+$, required 1043.5488). $[\alpha]_D^{23}$−27 (c 0.06, CHCl$_3$).

Compound 103

Method 2 was followed providing Compound 103 in 31% yield. $^1$H NMR (600 MHz, CDCl$_3$) δ 9.81 (s, 1H), 8.09 (s, 1H), 7.96 (s, 1H), 7.85 (d, J=8.1 Hz, 1H), 7.45 (d, J=8.0 Hz, 1H), 7.38 (d, J=8.0 Hz, 1H), 7.22-7.06 (m, 3H), 6.71 (s, 1H), 6.16 (s, 1H), 6.07 (s, 1H), 5.90 (dd, J=10.2, 4.7 Hz, 1H), 5.51 (s, 1H), 5.35 (d, J=10.9 Hz, 1H), 4.21-4.10 (m, 2H), 3.87 (s, 3H), 3.83 (s, 3H), 3.79 (s, 1H), 3.65 (s, 3H), 3.45-3.31 (m, 2H), 3.25-3.18 (m, 1H), 3.14-3.09 (m, 2H), 3.07-2.99 (m, 3H), 2.86 (d, J=16.2 Hz, 1H), 2.77 (s, 3H), 2.73 (s, 1H), 2.68 (d, J=13.8 Hz, 1H), 2.53-2.43 (m, 2H), 2.35-2.30 (m, 4H), 2.28-2.17 (m, 4H), 2.14 (s, 3H), 1.88-1.80 (m, 1H), 1.45-1.35 (m, 1H), 1.28 (s, 3H), 0.94-0.85 (m, 6H), 0.80 (t, J=7.4 Hz, 3H); HRESI-TOF m/z 985.5069 ($C_{56}H_{68}N_6O_{10}$+H$^+$, required 985.5069). $[\alpha]_D^{23}$−59 (c 0.04, CHCl$_3$).

Compound 104

Generated via Boc deprotection of Compound 105 with 4 M HCl in dioxane (95% yield). $^1$H NMR (600 MHz, CDCl$_3$) δ 9.87 (s, 1H), 8.04 (s, 1H), 7.80 (s, 1H), 7.77 (s, 1H), 7.50-7.43 (m, 1H), 7.19-7.06 (m, 3H), 6.74 (d, J=8.2 Hz, 1H), 6.67 (s, 1H), 6.14 (s, 1H), 6.01 (s, 1H), 5.88 (dd, J=10.3, 4.6 Hz, 1H), 5.50 (s, 1H), 5.33 (d, J=10.5 Hz, 1H), 4.05-4.00 (m, 2H), 3.88 (s, 1H), 3.84 (s, 3H), 3.83 (s, 3H), 3.79-3.73 (m, 1H), 3.61 (s, 3H), 3.45-3.36 (m, 2H), 3.35-3.28 (m, 1H), 3.27-3.22 (m, 2H), 3.18-3.05 (m, 1H), 2.86 (d, J=15.6 Hz, 1H), 2.74 (s, 3H), 2.72-2.66 (m, 2H), 2.50-2.43 (m, 2H), 2.38 (d, J=14.6 Hz, 1H), 2.28-2.17 (m, 6H), 2.14 (s, 3H), 2.05-2.01 (m, 2H), 1.90-1.78 (m, 2H), 0.95-0.81 (m, 6H), 0.79 (t, J=7.5 Hz, 3H); HRESI-TOF m/z 943.4959 ($C_{54}H_{66}N_6O_9$+H$^+$, required 943.4964). $[\alpha]_D^{23}$−43 (c 0.04, CHCl$_3$).

Compound 105

Method 2 was followed providing Compound 105 in 36% yield. $^1$H NMR (600 MHz, CDCl$_3$) δ 8.08 (d, J=8.0 Hz, 1H), 8.04 (s, 1H), 7.90-7.85 (m, 2H), 7.49-7.45 (m, 1H), 7.19-7.07 (m, 3H), 6.67 (s, 1H), 6.43 (s, 1H), 6.14 (s, 1H), 6.07 (s, 1H), 5.88 (dd, J=10.5, 4.7 Hz, 1H), 5.51 (s, 1H), 5.32 (d, J=10.4 Hz, 1H), 4.05-4.00 (m, 2H), 3.89-3.78 (m, 6H), 3.77 (s, 1H), 3.61 (s, 3H), 3.46-3.36 (m, 2H), 5.88 (td, J=9.5, 4.6 Hz, 1H), 3.29-3.18 (m, 2H), 3.17-3.06 (m, 2H), 2.85 (dd, J=16.1 Hz, 1H), 2.74 (s, 3H), 2.73-2.67 (m, 2H), 2.50-2.42 (m, 2H), 2.37-2.34 (m, 4H), 2.27-2.17 (m, 2H), 2.16-2.14 (m, 1H), 2.13 (s, 3H), 2.05-2.01 (m, 1H), 1.90-1.80 (m, 1H), 1.68-1.64 (m, 2H), 1.63-1.55 (m, 1H), 1.54 (s, 9H), 0.94-0.80 (m, 6H), 0.79 (t, J=7.4 Hz, 3H); HRESI-TOF m/z 1043.5466 ($C_{59}H_{74}N_6O_{11}$+H$^+$, required 1043.5488). $[\alpha]_D^{23}$−46 (c 0.06, CHCl$_3$).

Compound 106

Method 2 was followed providing Compound 106 in 33% yield. $^1$H NMR (600 MHz, CDCl$_3$) δ 9.84 (s, 1H), 8.02 (s, 1H), 7.55 (s, 1H), 7.53-7.50 (s, 1H), 7.46 (d, J=7.9 Hz, 1H), 7.38 (t, J=7.9 Hz, 1H), 7.17-7.05 (m, 3H), 7.04-7.01 (m, 1H), 6.64 (s, 1H), 6.11 (s, 1H), 6.09 (s, 1H), 5.85 (dd, J=10.7, 4.1 Hz, 1H), 5.48 (s, 1H), 5.30 (d, J=10.3 Hz, 1H), 4.03-3.95 (m, 2H), 3.92-3.81 (m, 5H), 3.81-3.77 (m, 5H), 3.75 (s, 1H), 3.58 (s, 3H), 3.43-3.33 (m, 2H), 3.36-3.27 (m, 2H), 3.27-3.20 (m, 5H), 3.18-3.09 (m, 1H), 2.95-2.88 (m, 1H), 2.82 (d, J=15.8 Hz, 1H), 2.72 (s, 3H), 2.61 (s, 1H), 2.48-2.38 (m, 2H), 2.35 (d, J=13.9 Hz, 1H), 2.23-2.15 (m, 2H), 2.11 (s, 3H), 1.87-1.75 (m, 1H), 1.68-1.60 (m, 4H), 1.38-1.30 (m, 1H), 0.94-0.86 (m, 2H), 0.82 (t, J=7.4 Hz, 3H), 0.76 (t, J=7.4 Hz, 3H); HRESI-TOF m/z 999.5221 ($C_{57}H_{70}N_6O_{10}$+H$^+$, required 999.5226). $[\alpha]_D^{23}$ −91 (c 0.08, CHCl$_3$).

Compound 107

Method 2 was followed providing Compound 107 in 28% yield. $^1$H NMR (600 MHz, CDCl$_3$) δ 8.69 (s, 1H), 8.22 (s, 1H), 7.99 (d, J=7.6 Hz, 2H), 7.92-7.86 (m, 2H), 7.61-7.47 (m, 2H), 7.46-7.40 (m, 3H), 7.19-7.06 (m, 3H), 6.69 (s, 1H), 6.08 (s 1H), 5.89 (dd, J=10.4, 4.7 Hz, 1H), 5.49 (s, 1H), 5.34 (d, J=10.2 Hz, 1H), 4.18-4.10 (m, 1H), 3.82 (s, 3H), 3.81-3.73 (m, 2H), 3.61 (s, 3H), 3.44-3.38 (m, 1H), 3.38-3.30 (m, 1H), 3.26 (s, 3H), 3.25-3.17 (m, 1H), 3.15-3.11 (m, 1H), 3.09-2.97 (m, 1H), 2.85 (d, J=15.9 Hz, 1H), 2.74 (s, 3H), 2.73-2.66 (m, 2H), 2.51-2.42 (m, 2H), 2.40-2.35 (m, 4H), 2.27-2.16 (m, 1H), 2.17-2.08 (m, 5H), 1.86-1.78 (m, 1H), 1.42-1.29 (m, 2H), 1.28 (s, 3H), 0.93-0.83 (m, 6H), 0.82 (t, J=7.5 Hz, 3H); HRESI-TOF m/z 1047.5220 ($C_{61}H_{70}N_6O_{10}$+H$^+$, required 1047.5226). $[\alpha]_D^{23}$ −5 (c 0.10, CHCl$_3$).

Compound 108

Method 2 was followed providing Compound 108 in 24% yield. $^1$H NMR (600 MHz, CDCl$_3$) δ 9.79 (s, 1H), 8.01 (s, 1H), 7.67 (d, J=15.7 Hz, 1H), 7.60-7.54 (m, 1H), 7.48 (d, J=8.3 Hz, 1H), 7.40-7.31 (m, 2H), 7.24-7.02 (m, 3H), 6.65 (s, 1H), 6.57 (d, J=15.4 Hz, 1H), 6.11 (s, 1H), 5.97 5.79 (m, 1H), 5.67-5.54 (m, 1H), 5.48 (s, 1H), 5.30 (d, J=10.4 Hz, 1H), 5.12 (s, 1H), 4.05-3.58 (m, 9H), 3.54 (s, 2H), 3.46-3.08 (m, 6H), 2.82 (d, J=14.0 Hz, 1H), 2.80-2.60 (m, 4H), 2.52-2.26 (m, 3H), 2.26-2.16 (m, 1H), 2.11 (s, 3H), 2.04 (s, 1H), 1.92-1.72 (m, 3H), 1.36-1.18 (m, 6H), 1.02-0.70 (m, 7H); HRESI-TOF m/z 940.4857 ($C_{54}H_{65}N_5O_9$+H$^+$, required 940.4855). $[\alpha]_D^{23}$ +0.14 (c 0.08, CHCl$_3$).

Compound 109

Method 2 was followed providing Compound 109 in 50% yield. $^1$H NMR (600 MHz, CDCl$_3$) δ 9.80 (s, 1H), 8.63 (s, 3H), 8.00 (s, 1H), 7.61 (d, J=15.7 Hz, 1H), 7.57-7.37 (m, 4H), 7.20-7.04 (m, 4H), 6.74 (d, J=15.7 Hz, 1H), 6.11 (s, 1H), 5.87 (s, 1H), 5.46 (s, 1H), 5.31 (d, J=10.2 Hz, 1H), 3.82 (s, 3H), 3.80 (s, 3H), 3.77 (d, J=9.5 Hz, 2H), 3.62 (s, 3H), 3.57 (s, 3H), 3.41-3.37 (m, 1H), 3.36 (d, J=4.2 Hz, 1H), 3.29 (ddd, J=11.2, 8.5, 5.4 Hz, 2H), 3.17 (s, 1H), 3.13-3.07 (m, 1H), 2.83 (d, J=16.1 Hz, 1H), 2.73 (s, 3H), 2.66 (s, 1H), 2.21-2.15 (m, 1H), 2.11 (s, 3H), 1.97 (s, 1H), 1.85-1.75 (m, 3H), 1.64 (s, 6H), 1.41 (t, J=7.3 Hz, 2H), 1.14 (t, J=7.3 Hz, 1H), 0.88 (t, J=7.0 Hz, 3H), 0.71 (t, J=7.5 Hz, 1H); HRESI-TOF m/z 941.4807 ($C_{54}H_{64}N_6O_9$+H$^+$, required 941.4807). $[\alpha]_D^{23}$ −2 (c 0.24, CHCl$_3$).

Compound 110

Method 2 was followed providing Compound 110 in 30% yield. $^1$H NMR (600 MHz, CDCl$_3$) δ 9.87 (s, 1H), 8.90 (s, 1H), 8.61 (d, J=5.0 Hz, 2H), 8.08 (s, 1H), 8.02 (s, 1H), 7.68 (d, J=15.7 Hz, 1H), 7.54 (d, J=7.9 Hz, 1H), 7.46-7.38 (m, 1H), 7.20 (t, J=7.6 Hz, 2H), 7.18-7.04 (m, 3H), 6.12 (s, 1H), 5.90 (d, J=8.6 Hz, 1H), 5.42 (s, 3H), 3.83 (s, 3H), 3.81 (s, 3H), 3.35 (s, 1H), 3.29 (dd, J=7.3, 5.7 Hz, 1H), 3.10 (dd, J=7.3, 4.8 Hz, 2H), 2.92 (s, 1H), 2.75 (s, 3H), 2.23-2.19 (m, 2H), 2.11 (s, 3H), 2.08 (d, J=5.0 Hz, 2H), 2.01 (dd, J=9.0, 5.4 Hz, 1H), 1.97 (s, 2H), 1.42 (t, J=7.3 Hz, 5H), 1.15 (d, J=7.3 Hz, 4H), 0.98 (t, J=7.2 Hz, 5H), 0.78 (t, J=7.5 Hz, 6H); HRESI-TOF m/z 941.4807 ($C_{54}H_{64}N_6O_9$+H$^+$, required 941.4807). $[\alpha]_D^{23}$ −1 (c 0.12, CHCl$_3$).

Compound 111

Method 2 was followed providing Compound 111 in 33% yield. $^1$H NMR (600 MHz, CDCl$_3$) δ 9.83 (s, 1H), 8.61 (d, J=4.4 Hz, 1H), 8.03 (s, 1H), 7.70-7.66 (m, 1H), 7.65 (d, J=15.2 Hz, 1H), 7.49 (d, J=7.9 Hz, 1H), 7.43 (d, J=7.5 Hz, 1H), 7.22 (dd, J=7.6, 4.8 Hz, 2H), 7.16-7.05 (m, 5H), 6.64 (s, 1H), 6.11 (s, 1H), 5.84 (dd, J=10.3, 4.7 Hz, 1H), 5.71 (s, 1H), 5.48 (s, 1H), 5.29 (d, J=10.3 Hz, 1H), 3.84 (d, J=13.7 Hz, 1H), 3.80 (s, 6H), 3.74 (s, 1H), 3.53 (s, 3H), 3.42-3.35 (m, 2H), 3.31-3.27 (m, 1H), 3.25-3.09 (m, 3H), 2.82 (d, J=16.2 Hz, 1H), 2.71 (s, 3H), 2.67-2.64 (m, 2H), 2.48-2.41 (m, 1H), 2.36 (t, J=13.5 Hz, 1H), 2.28 (d, J=14.1 Hz, 1H), 2.23-2.15 (m, 1H), 2.10 (s, 3H), 2.08 (t, J=4.3 Hz, 1H), 1.92 (d, J=14.9 Hz, 1H), 1.87-1.74 (m, $^3$H), 1.16-1.11 (m, 2H), 0.88 (t, J=6.9 Hz, 3H), 0.81 (t, J=7.3 Hz, 3H), 0.77 (t, J=7.4 Hz, 3H); HRESI-TOF m/z 941.4806 ($C_{54}H_{64}N_6O_9$+H$^+$, required 941.4807). $[\alpha]_D^{23}$ −1 (c 0.14, CHCl$_3$).

Compound 112

Method 2 was followed providing Compound 112 in 44% yield. $^1$H NMR (600 MHz, CDCl$_3$) δ 9.79 (s, 1H), 8.00 (s, 1H), 7.69 (s, 1H), 7.61-7.56 (m, 1H), 7.48 (d, J=8.6 Hz, 1H), 7.44-7.38 (m, 2H), 7.20 (d, J=7.4 Hz, 1H), 7.16-7.05 (m, 3H), 6.67-6.57 (m, 2H), 6.11 (s, 1H), 5.87 (s, 1H), 5.56 (s, 1H), 5.49-5.40 (m, 1H), 5.31 (s, 1H), 3.82 (s, 3H), 3.80 (s, 3H), 3.66 (s, 3H), 3.57 (d, J=2.8 Hz, 2H), 3.40-3.34 (m, 2H), 3.30 (d, J=5.2 Hz, 1H), 3.26-3.06 (m, 2H), 2.83 (d, J=16.4 Hz, 1H), 2.73 (d, J=10.7 Hz, 3H), 2.67 (s, 1H), 2.65-2.59 (m, 1H), 2.58-2.42 (m, 2H), 2.11 (s, 3H), 1.80 (s, 3H), 1.58-1.50 (m, 9H), 0.84-0.74 (m, 6H); HRESI-TOF m/z 930.4646 ($C_{53}H_{63}N_5O_{10}$+H$^+$, required 930.4647). $[\alpha]_D^{23}$ −4 (c 0.38, CHCl$_3$).

Compound 113

Method 2 was followed providing Compound 113 in 39% yield. $^1$H NMR (600 MHz, CDCl$_3$) δ 9.80 (s, 1H), 8.02 (s, 1H), 7.52-7.37 (m, 4H), 7.20-7.03 (m, 3H), 6.69-6.54 (m, 2H), 6.42-6.33 (m, 3H), 6.11 (s, 1H), 5.88 (s, 1H), 5.54 (s, 1H), 5.31 (s, 1H), 3.83-3.77 (m, 8H), 3.76 (d, J=17.0 Hz, 2H), 3.66 (d, J=6.5 Hz, 2H), 3.56 (s, 1H), 3.38 (s, 1H), 3.34-3.27 (m, 2H), 3.25-3.14 (m, 1H), 3.11 (s, 1H), 3.02 (t, J=18.1 Hz, 1H), 2.83 (d, J=16.7 Hz, 1H), 2.73 (d, J=13.0 Hz, 3H), 2.66 (s, 1H), 2.52 (m, 1H), 2.46 (s, 1H), 2.38 (d, J=12.8 Hz, 1H), 2.28 (d, J=14.2 Hz, 1H), 2.11 (s, 3H), 2.04 (s, 1H), 1.83-1.75 (d, J=11.1 Hz, 4H), 1.28-1.23 (m, 3H), 0.92 (d, J=6.7 Hz, 1H), 0.83-0.74 (m, 5H); HRESI-TOF m/z 930.4646 ($C_{53}H_{62}N_5O_{10}$+H$^+$, required 930.4647). $[\alpha]_D^{23}$ −2 (c 0.33, CHCl$_3$).

Compound 114

Method 2 was followed providing Compound 114 in 56% yield. $^1$H NMR (600 MHz, CDCl$_3$) δ 9.82 (s, 1H), 8.00 (s, 1H), 7.68 (d, J=15.7 Hz, 1H), 7.53 (t, J=2.0 Hz, 1H), 7.47 (s, 1H), 7.32 (d, J=14.5 Hz, 3H), 7.18-7.05 (m, 3H), 6.65 (s, 1H), 6.40 (d, J=17.2 Hz, 1H), 6.11 (s, 1H), 5.86 (s, 1H), 5.60 (s, 1H), 5.47 (s, 1H), 5.31 (d, J=10.1 Hz, 1H), 3.84-3.77 (m, 8H), 3.75 (s, 1H), 3.70-3.60 (m, 2H), 3.55 (d, J=6.3 Hz, 2H), 3.39 (d, J=5.3 Hz, 1H), 3.36 (dd, J=7.5, 2.9 Hz, 1H), 2.63 (s, 1H), 2.49 (d, J=13.8 Hz, 2H), 2.39 (d, J=12.6 Hz, 1H), 2.28 (d, J=14.1 Hz, 1H), 2.18 (s, 1H), 2.11 (s, 3H), 2.08 (d, J=2.0 Hz, 1H), 2.04 (s, 1H), 1.79 (d, J=11.2 Hz, 3H), 0.85-0.75 (m, 6H); HRESI-TOF m/z 946.4418 ($C_{53}H_{63}N_5O_9S$+H$^+$, required 946.4419). $[\alpha_D^{23}$ −6 (c 0.48, CHCl$_3$).

Compound 115

Method 1 was followed using 3.2 mg of 20'-aminovinblastine (6, 0.04 mmol) to provide Compound 115 as a white solid, yield: 36%. $^1$H NMR (600 MHz, CDCl$_3$) δ 8.98 (d, J=9.0 Hz, 1H), 8.44 (d, J=8.4 Hz, 1H), 8.14-8.03 (m, 3H), 7.92 (d, J=8.3 Hz, 1H), 7.87 (d, J=8.1 Hz, 1H), 7.60-7.48 (m, 4H), 7.14 (d, J=7.2 Hz, 1H), 7.11-7.08 (m, 1H), 6.65 (s, 1H), 6.11 (s, 1H), 5.95 (s, 1H), 5.84 (dd, J=9.8, 4.4 Hz, 1H), 5.48 (s, 1H), 5.29-5.28 (m, 1H), 4.05-4.01 (m, 1H), 3.79 (s, 3H), 3.77 (s, 3H), 3.75 (s, 1H), 3.52 (s, 3H), 3.45 (d, J=13.5 Hz, 1H), 3.38 (dd, J=16.1, 4.6 Hz, 1H), 3.31-3.28 (m, 2H), 3.20-3.10 (m, 2H), 2.75 (d, J=13.6 Hz, 1H), 2.71 (s, 3H), 2.66 (s, 1H), 2.47-2.42 (m, 1H), 2.40-2.36 (m, 2H), 2.23-2.18 (m, 1H), 2.10 (s, 3H), 2.04 (s, 1H), 1.86-1.77 (m, 3H), 1.36-1.33 (m, 3H), 1.26-1.24 (m, 4H), 0.89 (t, J=7.3 Hz, 3H), 0.82 (t, J=7.3 Hz, 3H); ESI-MS m/z 964.3 ($C_{57}H_{65}N_5O_9$+H$^+$, required 964.49).

Compound 116

Method 2 was followed providing Compound 116 in 34% yield. $^1$H NMR (600 MHz, CDCl$_3$) δ 8.63 (s, 1H), 8.15 (s, 1H), 8.08 (d, J=8.8 Hz, 1H), 8.03 (s, 1H), 7.96 (t, J=7.9 Hz, 1H), 7.92-7.84 (m, 2H), 7.57-7.51 (m, 2H), 7.43 (d, J=7.9 Hz, 1H), 7.16-7.09 (m, 2H), 7.06 (t, J=7.4 Hz, 1H), 6.67 (s, 1H), 6.28 (s, 1H), 6.13 (s, 1H), 5.85 (dd, J=13.5, 5.0 Hz, 1H), 5.31 (d, J=10.3 Hz, 1H), 3.83 (s, 3H), 3.80 (s, 3H), 3.76 (s, 1H), 3.59 (s, 3H), 3.46 (d, J=13.6 Hz, 1H), 3.42-3.26 (m, 4H), 3.17 (dd, J=13.5 Hz, 5.0 Hz, 1H), 3.14-3.08 (m, 1H), 2.87-2.75 (m, 2H), 2.73 (s, 3H), 2.68 (s, 1H), 2.54-2.40 (m, 3H), 2.27-2.15 (m, 2H), 2.11 (s, 3H), 1.87-1.78 (m, 2H), 1.44-1.33 (m, 3H), 0.88 (t, J=6.9, 3H), 0.82 (q, J=7.4 Hz, 6H); HRESI-TOF m/z 964.4852 ($C_{57}H_{65}N_5O_9$+H$^+$, required 964.4855). $[α]_D^{23}$−98 (c 0.3, CHCl$_3$).

Compound 117

Generated via Boc deprotection of Compound 118 with 4 M HCl in dioxane. $^1$H NMR (600 MHz, CDCl$_3$) δ 8.49 (s, 1H), 8.05 (s, 1H), 7.98 (d, J=9.2 Hz, 2H), 7.69 (d, J=8.6 Hz, 1H), 7.46 (d, J=7.9 Hz, 1H), 7.19-7.06 (m, 3H), 7.00 (s, 2H), 6.68 (s, 1H), 6.23 (s, 1H), 6.15 (s, 1H), 5.88 (dd, J=10.4, 4.5 Hz, 1H), 5.51 (s, 1H), 5.35-5.31 (m, 1H), 4.16-4.05 (m, 2H), 3.85-3.80 (m, 6H), 3.78 (s, 1H), 3.64-3.58 (m, 3H), 3.50-3.30 (m, 4H), 3.23-3.18 (m, 1H), 3.14-3.08 (m, 1H), 2.86 (d, J=16.1 Hz, 1H), 2.74 (s, 3H), 2.71 (s, 1H), 2.55-2.43 (m, 2H), 2.26-2.18 (m, 2H), 2.17-2.07 (m, 5H), 1.88-1.79 (m, 2H), 1.62-1.51 (2H), 1.42-1.32 (m, 1H), 1.28 (s, 3H), 0.92-0.29 (m, 8H); HRESI-TOF m/z 979.4962 ($C_{57}H_{66}N_6O_9$+H$^+$, required 979.4964). $[α]_D^{23}$−8 (c 0.12, CHCl$_3$).

Compound 118

Method 2 was followed providing desired product in 31% yield. $^1$H NMR (600 MHz, CDCl$_3$) δ 9.85 (s, 1H), 8.58 (s, 1H), 8.10 (s, 1H), 8.06-8.03 (m, 3H), 7.86 (d, J=8.6 Hz, 1H), 7.45 (d, J=8.3 Hz, 1H), 7.41-7.35 (m, 1H), 7.17-7.05 (m, 3H), 6.68 (s, 1H), 6.32 (d, J=12.1 Hz, 2H), 6.24 (s, 1H), 6.14 (s, 1H), 5.87 (dd, J=10.6, 4.7 Hz, 1H), 5.50 (s, 1H), 5.32 (d, J=10.4 Hz, 1H), 4.15-4.07 (m, 2H), 3.83 (s, 3H), 3.82 (s, 3H), 3.77 (s, 1H), 3.60-3.56 (m, 1H), 3.48-3.22 (m, 6H), 3.18-3.12 (m, 1H), 3.11-3.06 (m, 1H), 2.97 (s, 1H), 2.89 (s, 1H), 2.84 (d, J=16.1 Hz, 1H). 2.74 (s, 3H), 2.70 (d, J=7.2 Hz, 1H), 2.50-2.40 (m, 3H), 2.25-2.17 (m, 2H), 2.12 (s, 3H), 1.88-1.79 (m, 2H), 1.53 (s, 9H), 1.41-1.35 (m, 2H), 1.30-1.24 (m, 2H), 1.21-1.09 (m, 1H), 0.90-0.88 (m, 1H), 0.84 (t, J=7.4 Hz, 3H), 0.80 (t, J=7.4 Hz, 3H); HRESI-TOF m/z 1079.5482 ($C_{62}H_{74}N_6O_{11}$+H$^+$, required 1079.5488). $[α]_D^{23}$−54 (c 0.07, CHCl$_3$).

Compound 120

Method 2 was followed providing Compound 120 in 33% yield. $^1$H NMR (600 MHz, CDCl$_3$) δ 9.88 (s, 1H), 8.96 (d, J=1.8 Hz, 1H), 8.16-8.09 (m, 2H), 7.93 (d, J=8.5 Hz, 1H), 7.51 (d, J=7.9 Hz, 1H), 7.48-7.45 (m, 2H), 7.19-7.07 (m, 3H), 6.85 (dd, J=5.2, 3.5 Hz, 1H), 6.66 (s, 1H), 6.33 (s, 1H), 6.13 (s, 1H), 5.87 (dd, J=10.2, 4.6 Hz, 1H), 5.33-5.29 (m, 1H), 4.09-3.98 (m, 3H), 3.93 (s, 3H), 3.82 (s, 3H), 3.80-3.76 (m, 4H), 3.50-3.27 (m, 4H), 3.21-3.18 (m, 2H), 2.76 (d, J=13.8 Hz, 1H), 2.74 (s, 3H), 2.68 (s, 1H), 2.50-2.44 (m, 3H), 2.44-2.37 (m, 1H), 2.28-2.21 (m, 1H), 2.13 (s, 3H), 1.91-1.79 (m, 2H), 1.56-1.45 (m, 4H), 1.39-1.32 (m, 1H), 1.28 (s, 3H), 0.93-0.85 (m, 2H), 0.85-0.82 (m, 6H); HRESI-TOF m/z 994.4962 ($C_{58}H_{67}N_5O_{10}$+H+, required 994.4960). $[α]_D^{23}$+37 (c 0.07, CHCl$_3$).

Compound 121

Method 2 was followed using 8.4 mg of 20'-aminovinblastine (6, 0.01 mmol) to provide 4.0 mg of Compound 121 as a white solid, yield: 42%. $^1$H NMR (600 MHz, CDCl$_3$) δ 9.86 (br s, 1H), 8.05 (s, 1H), 7.76 (s, 2H), 7.48-7.46 (m, 1H), 7.19 (d, J=8.2 Hz, 1H), 7.16 (d, J=6.7 Hz, 1H), 7.12-7.10 (m, 2H), 6.66 (s, 1H), 6.14 (s, 1H), 6.10 (s, 1H), 5.88-5.87 (m, 1H), 5.50 (s, 1H), 5.33 (d, J=10.2 Hz, 1H), 4.00 (br s, 1H), 3.84 (s, 3H), 3.82 (s, 3H), 3.78-3.77 (m, 1H), 3.60 (s, 3H), 3.44-3.38 (m, 2H), 3.33 (td, J=9.5, 4.8 Hz, 1H), 3.26-3.23 (m, 1H), 3.14-3.10 (m, 2H), 2.91-2.87 (m, 2H), 2.84-2.83 (m, 1H), 2.82-2.81 (m, 2H), 2.75 (s, 3H), 2.71-2.69 (m, 1H), 2.48-2.43 (m, 1H), 2.39-2.36 (m, 1H), 2.20 (s, 3H), 2.13 (s, 1H), 1.88-1.85 (m, 1H), 1.83-1.82 (m, 4H), 1.61 (s, 3H), 1.54-1.51 (m, 1H), 1.44 (t, J=7.4 Hz, 1H), 1.37-1.33 (m, 2H), 1.28 (s, 2H), 0.92-0.89 (m, 1H), 0.84 (t, J=6.9 Hz, 3H), 0.80-0.78 (m, 3H); HRESI-TOF m/z 968.5164 ($C_{57}H_{69}N_5O_9$+H$^+$, required 968.5168). $[α]_D^{23}$−55 (c 0.069, CHCl$_3$).

Compound 122

Method 2 was followed using 4.5 mg of 20'-aminovinblastine (6, 0.006 mmol) to provide 0.97 mg of Compound 122 as a yellow solid, yield: 18%. $^1$H NMR (CDCl$_3$, 600 MHz) δ 9.81 (br s, 1H), 8.21 (s, 1H), 8.03 (s, 1H), 7.51 (t, J=7.5 Hz, 1H), 7.21-7.07 (m, 5H), 6.65-6.63 (m, 1H), 6.53 (s, 1H), 6.12 (s, 1H), 6.10 (d, J=3.0 Hz, 1H), 5.85 (dd, J=4.5, 10.5 Hz, 1H), 5.49-5.46 (m, 1H), 5.30 (d, J=10.2 Hz, 1H), 3.81-3.76 (m, 8H), 3.74 (s, 1H), 3.58-3.55 (m, 4H), 3.41-3.35 (m, 2H), 3.32-3.13 (m, 5H), 3.08-3.04 (m, 2H), 2.95-2.90 (m, 1H), 2.82 (d, J=16.2 Hz, 1H), 2.71 (s, 3H), 2.66 (s, 1H), 2.62-2.58 (m, 1H), 2.46-2.42 (m, 1H), 2.33-2.17 (m, 5H), 2.11 (s, 3H), 2.03-1.94 (m, 2H), 1.88-1.78 (m, 3H), 1.68-1.54 (m, 2H), 1.37-1.32 (m, 2H), 1.25-1.18 (m, 2H), 0.83-0.80 (m, 3H), 0.76-0.70 (m, 3H); IR (film) $ν_{max}$ 3726, 1737, 1373, 1218, 670 cm$^{-1}$; HRESI-TOF m/z 968.5169 ($C_{57}H_{69}N_5O_9$+H$^+$, required 968.5168). $[α]_D^{23}$+12 (c 0.049, CHCl$_3$).

Compound 123

Method 2 was followed providing Compound 123 in 32% yield. $^1$H NMR (600 MHz, CDCl$_3$) δ 8.05 (s, 1H), 7.94 (d, J=2.0 Hz, 1H), 7.76 (d, J=7.6 Hz, 1H), 7.47 (d, J=7.9 Hz, 1H), 7.39 (d, J=8.3 Hz, 1H), 7.16-7.06 (m, 3H), 6.64 (s, 1H), 6.11 (s, 1H), 6.06 (s, 1H), 5.88-5.82 (m, 1H), 5.48 (s, 1H), 5.30 (d, J=8.1 Hz, 1H), 4.00-3.95 (m, 1H), 3.88-3.86 (m, 1H), 3.82-3.79 (m, 6H), 3.75 (s, 1H), 3.56 (s, 3H), 3.44-3.33 (m, 2H), 3.32-3.28 (m, 1H), 3.27-3.23 (m, 1H), 3.15-3.11 (m, 2H), 2.82 (d, J=16.2 Hz, 1H), 2.71 (s, 3H), 2.66 (s, 1H), 2.48-2.39 (m, 2H), 2.37-2.32 (m, 3H), 2.23-2.18 (m, 1H), 2.12 (s, 1H), 2.11 (s, 3H), 1.92-1.90 (m, 1H), 1.88-1.77 (m, 2H), 1.70 (s, 3H), 1.65-1.53 (m, 7H), 1.36-1.25 (m, 8H), 0.96-0.85 (m, 2H), 0.83-0.75 (m, 7H); HRESI-TOF m/z 1024.5794 ($C_{61}H_{77}N_5O_9$+H$^+$, required 1024.5794). $[α]_D^{23}$−27 (c 0.08, CHCl$_3$).

Compound 124

Method 2 was followed using 4.3 mg of 20'-aminovinblastine (6, 0.005 mmol) to provide 1.1 mg of Compound 124 as a pale yellow solid, yield: 23%. $^1$H NMR (CDCl$_3$, 600 MHz) δ 9.84 (br s, 1H), 8.02 (s, 1H), 7.90 (s, 1H), 7.81 (d, J=9.0 Hz, 1H), 7.46-7.44 (m, 1H), 7.31 (d, J=7.8 Hz, 1H), 7.15-7.06 (m, 4H), 6.64 (s, 1H), 6.12 (s, 1H), 6.08 (s, 1H), 5.85 (dd, J=4.8, 10.2 Hz, 1H), 5.48 (s, 1H), 5.30 (d, J=10.2 Hz, 1H), 4.00 (br s, 1H), 3.81 (s, 3H), 3.80 (s, 3H), 3.75 (s, 1H), 3.59 (s, 3H), 3.41-3.35 (m, 3H), 3.30 (td, J=4.8, 9.6 Hz, 1H), 3.26-3.18 (m, 3H), 3.14-3.11 (m, 1H), 3.09-2.92 (m, 5H), 2.83 (d, J=15.6 Hz, 1H), 2.72 (s, 3H), 2.68-2.66 (m, 1H), 2.48-2.41 (m, 2H), 2.35 (d, J=13.8 Hz, 1H), 2.22-2.18 (m, 2H), 2.10-2.04 (m, 4H), 1.89-1.78 (m, 3H), 1.33-1.25 (m, 6H), 0.85-0.76 (m, 6H); IR (film) $v_{max}$ 2927, 1737, 1459, 1237, 1038, 667 cm$^{-1}$; HRESI-TOF m/z 954.5014 ($C_{56}H_{67}N_5O_9$+H$^+$, required 954.5011). [u]$_D^{23}$ −9 (c 0.055, CHCl$_3$)

Compound 125

Method 2 was followed using 6.7 mg of 20'-aminovinblastine (6, 0.008 mmol) to provide 4.0 mg of Compound 125 as a white solid, yield: 51%. $^1$H NMR (CDCl$_3$, 600 MHz) δ 9.83 (br s, 1H), 8.04 (s, 1H), 7.52 (d, J=7.8 Hz, 1H), 7.23-7.21 (m, 1H), 7.17-7.10 (m, 5H), 6.63 (s, 1H), 6.11 (s, 1H), 5.85 (dd, J=4.8, 10.8 Hz, 1H), 5.48 (s, 1H), 5.45 (s, 1H), 5.30 (d, J=10.2 Hz, 1H), 3.84 (br s, 1H), 3.81 (s, 3H), 3.80 (s, 3H), 3.74 (s, 1H), 3.59 (s, 3H), 3.42-3.35 (m, 3H), 3.31-3.28 (m, 3H), 3.24-3.16 (m, 1H), 3.06-3.04 (m, 1H), 2.82 (d, J=16.2 Hz, 1H), 2.71 (br s, 4H), 2.66 (s, 1H), 2.59 (d, J=13.2 Hz, 1H), 2.44 (td, J=6.6, 10.5 Hz, 1H), 2.31 (d, J=13.2 Hz, 1H), 2.24-2.17 (m, 2H), 1.88 (d, J=14.4 Hz, 1H), 1.84-1.78 (m, 3H), 1.63-1.62 (m, 2H), 1.38-1.31 (m, 2H), 1.28-1.25 (m, 2H), 1.22-1.15 (m, 2H), 0.82 (t, J=7.2 Hz, 3H), 0.71 (t, J=7.5 Hz, 3H); IR (film) $v_{max}$ 3464, 2924, 1739, 1236, 1040, 748 cm$^{-1}$; HRESI-TOF m/z 954.4993 ($C_{56}H_{67}N_5O_9$+H$^+$, required 954.5011). [α]$_D^{23}$ +11 (c 0.20, CHCl$_3$).

Compound 126

Method 2 was followed using 4.3 mg of 20'-aminovinblastine (6, 0.005 mmol) to provide 1.2 mg of Compound 126 as a white solid, yield: 35%. $^1$H NMR (CDCl$_3$, 600 MHz) δ 9.84 (br s, 1H), 8.03 (s, 1H), 7.75 (s, 1H), 7.45 (d, J=7.8 Hz, 1H), 7.20 (d, J=7.8 Hz, 1H), 7.15-7.06 (m, 3H), 6.64 (s, 1H), 6.12 (s, 1H), 6.07 (s, 1H), 5.85 (dd, J=4.5, 10.5 Hz, 1H), 5.48 (s, 1H), 5.30 (d, J=10.2 Hz, 1H), 3.99 (br s, 1H), 3.81 (s, 3H), 3.80 (s, 3H), 3.75 (s, 1H), 3.58 (s, 3H), 3.42-3.36 (m, 3H), 3.31 (td, J=4.2, 9.6 Hz, 1H), 3.24-3.20 (m, 2H), 3.14-3.10 (m, 1H), 2.90-2.88 (m, 1H), 2.84-2.81 (m, 3H), 2.72 (s, 3H), 2.69-2.66 (m, 2H), 2.48-2.41 (m, 3H), 2.36-2.34 (m, 1H), 2.22-2.17 (m, 2H), 2.11 (s, 3H), 2.00 (br s, 1H), 1.86-1.77 (m, 2H), 1.69-1.60 (m, 5H), 1.36-1.32 (m, 3H), 1.29-1.23 (m, 3H), 0.82 (t, J=7.2 Hz, 3H), 0.77 (t, J=7.2 Hz, 3H); IR (film) $v_{max}$ 2918, 2850, 1739, 1488, 1226, 1040, 771 cm$^{-1}$; HRESI-TOF m/z 982.5335 ($C_{58}H_{71}N_5O_9$+H$^+$, required 982.5324). [α]$_D^{23}$ −8 (c 0.09, CHCl$_3$).

Compound 127

Method 2 was followed using 4.9 mg of 20'-aminovinblastine (6, 0.006 mmol) to provide 3.2 mg of Compound 127 as white solid, yield: 52%. $^1$H NMR (CDCl$_3$, 600 MHz) δ 9.84 (br s, 1H), 8.86 (br s, 1H), 8.44 (s, 1H), 8.11 (d, J=9.0 Hz, 1H), 8.08-7.99 (m, 3H), 7.53-7.44 (m, 4H), 7.15-7.04 (m, 3H), 6.70 (s, 1H), 6.33 (s, 1H), 6.15 (s, 1H), 5.86 (dd, J=4.8, 10.2 Hz, 1H), 5.50 (s, 1H), 5.31 (d, J=10.8 Hz, 1H), 4.24 (br s, 1H), 4.10 (br s, 1H), 3.84-3.75 (m, 7H), 3.65 (s, 1H), 3.49-3.25 (m, 6H), 3.18-3.12 (m, 2H), 2.96 (br s, 2H), 2.83 (d, J=16.2 Hz, 1H), 2.75-2.70 (m, 3H), 2.50-2.46 (m, 2H), 2.24-2.19 (m, 2H), 2.26-2.19 (m, 2H), 2.12 (s, 3H), 1.88-1.81 (m, 2H), 1.42-1.26 (m, 8H), 0.92-0.81 (m, 6H); IR (film) $v_{max}$ 3728, 1737, 1366, 1227, 670 cm$^{-1}$; HRESI-TOF m/z 1014.5010 ($C_{61}H_{67}N_5O_9$+H$^+$, required 1014.5011). [α]$_D^{23}$ −32 (c 0.06, CHCl$_3$).

Compound 128

Method 2 was followed using 5.2 mg of 20'-aminovinblastine (6, 0.006 mmol) to provide 3.5 mg of Compound 128 as a white solid, yield: 60%. $^1$H NMR (CDCl$_3$, 600 MHz) δ 9.94 (br s, 1H), 8.80-8.78 (m, 2H), 8.01 (s, 1H), 7.90 (s, 1H), 7.85-7.84 (m, 1H), 7.46 (d, J=7.8 Hz, 1H), 7.16-7.07 (m, 3H), 6.66 (s, 1H), 6.15 (s, 1H), 6.12 (s, 1H), 5.86 (dd, J=4.8, 10.2 Hz, 1H), 5.48 (s, 1H), 5.32-5.30 (m, 1H), 3.98 (br s, 1H), 3.81-3.80 (m, 6H), 3.75 (s, 1H), 3.60 (s, 3H), 3.42-3.29 (m, 3H), 3.23-3.20 (m, 1H), 3.11-3.07 (m, 2H), 2.95 (s, 1H), 2.88 (s, 1H), 2.85-2.82 (m, 1H), 2.72-2.68 (m, 4H), 2.52-2.47 (m, 1H), 2.40 (d, J=13.8 Hz, 1H), 2.33-2.26 (m, 1H), 2.22-2.17 (m, 1H), 2.11 (s, 3H), 1.97-1.71 (m, 6H), 1.36-1.33 (m, 2H), 1.24 (s, 1H), 0.83 (t, J=7.5 Hz, 3H), 0.77 (t, J=7.2 Hz, 3H); IR (film) $v_{max}$ 3467, 2928, 1730, 1227, 1039, 736 cm$^{-1}$; HRESI-TOF m/z 915.4660 ($C_{52}H_{62}N_6O_9$+H$^+$, required 915.4651).

Compound 129

Method 2 was followed using 5.2 mg of 20'-aminovinblastine (6, 0.006 mmol) to provide 2.8 mg of Compound 129 as a pale yellow resin, yield: 60%. $^1$H NMR (CDCl$_3$, 600 MHz) δ 9.95 (br s, 1H), 9.30 (s, 1H), 8.75-8.74 (m, 1H), 8.36 (br s, 1H), 8.01 (s, 1H), 7.46-7.44 (m, 2H), 7.16-7.06 (m, 3H), 6.66 (s, 1H), 6.12-6.10 (m, 2H), 5.86 (dd, J=4.5, 10.5 Hz, 1H), 5.48 (s, 1H), 5.31-5.30 (m, 1H), 4.03-3.96 (m, 1H), 3.81-3.80 (m, 6H), 3.75 (s, 1H), 3.62 (s, 3H), 3.43-3.37 (m, 2H), 3.30 (td, J=4.6, 9.6 Hz, 1H), 3.24-3.20 (m, 1H), 3.12-3.08 (m, 2H), 2.96 (s, 1H), 2.88 (s, 1H), 2.85-2.82 (m, 1H), 2.72 (s, 3H), 2.69 (s, 1H), 2.50-2.45 (m, 1H), 2.40 (d, J=13.8 Hz, 1H), 2.32 (d, J=13.8 Hz, 1H), 2.22-2.16 (m, 1H), 2.11 (s, 3H), 1.95 (br s, 1H), 1.86-1.69 (m, 5H), 1.36-1.33 (m, 2H), 1.24 (s, 1H), 0.82 (t, J=7.2 Hz, 3H), 0.78 (t, J=7.5 Hz, 3H); IR (film) $v_{max}$ 3467, 2921, 1735, 1227, 1039, 737 cm$^{-1}$; HRESI-TOF m/z 915.4657 ($C_{52}H_{62}N_6O_9$+H$^+$, required 915.4651).

Compound 130

Method 2 was followed using 4.6 mg of 20'-aminovinblastine (6, 0.006 mmol) to provide 3.1 mg of Compound 130 as a white solid, yield: 60%. $^1$H NMR (CDCl$_3$, 600 MHz) δ 10.0 (br s, 1H), 8.63 (s, 1H), 8.47 (s, 1H), 8.24 (d, J=7.8 Hz, 1H), 8.05 (s, 1H), 7.88 (t, J=7.8 Hz, 1H), 7.46 (d, J=7.8 Hz, 1H), 7.42-7.41 (m, 1H), 7.14-7.06 (m, 3H), 6.57 (s, 1H), 6.08 (s, 1H), 5.84 (dd, J=4.8, 10.2 Hz, 1H), 5.46 (s, 1H), 5.30-5.27 (m, 1H), 3.85-3.83 (m, 1H), 3.79 (s, 6H) 3.75 (s, 1H), 3.49 (s, 3H), 3.41-3.28 (m, 4H), 3.21-3.17 (m, 1H), 2.96 (s, 1H), 2.89 (s, 1H), 2.85-2.82 (m, 1H), 2.70 (s, 3H), 2.65 (s, 1H), 2.48-2.39 (m, 2H), 2.27-2.16 (m, 2H), 2.10 (s, 3H), 1.83-1.75 (m, 2H), 1.62-1.55 (m, 5H), 1.33-1.13 (m, 3H), 0.88-0.77 (m, 6H); IR (film) $v_{max}$ 1738, 1367, 1218 cm$^{-1}$; HRESI-TOF m/z 915.4663 ($C_{52}H_{62}N_6O_9$+H$^+$, required 915.4651).

Compound 131

Method 2 was followed providing Compound 129 as an off-white resin in 61% yield. $^1$H NMR (CDCl$_3$, 600 MHz) δ 9.83 (br s, 1H), 9.47 (s, 1H), 8.75 (d, J=2.4 Hz, 1H), 8.60 (s, 1H), 8.14 (s, 1H), 8.02 (s, 1H), 7.48 (d, J=8.4 Hz, 1H), 7.14-7.07 (m, 3H), 6.57 (s, 1H), 6.08 (s, 1H), 5.84 (dd, J=4.8, 10.2 Hz, 1H), 5.47 (s, 1H), 5.28 (d, J=10.2 Hz, 1H), 3.80 (s, 3H), 3.75-3.73 (m, 5H), 3.58 (br s, 1H), 3.42-3.28 (m, 4H), 3.17-3.15 (m, 1H), 3.13-3.05 (m, 4H), 2.81 (d, J=16.2 Hz, 1H), 2.73 (d, J=13.8 Hz, 1H), 2.70 (s, 3H), 2.64 (s, 1H), 2.46-2.41 (m, 1H), 2.38 (d, J=12.6 Hz, 1H), 2.22-2.16 (m, 2H), 2.10 (s, 3H), 1.93 (br s, 1H), 1.84-1.77 (m, 2H), 1.38 (br s, 2H), 1.33-1.25 (m, 4H), 0.84-0.78 (m, 6H); IR (film) $v_{max}$ 3725, 1739, 1367, 1218, 772 cm$^1$; HRESI-TOF m/z 916.4603 ($C_{51}H_{61}N_7O_9$+H$^+$, required 916.4603). [α]$_D^{23}$ +17 (c 0.04, CHCl$_3$).

Compound 132

Method 2 was followed providing Compound 132 in 29% yield. $^1$H NMR (600 MHz, CDCl$_3$) δ 9.76 (s, 1H), 9.45 (dd, J=5.4, 1.2 Hz, 1H), 8.17 (s, 1H), 8.04 (s, 1H), 8.03 (s, 1H), 7.48 (d, J=8.0 Hz, 1H), 7.48 (d, J=8.0 Hz, 1H), 7.20-7.09 (m, 3H), 6.70 (s, 1H), 6.17 (s, 1H), 6.15 (s, 1H), 5.91-5.85 (m, 1H), 5.51 (s, 1H), 5.33 (d, J=10.1 Hz, 1H), 4.01 (t, J=13.3

Hz, 1H), 3.87 (d, J=13.3 Hz, 1H), 3.84 (s, 3H), 3.83 (s, 3H), 3.78 (s, 1H), 3.66 (s, 3H), 3.47 (d, J=13.3 Hz, 1H), 3.44-3.39 (m, 1H), 3.38-3.31 (m, 1H), 3.31-3.21 (m, 1H), 3.16 (dd, J=14.7, 5.1 Hz, 1H), 3.12-3.02 (m, 1H), 2.84 (d, J=16.1 Hz, 1H), 2.75 (s, 3H), 2.73 (s, 1H), 2.70 (s, 1H), 2.48 (td, J=10.4, 6.6 Hz, 1H), 2.41 (d, J=13.0 Hz, 1H), 2.33 (d, J=13.0 Hz, 1H), 2.27-2.20 (m, 1H), 2.14 (s, 3H), 1.96-1.78 (m, 3H), 1.68-1.58 (m, 1H), 1.42-1.36 (m, 2H), 1.30-1.26 (m, 2H), 0.96-0.87 (m, 1H), 0.85 (t, J=7.5 Hz, 3H), 0.81 (t, J=7.5 Hz, 3H); HRESI-TOF m/z 916.4603 ($C_{51}H_{61}N_7O_9$+H$^+$, required 916.4603). $[\alpha]_D^{23}$ −1.3 (c 0.09, CHCl$_3$).

Compound 133

Method 1 was followed providing Compound 133 as a yellow resin in 60% yield. $^1$H NMR (CDCl$_3$, 600 MHz) δ 8.20 (s, 1H), 8.00 (s, 1H), 7.47-7.41 (m, 2H), 7.16-7.06 (m, 3H), 6.91 (s, 1H), 6.65 (s, 1H), 6.12 (s, 1H), 5.85 (dd, J=4.2, 10.2 Hz, 1H), 5.78 (s, 1H), 5.47 (s, 1H), 5.31-5.29 (m, 1H), 3.97-3.92 (m, 2H), 3.82 (s, 3H), 3.80 (s, 3H), 3.75 (s, 1H), 3.62 (s, 3H), 3.40-3.36 (m, 2H), 3.30 (td, J=4.6, 9.5 Hz, 1H), 3.23 (t, J=12.0 Hz, 1H), 3.17-3.08 (m, 3H), 2.83 (d, J=16.2 Hz, 1H), 2.72 (s, 3H), 2.68 (s, 1H), 2.48-2.42 (m, 1H), 2.30 (d, J=13.2 Hz, 1H), 2.21-2.16 (m, 1H), 2.11 (s, 3H), 2.07-2.00 (m, 1H), 1.84-1.72 (m, 3H), 1.36-1.30 (m, 3H), 1.27-1.24 (m, 2H), 0.83-0.79 (m, 6H); IR (film) ν$_{max}$ 3462, 2949, 1735, 1502, 1227, 1039, 735 cm$^{-1}$; HRESI-TOF m/z 904.4491 ($C_{51}H_{61}N_5O_{10}$+H$^+$, required 904.4491).

Compound 134

Method 1 was followed using 3.5 mg of 20'-aminovinblastine (6, 0.004 mmol) to provide Compound 134 as a white solid, yield: 51%. $^1$H NMR (600 MHz, CDCl$_3$) δ 9.86 (s, 1H), 8.04 (s, 1H), 7.49-7.47 (m, 2H), 7.15 (d, J=3.4 Hz, 1H), 7.12 (d, J=7.0 Hz, 1H), 7.09-7.06 (m, 2H), 6.59 (s, 1H), 6.51 (dd, J=3.3, 1.6 Hz, 1H), 6.45 (s, 1H), 6.09 (s, 1H), 5.83 (dd, J=10.1, 4.3 Hz, 1H), 5.46 (s, 1H), 5.28 (d, J=10.1 Hz, 1H), 3.79 (s, 3H), 3.77 (s, 3H), 3.73 (s, 1H), 3.68-3.59 (m, 1H), 3.48 (s, 3H), 3.41-3.35 (m, 3H), 3.29-3.24 (m, 3H), 3.15-3.12 (m, 2H), 2.81 (d, J=16.2 Hz, 1H), 2.70 (s, 3H), 2.67 (d, J=13.9 Hz, 1H), 2.64 (s, 1H), 2.43 (td, J=10.4, 6.7 Hz, 1H), 2.38 (d, J=12.8 Hz, 1H), 2.28 (d, J=13.7 Hz, 1H), 2.20-2.14 (m, 1H), 2.09 (s, 3H), 1.83-1.75 (m, 4H), 1.30 (td, J=13.4, 5.6 Hz, 2H), 1.26-1.24 (m, 1H), 0.79 (td, J=7.3, 2.3 Hz, 6H); HRESI-TOF m/z 904.4491 ($C_{51}H_{61}N_5O_{10}$+H$^+$, required 904.4491).

Compound 135

Method 1 was followed using 6.0 mg of 20'-aminovinblastine (6, 0.007 mmol) to provide 6.3 mg of Compound 135 as a white solid, yield: 90%. $^1$H NMR (600 MHz, CDCl$_3$) δ 9.82 (br s, 1H), 9.76 (br s, 1H), 8.15 (s, 1H), 8.05 (s, 1H), 8.00 (s, 1H), 7.62 (s, 1H), 7.36-7.34 (m, 1H), 7.20-7.18 (m, 1H), 7.11-7.07 (m, 1H), 6.65 (s, 1H), 6.43 (s, 1H), 6.11 (s, 1H), 5.90-5.85 (m, 1H), 5.47 (s, 1H), 5.31-5.29 (m, 1H), 4.00 (s, 1H), 3.83-3.81 (m, 3H), 3.79 (s, 3H), 3.74-3.60 (m, 4H), 3.40-3.35 (m, 2H), 3.30-3.28 (m, 1H), 3.22-3.15 (m, 1H), 3.09 (dd, J=7.3, 4.7 Hz, 2H), 2.83 (t, J=12.7 Hz, 1H), 2.71 (s, 3H), 2.62 (s, 1H), 2.42-2.40 (m, 1H), 2.17 (s, 1H), 2.16 (s, 1H), 2.10 (s, 3H), 1.81-1.77 (m, 2H), 1.62-1.56 (m, 3H), 1.41 (t, J=7.3 Hz, 1H), 1.35-1.30 (m, 2H), 1.28-1.25 (m, 4H), 0.87 (t, J=6.9 Hz, 3H), 0.80 (t, J=5.4 Hz, 3H); HRESI-TOF m/z 920.4262 ($C_{51}H_{61}N_5O_9S$+H$^+$, required 920.4263).

Compound 136

Method 2 was followed providing Compound 136 as a white solid in 57% yield. $^1$H NMR (CDCl$_3$, 600 MHz) δ 9.84 (s, 1H), 8.02 (s, 1H), 7.78 (s, 1H), 7.48-7.45 (m, 2H), 7.15-7.06 (m, 3H), 6.64 (s, 1H), 6.12 (s, 1H), 6.02 (s, 1H), 5.85 (dd, J=4.5, 10.5 Hz, 1H), 5.48 (s, 1H), 5.29 (d, J=10.2 Hz, 1H), 3.93-3.89 (m, 1H), 3.81-3.80 (m, 6H), 3.75 (s, 1H), 3.57 (s, 3H), 3.41-3.35 (m, 2H), 3.30 (td, J=9.6, 4.8 Hz, 1H), 3.26-3.18 (m, 1H), 3.15-3.12 (m, 1H), 2.82 (d, J=16.2 Hz, 1H), 2.72 (s, 3H), 2.68-2.63 (m, 3H), 2.48-2.40 (m, 3H), 2.34 (d, J=13.8 Hz, 1H), 2.22-2.17 (m, 2H), 2.11 (s, 3H), 1.96 (br s, 1H), 1.85-1.77 (m, 2H), 1.49 (br s, 1H), 1.35-1.31 (m, 2H), 1.10 (br s, 1H), 0.82-0.80 (m, 6H); IR (film) ν$_{max}$ 2921, 1740, 1649, 1503, 1242, 745 cm$^{-1}$; HRESI-TOF m/z 920.4268 ($C_{51}H_{61}N_5O_9S$+H$^+$, required 920.4263). $[\alpha]_D^{23}$ −12 (c 0.16, CHCl$_3$).

Compound 137

Method 2 was followed using 5.6 mg of 20'-aminovinblastine (6, 0.007 mmol) to provide Compound 137 as a white solid, yield: 41%. $^1$H NMR (600 MHz, CDCl$_3$) δ 9.86 (s, 1H), 8.26 (s, 1H), 8.03 (s, 1H), 7.88 (s, 1H), 7.48 (d, J=8.6 Hz, 1H), 7.14-7.11 (m, 1H), 7.09-7.06 (m, 1H), 6.57 (s, 1H), 6.08 (s, 1H), 5.83 (dd, J=10.4, 4.5 Hz, 1H), 5.46 (s, 1H), 5.29-5.27 (m, 3H), 3.79 (s, 3H), 3.75 (s, 3H), 3.72 (s, 1H), 3.55 (d, J=11.6 Hz, 1H), 3.45 (s, 2H), 3.39-3.35 (m, 3H), 3.29 (t, J=12.9 Hz, 2H), 3.16 (dt, J=17.3, 7.7 Hz, 2H), 2.81 (d, J=16.0 Hz, 1H), 2.69 (s, 3H), 2.64 (s, 1H), 2.45-2.41 (m, 1H), 2.36 (d, J=12.8 Hz, 1H), 2.25 (d, J=14.4 Hz, 1H), 2.19-2.13 (m, 2H), 2.09 (s, 3H), 1.83-1.76 (m, 3H), 1.33-1.23 (m, 7H), 0.80-0.77 (m, 6H); HRESI-TOF m/z 905.4444 ($C_{50}H_{60}N_6O_{10}$+H$^+$, required 905.4443).

Compound 138

Method 2 was followed providing Compound 138 in 47% yield. $^1$H NMR (600 MHz, CDCl$_3$) δ 9.77 (s, 1H), 8.02 (s, 1H), 7.96 (s, 1H), 7.79 (s, 1H), 7.49 (d, J=7.4 Hz, 1H), 7.18-7.06 (m, 3H), 6.61 (s, 1H), 6.34 (s, 1H), 6.10 (s, 1H), 5.85 (dd, J=10.0, 4.4 Hz, 1H), 5.48 (s, 1H), 5.29 (d, J=10.0 Hz, 1H), 3.80 (s, 3H), 3.78 (s, 3H), 3.49 (s, 3H), 3.45-3.37 (m, 2H), 3.37-3.27 (m, 2H), 3.22-3.16 (m, 3H), 3.14-3.10 (m, 1H), 2.81 (d, J=16.1 Hz, 1H), 2.71 (s, 3H), 2.68 (s, 1H), 2.65 (s, 1H), 2.44 (td, J=10.4, 6.6 Hz, 1H), 2.36 (d, J=13.3 Hz, 1H), 2.27-2.16 (m, 1H), 2.11 (s, 3H), 2.11-2.03 (m, 2H), 2.02-1.94 (m, 1H), 1.86-1.76 (m, 1H), 1.36-1.23 (s, 5H), 0.95-0.83 (m, 1H), 0.83-0.78 (m, 8H); HRESI-TOF m/z 905.4444 ($C_{50}H_{60}N_6O_{10}$+H$^+$, required 905.4443). $[\alpha]_D^{23}$ −10 (c 0.06, CHCl$_3$).

Compound 139

Method 2 was followed using 5.6 mg of 20'-aminovinblastine (6, 0.007 mmol) to provide Compound 139 as a white solid, yield: 52%. $^1$H NMR (600 MHz, CDCl$_3$) δ 9.87 (s, 1H), 8.78 (s, 1H), 8.17 (s, 1H), 8.04 (s, 1H), 7.68 (s, 1H), 7.47 (d, J=8.0 Hz, 1H), 7.12 (t, J=7.3 Hz, 1H), 7.08-7.06 (m, 1H), 6.56 (s, 1H), 6.08 (s, 1H), 5.84-5.81 (m, 1H), 5.46 (s, 1H), 5.29 (s, 1H), 5.27 (d, J=10.2 Hz, 1H), 3.78 (s, 3H), 3.75 (s, 3H), 3.72 (s, 1H), 3.40-3.34 (m, 4H), 3.27 (dd, J=10.9, 6.4 Hz, 3H), 3.19-3.16 (m, 1H), 3.12 (s, 1H), 2.95 (s, 1H), 2.87 (s, 1H), 2.80 (d, J=16.1 Hz, 1H), 2.69 (s, 3H), 2.63 (s, 1H), 2.43 (dd, J=16.9, 10.7 Hz, 1H), 2.38 (d, J=13.2 Hz, 1H), 2.26 (d, J=15.0 Hz, 1H), 2.20-2.15 (m, 2H), 2.09 (s, 3H), 1.83-1.73 (m, 3H), 1.30-1.24 (m, 5H), 0.81-0.76 (m, 6H); HRESI-TOF m/z 921.4192 ($C_{50}H_{60}N_6O_9S$+H$^+$, required 921.4215).

Compound 140

Method 2 was followed providing Compound 140 in 37% yield. $^1$H NMR (600 MHz, CDCl$_3$) δ 8.92 (s, 1H), 8.90 (s, 1H), 8.62 (s, 1H), 8.14 (s, 1H), 8.04 (s, 1H), 7.49 (d, J=8.0 Hz, 1H), 7.20-7.08 (m, 3H), 6.68 (s, 1H), 6.14 (s, 1H), 6.04 (s, 1H), 5.87 (dd, J=10.4, 4.8 Hz, 1H), 5.50 (s, 1H), 5.35-5.30 (m, 1H), 3.99-3.91 (m, 1H), 3.85-3.80 (m, 9H), 3.63 (s, 3H), 3.48-3.36 (m, 3H), 3.37-3.24 (m, 3H), 3.18-3.13 (m, 2H), 2.88-2.82 (m, 2H), 2.79-2.67 (m, 3H), 2.52-2.39 (m, 2H), 2.29-2.31 (m, 1H), 2.20 (s, 1H), 2.13 (s, 2H), 1.89-1.79 (m, 2H), 1.38-1.30 (m, 3H), 0.93-0.81 (m, 8H);

HRESI-TOF m/z 921.4192 ($C_{50}H_{60}N_6O_9S+H^+$, required 921.4215). $[\alpha]_D^{23}$ –13 (c 0.04, CHCl$_3$).

Compound 141

Method 2 was followed providing Compound 141 in 50% yield. $^1$H NMR (600 MHz, CDCl$_3$) δ 8.05 (s, 1H), 7.86 (s, 1H), 7.54 (s, 1H), 7.52-7.46 (m, 1H), 7.20-7.14 (m, 1H), 7.15-7.07 (m, 2H), 6.68 (s, 1H), 6.15 (s, 1H), 5.92-5.84 (m, 2H), 5.51 (s, 1H), 5.32 (d, J=10.0 Hz, 1H), 3.97-3.90 (m, 4H), 3.85-3.81 (m, 7H), 3.66 (s, 3H), 3.49-3.36 (m, 5H), 3.36-3.25 (m, 2H), 3.26-3.18 (m, 1H), 3.20-3.08 (m, 1H), 2.85-2.83 (m, 1H), 2.75-2.69 (m, 4H), 2.47 (td, J=10.5, 6.7 Hz, 1H), 2.41 (d, J=13.1 Hz, 1H), 2.32 (d, J=13.2 Hz, 1H), 2.27-2.18 (m, 1H), 2.13 (s, 3H), 2.07 (s, 2H), 1.83-1.80 (m, 1H), 1.75-1.65 (m, 1H), 1.55-1.49 (m, 1H), 1.40-1.29 (m, 3), 0.93-086 (m, 1H), 0.86-0.81 (m, 6H); HRESI-TOF m/z 918.4759 ($C_{51}H_{63}N_7O_9+H^+$, required 918.4760). $[\alpha]_D^{23}$ –132 (c 0.06, CHCl$_3$).

Compound 143

Method 2 was followed providing Compound 143 as a white solid in 23% yield. $^1$H NMR (CDCl$_3$, 600 MHz) δ 9.85 (br s, 1H), 8.49 (d, J=1.8 Hz, 1H), 8.04 (s, 1H), 7.49 (d, J=8.4 Hz, 1H), 7.14-7.07 (m, 2H), 6.93 (s, 1H), 6.87 (d, J=1.2 Hz, 1H), 6.62 (s, 1H), 6.10 (s, 1H), 5.84 (dd, J=4.2, 10.2 Hz, 1H), 5.48 (s, 1H), 5.28 (d, J=10.2 Hz, 1H), 3.81-3.78 (m, 4H), 3.77 (s, 3H), 3.73 (s, 1H), 3.56 (d, J=13.8 Hz, 1H), 3.48 (s, 1H), 3.42 (d, J=12.6 Hz, 1H), 3.39-3.35 (m, 1H), 3.33-3.27 (m, 2H), 3.19-3.13 (m, 2H), 2.83-2.72 (m, 2H), 2.70 (s, 3H), 2.64 (s, 1H), 2.46-2.42 (m, 1H), 2.37 (d, J=13.2 Hz, 1H), 2.26 (d, J=14.4 Hz, 1H), 2.22-2.17 (m, 2H), 2.13 (s, 1H), 2.10 (s, 3H), 1.87-1.76 (m, 2H), 1.64-1.60 (m, 2H), 1.33-1.18 (m, 5H), 0.89-0.79 (m, 6H); IR (film) $\nu_{max}$ 2968, 1744, 1366, 1211 cm$^{-1}$; HRESI-TOF m/z 905.4447 ($C_{50}H_{60}N_6O_{10}+H^+$, required 905.4443). $[\alpha]_D^{23}$ +2 (c 0.065, CHCl$_3$).

Compound 144

Method 2 was followed providing Compound 144 in 47% yield. $^1$H NMR (600 MHz, CDCl$_3$) δ 8.05 (s, 1H), 7.59 (d, J=7.7 Hz, 1H), 7.48-7.41 (m, 2H), 7.40-7.36 (m, 1H), 7.28-7.22 (m, 2H), 7.18 (t, J=7.4 Hz, 1H), 7.15 (d, J=8.1 Hz, 1H), 6.85-6.83 (m, 1H), 6.49-6.47 (m, 1H), 6.14 (s, 1H), 5.92 (dd, J=10.4, 4.8 Hz, 1H), 5.48 (d, J=15.7 Hz, 1H), 5.43 (s, 1H), 5.32 (s, 1H), 4.10-4.05 (m, 2H), 3.87-3.83 (m, 9H), 3.68 (d, J=9.7 Hz, 3H), 3.63 (s, 1H), 3.51-3.43 (m, 3H), 3.40-3.37 (m, 1H), 3.09 (s, 1H), 3.04-3.01 (m, 2H), 2.98-2.97 (m, 2H), 2.94 (s, 1H), 2.80-2.77 (m, 2H), 2.57-2.47 (m, 2H), 2.16-2.07 (m, 5H), 1.95-1.85 (m, 5H), 1.63-1.62 (m, 2H), 1.34-1.32 (m, 1H), 0.97-0.85 (m, 5H), 0.85-0.79 (m, 4H); HRESI-TOF m/z 922.4961 ($C_{52}H_{67}N_5O_{10}+H^+$, required 922.4960). $[\alpha]_D^{23}$ +54 (c 0.08, CHCl$_3$).

Compound 145

Method 2 was followed providing Compound 145 in 58% yield. $^1$H NMR (600 MHz, CDCl$_3$) δ 9.74 (s, 1H), 8.03 (s, 1H), 7.51 (d, J=7.8 Hz, 1H), 7.20-7.05 (m, 3H), 6.62 (s, 1H), 6.10 (s, 1H), 5.88-5.82 (m, 1H), 5.48 (s, 1H), 5.35 (s, 1H), 5.32-5.27 (m, 1H), 3.81 (s, 3H), 3.80 (s, 3H), 3.74 (s, 1H), 3.72-3.61 (m, 1H), 3.59 (s, 3H), 3.59-3.54 (m, 1H), 3.44-3.34 (m, 2H), 3.33-3.25 (m, 2H), 3.24-3.16 (m, 4H), 3.11-3.05 (m, 1H), 2.96 (s, 2H), 2.84-2.77 (m, 2H), 2.77-2.69 (m, 3H), 2.65 (s, 1H), 2.63-2.58 (m, 1H), 2.48-2.36 (m, 1H), 2.33-2.19 (m, 2H), 2.19-2.15 (m, 1H), 2.11 (s, 3H), 2.10-2.07 (m, 1H), 1.97-1.90 (m, 1H), 1.85-1.75 (m, 2H), 1.36-1.30 (m, 1H), 1.27-1.23 (m, 4H), 1.23-1.11 (m, 2H), 0.95-0.83 (m, 1H), 0.81 (t, J=7.4 Hz, 3H), 0.70 (t, J=7.4 Hz, 3H); HRESI-TOF m/z 938.4731 ($C_{52}H_{67}N_5O_9S+H^+$, required 938.4732). $[\alpha]_D^{23}$ –12 (c 0.08, CHCl$_3$).

Compound 146

Compound 146 was prepared from Compound 147 upon treatment with TFA in CH$_2$Cl$_2$ (1:1) for 5 min followed by quench of the reaction with the addition of aq. NaHCO$_3$ and product extraction with CH$_2$Cl$_2$. $^1$H NMR (600 MHz, CDCl$_3$) δ 8.00 (s, 1H), 7.50 (d, J=7.9 Hz, 1H), 7.13 (m, 4H), 6.63 (s, 1H), 6.09 (s, 1H), 5.86 (dd, J=10.2, 4.9 Hz, 1H), 5.48 (s, 1H), 5.31 (d, J=8.7 Hz, 2H), 3.80 (s, 4H), 3.78 (s, 3H), 3.76 (s, 1H), 3.74 (q, J=5.4, 4.8 Hz, 3H), 3.71-3.68 (m, 1H), 3.64 (t, J=6.1 Hz, 1H), 3.54 (s, 3H), 3.48 (q, J=7.0 Hz, 1H), 3.43-3.34 (m, 3H), 3.31 (d, J=4.7 Hz, 1H), 3.22 (s, 2H), 3.11 (t, J=7.3 Hz, 2H), 2.81 (m, 1H), 2.71 (s, 3H), 2.65 (s, 1H), 2.54 (s, 1H), 2.44 (t, J=7.9 Hz, 1H), 2.33 (d, J=8.3 Hz, 2H), 2.23-2.16 (m, 2H), 2.11 (s, 4H), 1.98 (d, J=15.4 Hz, 1H), 1.81 (m, 6H), 1.41 (t, J=7.3 Hz, 2H), 1.21 (t, J=7.0 Hz, 4H), 0.88 (t, J=6.9 Hz, 3H); HRESI-TOF m/z 921.5056 ($C_{52}H_{68}N_6O_9+H^+$, required 921.5058).

Compound 147

Method 2 was followed providing Compound 147 in 56% yield. $^1$H NMR (600 MHz, CDCl$_3$) δ 8.03 (s, 1H), 7.45-7.39 (m, 1H), 7.22 (d, J=7.6 Hz, 1H), 7.15 (m, 3H), 6.40 (s, 1H), 6.10 (s, 1H), 5.89 (dd, J=10.5, 4.8 Hz, 1H), 5.44 (m, 2H), 5.30 (s, 3H), 4.50 (d, J=14.1 Hz, 1H), 3.82 (d, J=2.7 Hz, 4H), 3.79 (s, 3H), 3.76-3.73 (m, 6H), 3.71 (s, 1H), 3.64 (d, J=7.8 Hz, 4H), 3.61 (d, J=6.3 Hz, 1H), 3.59 (s, 3H), 3.45 (d, J=12.7 Hz, 1H), 3.36-3.33 (m, 2H), 3.29 (d, J=5.7 Hz, 1H), 3.09 (d, J=13.1 Hz, 1H), 3.00 (d, J=16.2 Hz, 1H), 2.91 (s, 1H), 2.90-2.81 (m, 4H), 2.73 (s, 3H), 2.65 (s, 1H), 2.49 (ddt, J=10.9, 7.0, 3.9 Hz, 3H), 2.31 (s, 2H), 2.22 (s, 1H), 2.11 (s, 4H), 2.08 (q, J=2.1, 1.7 Hz, 1H), 2.04 (s, 1H), 2.01 (d, J=6.6 Hz, 1H), 1.87-1.83 (m, 9H), 0.89 (m, 1H), 0.79 (t, J=7.5 Hz, 3H); HRESI-TOF m/z 1021.5642 ($C_{57}H_{76}N_6O_{11}+H^+$, required 1021.5645). $[\alpha]_D^{23}$ +34 (c 0.26, CHCl$_3$).

Compound 148

Method 2 was followed providing Compound 148 in 61% yield. $^1$H NMR (600 MHz, CDCl$_3$) δ 8.04 (s, 1H), 7.58-7.50 (m, 1H), 7.19-7.17 (m, 1H), 7.15-7.13 (m, 2H), 7.12-7.10 (m, 1H), 6.65 (s, 1H), 6.12 (s, 1H), 5.88 (dd, J=10.4, 4.5 Hz, 1H), 5.54 (s, 1H), 5.50 (s, 1H), 5.32 (d, J=10.2 Hz, 1H), 5.14 (s, 1H), 3.87-3.67 (m, 9H), 3.59 (s, 3H), 3.59-3.50 (m, 1H), 3.44-3.36 (m, 3H), 3.36-3.17 (m, 5H), 3.10 (q, J=7.3 Hz, 2H), 3.01 (dd, J=7.9, 5.7 Hz, 1H), 2.90-2.81 (m, 2H), 2.73 (s, 3H), 2.68 (s, 1H), 2.46 (td, J=10.7, 6.7 Hz, 1H), 2.26-2.02 (m, 8H), 1.99 (s, 2H), 1.87-1.79 (m, 2H), 1.70 (s, 3H), 1.45-1.35 (m, 7H), 0.89-0.81 (m, 6H), 0.74 (t, J=7.4 Hz, 3H); HRESI-TOF m/z 935.5278 ($C_{53}H_{70}N_6O_9+H^+$, required 935.5277). $[\alpha]_D^{23}$ –19 (c 0.06, CHCl$_3$).

Compound 149

Method 2 was followed providing Compound 149 in 33% yield. $^1$H NMR (600 MHz, CDCl$_3$) δ 9.86 (s, 1H), 9.06-8.95 (m, 1H), 8.63 (s, 1H), 8.20 (s, 1H), 8.05 (s, 1H), 7.96 (d, J=8.4 Hz, 1H), 7.54-7.37 (m, 2H), 7.18-7.01 (m, 2H), 6.63 (s, 1H), 6.31 (s, 1H), 6.13 (s, 1H), 5.85 (s, 1H), 5.46 (m, 1H), 5.36-5.26 (m, 1H), 3.92 (d, J=12.8 Hz, 1H), 3.84-3.73 (m, 3H), 3.73-3.56 (m, 2H), 3.52 (s, 1H), 3.46-3.34 (m, 2H), 3.34-3.22 (m 2H), 3.22-3.05 (m, 2H), 2.82 (d, J=16.3 Hz, 1H), 2.78-2.60 (m, 3H), 2.57-2.31 (m, 3H), 2.28-2.14 (m, 2H), 2.11 (s, 1H), 2.09-1.95 (m, 2H), 1.93-1.76 (m, 2H), 1.19-0.95 (m, 4H), 0.92-0.61 (m, 7H); HRESI-TOF m/z 965.4608 ($C_{56}H_{64}N_6O_9+H^+$, required 965.4807). $[\alpha]_D^{23}$ –10 (c 0.1, CHCl$_3$).

Compound 151

Method 2 was followed providing Compound 151 in 39% yield. $^1$H NMR (600 MHz, CDCl$_3$) δ 9.82 (s, 1H), 9.49 (s, 1H), 9.00 (s, 1H), 8.25-8.10 (m, 2H), 8.01 (d, J=4.6 Hz, 1H), 7.79 (t, J=7.5 Hz, 1H), 7.68-7.50 (m, 1H), 7.51-7.34 (m, 1H), 7.18-7.01 (m, 3H), 6.69 (s, 1H), 6.24 (s, 1H), 6.14 (s, 1H), 5.86 (d, J=7.1 Hz, 1H), 5.49 (s, 1H), 5.32 (d, J=10.2 Hz, 1H), 3.91-3.74 (m, 7H), 3.63 (s, 3H), 3.58-3.29 (m, 4H), 2.83 (d, J=16.1 Hz, 1H), 2.75-2.69 (m, 4H), 2.51-2.36 (m, 2H), 2.26-2.15 (m, 1H), 2.12 (s, 3H), 2.07-2.01 (m, 1H), 1.90-1.77 (m, 2H), 1.43-1.32 (m, 2H), 1.30-1.17 (m, 5H), 0.93-0.77 (m, 8H); HRESI-TOF m/z 965.4811 ($C_{56}H_{64}N_6O_9$+H$^+$, required 965.4807). [α]$_D^{23}$ −48 (c 0.3, CHCl$_3$).

Compound 152

Method 2 was followed providing Compound 152 in 29% yield. $^1$H NMR (600 MHz, CDCl$_3$) δ 9.86 (s, 1H), 8.64 (s, 1H), 8.37 (d, J=8.6 Hz, 1H), 8.34 (d, J=8.6 Hz, 1H), 8.06-8.03 (m, 1H), 7.89-7.84 (m, 1H), 7.74-7.67 (m, 1H), 7.62-7.49 (m, 2H), 7.16-7.04 (m, 3H), 6.58 (s, 1H), 6.07 (s, 1H), 5.86-5.80 (m, 1H), 5.47 (s, 1H), 5.27 (d, J=10.2 Hz, 1H), 3.94-3.86 (m, 2H), 3.81 (s, 3H), 3.79 (3H), 3.73 (s, 1H), 3.70 (s, 3H), 3.48 (d, J=13.3 Hz, 1H), 3.42-3.34 (m, 2H), 3.32-3.26 (m, 2H), 2.81 (d, J=15.9 Hz, 1H), 2.77 (d, J=13.6 Hz, 1H), 2.69 (s, 3H), 2.63 (s, 1H), 2.48-2.37 (m, 2H), 2.30-2.25 (m, 1H), 2.23-2.17 (m, 2H), 2.09 (s, 3H), 1.88-1.73 (m, 2H), 1.62-1.54 (m, 4H), 1.35-1.24 (m, 3H), 0.90-0.86 (m, 1H), 0.83 (t, J=7.4 Hz, 3H), 0.78 (t, J=7.4 Hz, 3H); HRESI-TOF m/z 965.4804 ($C_{56}H_{64}N_6O_9$+H$^+$, required 965.4807). [α]$_D^{23}$ 6 (c 0.12, CHCl$_3$).

Compound 153

Method 2 was followed using 7.0 mg of 20'-aminovinblastine (6, 0.009 mmol) to provide 2.8 mg of Compound 153 as a white solid, yield: 34%. $^1$H NMR (600 MHz, CDCl$_3$) δ 9.76 (br s, 1H), 8.93 (s, 1H), 8.69-8.62 (m, 1H), 8.36-8.34 (m, 1H), 8.22 (d, J=6.3 Hz, 1H), 8.04-7.98 (m, 2H), 7.72 (s, 1H), 7.46-7.44 (d, J=12.8 Hz, 1H), 7.35 (d, J=5.9 Hz, 1H), 7.21 (d, J=8.4 Hz, 1H), 7.15-7.11 (m, 1H), 6.73 (s, 1H), 6.30 (s, 1H), 6.16-6.12 (m, 1H), 5.92-5.90 (m, 1H), 5.49 (m, 1H), 5.35 (s, 1H), 3.89-3.87 (m, 3H), 3.85-3.78 (m, 4H), 3.74 (s, 1H), 3.67 (s, 3H), 3.42-3.38 (m, 2H), 3.34-3.27 (m, 2H), 3.13-3.10 (m, 2H), 2.98 (s, 1H), 2.91 (s, 3H), 2.75-2.72 (m, 1H), 2.37 (t, J=7.5 Hz, 1H), 2.20-2.19 (m, 1H), 2.14 (s, 3H), 2.04-1.99 (m, 1H), 1.86-1.79 (m, 4H), 1.69-1.65 (m, 1H), 1.44 (t, J=7.4 Hz, 2H), 1.30-1.28 (m, 5H), 0.90 (t, J=7.0 Hz, 3H), 0.86-0.82 (m, 3H); ESI-TOF m/z 965.5 ($C_{56}H_{64}N_6O_9$+H$^+$, required 965.48). [α]$_D^{23}$ −10 (c 0.14, CHCl$_3$).

Compound 154

Method 2 was followed using 8.0 mg of 20'-aminovinblastine (6, 0.010 mmol) to provide 3.7 mg of Compound 154 as a white solid, yield: 39%. $^1$H NMR (600 MHz, CDCl$_3$) δ 9.48 (br s, 2H), 8.73 (s, 1H), 8.61 (s, 1H), 8.29 (s, 1H), 8.22 (s, 1H), 8.04-8.03 (m, 1H), 7.90-7.88 (m, 1H), 7.76-7.72 (m, 1H), 7.59-7.55 (m, 1H), 7.39-7.37 (m, 1H), 7.24-7.21 (m, 1H), 7.15-7.11 (m, 1H), 6.55-6.52 (m, 1H), 6.16-6.15 (m, 1H), 5.94-5.91 (m, 1H), 5.45-5.44 (m, 1H), 5.38-5.36 (m, 1H), 4.01 (s, 1H), 3.90 (s, 3H), 3.84 (s, 3H), 3.78 (s, 1H), 3.74 (s, 3H), 3.51-3.44 (m, 1H), 3.37-3.24 (m, 2H), 3.19-3.13 (m, 1H), 3.01-2.96 (m, 2H), 2.85-2.83 (m, 1H), 2.80 (s, 3H), 2.68-2.67 (m, 1H), 2.45-2.38 (m, 1H), 2.25-2.23 (m, 1H), 2.14 (s, 3H), 2.05-2.03 (m, 1H), 1.65-1.52 (m, 5H), 1.28-1.24 (m, 7H), 0.90 (t, J=6.9 Hz, 3H), 0.86-0.84 (m, 3H); HRESI-TOF m/z 965.4807 ($C_{56}H_{64}N_6O_9$+H$^+$, required 965.4807).

Compound 155

Method 1 was followed providing Compound 155 as a yellow solid in 60% yield. $^1$H NMR (CDCl$_3$, 600 MHz) δ 8.93-8.91 (m, 3H), 8.83 (s, 1H), 8.66 (s, 1H), 8.41-8.39 (m, 1H), 8.26 (d, J=9.0 Hz, 1H), 8.07 (br s, 1H), 7.43 (d, J=7.8 Hz, 1H), 7.13-7.04 (m, 3H), 6.62 (s, 1H), 6.35 (s, 1H), 6.13 (s, 1H), 5.84 (dd, J=4.8, 10.2 Hz, 1H), 5.47 (s, 1H), 5.30-5.28 (m, 1H), 3.93 (t, J=13.8 Hz, 1H), 3.82 (s, 3H), 3.80 (s, 3H), 3.75 (s, 3H), 3.60 (s, 3H), 3.51 (d, J=13.2 Hz, 1H), 3.38-3.34 (m, 2H), 3.29-3.24 (m, 2H), 3.19-3.14 (m, 2H), 2.91 (d, J=13.8 Hz, 1H), 2.79 (d, J=15.6 Hz, 1H), 2.72 (s, 3H), 2.66 (s, 1H), 2.61-2.58 (m, 1H), 2.50-2.42 (m, 2H), 2.22-2.17 (m, 1H), 2.10 (s, 3H), 2.08-1.98 (m, 2H), 1.87-1.76 (m, 2H), 1.70-1.67 (m, 1H), 1.52-1.51 (m, 1H), 1.34-1.24 (m, 3H), 0.89-0.84 (m, 3H), 0.82-0.79 (m, 3H); IR (film) ν$_{max}$ 3463, 2927, 1736, 1457, 1228, 1038, 731, 477 cm$^{-1}$; HRESI-TOF m/z 966.4739 ($C_{55}H_{63}N_7O_9$+H$^+$, required 966.4760).

Compound 156

Method 2 was followed providing Compound 156 in 56% yield. $^1$H NMR (600 MHz, CDCl$_3$) δ 9.79 (s, 1H), 9.69 (d, J=7.1 Hz, 2H), 8.35 (d, J=7.9 Hz, 1H), 8.04 (s, 1H), 7.31 (d, J=8.0 Hz, 1H), 7.17 (t, J=7.9 Hz, 2H), 7.16-7.03 (m, 4H), 6.40 (s, 1H), 6.13 (s, 1H), 5.89 (dd, J=10.3, 4.8 Hz, 1H), 5.43 (d, J=6.6 Hz, 1H), 5.32 (d, J=10.3 Hz, 1H), 4.14-4.09 (m, 1H), 3.88 (s, 3H), 3.80 (s, 6H), 3.65 (s, 1H), 3.35 (s, 3H), 3.22 (d, J=12.4 Hz, 1H), 2.94 (s, 1H), 2.75 (s, 3H), 2.18 (s, 1H), 2.11 (s, 3H), 2.04 (s, 2H), 1.84 (t, J=12.0 Hz, 2H), 1.79-1.73 (m, 2H), 1.62 (s, 3H), 1.02 (t, J=7.5 Hz, 3H), 0.78 (t, J=7.5 Hz, 3H), 0.53 (t, J=7.3 Hz, 3H); HRESI-TOF m/z 966.4762 ($C_{55}H_{63}N_7O_9$+H$^+$, required 966.4760). [α]$_D^{23}$ −2 (c 0.19, CHCl$_3$).

Compound 157

Method 2 was followed providing Compound 157 in 54% yield. $^1$H NMR (600 MHz, CDCl$_3$) δ 8.24 (s, 1H), 8.10 (s, 1H), 7.99 (dd, J=8.1, 1.3 Hz, 1H), 7.81-7.78 (m, 2H), 7.74 (d, J=8.1 Hz, 1H), 7.68 (d, J=8.1 Hz, 1H), 7.44 (s, 1H), 7.37 (d, J=8.0 Hz, 1H), 7.23-7.11 (m, 4H), 6.88-6.84 (m, 2H), 6.16 (s, 1H), 5.91 (dd, J=10.3, 5.0 Hz, 1H), 5.44 (s, 1H), 5.32 (s, 1H), 3.96-3.82 (m, 7H), 3.78-3.73 (m, 3H), 3.32-3.21 (m, 4H), 3.12-3.05 (m, 3H), 2.95 (s, 1H), 2.79 (s, 1H), 2.72-2.69 (m, 2H), 2.29-2.23 (m, 2H), 2.16-2.03 (m, 6H), 1.40-1.23 (m, 5H), 0.99 (t, J=7.4 Hz, 3H), 0.92-0.78 (m, 7H); HRESI-TOF m/z 954.4649 ($C_{55}H_{63}N_5O_{10}$+H$^+$, required 954.4647). [α]$_D^{23}$ −9 (c 0.23, CHCl$_3$).

Compound 158

Method 1 was followed providing Compound 158 as a pale pink resin in 60% yield. $^1$H NMR (CDCl$_3$, 600 MHz) δ 9.83 (br s, 1H), 8.60 (br s, 1H), 8.15 (dd, J=2.7, 5.7 Hz, 1H), 8.00 (s, 1H), 7.53 (dd, J=2.7, 6.3 Hz, 1H), 7.44 (d, J=7.8 Hz, 1H), 7.39-7.35 (m, 2H), 7.15-7.05 (m, 3H), 6.67 (s, 1H), 6.13 (s, 1H), 5.90 (s, 1H), 5.86 (dd, J=4.5, 10.5 Hz, 1H), 5.48 (s, 1H), 5.31-5.29 (m, 1H), 4.04 (br s, 1H), 3.82 (s, 3H), 3.80 (s, 3H), 3.76 (s, 1H), 3.58 (s, 3H), 3.49 (s, 1H), 3.42 (d, J=13.2 Hz, 1H), 3.38 (dd, J=4.8, 16.2 Hz, 1H), 3.31 (td, J=9.6, 4.8 Hz, 1H), 3.26-3.13 (m, 3H), 3.09-3.06 (m, 1H), 2.83 (d, J=16.2 Hz, 1H), 2.72 (s, 3H), 2.68 (s, 1H), 2.48-2.42 (m, 1H), 2.32 (d, J=13.2 Hz, 1H), 2.23-2.18 (m, 1H), 2.11 (s, 3H), 2.06-2.03 (m, 2H), 1.85-1.79 (m, 3H), 1.49 (br s, 1H), 1.35 (dd, J=14.4, 6.0 Hz, 2H), 1.27-1.25 (m, 1H), 0.87-0.81 (m, 6H); IR (film) ν$_{max}$ 3468, 2929, 1736, 1501, 1226, 1039, 738 cm$^{-1}$; HRESI-TOF m/z 954.4646 ($C_{55}H_{63}N_5O_{10}$+H$^+$, required 954.4647).

Compound 159

Method 1 was followed providing Compound 159 as a pale pink resin in 60% yield. $^1$H NMR (CDCl$_3$, 600 MHz) δ 9.83 (br s, 1H), 8.60 (br s, 1H), 8.15 (dd, J=2.7, 5.7 Hz, 1H), 8.00 (s, 1H), 7.53 (dd, J=2.7, 6.3 Hz, 1H), 7.44 (d, J=7.8 Hz, 1H), 7.39-7.35 (m, 2H), 7.15-7.05 (m, 3H), 6.67 (s, 1H), 6.13 (s, 1H), 5.90 (s, 1H), 5.86 (dd, J=4.5, 10.5 Hz, 1H), 5.48 (s, 1H), 5.31-5.29 (m, 1H), 4.04 (br s, 1H), 3.82 (s, 3H), 3.80 (s, 3H), 3.76 (s, 1H), 3.58 (s, 3H), 3.49 (s, 1H), 3.42 (d, J=13.2 Hz, 1H), 3.38 (dd, J=4.8, 16.2 Hz, 1H), 3.31 (td, J=4.8, 9.6 Hz, 1H), 3.26-3.13 (m, 3H), 3.09-3.06 (m, 1H), 2.83 (d, J=16.2 Hz, 1H), 2.72 (s, 3H), 2.68 (s, 1H), 2.48-2.42 (m, 1H), 2.32 (d, J=13.2 Hz, 1H), 2.23-2.18 (m, 1H), 2.11 (s, 3H), 2.06-2.03 (m, 2H), 1.85-1.79 (m, 3H), 1.49 (br s, 1H), 1.35 (dd, J=6.0, 14.4 Hz, 2H), 1.27-1.25 (m, 1H), 0.87-0.81 (m, 6H); IR (film) $v_{max}$ 3468, 2929, 1736, 1501, 1226, 1039, 738 HRESI-TOF m/z 954.4646 ($C_{55}H_{63}N_5O_{10}$+H$^+$, required 959.4647).

Compound 160

Method 2 was followed using 4.1 mg of 20'-aminovinblastine (6, 0.005 mmol) to provide Compound 160 as a white solid, yield: 58%. $^1$H NMR (600 MHz, CDCl$_3$) δ 9.86 (s, 1H), 8.05 (d, J=0.6 Hz, 1H), 7.67 (d, J=7.8 Hz, 1H), 7.58 (s, 1H), 7.50 (s, 1H), 7.48 (d, J=7.8 Hz, 1H), 7.36 (t, J=7.5 Hz, 1H), 7.27-7.25 (m, 1H), 7.13 (t, J=7.4 Hz, 1H), 7.08 (dd, J=7.6, 3.4 Hz, 2H), 6.82 (s, 1H), 6.58 (s, 1H), 6.09 (s, 1H), 5.83 (dd, J=10.1, 4.2 Hz, 1H), 5.46 (s, 1H), 5.27 (d, J=10.2 Hz, 1H), 3.84 (s, 1H), 3.79 (s, 3H), 3.75 (s, 3H), 3.73 (s, 1H), 3.45 (d, J=13.3 Hz, 2H), 3.36 (dd, J=16.3, 4.7 Hz, 2H), 3.32-3.26 (m, 2H), 3.19 (d, J=11.8 Hz, 3H), 2.80 (d, J=16.3 Hz, 1H), 2.75-2.73 (m, 1H), 2.70 (s, 3H), 2.63 (s, 1H), 2.45-2.40 (m, 2H), 2.30 (d, J=12.1 Hz, 1H), 2.21-2.16 (m, 1H), 2.09 (s, 3H), 1.84-1.75 (m, 6H), 1.34-1.28 (m, 2H), 1.26-1.24 (m, 1H), 0.83 (t, J=7.4 Hz, 3H), 0.78 (t, J=7.3 Hz, 3H); HRESI-TOF m/z 954.4646 ($C_{55}H_{63}N_5O_{10}$+H$^+$, required 954.4647).

Compound 161

Method 2 was followed providing Compound 161 as a white resin in 24% yield. $^1$H NMR (CDCl$_3$, 600 MHz) δ 9.83 (br s, 1H), 8.00-7.97 (m, 2H), 7.82 (d, J=1.8 Hz, 1H), 1.46-7.43 (m, 1H), 7.15-7.06 (m, 3H), 6.84 (d, J=8.4 Hz, 1H), 6.65 (s, 1H), 6.12 (s, 1H), 6.00 (s, 1H), 5.85 (dd, J=4.5, 10.5 Hz, 1H), 5.48 (s, 1H), 5.30 (d, J=9.6 Hz, 1H), 4.62 (t, J=8.7 Hz, 2H), 4.03 (br s, 1H), 3.82 (s, 3H), 3.80 (s, 3H), 3.75 (s, 1H), 3.59 (s, 3H), 3.41-3.35 (m, 2H), 3.33-3.17 (m, 5H), 3.13-3.05 (m, 2H), 2.83 (d, J=15.6 Hz, 1H), 2.72 (s, 3H), 2.68 (s, 1H), 2.48-2.42 (m, 1H), 2.36-2.33 (m, 1H), 2.21-2.17 (m, 2H), 2.11 (s, 3H), 1.85-1.78 (m, 3H), 1.40 (t, J=7.5 Hz, 2H), 1.37-1.32 (m, 2H), 1.29-1.26 (m, 1H), 0.82 (t, J=7.5 Hz, 3H), 0.77 (t, J=7.2 Hz, 3H); IR (film) $v_{max}$ 3583, 3022, 2970, 1740, 1367, 1217, 774 cm$^{-1}$; HRESI-TOF m/z 956.4806 ($C_{55}H_{65}N_5O_{10}$+H$^+$, required 956.4804). $[\alpha]_D^{23}$−11 (c 0.059, CHCl$_3$).

Compound 162

Method 2 was followed providing Compound 162 in 52% yield. $^1$H NMR (600 MHz, CDCl$_3$) δ 8.19 (s, 1H), 8.04 (s, 1H), 7.94 (d, J=7.7 Hz, 1H), 7.89 (dt, J=7.5, 0.9 Hz, 1H), 7.50-7.37 (m, 3H), 7.19-7.06 (m, 3H), 6.68 (s, 1H), 6.21 (s, 1H), 6.15 (s, 1H), 5.88 (dd, J=10.4, 4.6 Hz, 1H), 5.51 (s, 1H), 5.34-5.31 (m, 2H), 4.04-4.02 (m, 1H), 3.85-3.76 (m, 6H), 3.57 (s, 2H), 3.48-3.29 (m, 4H), 3.29-3.25 (m, 2H), 3.16-3.11 (m, 1H), 2.87-2.84 (m, 2H), 2.75 (s, 3H), 2.71-2.68 (m, 3H), 2.52-2.33 (m, 4H), 2.25-2.20 (m, 3H), 2.18-2.05 (m, 3H), 1.88-1.79 (m, 2H), 1.38 (dt, J=14.0, 6.9 Hz, 3H), 0.92-0.83 (m, 7H); HRESI-TOF m/z 970.4961 ($C_{55}H_{63}N_5O_9S$+H$^+$, required 970.4960). $[\alpha]_D^{23}$−46 (c 0.09, CHCl$_3$).

Compound 163

Method 1 was followed using 6.0 mg of 20'-aminovinblastine (6, 0.007 mmol) to provide Compound 163 as a white solid, yield: 41%. $^1$H NMR (600 MHz, CDCl$_3$) δ 9.82 (br s, 2H), 8.67 (s, 1H), 8.46 (s, 1H), 8.00 (s, 1H), 7.91-7.85 (m, 1H), 7.56-7.51 (m, 1H), 7.44 (s, 1H), 7.12 (s, 1H), 6.69 (s, 1H), 6.47 (s, 1H), 6.20-6.19 (m, 1H), 6.14 (s, 1H), 5.88 (s, 1H), 5.50-5.43 (m, 1H), 5.34 (s, 1H), 4.19-4.14 (m, 1H), 3.91 (s, 3H), 3.88 (s, 3H), 3.84-3.81 (m, 4H), 3.48 (d, J=5.0 Hz, 1H), 3.45-3.43 (m, 1H), 3.41-3.37 (m, 1H), 3.31 (s, 1H), 3.22-3.21 (m, 1H), 3.16-3.15 (m, 1H), 2.91 (dd, J=16.1, 0.4 Hz, 1H), 2.81 (s, 1H), 2.76 (s, 1H), 2.56-2.51 (m, 1H), 2.31-2.25 (m, 1H), 2.19 (s, 3H), 2.10-2.08 (m, 1H), 1.95- 1.92 (m, 4H), 1.89-1.86 (m, 1H), 1.36-1.34 (m, 7H), 0.96 (t, J=6.7 Hz, 3H), 0.90 (t, J=7.4 Hz, 3H); HRESI-TOF m/z 970.4961 ($C_{55}H_{63}N_5O_9S$+H$^+$, required 970.4960). $[\alpha]_D^{23}$−43 (c 0.24, CHCl$_3$).

Compound 164

Method 2 was followed using 7.0 mg of 20'-aminovinblastine (6, 0.009 mmol) to provide 2.8 mg of Compound 164 as a pale white solid, yield: 39%. $^1$H NMR (600 MHz, CDCl$_3$) δ 9.84 (br s, 2H), 8.51 (d, J=8.0 Hz, 1H), 8.04 (s, 1H), 7.90 (d, J=7.9 Hz, 1H), 7.51-7.42 (m, 2H), 7.18-7.09 (m, 2H), 6.70 (s, 1H), 6.15 (s, 1H), 6.01 (s, 1H), 5.89-5.87 (m, 1H), 5.51 (s, 1H), 5.33 (d, J=10.2 Hz, 1H), 4.04-4.01 (m, 1H), 3.83 (s, 3H), 3.78 (s, 3H), 3.71-3.69 (m, 1H), 3.61 (s, 3H), 3.47-3.45 (m, 1H), 3.41 (dd, J=16.0, 4.4 Hz, 1H), 3.34 (td, J=9.5, 4.6 Hz, 1H), 3.28-3.26 (m, 1H), 3.17-3.14 (m, 2H), 2.86 (d, J=16.1 Hz, 1H), 2.75 (s, 3H), 2.72-2.70 (m, 1H), 2.51-2.44 (m, 1H), 2.39-2.37 (m, 1H), 2.24-2.22 (m, 1H), 2.14 (s, 3H), 1.88-1.81 (m, 2H), 1.66-1.58 (m, 6H), 1.43-1.36 (m, 2H), 1.31-1.26 (m, 3H), 0.95-0.84 (m, 6H); HRESI-TOF m/z 970.4961 ($C_{55}H_{63}N_5O_9S$+H$^+$, required 970.4960).

Compound 165

Method 2 was followed using 7.0 mg of 20'-aminovinblastine (6, 0.009 mmol) to provide 3.0 mg of Compound 165 as a pale white solid, yield: 368. $^1$H NMR (600 MHz, CDCl$_3$) δ 9.86 (br s, 1H), 8.19 (br s, 1H), 8.04 (s, 1H), 7.93 (d, J=7.6 Hz, 1H), 7.89 (d, J=7.7 Hz, 1H), 7.47 (d, J=7.8 Hz, 1H), 7.44-7.40 (m, 2H), 7.16-7.09 (m, 2H), 6.68 (s, 1H), 6.21 (s, 1H), 6.15 (s, 1H), 5.89-5.87 (m, 1H), 5.51 (s, 1H), 5.33 (d, J=10.2 Hz, 1H), 4.03 (br s, 1H), 3.86 (s, 3H), 3.83 (s, 3H), 3.80-3.78 (m, 1H), 3.57 (s, 3H), 3.46-3.39 (m, 2H), 3.33 (td, J=9.5, 4.6 Hz, 1H), 3.29-3.27 (m, 1H), 3.18-3.12 (m, 2H), 2.85 (d, J=15.9 Hz, 1H), 2.75 (s, 3H), 2.70-2.69 (m, 1H), 2.44-2.40 (m, 1H), 2.24-2.20 (m, 1H), 2.14 (s, 3H), 2.04-2.01 (m, 1H), 1.88-1.81 (m, 2H), 1.60-1.57 (m, 6H), 1.40-1.36 (m, 1H), 1.31-1.25 (m, 3H), 0.92-0.83 (m, 6H); HRESI-TOF m/z 970.4961 ($C_{55}H_{63}N_5O_9S$+H$^+$, required 970.4960).

Compound 166

Method 2 was followed using 4.4 mg of 20'-aminovinblastine (6, 0.005 mmol) to provide 2.0 mg of Compound 166 as a white solid, yield: 38%. $^1$H NMR (600 MHz, CDCl$_3$) δ 9.87 (s, 1H), 8.40 (s, 1H), 8.07 (d, J=8.1 Hz, 1H), 7.92 (s, 1H), 7.48 (d, J=8.5 Hz, 1H), 7.41 (d, J=7.8 Hz, 1H), 7.12-7.09 (m, 1H), 7.07-7.03 (m, 1H), 6.63 (s, 1H), 6.18 (s, 1H), 6.12 (s, 1H), 5.84 (dd, J=9.9, 4.3 Hz, 1H), 5.47 (s, 1H), 5.29 (s, 3H), 4.05-3.97 (m, 2H), 3.89-3.86 (m, 2H), 3.81 (s, 2H), 3.79 (s, 3H), 3.74 (s, 1H), 3.61 (s, 2H), 3.57 (d, J=16.5 Hz, 1H), 3.41-3.35 (m, 2H), 3.31-3.27 (m, 1H), 3.25-3.19 (m, 2H), 3.16-3.13 (m, 1H), 3.06-3.03 (m, 1H), 2.82 (d, J=16.3 Hz, 1H), 2.72-2.69 (m, 2H), 2.61 (s, 6H), 2.47-2.42 (m, 2H), 2.21-2.16 (m, 2H), 2.10 (s, 3H), 1.85-1.77 (m, 2H), 1.37-1.30 (m, 2H), 1.24 (s, 3H), 0.83-0.77 (m, 6H); ESI-MS m/z 968.5 ($C_{55}H_{63}N_7O_9$+H$^+$, required 968.49).

Compound 167

Method 2 was followed providing Compound 167 in 49% yield. $^1$H NMR (600 MHz, CDCl$_3$) δ 9.81 (s, 1H), 8.31 (s, 1H), 8.24-8.13 (m, 1H), 8.12-8.01 (m, 1H), 7.90 (d, J=7.9 Hz, 1H), 7.47-7.38 (m, 1H), 7.24-6.98 (m, 3H), 6.66 (s, 1H), 6.13 (s, 2H), 5.97-5.68 (m, 2H), 5.49 (s, 1H), 5.30 (d, J=10.3 Hz, 1H), 3.96-3.73 (m, 7H), 3.64 (s, 3H), 3.52-3.28 (m, 4H), 3.27-3.18 (m, 1H), 3.18-3.04 (m, 2H), 2.93-2.78 (m, 2H), 2.78-2.64 (m, 4H), 2.58-2.34 (m, 3H), 2.29-2.14 (m, 2H), 2.11 (s, 3H), 2.05-1.93 (m, 1H), 1.93-1.74 (m, 3H), 1.44-1.23 (m, 4H), 1.05-0.71 (m, 7H); HRESI-TOF m/z 955.4602 ($C_{54}H_{62}N_6O_{10}$+H$^+$, required 955.4606). $[\alpha]_D^{23}$−8 (c 0.1, CHCl$_3$).

Compound 168

Method 2 was followed providing Compound 168 in 26% yield. $^1$H NMR (600 MHz, CDCl$_3$) δ 9.77 (s, 1H), 8.29 (s, 1H), 8.22-8.16 (m, 1H), 8.08-7.99 (m, 1H), 7.71 (d, J=8.6 Hz, 1H), 7.23-7.05 (m, 3H), 6.18-6.06 (m, 2H), 5.89 (d, J=7.8 Hz, 2H), 5.54-5.40 (m, 2H), 5.36-5.22 (m, 2H), 3.94-3.58 (m, 8H), 3.58-3.45 (m, 2H), 3.45-3.34 (m, 2H), 3.33-3.19 (m, 2H), 3.18-2.97 (m, 3H), 2.92-2.79 (m, 2H), 2.79-2.70 (m, 2H), 2.6 (d, J=4.9 Hz, 1H), 2.63 (s, 1H), 2.57-2.32 (m, 4H), 2.25-2.13 (m, 2H), 2.13-2.05 (m, 2H), 2.05-1.93 (m, 2H), 1.93-1.67 (m, 4H), 1.41-1.25 (m, 4H), 1.03-0.91 (m, 2H), 0.90-0.76 (m, 3H); HRESI-TOF m/z 955.4601 (C$_{54}$H$_{62}$N$_6$O$_{10}$+H$^+$, required 955.4606). [α]$_D^{23}$ −3 (c 0.8, CHCl$_3$).

Compound 169

Method 2 was followed providing Compound 169 in 31% yield. $^1$H NMR (600 MHz, CDCl$_3$) δ 9.80 (s, 1H), 8.06 (s, 1H), 7.81 (d, J=8.0 Hz, 1H), 7.69 (d, J=8.3 Hz, 1H), 7.49 (d, J=8.7 Hz, 3H), 7.44-7.40 (M, 1H), 7.17-7.07 (m, 3H), 6.54 (s, 1H), 6.11 (s, 1H), 5.84 (dd, J=10.4, 4.8 Hz, 1H), 5.45 (s, 1H), 5.31 (d, J=10.3 Hz, 1H), 3.84-3.79 (m, 4H), 3.79-3.72 (m, 5H), 3.65-3.56 (m, 2H), 3.51-3.39 (m, 3H), 3.35 (s, 1H), 3.33-3.21 (m, 1H), 2.30-2.22 (m, 1H), 2.18 (s, 1H), 2.10 (s, 3H), 1.79 (dq, J=14.6, 7.2 Hz, 2H), 1.41 (t, J=7.3 Hz, 3H), 0.92-0.81 (m, 7H), 0.77 (t, J=4.7 Hz, 3H); HRESI-TOF m/z 955.4605 (C$_{54}$H$_{62}$N$_6$O$_{10}$+H$^+$, required 955.4606). [α]$_D^{23}$ −10 (c 0.2, CHCl$_3$).

Compound 170

Method 2 was followed providing Compound 170 in 27% yield. $^1$H NMR (600 MHz, CDCl$_3$) δ 9.78 (s, 1H), 9.10 (s, 1H), 8.87 (s, 1H), 8.23 (d, J=8.6 Hz, 1H), 8.17 (d, J=8.8 Hz, 1H), 7.44 (d, J=9.7 Hz, 1H), 7.19-7.01 (m, 3H), 6.68 (s, 1H), 6.18 (s, 1H), 6.13 (s, 1H), 5.86 (d, J=8.5 Hz, 1H), 5.49 (s, 1H), 5.31 (d, J=10.2 Hz, 1H), 4.19-4.02 (m, 2H), 3.83 (s, 3H), 3.80 (s, 3H), 3.76 (s, 1H), 3.63 (s, 3H), 3.47-3.29 (m, 4H), 3.25-3.05 (m, 3H), 2.83 (d, J=16.3 Hz), 1H), 2.73 (s, 3H), 2.68 (s, 1H), 2.45 (d, J=13.1 Hz, 3H), 2.24-2.18 (m, 1H), 2.11 (s, 3H), 2.09-2.03 (m, 1H), 1.86-1.79 (m, 2H), 1.41-1.34 (m, 2H), 1.26 (s, 2H), 0.91-0.72 (m, 7H); HRESI-TOF m/z 971.4371 (C$_{54}$H$_{62}$N$_6$O$_9$S+H$^+$, required 971.4372). [α]$_D^{23}$ −23 (c 0.1, CHCl$_3$).

Compound 171

Method 2 was followed providing Compound 171 in 58% yield. $^1$H NMR (600 MHz, CDCl$_3$) δ 9.85 (s, 1H), 9.07 (s, 1H), 8.72 (s, 1H), 8.20-8.01 (m, 3H), 7.44 (d, J=8.0 Hz, 1H), 7.17-7.01 (m, 3H), 6.65 (s, 1H), 6.21 (s, 1H), 6.13 (s, 1H), 5.89-5.81 (m, 1H), 5.48 (s, 1H), 5.29 (d, J=10.4 Hz, 1H), 3.88-3.72 (m, 8H), 3.66-3.62 (m, 1H), 3.60 (s, 2H), 3.48-3.34 (m, 3H), 3.34-3.19 (m, 3H), 3.20-3.05 (m, 3H), 2.82 (d, J=16.6 Hz, 2H), 2.72 (s, 3H), 2.69-2.62 (m, 2H), 2.50-2.37 (m, 3H), 2.11 (s, 2H), 1.31-1.18 (m, 5H), 0.90-0.74 (m, 8H); HRESI-TOF m/z 971.4378 (C$_{54}$H$_{62}$N$_6$O$_9$S+H$^+$, required 971.4372). [α]$_D^{23}$ −14 (c 0.2, CHCl$_3$).

Compound 172

Method 2 was followed providing Compound 172 in 26% yield. $^1$H NMR (600 MHz, CDCl$_3$) δ 9.85 (s, 1H), 8.17 (d, J=8.1 Hz, 1H), 8.14-8.03 (m, 2H), 8.01-7.96 (m, 1H), 7.74 (s, 1H), 7.58-7.46 (m, 3H), 7.14-7.07 (m, 2H), 6.57 (s, 1H), 6.09 (s, 1H), 5.85-5.80 (m, 1H), 5.47 (s, 1H), 5.30 (s, 1H), 3.83-3.76 (m, 3H), 3.73 (s, 2H), 3.73 (s, 2H), 3.70-3.61 (m, 2H), 3.60-3.50 (m, 2H), 3.46 (d, J=12.8 Hz, 2H), 3.41-3.27 (m, 4H), 3.24 (d, J=12.4 Hz, 2H), 2.85-2.73 (m, 3H), 2.70 (s, 2H), 2.67-2.59 (m, 2H), 2.48-2.33 (m, 3H), 2.28-2.16 (m, 3H), 2.10 (s, 2H), 1.91-1.72 (m, 4H), 1.36-1.27 (m, 3H), 0.92-0.82 (m, 4H), 0.78 (t, J=7.3 Hz, 3H); HRESI-TOF m/z 971.4372 (C$_{54}$H$_{62}$N$_6$O$_9$S+H$^+$, required 971.4372). [α]$_D^{23}$ −6 (c 0.09, CHCl$_3$).

Compound 173

Method 2 was followed using 8.0 mg of 20'-aminovinblastine (6, 0.01 mmol) to provide 3.5 mg of Compound 173 as a white solid, yield: 37%. $^1$H NMR (600 MHz, CDCl$_3$) δ 9.84 (br s, 1H), 8.06-8.04 (m, 1H), 7.91 (s, 1H), 7.58-7.50 (m, 2H), 7.30-7.38 (m, 1H), 7.19-7.16 (m, 2H), 6.78-6.77 (m, 2H), 6.53 (s, 1H), 6.11 (s, 1H), 5.88 (s, 1H), 5.47 (s, 1H), 5.32 (d, J=9.8 Hz, 1H), 4.21 (t, J=4.6 Hz, 2H), 3.82-3.82 (m, 6H), 3.76 (br s, 1H), 3.63 (s, 3H), 3.51 (s, 1H), 3.42-3.37 (m, 2H), 3.31-3.25 (m, 2H), 3.15-3.10 (m, 2H), 2.91 (s, 1H), 2.82-2.79 (m, 2H), 2.74 (s, 3H), 2.66-2.62 (m, 1H), 2.45-2.41 (m, 1H), 2.32-2.30 (m, 1H), 2.19 (s, 3H), 2.13-2.12 (m, 2H), 2.11-2.09 (m, 1H), 2.01 (br s, 1H), 1.69-1.66 (m, 4H), 1.55-1.52 (m, 2H), 1.33-1.28 (m, 5H), 0.89-0.84 (m, 6H); HRESI-TOF m/z 970.4961 (C$_{56}$H$_{67}$N$_5$O$_{10}$+H$^+$, required 970.4960). [α]$_D^{23}$ −76 (c 0.06, CHCl$_3$).

Compound 174

Method 1 was followed providing Compound 174 as a pale yellow resin in 75% yield. $^1$H NMR (CDCl$_3$, 600 MHz) δ 9.85 (br s, 1H), 8.04 (s, 1H), 7.61 (s, 1H), 7.48-7.44 (m, 2H), 7.15-7.06 (m, 3H), 6.90 (d, J=8.4 Hz, 1H), 6.64 (s, 1H), 6.12 (s, 1H), 6.03-6.02 (m, 2H), 5.85 (dd, J=9.9, 4.5 Hz, 1H), 5.48 (s, 1H), 5.31-5.29 (m, 1H), 3.99-3.94 (m, 2H), 3.82 (s, 3H), 3.80 (s, 3H), 3.75 (s, 1H), 3.63 (s, 3H), 3.39-3.35 (m, 2H), 3.30 (td, J=9.5, 4.8 Hz, 1H), 3.23-3.21 (m, 1H), 3.17-3.10 (m, 2H), 2.83 (d, =15.6 Hz, 1H), 2.72 (s, 3H), 2.67 (s, 1H), 2.47-2.41 (m, 2H), 2.36 (d, J=14.4 Hz, 3H), 2.21-2.16 (m, 1H), 2.11 (s, 3H), 2.00 (br s, 1H), 1.85-1.78 (m, 3H), 1.63 (br s, 2H), 1.42 (br s, 1H), 1.37 (dd, J=14.7, 6.9 Hz, 2H), 1.25 (s, 1H), 0.82-0.77 (m, 6H); IR (film) ν$_{max}$ 3467, 2927, 1738, 1479, 1244, 1038 cm$^{−1}$; HRESI-TOF m/z 958.4593 (C$_{54}$H$_{63}$N$_5$O$_{11}$+H$^+$, required 958.4597).

Compound 175

Method 1 was followed providing Compound 175 as a pale yellow resin in 29% yield. $^1$H NMR (CDCl$_3$, 600 MHz) δ 9.87 (br s, 1H), 8.06 (s, 1H), 7.53-7.45 (m, 3H), 7.15-7.06 (m, 3H), 6.95 (d, J=8.4 Hz, 1H), 6.63 (s, 1H), 6.12 (s, 1H), 5.97 (s, 1H), 5.85-5.84 (m, 1H), 5.47 (s, 1H), 5.29 (d, J=10.2 Hz, 1H), 4.28-4.27 (m, 4H), 3.94 (br s, 1H), 3.81 (s, 3H), 3.80 (s, 3H), 3.74 (s, 1H), 3.62 (s, 3H), 3.39-3.35 (m, 2H), 3.30 (td, J=9.5, 4.4 Hz, 1H), 3.23-3.11 (m, 3H), 2.82 (d, J=16.2 Hz, 1H), 2.71 (s, 3H), 2.66 (s, 1H), 2.46-2.35 (m, 3H), 2.21-2.16 (m, 2H), 2.11 (s, 3H), 1.94 (br s, 1H), 1.85-1.77 (m, 3H), 1.48 (br s, 2H), 1.32 (dd, J=13.8, 6.6 Hz, 2H), 1.27-1.25 (m, 2H), 0.82-0.76 (m, 6H); IR (film) ν$_{max}$ 2927, 1738, 1494, 1230, 1065, 748 cm$^{−1}$; HRESI-TOF m/z 972.4760 (C$_{55}$H$_{65}$N$_5$O$_{11}$+H$^+$, required 972.4753).

Compound 176

Method 2 was followed using 8.0 mg of 20'-aminovinblastine (6, 0.010 mmol) to provide 2.9 mg of Compound 176 as a white solid, yield: 30%. $^1$H NMR (600 MHz, CDCl$_3$) δ 9.76 (br s, 1H), 8.04 (s, 1H), 7.89 (d, J=8.6 Hz, 1H), 7.78 (s, 1H), 7.57 (d, J=2.1 Hz, 1H), 7.48 (d, J=8.1 Hz, 1H), 7.26 (d, J=8.1 Hz, 1H), 7.21 (d, J=7.2 Hz, 1H), 7.18 (d, J=8.0 Hz, 1H), 6.96 (dd, J=8.3, 2.0 Hz, 1H), 6.87 (d, J=2.0 Hz, 1H), 6.65 (d, J=8.6 Hz, 1H), 6.13 (s, 1H), 5.90 (dd, J=10.1, 4.2 Hz, 1H), 5.45 (s, 1H), 4.31-4.30 (m, 1H), 4.25 (t, J=4.4 Hz, 2H), 3.83 (s, 3H), 3.82 (s, 3H), 3.79-3.76 (m, 1H), 3.67 (s, 3H), 3.63-3.59 (m, 2H), 3.47-3.41 (m, 3H), 3.37-3.34 (m, 1H), 3.33-3.12 (m, 2H), 2.98 (s, 1H), 2.95-2.93 (m, 3H), 2.91-2.90 (m, 1H), 2.78 (s, 3H), 2.69-2.65 (m, 1H), 2.55-2.51 (m, 1H), 2.13 (s, 3H), 2.09-2.05 (m, 1H), 1.84-1.79 (m, 2H), 1.62-1.60 (m, 3H), 1.31-1.26 (m, 7H), 0.90-0.89 (m, 3H), 0.81 (t, J=7.3 Hz, 3H); ESI-MS m/z 985.5 (C$_{56}$H$_{68}$N$_6$O$_{10}$+H$^+$, required 985.51).

Compound 177

Generated via Boc deprotection of Compound 178 with 4 M HCl in dioxane. $^1$H NMR (600 MHz, CDCl$_3$) δ 9.85 (s, 1H), 8.00 (s, 1H), 7.57-7.52 (m, 1H), 7.47 (d, J=8.0 Hz, 1H), 7.22-7.07 (m, 3H), 6.69 (s, 1H), 6.15 (s, 2H), 6.05 (s, 1H), 5.88 (dd, J=10.4, 4.8 Hz, 1H), 5.50 (s, 1H), 5.35-5.34 (m, 1H), 4.18-4.10 (m, 3H), 3.89-3.79 (m, 8H), 3.77 (s, 1H), 3.66-3.56 (m, 3H), 3.44-3.38 (m, 2H), 3.35-3.32 (m, 1H), 3.27-3.11 (m, 2H), 3.08-3.05 (m, 3H), 2.86 (d, J=16.0 Hz, 1H), 2.77 (s, 3H), 2.73-2.65 (m, 3H), 2.52-2.43 (m, 2H), 2.36 (d, J=13.6 Hz, 2H), 2.25-2.18 (m, 2H), 2.14 (s, 3H), 1.88-1.80 (m, 2H), 1.28 (s, 3H), 0.92-0.88 (m, 2H), 0.86 (t, J=7.4 Hz, 3H), 0.79 (t, J=7.4 Hz, 3H); HRESI-TOF m/z 955.4965 (C$_{55}$H$_{66}$N$_6$O$_9$+H$^+$, required 955.4964). [α]$_D^{23}$ −294 (c 0.05, CHCl$_3$).

Compound 178

Method 2 was followed providing Compound 178 in 29% yield. $^1$H NMR (600 MHz, CDCl$_3$) δ 9.87 (s, 1H), 8.05 (s, 1H), 7.68 (s, 1H), 7.48 (d, J=8.0 Hz, 1H), 7.26 (d, J=7.5 Hz, 1H), 7.18-7.12 (m, 1H), 7.12-7.06 (m, 2H), 6.65 (s, 1H), 6.13 (s, 2H), 5.87 (dd, J=10.3, 4.8 Hz, 1H), 5.50 (s, 1H), 5.34-5.29 (m, 1H), 4.05-4.00 (m, 3H), 3.83-3.80 (m, 6H), 3.77 (s, 1H), 3.60-3.50 (m, 4H), 3.46-3.36 (m, 3H), 3.32 (td, J=9.3, 4.5 Hz, 1H), 3.31-3.25 (m, 2H), 3.18-3.11 (m, 5H), 2.85 (d, J=16.2 Hz, 1H), 2.74-2.66 (m, 5H), 2.51-2.40 (m, 2H), 2.37-2.34 (m, 1H), 2.25-2.18 (m, 1H), 2.13 (s, 3H), 1.89-1.77 (m, 2H), 1.58 (s, 9H), 1.37-1.31 (m, 2H), 1.30-1.26 (m, 2H), 0.95-0.88 (m, 1H), 0.86-0.78 (m, 7H); HRESI-TOF m/z 1055.5482 (C$_{60}$H$_{74}$N$_6$O$_{11}$+H$^+$, required 1055.5488). [α]$_D^{23}$ −39 (c 0.06, CHCl$_3$).

Compound 179

Method 3 was followed providing Compound 179 in 43% yield. $^1$H NMR (600 MHz, CDCl$_3$) δ 9.76 (s, 1H), 8.02 (m, 3H), 7.53 (s, 4H), 7.44 (d, J=8.0 Hz, 1H), 7.10 (m, 3H), 6.10 (s, 1H), 5.86 (s, 1H), 5.55-5.40 (m, 1H), 3.82 (s, 3H), 3.79 (s, 4H), 3.74 (d, J=15.5 Hz, 2H), 3.66 (m, 4H), 3.40-3.33 (m, 2H), 3.28 (d, J=12.8 Hz, 1H), 3.18-3.10 (m, 1H), 3.09-2.97 (m, 1H), 2.80 (m, 2H), 2.71 (d, J=5.2 Hz, 3H), 2.64 (s, 1H), 2.58 (d, J=13.5 Hz, 1H), 2.46 (s, 2H), 2.25-2.11 (m, 2H), 2.10 (s, 4H), 1.77 (s, 4H), 1.41 (t, J=7.3 Hz, 1H), 1.32 (dt, J=14.1, 7.2 Hz, 2H), 0.88 (t, J=6.9 Hz, 1H), 0.80 (br s, 4H), 0.60 (br s, 3H); HRESI-TOF m/z 950.4298 (C$_{52}$H$_{63}$N$_5$O$_{10}$S+H$^+$, required 950.4296).

Compound 180

Method 3 was followed providing Compound 180 in 41% yield. $^1$H NMR (600 MHz, CDCl$_3$) δ 9.80 (s, 1H), 8.00 (s, 1H), 7.94-7.83 (m, 2H), 7.49-7.41 (m, 1H), 7.36-7.28 (m, 2H), 7.19-7.05 (m, 3H), 6.11 (d, J=7.7 Hz, 1H), 5.85 (s, 1H), 5.50-5.37 (m, 1H), 5.30 (s, 1H), 3.82 (s, 3H), 3.79 (s, 3H), 3.76-3.72 (m, 2H), 3.69-3.64 (m, 3H), 3.40-3.32 (m, 2H), 3.30-3.25 (m, 1H), 3.15-3.05 (m, 2H), 2.81 (m, 2H), 2.73-2.68 (m, 3H), 2.64 (s, 1H), 2.45-2.40 (m, 5H), 2.10 (s, 3H), 2.09-2.06 (m, 1H), 1.78 (s, 4H), 1.63 (s, 4H), 1.41 (t, J=7.3 Hz, 1H), 1.33 (dd, J=14.3, 7.2 Hz, 2H), 1.26-1.23 (m, 2H), 1.14 (t, J=7.3 Hz, 1H), 0.80 (br s, 4H), 0.60 (br s, 3H); HRESI-TOF m/z 962.4497 (C$_{53}$H$_{65}$N$_5$O$_{10}$S+H$^+$, required 962.4494). [α]$_D^{23}$ +3 (c 0.35, CHCl$_3$).

Compound 181

Method 3 was followed providing Compound 181 in 42% yield. $^1$H NMR (600 MHz CDCl$_3$) δ 7.96 (d, J=8.6 Hz, 1H), 7.21-7.06 (m, 5H), 6.98 (dd, J=8.7, 6.7 Hz, 2H), 6.84 (d, J=11.2 Hz, 1H), 6.11 (d, J=8.6 Hz, 1H), 5.92-5.78 (m, 2H), 5.50-5.45 (m, 1H), 5.29 (d, J=10.4 Hz, 1H), 3.87-3.82 (m, 4H), 3.75 (s, 2H), 3.73 (d, J=6.7 Hz, 2H), 3.64 (d, J=11.0 Hz, 3H), 3.41-3.34 (m, 3H), 3.31-3.26 (m, 2H), 3.11 (q, J=7.4 Hz, 3H), 2.73-2.68 (m, 6H), 2.21-2.14 (m, 2H), 2.13-2.10 (m, 4H), 1.97 (s, 2H), 1.80 (m, 5H), 1.40 (t, J=7.3 Hz, 4H), 1.16-1.11 (m, 2H), 0.81 (t, J=7.3 Hz, 4H), 0.61 (t, J=7.3 Hz, 23); HRESI-TOF m/z 980.4403 (C$_{53}$H$_{65}$N$_5$O$_{10}$S+H$^+$, required 980.4401).

Compound 182

Method 3 was followed providing Compound 182 in 22% yield. $^1$H NMR (600 MHz, CDCl$_3$) δ 9.74 (s, 1H), 8.83 (s, 1H), 8.36 (m, 3H), 7.99 (s, 1H), 7.75 (s, 1H), 7.46-7.37 (m, 1H), 7.10 (m, 4H), 6.10 (s, 1H), 5.86 (s, 1H), 5.51-5.38 (m, 1H), 5.31 (d, J=7.8 Hz, 1H), 4.11 (m, 1H), 3.83 (s, 3H), 3.80 (s, 3H), 3.80-3.78 (m, 1H), 3.74 (d, J=10.7 Hz, 2H), 3.67 (s, 3H), 3.60 (d, J=14.3 Hz, 3H), 3.37 (m, 4H), 2.92 (d, J=14.3 Hz, 1H), 2.81 (m, 3H), 2.71 (s, 4H), 2.65 (m, 2H), 2.43 (s, 2H), 2.11 (s, 4H), 2.07 (d, J=3.4 Hz, 1H), 1.81-1.74 (m, 5H), 0.88 (t, J=7.4 Hz, 3H); HRESI-TOF m/z 995.4143 (C$_{52}$H$_{62}$N$_6$O$_{12}$S+H$^+$, required 995.4146).

Compound 183

Method 3 was followed providing Compound 183 in 41% yield. $^1$H NMR (600 MHz, CDCl$_3$) δ 9.81 (s, 1H), 8.25 (d, J=7.9 Hz, 1H), 8.00 (s, 1H), 7.96 (dd, J=7.9, 1.3 Hz, 1H), 7.73 (m, 2H), 7.44 (d, J=7.9 Hz, 1H), 7.16-7.04 (m, 3H), 6.57 (s, 1H), 6.10 (s, 1H), 5.84 (s, 1H), 5.64 (s, 1H), 5.46 (d, J=6.7 Hz, 1H), 5.28 (d, J=10.2 Hz, 1H), 3.82 (s, 3H), 3.78 (s, 3H), 3.78-3.75 (m, 1H), 3.72 (s, 1H), 3.58 (s, 3H), 3.50 (d, J=9.3 Hz, 1H), 3.41 (s, 1H), 3.38 (dd, J=5.1, 1.5 Hz, 1H), 3.36-3.34 (m, 1H), 3.28 (td, J=9.5, 4.6 Hz, 1H), 3.17 (s, 1H), 3.02-2.90 (m, 2H), 2.81 (t, J=15.2 Hz, 2H), 2.75-2.65 (m, 4H), 2.63 (s, 1H), 2.42 (s, 1H), 2.22 (dd, J=15.2, 8.1 Hz, 1H), 2.16 (m, 1H), 2.10 (s, 3H), 1.78 (m, 4H), 1.27-1.23 (m, 4H), 0.88 (dd, J=8.0, 6.1 Hz, 1H), 0.79 (t, J=7.4 Hz, 3H), 0.74 (br s, 3H); HRESI-TOF m/z 995.4229 (C$_{52}$H$_{62}$N$_6$O$_{12}$S+H$^+$, required 995.4219). [α]$_D^{23}$ +3 (c 0.35, CHCl$_3$).

Compound 184

Method 3 was followed providing Compound 184 in 54% yield. $^1$H NMR (600 MHz, CDCl$_3$) δ 9.80 (s, 1H), 8.05 (s, 1H), 7.44 (d, J=8.2 Hz, 1H), 7.10 (m, 3H), 6.97 (m, 2H), 6.10 (s, 1H), 5.85 (s, 1H), 5.46 (m, 1H), 4.66 (m, 1H), 3.81 (s, 3H), 3.79 (s, 3H), 3.74 (d, J=7.7 Hz, 2H), 3.67-3.61 (m, 3H), 3.40-3.36 (m, 1H), 3.35 (d, J=4.6 Hz, 1H), 3.31-3.25 (m, 2H), 3.13-3.07 (m, 2H), 2.80 (m 1H), 2.72 (m, 9H), 2.63 (s, 1H), 2.41 (d, J=4.8 Hz, 2H), 2.30 (s, 4H), 2.10 (s, 3H), 1.97 (s, 1H), 1.78 (dt, J=14.8, 7.5 Hz, 3H), 1.41 (t, J=7.3 Hz, 2H), 1.14 (t, J=7.3 Hz, 2H), 0.87 (t, J=7.1 Hz, 1H), 0.79 (t, J=7.4 Hz, 3H), 0.75-0.71 (m, 2H), 0.56-0.52 (m, 2H); HRESI-TOF m/z 992.4768 (C$_{56}$H$_{65}$N$_5$O$_{10}$S+H$^+$, required 992.4765).

Compound 185

Method 3 was followed providing Compound 185 in 22% yield. $^1$H NMR (600 MHz, CDCl$_3$) δ 9.69 (s, 1H), 8.54 (m, 2H), 7.65 (m, 4H), 7.47-7.36 (m, 2H), 7.21-7.02 (m, 3H), 6.08 (m, 1H), 5.86 (m, 1H), 5.48 (d, J=10.6 Hz, 1H), 5.41 (s, 1H), 5.34-5.27 (m, 2H), 4.12 (d, J=7.0 Hz, 1H), 3.98-3.89 (m, 1H), 3.74 (s, 2H), 3.70 (s, 3H), 3.52 (s, 3H), 3.35 (s, 3H), 3.26 (s, 1H), 3.13 (d, J=13.1 Hz, 1H), 2.94 (m, 2H), 2.81 (m, 2H), 2.63 (s, 2H), 2.46 (m, 3H), 2.09-2.04 (m, 2H), 1.83-1.73 (m, 4H), 0.86-0.84 (m, 5H), 0.81-0.76 (m, 6H), 0.60-0.53 (m, 4H); HRESI-TOF m/z 1000.4525 (C$_{56}$H$_{65}$N$_5$O$_{10}$S+H$^+$, required 1000.4525). [α]$_D^{23}$ 0.02 (c 0.15, CHCl$_3$).

Compound 186

Method 3 was followed providing Compound 186 in 30% yield. $^1$H NMR (600 MHz, CDCl$_3$) δ 9.80 (s, 1H), 8.55 (m, 1H), 8.33 (m, 2H), 8.03 (m, 1H), 7.63 (t, J=8.1 Hz, 1H), 7.53 (s, 1H), 7.43 (s, 1H), 7.23-7.07 (m, 4H), 6.10 (s, 1H), 5.84 (s, 1H), 5.45 (m, 3H), 3.83 (s, 3H), 3.79 (s, 3H), 3.74-3.62 (m, 5H), 3.36 (dd, J=15.0, 4.7 Hz, 3H), 3.28 (qd, J=7.3, 6.5, 4.8 Hz, 2H), 3.10 (dd, J=7.1, 6.5 Hz, 1H), 2.99 (m, 1H), 2.88 (d, J=7.6 Hz, 6H), 2.79 (m, 2H), 2.70 (s, 3H), 2.62 (s, 1H), 2.45 (m, 2H), 2.22-2.14 (m, 1H), 2.10 (s, 3H), 1.97 (s, 1H), 1.78 (dd, J=14.5, 7.5 Hz, 2H), 1.41 (t, J=7.3 Hz, 1H), 1.25 (t, J=1.7 Hz, 3H), 1.14 (t, J=7.3 Hz, 1H), 0.88 (t, J=7.0 Hz, 1H), 0.78 (t, J=7.4 Hz, 3H), 0.58-0.48 (m, 1H), 0.32-0.25 (m, 2H); HRESI-TOF m/z 1043.4873 ($C_{56}H_{65}N_5O_{10}S+H^+$, required 1043.4874). $[\alpha]_D^{23}$ 0.04 (c 0.35, $CHCl_3$).

Compound 187

$^1H$ NMR (600 MHz, $CDCl_3$) δ 9.81 (br s, 1H), 8.00 (br s, 1H), 7.40 (dd, J=8.4, 5.4 Hz, 1H), 6.86 (t, J=9.0 Hz, 1H), 6.77 (dd, J=9.6, 1.8 Hz, 1H), 6.56 (s, 1H), 6.10 (s, 1H), 5.88 (dd, J=10.2, 4.2 Hz, 1H), 5.47 (s, 1H), 5.30 (d, J=10.2 Hz, 1H), 3.91 (t, J=14.4 Hz, 1H), 3.79 (s, 6H), 3.74 (s, 1H), 3.70-3.60 (m, 1H), 3.63 (s, 3H), 3.44-3.26 (m, 3H), 3.20-3.00 (m, 2H), 2.86-2.75 (m, 3H), 2.70 (s, 3H), 2.64 (s, 1H), 2.50-2.38 (m, 2H), 2.32-2.24 (m, 1H), 2.22-2.14 (m, 1H), 2.11 (s, 3H), 1.90-1.75 (m, 3H), 1.50-1.20 (m, 6H), 0.89 (t, J=7.2 Hz, 3H), 0.78 (t, J=7.2 Hz, 3H); IR (film) $v_{max}$ 2947, 1740, 1650, 1618, 1504, 1459, 1235, 1140, 1041 $cm^{-1}$; HRESI-TOF m/z 829.4179 ($C_{46}H_{57}FN_4O_9+H^+$, required 829.4182). $[\alpha]_D^{23}$+5 (c 0.44, $CHCl_3$).

Compound 188

Method 1 was followed providing Compound 188. $^1H$ NMR (600 MHz, $CDCl_3$) δ 9.76 (s, 1H), 8.11 (d, J=8.3 Hz, 1H), 7.97 (s, 1H), 7.34 (dd, J=8.7, 4.1 Hz, 2H), 6.83 (td, J=9.2, 2.3 Hz, 1H), 6.76 (dd, J=9.4, 2.2 Hz, 1H), 6.60 (s, 1H), 6.12 (s, 1H), 6.03 (s, 1H), 5.91-5.81 (m, 1H), 5.50-5.42 (m, 1H), 5.34-5.21 (m, 1H), 4.03-3.93 (m, 1H), 3.84-3.78 (m, 6H), 3.77-3.72 (m, 1H), 3.61 (s, 3H), 3.50 (dd, J=15.8, 5.1 Hz, 1H), 3.45-3.28 (m, 3H), 3.24-3.17 (m, 1H), 3.11 (t, J=13.1 Hz, 2H), 3.07-3.00 (m, 1H), 2.82 (d, J=15.9 Hz, 1H), 2.72 (s, 3H), 2.66 (d, J=17.6 Hz, 3H), 2.56-2.49 (m, 1H), 2.49-2.40 (m, 2H), 2.36-2.29 (m, 1H), 2.24-2.20 (m, 1H), 2.11 (s, 3H), 2.07 (s, 1H), 2.03-1.95 (m, 1H), 1.88-1.78 (m, 2H), 1.68-1.61 (m, 1H), 1.38-1.31 (m, 2H), 1.17-1.09 (m, 1H), 0.87-0.82 (m, 1H), 0.80-0.76 (m, 6H); HRESI-TOF m/z 1016.4426 ($C_{54}H_{61}F_4N_5O_{10}+H^+$, required 1016.4427).

Compound 189

Method 2 was followed providing Compound 189. $^1H$ NMR (600 MHz, $CDCl_3$) δ 9.79 (s, 1H), 7.99 (s, 1H), 7.72 (s, 2H), 7.33 (dd, J=8.8, 5.2 Hz, 1H), 7.17 (d, J=8.4 Hz, 1H), 6.82 (td, J=9.1, 2.3 Hz, 1H), 6.75 (dd, J=9.5, 2.3 Hz, 1H), 6.58 (s, 1H), 6.11 (s, 1H), 6.05 (s, 1H), 5.91-5.82 (m, 1H), 5.48 (s, 1H), 5.30 (d, J=10.1 Hz, 1H), 4.05-3.87 (m, 1H), 3.84-3.77 (m, 6H), 3.75 (s, 1H), 3.59 (s, 3H), 3.44-3.26 (m, 4H), 3.24-3.04 (m, 4H), 3.05-2.95 (m, 1H), 2.89-2.76 (m, 5H), 2.72 (s, 3H), 2.69-2.60 (m, 2H), 2.43 (d, J=13.3 Hz, 2H), 2.35 (d, J=13.9 Hz, 1H), 2.24-2.16 (m, 1H), 2.11 (s, 3H), 1.82-1.77 (m, 6H), 1.33 (dt, J=14.6, 7.2 Hz, 3H), 0.82-0.70 (m, 6H); HRESI-TOF m/z 986.5074 ($C_{57}H_{68}FN_5O_9+H^+$, required 986.5074).

Compound 190

Method 1 was followed providing Compound 190 in 70% yield. $^1H$ NMR (500 MHz, $CDCl_3$) δ 9.74 (s, 1H), 7.97 (s, 1H), 7.66 (s, 1H), 7.56 (s, 1H), 7.33 (dd, J=8.8, 5.2 Hz, 1H), 6.95 (d, J=8.3 Hz, 1H), 6.83 (t, J=9.1 Hz, 1H), 6.75 (d, J=9.5 Hz, 1H), 6.59 (s, 1H), 6.11 (s, 1H), 6.05 (s, 1H), 5.88 (dd, J=10.4, 4.7 Hz, 1H), 5.48 (s, 1H), 5.31 (d, J=10.2 Hz, 1H), 3.97 (s, 4H), 3.92 (s, 3H), 3.85-3.78 (m, 6H), 3.76 (s, 1H), 3.60 (s, 3H), 3.44-3.26 (m, 3H), 3.23-3.16 (m, 2H), 3.16-3.08 (m, 1H), 3.01 (d, J=12.6 Hz, 1H), 2.82 (d, J=16.1 Hz, 1H), 2.72 (s, 3H), 2.68 (d, J=13.8 Hz, 2H), 2.64 (s, 1H), 2.48-2.41 (m, 2H), 2.35 (d, J=14.0 Hz, 1H), 2.25-2.16 (m, 1H), 2.11 (s, 3H), 2.04-1.98 (m, 1H), 1.90-1.76 (m, 3H), 1.39-1.30 (m, 2H), 0.91-0.81 (m, 3H), 0.78 (t, J=7.3 Hz, 6H); HRESI-TOF m/z 992.4813 ($C_{55}H_{66}FN_5O_{11}+H^+$, required 992.4816).

II. Reexamination of Reported Ritter Amidation 20'-Acetamidoleurosidine (8)

From Ritter reaction: $^1H$ NMR (600 MHz, $CDCl_3$) δ 9.81 (s, 1H), 7.98 (s, 1H), 7.52 (d, J=7.8 Hz, 1H), 7.21-7.14 (m, 1H), 7.14-7.08 (m, 3H), 6.50 (s, 1H), 6.16 (s, 1H), 6.08 (s, 1H), 5.88-5.80 (m, 1H), 5.45 (s, 1H), 5.28 (d, J=10.2 Hz, 1H), 3.79 (s, 3H), 3.77 (s, 1H), 3.76 (s, 3H), 3.66-3.61 (m, 1H), 3.59 (s, 3H), 3.40-3.34 (m, 1H), 3.33-3.27 (m, 1H), 3.27-3.21 (m, 2H), 3.15 (t, J=14.4 Hz, 1H), 3.04 (dd, J=14.5, 5.9 Hz, 1H), 2.97 (d, J=10.7 Hz, 1H), 2.91-2.83 (m, 1H), 2.83-2.77 (m, 1H), 2.73 (s, 3H), 2.71-2.64 (m, 2H), 2.63 (s, 1H), 2.47-2.41 (m, 1H), 2.31 (dq, J=14.8, 7.5 Hz, 1H), 2.27-2.22 (m, 1H), 2.22-2.15 (m, 1H), 2.09 (s, 3H), 1.88 (s, 3H), 1.78 (dt, J=14.4, 7.4 Hz, 1H), 1.75-1.68 (m, 1H), 1.43 (dq, J=14.3, 7.2 Hz, 1H), 1.36-1.27 (m, 1H), 1.07-0.99 (m, 1H), 0.96 (d, J=15.1 Hz, 1H), 0.81 (t, J=7.4 Hz, 3H), 0.78 (t, J=7.4 Hz, 3H); $^{13}C$ NMR (151 MHz, $CDCl_3$) δ 174.5, 171.8, 171.1, 169.8, 158.1, 153.1, 135.0, 130.9, 130.2, 129.4, 124.6, 123.3, 123.0, 122.6, 119.2, 118.3, 117.0, 110.8, 94.5, 83.5, 79.8, 76.6, 65.8, 56.8, 56.0, 54.4, 53.4, 52.6, 52.4, 50.5, 44.7, 43.5, 42.8, 38.6, 37.1, 30.9, 30.7, 30.1, 24.7, 21.3, 8.6, 8.2; IR (film) $v_{max}$ 3467, 2958, 1738, 1666, 1459, 1229, 1039, 749 $cm^{-1}$; HRESI-TOF m/z 852.4547 ($C_{48}H_{61}N_5O_9+H^+$, required 852.4542). $[\alpha]_D^{23}$+13 (c 0.31, $CHCl_3$). Identical in all aspects with reported data and an authentic sample including HPLC and TLC comigration.[41]

Leurosidine $^1H$ NMR (400 MHz, $CDCl_3$) δ 9.80 (br s, 1H), 7.95 (s, 1H), 7.54 (d, J=7.8 Hz, 1H), 7.20-7.05 (m, 3H), 6.57 (s, 1H), 6.10 (s, 1H), 5.86 (dd, J=9.7, 3.5 Hz, 1H), 5.47 (s, 1H), 5.31 (d, J=9.7 Hz, 1H), 3.80 (s, 6H), 3.74 (s, 1H), 3.60 (s, 3H), 3.43-3.23 (m, 4H), 3.21-3.08 (m, 2H), 2.98-2.92 (m, 1H), 2.72 (s, 3H), 2.87-2.67 (m, 3H), 2.50-2.40 (m, 1H), 2.28-2.11 (m, 6H), 2.11 (s, 3H), 1.84-1.73 (m, 3H), 1.59-1.52 (m, 1H), 1.41-1.16 (m, 2H), 0.95 (t, J=7.5 Hz, 3H), 0.82 (t, J=7.4 Hz, 3H); HRESI-TOF m/z 811.4249 ($C_{46}H_{58}N_4O_9+H^+$, required 811.4276). $[\alpha]_D^{23}$+60 (c 0.24, $CHCl_3$). Identical in all aspects with reported data.[41]

20'-Acetamidovinblastine (10)

20'-aminovinblastine (6, 30 mg, 37 μmol) was dissolved in 1 mL of anhydrous $CH_2Cl_2$. i-$Pr_2NEt$ (13 μL, 74 μmol) and acetyl chloride (4 μL, 56 μmol) were added and the resulting mixture was stirred for 30 min, then diluted with saturated aqueous $NaHCO_3$ (2 mL). The mixture was extracted with 10% MeOH/$CH_2Cl_2$ (4×2 mL), and washed with saturated aqueous NaCl (4 mL). The combined organic extracts were dried ($Na_2SO_4$) and concentrated under reduced pressure. The crude product was purified by PTLC ($SiO_2$, 97:3:3 EtOAc/MeOH/$Et_3N$) to give 10 (21.5 mg, 68%, white solid): $^1H$ NMR (600 MHz, $CDCl_3$) δ 9.79 (s, 1H), 8.01 (s, 1H), 7.50 (d, J=7.9 Hz, 1H), 7.20-7.04 (m, 3H), 6.62 (s, 1H), 6.09 (s, 1H), 5.88-5.82 (m, 1H), 5.47 (s, 1H), 5.40 (s, 1H), 5.30 (d, J=10.2 Hz, 1H), 3.79 (s, 7H), 3.73 (s, 1H), 3.59 (s, 3H), 3.55-3.47 (m, 3H), 3.43-3.34 (m, 2H), 3.33-3.15 (m, 4H), 3.14-3.06 (m, 1H), 2.84-2.77 (m, 1H), 2.70 (s, 3H), 2.65 (s, 1H), 2.59 (s, 1H), 2.48-2.40 (m, 1H), 2.33 (s, 1H), 2.23-2.16 (m, 2H), 2.14 (s, 3H), 2.10 (s, 3H), 1.97-1.89 (m, 1H), 1.86-1.73 (m, 3H), 1.70-1.62 (m, 1H), 1.61-1.51 (m, 1H), 1.42-1.30 (m, 2H), 1.22-1.14 (m, 1H), 0.81 (t, J=7.4 Hz, 3H), 0.75 (t, J=7.5 Hz, 3H); $^{13}C$ NMR (150 MHz, $CDCl_3$) 175.5, 172.6, 171.8, 170.8, 158.9, 153.7, 135.6, 132.9, 130.8, 130.2, 125.4, 124.4, 123.7, 123.1, 119.8, 119.2, 116.7, 111.4, 84.3, 80.5, 77.3, 66.5, 63.4, 56.8, 55.9, 55.4, 54.1, 53.2, 53.1, 51.3, 51.2, 50.7, 43.6, 39.2, 31.8, 31.7, 31.5, 30.6, 30.2, 25.7, 22.0, 9.3, 8.1; IR (film) $v_{max}$ 3459, 2956, 1738, 1668, 1457, 1230, 1043, 729 $cm^{-1}$;

HRESI-TOF m/z 852.4539 (C$_{48}$H$_{61}$N$_5$O$_9$+H$^+$, required 852.4542). [α]$_n^{23}$+3 (c 0.26, CHCl$_3$). Identical in all aspects with reported data.[41]

20'-acetamidoleurosidine (8)

20'-aminoleurosidine (35 mg, 43 μmol) was dissolved in 1 mL of anhydrous CH$_2$Cl$_2$. i-Pr$_2$NEt (15 μL, 86 μmol) and acetyl chloride (4.6 μL, 64 μmol) were added and the resulting mixture was stirred for 30 min, then diluted with saturated aqueous NaHCO$_3$ (2 mL). The mixture was extracted with 10% MeOH/CH$_2$Cl$_2$ (4×2 mL), and washed with saturated aqueous NaCl (4 mL). The combined organic extracts were dried (Na$_2$SO$_4$) and concentrated under reduced pressure. The crude product was purified by PTLC (SiO$_2$, 97:3:3 EtOAc/MeOH/Et$_3$N) to give 8 (25 mg, 68%, white solid): $^1$H NMR (600 MHz, CDCl$_3$) δ 9.81 (s, 1H), 7.98 (s, 1H), 7.52 (d, J=7.8 Hz, 1H), 7.21-7.14 (m, 1H), 7.14-7.08 (m, 3H), 6.50 (s, 1H), 6.16 (s, 1H), 6.08 (s, 1H), 5.88-5.80 (m, 1H), 5.45 (s, 1H), 5.28 (d, J=10.2 Hz, 1H), 3.79 (s, 3H), 3.77 (s, 1H), 3.76 (s, 3H), 3.66-3.61 (m, 1H), 3.59 (s, 3H), 3.40-3.34 (m, 1H), 3.33-3.27 (m, 1H), 3.27-3.21 (m, 2H), 3.15 (t, J=14.4 Hz, 1H), 3.04 (dd, J=14.5, 5.9 Hz, 1H), 2.97 (d, J=10.7 Hz, 1H), 2.91-2.83 (m, 1H), 2.83-2.77 (m, 1H), 2.73 (s, 3H), 2.71-2.64 (m, 2H), 2.63 (s, 1H), 2.47-2.41 (m, 1H), 2.31 (dq, J=14.8, 7.5 Hz, 1H), 2.27-2.22 (m, 1H), 2.22-2.15 (m, 1H), 2.09 (s, 3H), 1.88 (s, 3H), 1.78 (dt, J=14.4, 7.4 Hz, 1H), 1.75-1.68 (m, 1H), 1.43 (dq, J=14.3, 7.2 Hz, $^1$H), 1.36-1.27 (m, 1H), 1.07-0.99 (m, 1H), 0.96 (d, J=15.1 Hz, 1H), 0.81 (t, J=7.4 Hz, 3H), 0.78 (t, J=7.4 Hz, 3H); $^{13}$C NMR (151 MHz, CDCl$_3$) δ 174.5, 171.8, 171.1, 169.80, 158.1, 153.1, 135.0, 130.9, 130.2, 129.4, 124.6, 123.3, 123.0, 122.6, 119.2, 118.3, 117.0, 110.8, 94.5, 83.5, 79.8, 76.6, 65.8, 56.8, 56.0, 54.4, 53.4, 52.6, 52.4, 50.5, 44.7, 43.5, 42.8, 38.6, 37.1, 30.9, 30.7, 30.1, 24.7, 21.3, 8.6, 8.2; IR (film) ν$_{max}$ 3467, 2958, 1738, 1666, 1459, 1229, 1039, 749 cm$^{-1}$; HRESI-TOF m/z 852.4547 (C$_{48}$H$_{61}$H$_5$O$_9$+H$^+$, required 852.4542). [α]$_D^{23}$+13 (c 0.31, CHCl$_3$). Identical in all aspects with reported data and an authentic sample [Leggans et al., Org. Lett. 2012, 14:1428-1431].

$^1$H NMR Spectra Comparison

| δ$_H$ of prepared 20'-acetamido-leurosidine (600 MHz, δ in ppm, J in Hz) | δ$_H$ of literature proposed 20'-acetamidovinblastine (δ in ppm, J in Hz) | δ$_H$ of synthesized 20'-acetamidovinblastine (600 MHz, δ in ppm, J in Hz) |
|---|---|---|
| 1.88 (s, 3H) | 1.87 (s, acetyl methyl) | 2.10 (s, 3H) |
| 2.09 (s, 3H) | 2.09 (s, acetoxy) | 2.14 (s, 3H) |
| 2.73 (s, 3H) | 2.74 (N-1, methyl) | 2.70 (s, 3H) |
| 3.59 (s, 3H) | 3.60 (carbomethoxy) | 3.59 (s, 3H) |
| 3.76 (s, 3H) | 3.78 | 3.79 (s, 6H) |
| 3.79 (s, 3H) | 3.80 | |
| 5.28 (d, J = 10.0 Hz, 1H) | 5.25 (multiple) | 5.30 (dt, J = 10.2, 1.9 Hz, 1H) |
| 5.45 (s, 1H) | 5.46 (singlet, 1H) | 5.47 (s, 1H) |
| 5.85 (m, 1H) | 5.85 (multiplet) | 5.85 (m, 1H) |
| 6.08 (s, 1H) | 6.09 (ring hydrogen) 6.40 (NH) | 6.09 (s, 1H) |
| 6.50 (s, 1H) | 6.51 (ring hydrogen) | 6.62 (s, 1H) |

III. Purity of Tested and Active Compounds

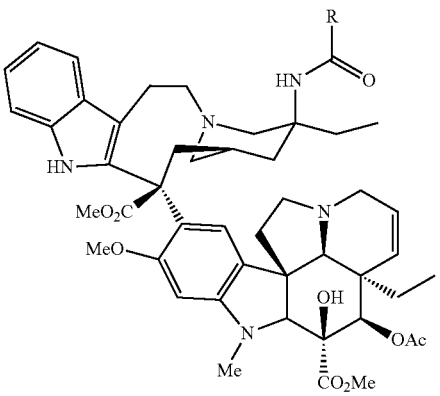

| Compound | % Purity |
|---|---|
| 10 | 99 |
| 12 | 96 |
| 13 | 95 |
| 14 | 98 |
| 15 | 99 |
| 16 | 95 |
| 17 | 95 |
| 18 | 98 |
| 19 | 99 |
| 20 | 98 |
| 21 | 97 |
| 22 | 97 |
| 23 | 95 |
| 24 | 99 |
| 25 | 99 |
| 26 | 97 |
| 27 | 95 |
| 28 | 97 |
| 29 | 98 |
| 30 | 95 |
| 31 | 98 |
| 32 | 99 |
| 33 | 99 |
| 34 | 97 |
| 35 | 95 |
| 36 | 99 |
| 37 | 99 |
| 38 | 95 |
| 39 | 98 |
| 40 | 98 |
| 41 | 97 |
| 42 | 98 |
| 43 | 99 |
| 44 | 96 |
| 45 | 99 |
| 46 | 96 |
| 47 | 96 |
| 48 | 99 |
| 49 | 98 |
| 50 | 95 |
| 51 | 98 |
| 52 | 95 |
| 53 | 97 |
| 54 | 97 |
| 55 | 95 |
| 56 | 95 |
| 57 | 98 |
| 58 | 95 |
| 59 | 97 |
| 60 | 99 |
| 61 | 95 |
| 62 | 99 |
| 63 | 96 |
| 64 | 98 |
| 65 | 98 |
| 66 | 98 |
| 67 | 99 |

93
-continued
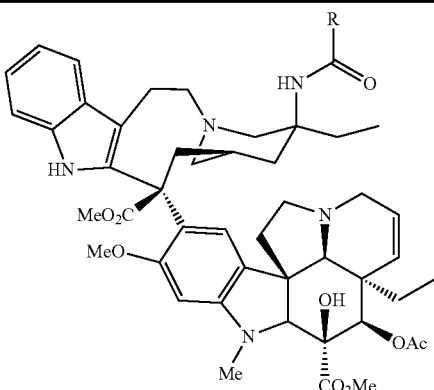
94
-continued
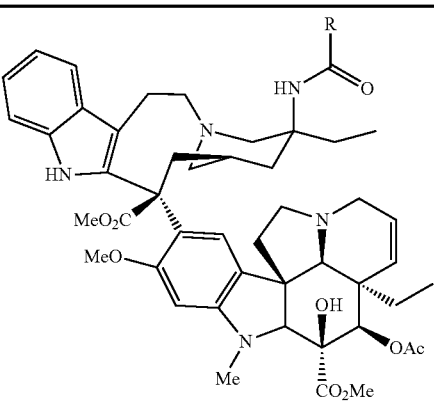
| Compound | % Purity |
|---|---|
| 68 | 99 |
| 69 | 96 |
| 70 | 98 |
| 71 | 96 |
| 72 | 97 |
| 73 | 95 |
| 74 | 96 |
| 75 | 97 |
| 76 | 99 |
| 77 | 96 |
| 78 | 99 |
| 79 | 99 |
| 80 | 97 |
| 81 | 99 |
| 82 | 99 |
| 83 | 96 |
| 84 | 99 |
| 85 | 99 |
| 86 | 96 |
| 87 | 96 |
| 88 | 97 |
| 89 | 98 |
| 90 | 95 |
| 91 | 95 |
| 92 | 95 |
| 93 | 99 |
| 94 | 99 |
| 95 | 97 |
| 97 | 99 |
| 98 | 99 |
| 99 | 99 |
| 100 | 97 |
| 101 | 99 |
| 102 | 98 |
| 103 | 99 |
| 104 | 96 |
| 105 | 97 |
| 106 | 99 |
| 107 | 95 |
| 108 | 98 |
| 109 | 98 |
| 110 | 99 |
| 111 | 99 |
| 112 | 98 |
| 113 | 96 |
| 114 | 98 |
| 115 | 98 |
| 116 | 96 |
| 117 | 99 |
| 118 | 96 |
| 119 | 96 |
| 120 | 96 |
| 121 | 99 |
| 122 | 98 |
| 123 | 99 |
| 124 | 99 |
| 125 | 95 |
| 126 | 98 |
| Compound | % Purity |
|---|---|
| 127 | 97 |
| 128 | 95 |
| 129 | 95 |
| 130 | 95 |
| 131 | 97 |
| 133 | 99 |
| 134 | 98 |
| 135 | 95 |
| 137 | 98 |
| 138 | 98 |
| 139 | 97 |
| 140 | 98 |
| 141 | 98 |
| 143 | 95 |
| 144 | 97 |
| 145 | 99 |
| 146 | 97 |
| 147 | 99 |
| 148 | 98 |
| 149 | 96 |
| 151 | 99 |
| 152 | 99 |
| 153 | 98 |
| 154 | 95 |
| 155 | 96 |
| 156 | 99 |
| 157 | 99 |
| 158 | 99 |
| 159 | 98 |
| 160 | 97 |
| 161 | 98 |
| 162 | 99 |
| 163 | 99 |
| 164 | 98 |
| 165 | 99 |
| 166 | 99 |
| 167 | 97 |
| 168 | 99 |
| 169 | 96 |
| 170 | 98 |
| 171 | 99 |
| 172 | 95 |
| 173 | 99 |
| 174 | 99 |
| 175 | 99 |
| 176 | 95 |
| 177 | 99 |
| 178 | 97 |
| 179 | 96 |
| 180 | 98 |
| 181 | 97 |
| 182 | 99 |
| 183 | 99 |
| 184 | 97 |
| 185 | 98 |
| 186 | 98 |

-continued

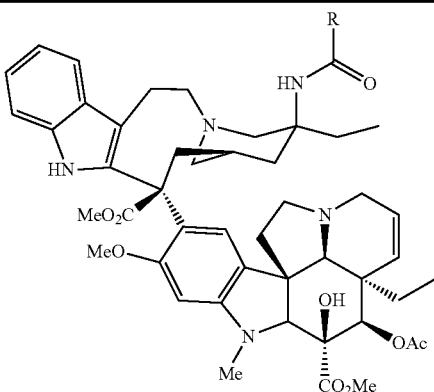

| Compound | % Purity |
|---|---|
| 188 | 97 |
| 189 | 99 |
| 190 | 99 |

Each of the patents, patent applications and articles cited herein is incorporated by reference.

The foregoing description and the examples are intended as illustrative and are not to be taken as limiting. Still other variations within the spirit and scope of this invention are possible and will readily present themselves to those skilled in the art.

The invention claimed is:

1. A 20'-carboxamide-substituted vinca alkaloid compound or a pharmaceutically acceptable salt thereof, wherein said compound corresponds in structure to a compound shown in Table A, below,

TABLE A

| Vinca Compound | $R^1$ | $R^2$ | $R^3$ |
|---|---|---|---|
| Vinblastine | —CH$_3$ | —C(O)—OCH$_3$ | —O—C(O)—CH$_3$ |
| Vincristine | —CHO | —C(O)—OCH$_3$ | —O—C(O)—CH$_3$ |
| Vindesine | —CH$_3$ | —C(O)—NH$_2$ | —OH | wherein

Y— is fluoro (—F) or hydrido (—H), and $R^a$— is a ring system containing up to a total of three 5-, 6- or 7-membered rings that are fused or otherwise directly bonded to each other, said ring system being carbocyclic or heterocyclic in which ring atoms other than carbon are the same or different and are nitrogen (N), oxygen (O) or sulfur (S), and said heterocyclic ring system contains up to three ring heteroatoms, and up to four substituents that are the same or different are present bonded to ring atoms of said ring system, said substituents being selected from the group consisting of $C_1$-$C_7$ hydrocarbyl, trifluoromethyl, phenyl, halogen (fluoro, chloro or bromo), cyano, nitro, $C_1$-$C_7$ acyl, amino, mono- or di-$C_1$-$C_7$ hydrocarbylamino, a nitrogen-bonded heterocyclic ring of 5- or 6 members that can contain 1 or 2 additional ring hetero atoms selected from oxygen, nitrogen, and sulfur, acylamido containing 1-7 carbon atoms, sulfonylamido containing 1-7 carbon atoms, oxycarbonylamido containing 1-7 carbon atoms, $C_1$-$C_7$ hydrocarbyloxy, N—$C_1$-$C_7$ hydrocarbyl acylamido containing 1-7 carbon atoms in the acyl group, N—$C_1$-$C_7$ hydrocarbyl sulfonylamido containing 1-7 carbon atoms in the sulfonamido group, N—$C_1$-$C_7$ hydrocarbyl oxycarbonylamido containing 1-7 carbon atoms in the oxycarbonyl group, trifluoromethoxy, trifluoromethylamino, trifluoromethylamino oxycarbonyl containing 1-7 carbon atoms in the oxycarbonyl group, and $C_1$-$C_7$ hydrocarbylthioxy group.

2. The 20'-carboxamide-substituted vinca alkaloid compound or pharmaceutically acceptable salt thereof according to claim 1, wherein said ring system contains one or two rings.

3. The 20'-carboxamide-substituted vinca alkaloid compound or pharmaceutically acceptable salt thereof according to claim 2, wherein said ring system contains one aromatic ring.

4. The 20'-carboxamide-substituted vinca alkaloid compound or pharmaceutically acceptable salt thereof according to claim 3, wherein said one aromatic ring is carbocyclic.

5. The 20'-carboxamide-substituted vinca alkaloid compound or pharmaceutically acceptable salt thereof according to claim 4, wherein said one carbocyclic aromatic ring is a single 6-membered ring.

6. The 20'-carboxamide-substituted vinca alkaloid compound or pharmaceutically acceptable salt thereof according to claim 4, wherein said compound corresponds in structure to a compound shown in Table A, below,
TABLE A
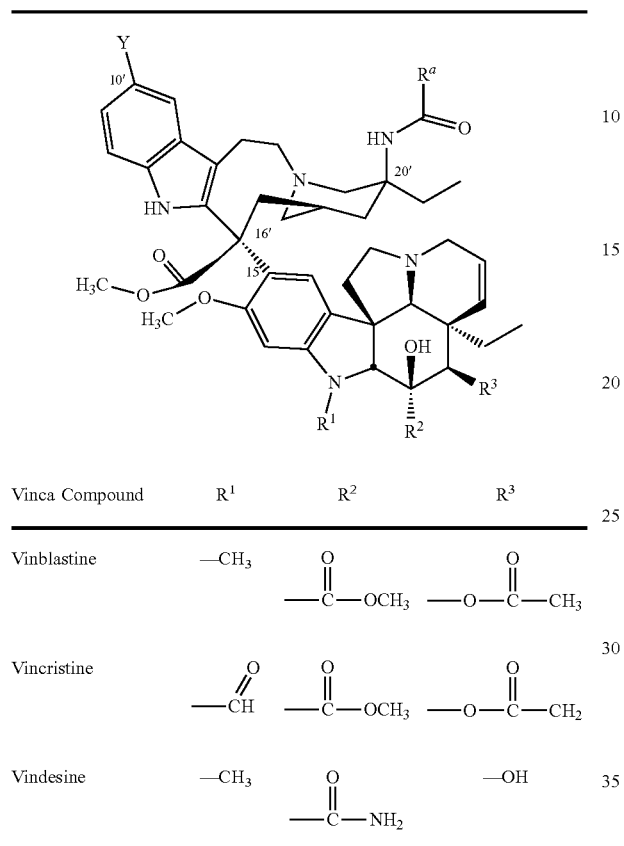
| Vinca Compound | R¹ | R² | R³ |
|---|---|---|---|
| Vinblastine | —CH₃ | —C(O)—OCH₃ | —O—C(O)—CH₃ |
| Vincristine | —CH(O) | —C(O)—OCH₃ | —O—C(O)—CH₂ |
| Vindesine | —CH₃ | —C(O)—NH₂ | —OH |
wherein
Y— is fluoro (—F) or hydrido (—H), and
R$^a$— is a ring system selected from the group consisting of one or more of those shown below:
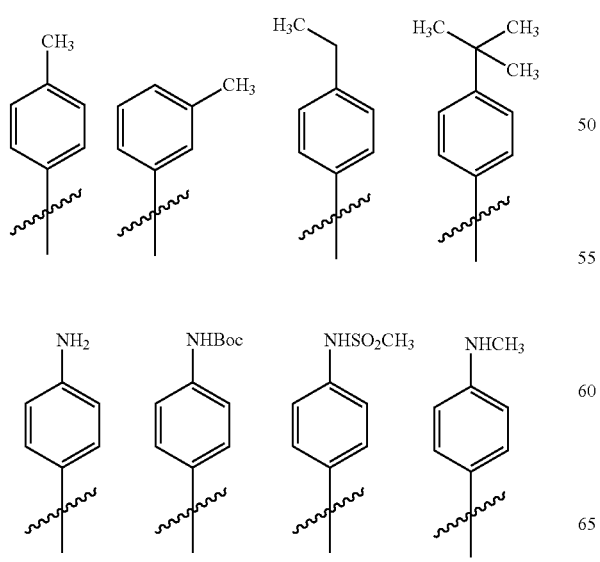
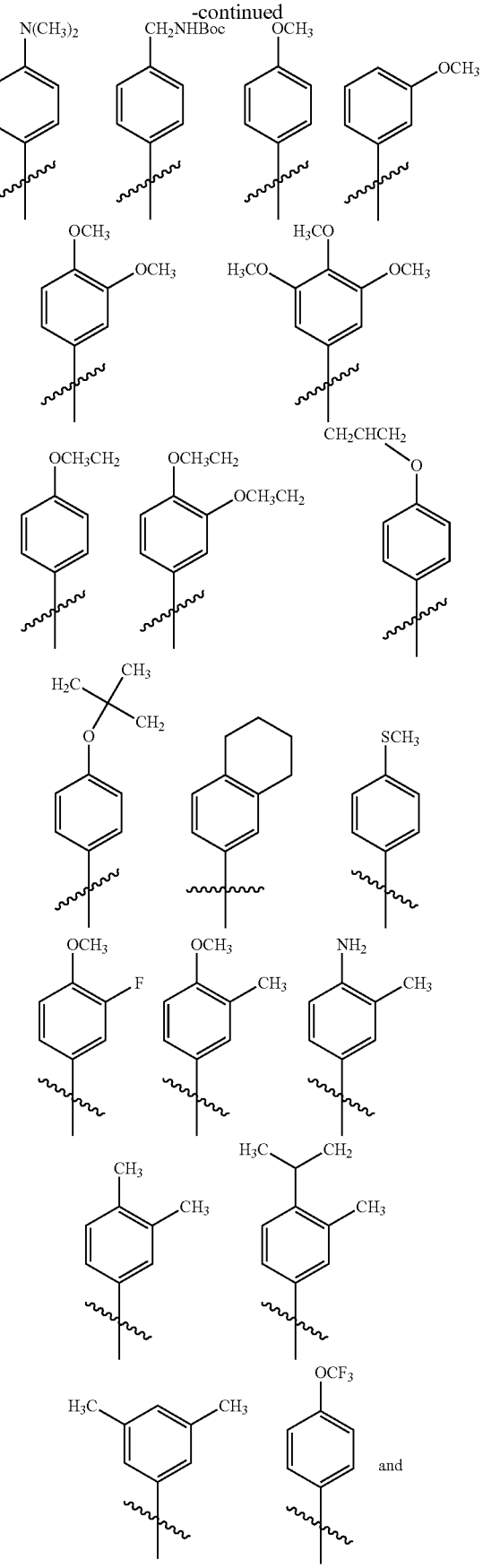
and

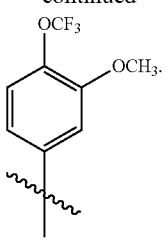

7. The 20′-carboxamide-substituted vinca alkaloid compound or pharmaceutically acceptable salt thereof according to claim 4, wherein said ring system contains two fused rings at least one of which is an aromatic carbocyclic ring.

8. The 20′-carboxamide-substituted vinca alkaloid compound or pharmaceutically acceptable salt thereof according to claim 7, wherein said compound corresponds in structure to a compound shown in Table A, below,

TABLE A

| Vinca Compound | R¹ | R² | R³ |
|---|---|---|---|
| Vinblastine | —CH₃ | —C(=O)—OCH₃ | —O—C(=O)—CH₃ |
| Vincristine | —CH(=O) | —C(=O)—OCH₃ | —O—C(=O)—CH₃ |
| Vindesine | —CH₃ | —C(=O)—NH₂ | —OH | wherein
Y— is fluoro (—F) or hydrido (—H), and
R$^a$— is a ring system selected from the group consisting of one or more of those shown below:

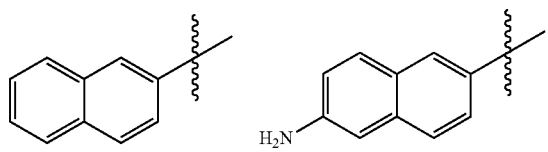

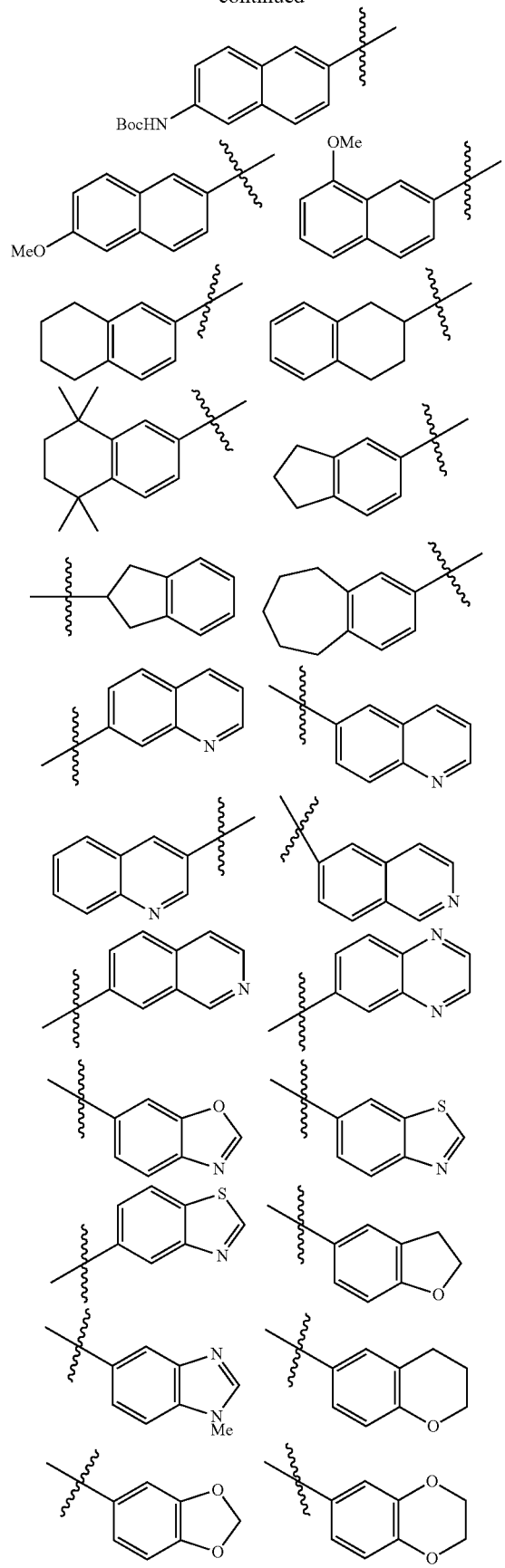

-continued

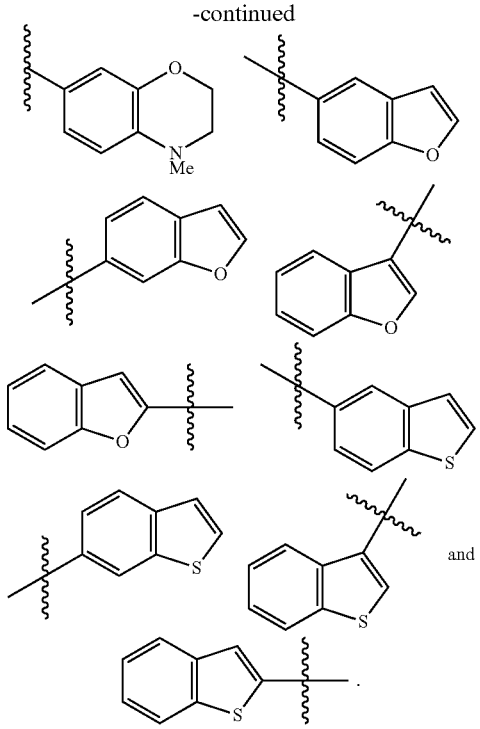

9. The 20'-carboxamide-substituted vinca alkaloid compound or pharmaceutically acceptable salt thereof according to claim 5, wherein said aromatic carbocyclic ring is bonded directly to the depicted carbonyl group.

10. The 20'-carboxamide-substituted vinca alkaloid compound or pharmaceutically acceptable salt thereof according to claim 9, wherein a heterocyclic ring is fused to said carbocyclic aromatic ring.

11. The 20'-carboxamide-substituted vinca alkaloid compound or pharmaceutically acceptable salt thereof according to claim 10, wherein said compound corresponds in structure to a compound shown in Table A, below,

TABLE A

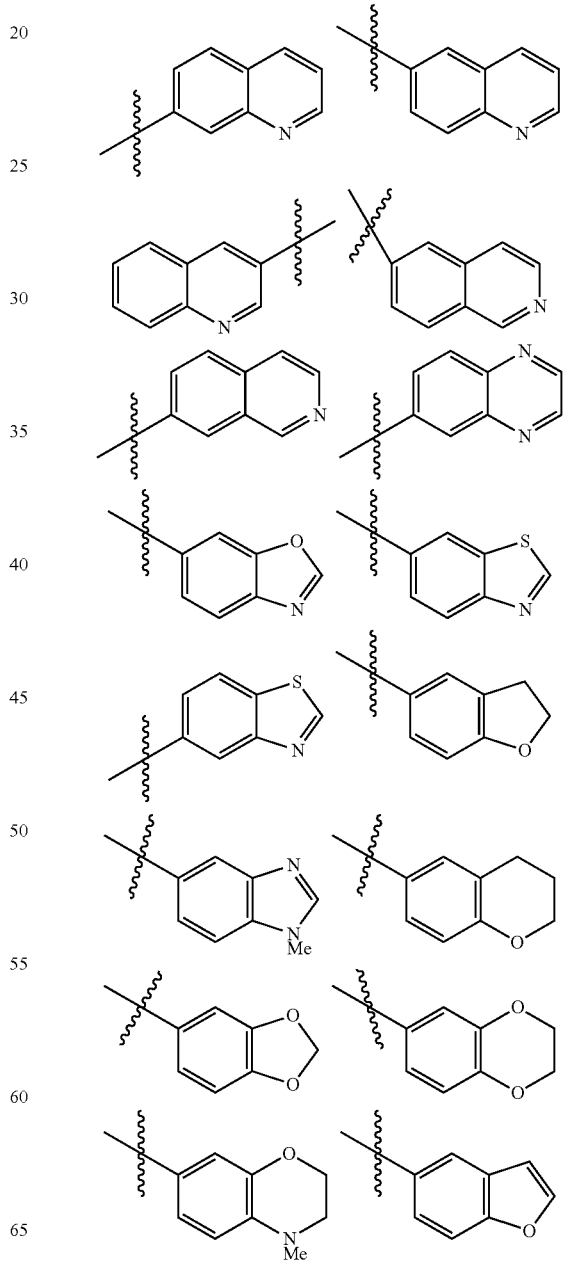

| Vinca Compound | $R^1$ | $R^2$ | $R^3$ |
|---|---|---|---|
| Vinblastine | —CH$_3$ | —C(O)—OCH$_3$ | —O—C(O)—CH$_3$ |
| Vincristine | —CH(O) | —C(O)—OCH$_3$ | —O—C(O)—CH$_3$ |
| Vindesine | —CH$_3$ | —C(O)—NH$_2$ | —OH | wherein

Y— is fluoro (—F) or hydrido (—H), and $R^a$— is a ring system selected from the group consisting of one or more of those shown below:

-continued

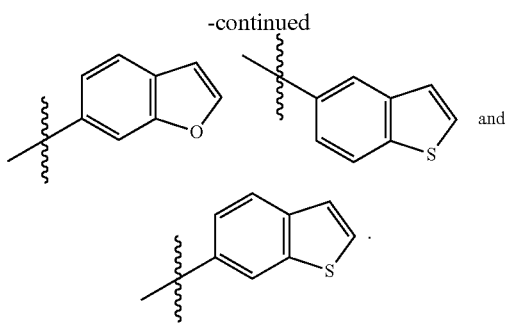

and

12. The 20'-carboxamide-substituted vinca alkaloid compound or pharmaceutically acceptable salt thereof according to claim 3, wherein said at least one aromatic ring is heterocyclic.

13. The 20'-carboxamide-substituted vinca alkaloid compound or pharmaceutically acceptable salt thereof according to claim 12, wherein said heterocyclic aromatic ring contains 5-members.

14. The 20'-carboxamide-substituted vinca alkaloid compound or pharmaceutically acceptable salt thereof according to claim 13, wherein said 5-membered heterocyclic aromatic ring contains two heteroatoms in the ring.

15. The 20'-carboxamide-substituted vinca alkaloid compound or pharmaceutically acceptable salt thereof according to claim 12, wherein said heterocyclic aromatic ring contains 5- or 6-members and contains one hetero atom in the ring.

16. The 20'-carboxamide-substituted vinca alkaloid compound or pharmaceutically acceptable salt thereof according to claim 12, wherein said compound corresponds in structure to a compound shown in Table A, below,

TABLE A

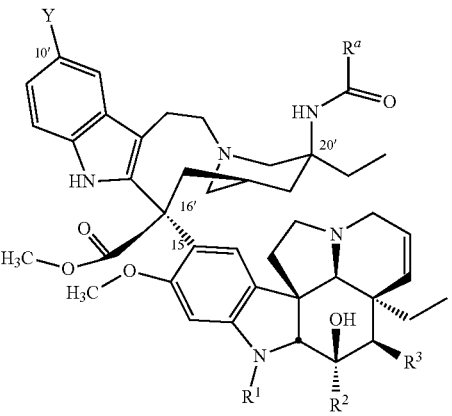

| Vinca Compound | $R^1$ | $R^2$ | $R^3$ |
|---|---|---|---|
| Vinblastine | —CH$_3$ | —C(=O)—OCH$_3$ | —O—C(=O)—CH$_3$ |
| Vincristine | —CHO | —C(=O)—OCH$_3$ | —O—C(=O)—CH$_3$ |
| Vindesine | —CH$_3$ | —C(=O)—NH$_2$ | —OH | wherein
Y— is fluoro (—F) or hydrido (—H), and
$R^a$— is a ring system selected from the group consisting of one or more of those shown below:

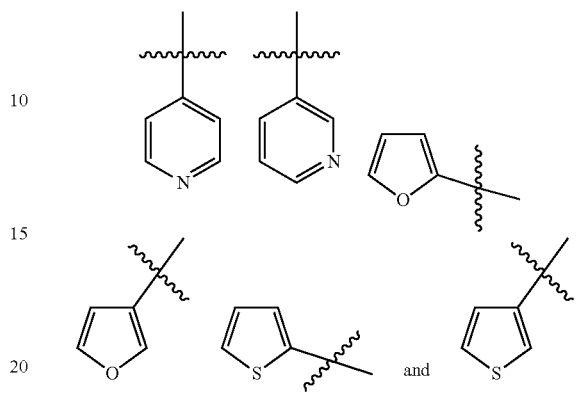

and

17. The 20'-carboxamide-substituted vinca alkaloid compound or pharmaceutically acceptable salt thereof according to claim 1, wherein said ring system, Ra-, is free of substituents other than fluoro bonded at a ring position beta- to the depicted carbonyl group to which Ra- is bonded.

18. The 20'-carboxamide-substituted vinca alkaloid compound or pharmaceutically acceptable salt thereof according to claim 1, wherein the substituents present are electron donating.

19. The 20'-carboxamide-substituted vinca alkaloid compound or pharmaceutically acceptable salt thereof according to claim 1, wherein Y— is fluoro.

20. The 20'-carboxamide-substituted vinca alkaloid compound or pharmaceutically acceptable salt thereof according to claim 19, wherein said compound corresponds in structure to a compound shown in Table A, below,

TABLE A

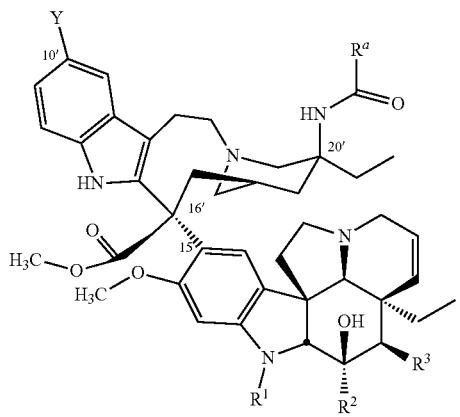

| Vinca Compound | $R^1$ | $R^2$ | $R^3$ |
|---|---|---|---|
| Vinblastine | —CH$_3$ | —C(=O)—OCH$_3$ | —O—C(=O)—CH$_3$ |
| Vincristine | —CHO | —C(=O)—OCH$_3$ | —O—C(=O)—CH$_3$ |

TABLE A-continued

| Vindesine | —CH₃ | $-\overset{O}{\underset{\|}{C}}-NH_2$ | —OH | wherein

R$^a$— is a ring system selected from the group consisting of those shown below:

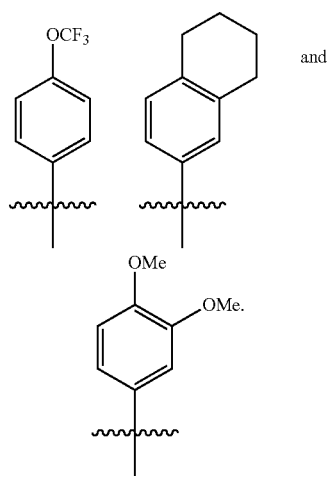

21. A pharmaceutical composition that comprises a cancerous cell proliferation-inhibiting amount of a 20'-carboxamide-substituted vinca alkaloid compound of claim 1 or a pharmaceutically acceptable salt thereof dissolved or dispersed in a physiologically acceptable carrier.

22. A method of inhibiting the growth of cancerous cells that comprises contacting said cancerous cells with a cancerous cell proliferation-inhibiting amount of a 20'-carboxamide-substituted vinca alkaloid compound of claim 1 or a pharmaceutically acceptable salt thereof.

23. The method according to claim 22, wherein said cancerous cells are contacted a plurality of times.

24. The method according to claim 22, wherein said cancerous cells are contacted in vitro.

25. The method according to claim 22, wherein said contacted cancerous cells are leukemia cells.

26. The method according to claim 22, wherein said contacted cancerous cells are colon cancer cells.

27. The method according to claim 22, wherein said contacted cancerous cells are non small cell lung cancer cells.

28. The method according to claim 22, wherein said contacted cancerous cells are colon cancer cells that overexpress phosphoglycoprotein (Pgp).

* * * * *